US010604810B2

(12) United States Patent
Kozono et al.

(10) Patent No.: US 10,604,810 B2
(45) Date of Patent: Mar. 31, 2020

(54) COLORECTAL CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoko Kozono, Kamakura (JP); Hitoshi Nobumasa, Kamakura (JP); Satoshi Kondou, Kamakura (JP); Hiroko Sudo, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 264 days.

(21) Appl. No.: 15/318,312

(22) PCT Filed: Jun. 12, 2015

(86) PCT No.: PCT/JP2015/066970
§ 371 (c)(1),
(2) Date: Dec. 12, 2016

(87) PCT Pub. No.: WO2015/190586
PCT Pub. Date: Dec. 17, 2015

(65) Prior Publication Data
US 2017/0130274 A1    May 11, 2017

(30) Foreign Application Priority Data

Jun. 13, 2014  (JP) ................. 2014-122686
Mar. 30, 2015  (JP) ................. 2015-070182

(51) Int. Cl.
| | | |
|---|---|---|
| C12Q 1/68 | (2018.01) | |
| C12P 19/34 | (2006.01) | |
| C12Q 1/6886 | (2018.01) | |
| C12N 15/113 | (2010.01) | |
| G01N 33/53 | (2006.01) | |
| C12M 1/00 | (2006.01) | |
| C12N 15/09 | (2006.01) | |
| G01N 33/574 | (2006.01) | |

(52) U.S. Cl.
CPC ............ C12Q 1/6886 (2013.01); C12M 1/00 (2013.01); C12N 15/09 (2013.01); C12N 15/113 (2013.01); C12Q 1/68 (2013.01); G01N 33/53 (2013.01); G01N 33/574 (2013.01); C12Q 2600/118 (2013.01); C12Q 2600/158 (2013.01); C12Q 2600/178 (2013.01)

(58) Field of Classification Search
CPC .. C12Q 1/6886; C12Q 2600/178; C12Q 1/68; C12Q 1/6876
See application file for complete search history.

(56) References Cited

U.S. PATENT DOCUMENTS

| | | | |
|---|---|---|---|
| 2001/0053519 A1* | 12/2001 | Fodor ................. | B01J 19/0046 435/6.11 |
| 2008/0306006 A1 | 12/2008 | Croce et al. | |
| 2012/0088687 A1 | 4/2012 | Goel et al. | |
| 2012/0231970 A1 | 9/2012 | Nakagama et al. | |
| 2013/0102487 A1 | 4/2013 | Gironella i Cos et al. | |

FOREIGN PATENT DOCUMENTS

| | | |
|---|---|---|
| JP | 2009-531019 A | 9/2009 |
| WO | WO 2007/081204 A2 | 7/2007 |
| WO | WO 2007/081740 A2 | 7/2007 |
| WO | WO 2009/008720 A2 | 1/2009 |
| WO | WO 2011/076142 A1 | 6/2011 |

OTHER PUBLICATIONS miScript™ miRNA PCR Array (384-well, 384HC) Human miRBase Profiler HC Plate 6, Qiagen, pp. 1-10 printed from https://b2b.qiagen.com/~/media/genetable/mi/hs/34/mihs-3406z . (Year: 2012).*
Sheng, W. et al. Oncology Reports 36: 3387-3396, (Year: 2016).*
Meng, Q.-L. et al. BMC Microbiology 2014, 14:37, Feb. 12, (Year: 2014).*
Hoshikawa, Y. et al. Physiol Genomics 12: 209-219, (Year: 2003).*
Cheung V.G.et al. Nature Genetics, pp. 422-425, vol. 33, Mar. (Year: 2003).*
Cobb, J. P. et al. Crit Care Med, pp. 2711-2721, vol. 30, No. 12 (Year: 2002).*
Shivapurkar N, Weiner LM, Marshall JL, Madhavan S, Deslattes Mays A, et al. (Jan. 6, 2014) Recurrence of Early Stage Colon Cancer Predicted by Expression Pattern of Circulating microRNAs. PLoS ONE 9(1): e84686. doi:10.1371/journal.pone.0084686 (Year: 2014).*
Allison et al., "A comparison of fecal occult-blood tests for colorectal-cancer screening", The New England Journal of Medicine, vol. 334, No. 3, 1996, pp. 155-159.
American Cancer Society, "Colorectal Cancer", 2013, pp. 5-6, 17-28, 33, 45-54, and 67-71.
Eto et al., "Prospect of microRNA toward laboratory medicine Gastrointestinal Cancer and microRNA", Clinical Chemistry, vol. 43, 2014, pp. 99-105.
International Search Report for PCT/JP2015/066970 (PCT/ISA/210) dated Sep. 8, 2015.
Kozomara et al., "miRBase: annotating high confidence microRNAs using deep sequencing data", Nucleic Acids Research, vol. 42, 2014, Database issue, pp. D68-D73.

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or a device for the detection of colorectal cancer and a method for detecting colorectal cancer. The present invention provides a kit or a device for the detection of colorectal cancer, comprising a nucleic acid capable of specifically binding to a miRNA in a sample from a subject, and a method for detecting colorectal cancer, comprising measuring the miRNA in vitro.

6 Claims, 4 Drawing Sheets
Specification includes a Sequence Listing.

(56) References Cited

OTHER PUBLICATIONS

Palmqvist et al., "Prediagnostic levels of carcinoembryonic antigen and CA 242 in colorectal cancer: a matched case-control study", Diseases of colon and rectum, vol. 46, No. 11, 2003, pp. 1538-1544.
Sobin, et al., "TNM Classification of Malignant Tumours", International Union Against Cancer, 7th edition, 2010, pp. 94-99.
Takizawa et al., "The difference of serum RNA profile: RNA extraction and detection method", Cancer Research, vol. 73, No. 8 (Suppl. 1), Abstract No. 5294, 2013, 1 page.
Takizawa et al. "Simultaneous Profiling of Multiple miRNAs in FFPE or Serum Samples Using DNA Chip 3D-Gene", BIO Clinica, vol. 28, No. 9, 2013, pp. 872 to 873.
Written Opinion of the International Searching Authority for PCT/JP2015/066970 (PCT/ISA/237) dated Sep. 8, 2015.
Partial Supplementary European Search Report, dated Dec. 15, 2017, for European Application No. 15806013.7.
Ladewig et al., "*Homo sapiens* microRNA 6726 (MIR6726), microRNA", NCBI Reference Sequence: NR_106784.1, Apr. 3, 2014, https://www.ncbi.nlm.nih.gov/nuccore/563318489?sat=18&satkey=18644989.
Chinese Office Action for Chinese Application No. 201580031244.9, dated Nov. 14, 2019.
Tian et al,. "Serum microRNAs as promising novel biomarkers for hereditary nonpolyposis colorectal cancer," WCJD, vol. 21, issue 11, Apr. 18, 2013, pp. 1040-1045, with abstract.

\* cited by examiner

Fig. 1

```
                              guuu      c     c      c
hsa-miR-3679-5p           ca                                   hsa-mir-3679
(SEQ ID NO: 11)    a         ugg  gggaaggga                    (SEQ ID NO: 205)
       ↓                     |||  |||||||||
cguggaggau                   acc  ccuucccuu
||||||||||               aug                  aucu
guacuucucua            -c                      ↑
                                          hsa-miR-3679-3p
                                          (SEQ ID NO: 78)
```

COLORECTAL CANCER DETECTION KIT OR DEVICE, AND DETECTION METHOD

TECHNICAL FIELD

The present invention relates to a kit or a device for the detection of colorectal cancer, comprising a nucleic acid capable of specifically binding to a particular miRNA, which is used for examining the presence or absence of colorectal cancer in a subject, and a method for detecting colorectal cancer, comprising measuring an expression level of the miRNA using the nucleic acid.

BACKGROUND ART

The large intestine is an organ that stores residual bowel contents after digestion and absorption, and produces feces while absorbing water. The large intestine begins with the cecum, which is then connected to the ascending colon, the transverse colon, the descending colon, the sigmoid colon, the rectum, and the anal canal. According to the 2011 type-specific cancer statistics in Japan disclosed by the Center for Cancer Control and Information Services, National Cancer Center, the number of individuals affected by colorectal cancer was 112,772 people. Namely, it is estimated that one in approximately 14 Japanese people experience colorectal cancer. The number of incidences of this cancer takes the 2nd place by cancer site. The number of colorectal cancer deaths in men and women together climbs to 45,744 people and takes the 3rd place by cancer site. It is estimated that one in approximately 20 Americans develop colorectal cancer. The estimated number of American individuals affected by colorectal cancer climbed to 96,830 people in 2014, among which approximately 40,000 people reportedly died (Non Patent Literature 1).

The progression stages of colorectal cancer are specified in Non Patent Literature 2 and classified into stage 0 (Tis/N0/M0), stage I (T1 to T2/N0/M0), stage II (T3 to T4/N0/M0), stage IIA (T3/N0/M0), stage IIB (T4a/N0/M0), stage IIC (T4b/N0/M0), stage III (N1 to N2/M0), stage IIIA (T1 to T2/N1/M0 and T1N2a/M0), stage IIIB (T3 to T4a/N1/M0 and T2 to T3/N2a/M0 and T1 to T2/N2b/M0), stage IIIC (T4a/N2a/M0 and T3 to T4a/N2b/M0 and T4b/N1 to N2/M0), stage IVA (M1a), and stage IVB (M1b) according to the degrees of tumor spread (Tis and T1 to T4), lymph node metastasis (N0, N1a to N1c, and N2a to N2b), and distant metastasis (M0 and M1a to M1b).

The survival rate of colorectal cancer differs depending on the stages of progression. Non Patent Literature 1 has reported the following respective statistic values of colon cancer and rectal cancer. The 5-year relative survival rate of colon cancer is reportedly 74% for stage I, 67% for stage IIA, 59% for stage IIB, 37% for stage IIC, 73% for stage IIIA, 46% for stage IIIB, 28% for stage IIIC, and 6% for stage IV. Also, the 5-year relative survival rate of rectal cancer is reportedly 74% for stage I, 65% for stage IIA, 52% for stage IIB, 32% for stage IIC, 74% for stage IIIA, 45% for stage IIIB, 33% for stage IIIC, and 6% for stage IV. Evidently, colorectal cancer at an early stage of progression leads to a high survival rate. Thus, the early detection and treatment of colorectal cancer makes a significant contribution to improvement in survival rate.

The treatment of colorectal cancer is mainly laparotomy or laparoscopic surgery, which is often used in combination with postoperative anticancer drug treatment or radiotherapy (Non Patent Literature 1). Particularly, early colorectal cancer may be adaptable to endoscopic surgery which permits treatment without abdominal resection.

As described in Non Patent Literature 1, fecal occult blood test and endoscopy are widely prevalent as tests of colorectal cancer. Particularly, the fecal occult blood test is inexpensive and noninvasive and is also carried out at home. Therefore, the American Cancer Society recommends taking the fecal occult blood test every year. In order to further examine a tumor site and spread of the cancer, an imaging test such as barium enema, CT, or MRI is also carried out in addition to the colonoscopy. Alternatively, tests on blood tumor markers such as CEA and CA19-9 may be carried out for the purpose of observing the prognosis or the therapeutic effects on patients already diagnosed with colorectal cancer (Non Patent Literature 1).

As shown in Patent Literatures 1 to 4, there are reports, albeit at a research stage, on the detection of colorectal cancer using the expression levels of microRNAs (miRNAs) or combinations of the expression levels of miRNAs and the expression levels of additional protein markers in biological samples including blood.

Patent Literature 1 discloses a method for detecting colorectal cancer or other cancers using hsa-miR-92a-2-5p, hsa-miR-128-2-5p, and hsa-miR-24-3p in colorectal cancer tissues.

Patent Literature 2 discloses a method for detecting colorectal cancer using hsa-miR-1233-5p and hsa-miR-1225-3p in plasma.

Patent Literature 3 discloses a method for detecting colorectal cancer using multiple miRNAs such as hsa-miR-1231, hsa-miR-423-5p, and hsa-miR-1268a in large intestine tissues or feces.

Patent Literature 4 discloses a method for detecting colorectal cancer using hsa-miR-150-3p, miR-92a-2-5p, and the like in tissues.

CITATION LIST

Patent Literature

Patent Literature 1: International Publication No. WO 2007/081740
Patent Literature 2: U.S. Patent Application Publication No. 2013/102487
Patent Literature 3: U.S. Patent Application Publication No. 2012/088687
Patent Literature 4: JP Patent Publication (Kohyo) No. 2009-531019 A (2009)

Non Patent Literature

Non Patent Literature 1: American Cancer Society, "Colorectal Cancer", 2013, p. 5 to 6, 17 to 28, 33 to, 45 to 54, and 67 to 71
Non Patent Literature 2: Sobin, L. et al., "TNM Classification of Malignant Tumours, the 7th edition", 2010, p. 94-99
Non Patent Literature 3: Allison, J E. et al., 1996, The New England Journal of Medicine, Vol. 334 (3), p. 155-9
Non Patent Literature 4: Palmqvist, R. et al., 2007, Diseases of colon and rectum, Vol. 46 (11), p. 1538-44

SUMMARY OF INVENTION

Technical Problem

An object of the present invention is to find a novel tumor marker for colorectal cancer and to provide a method that can effectively detect colorectal cancer using a nucleic acid capable of specifically binding to the marker. The fecal occult blood test, which is widely used at present as a first test of colorectal cancer, produces positive results even for non-cancerous reasons such as hemorrhoid, whereas this test fails to detect early colorectal cancer without bleeding and overlooks 90% or more of abnormalities in the large intestine (including cancer) according to the report (Non Patent Literature 1). The specific sensitivity of the fecal occult blood test differs largely from 37% to 79.4% depending on a testing kit used, and its specificity is reportedly 86.7% to 97.7% (Non Patent Literature 3). Although the colonoscopy is known to have high examination accuracy, this examination is difficult to apply as a primary screening because of the necessity of pretreatment or sedatives on patients, relatively high cost, etc. (Non Patent Literature 1). The tumor markers such as CEA and CA19-9 in blood may elevate in cancers other than colorectal cancer and therefore allegedly fail to determine the presence or absence of colorectal cancer. The false diagnosis of other cancers as colorectal cancer wastes appropriate therapeutic opportunity or places unnecessary economical and physical burdens on patients due to the application of wrong medicine. Therefore, use of CEA or CA19-9 is often limited to the observation of the prognosis and of therapeutic effects on patients already diagnosed with colorectal cancer (Non Patent Literature 1). The report states that the CEA test has specificity of 99%, but sensitivity of only 12%, suggesting that the significance of tumor marker measurement as a colorectal cancer screening test is poor (Non Patent Literature 4).

As described below, there are reports, albeit at a research stage, on the determination of colorectal cancer using the expression levels of microRNAs (miRNAs) in biological samples including blood, none of which, however, have yet been brought into practical use.

Patent Literature 1 discloses a method for detecting colorectal cancer or other cancers using hsa-miR-92a-2-5p, hsa-miR-128-2-5p, and hsa-miR-24-3p in colorectal cancer tissues. This detection method, however, requires obtaining colorectal cancer tissue samples by surgical operation, and this step places a heavy physical burden on patients. Therefore, this method is not favorable as an examination method. In addition, this detection method does not describe specific colorectal cancer detection performance such as accuracy, sensitivity, or specificity and is thus industrially less practical.

Patent Literature 3 discloses a method for detecting colorectal cancer using multiple miRNAs such as hsa-miR-1231, hsa-miR-423-5p, and hsa-miR-1268a in large intestine tissues or feces. Since surgical operation for obtaining colorectal cancer tissues places a heavy physical burden on patients, this method is not favorable as an examination method. In addition, although the collection of fecal samples is noninvasive, test substances may exist unevenly in feces. This tends to cause unfavorable variations in testing results.

Patent Literature 4 discloses a method for detecting colorectal cancer using hsa-miR-150-3p, miR-92a-2-5p, and the like in tissues. This literature, however, neither describes detection performance such as accuracy, sensitivity, or specificity nor describes a specific method for determining colorectal cancer using blood. Therefore, this method is industrially less practical. In addition, these miRNA markers were not validated in an independent sample group and are thus less reliable.

As mentioned above, the existing tumor markers exhibit low performance in the detection of colorectal cancer, or neither performance nor detection methods are specifically shown as to the markers at a research stage. Therefore, use of these markers might lead to imposing needless extra examination due to the false detection of healthy subjects as being colorectal cancer patients, or might waste therapeutic opportunity because of overlooking colorectal cancer patients. In addition, the measurement of several dozens to several hundreds of miRNAs increases examination cost and is therefore difficult to use in large-scale screening such as medical checkup. Furthermore, the collection of colorectal tissues for measuring the tumor markers is highly invasive to patients and is not favorable. Hence, there is a demand for a highly accurate colorectal cancer marker that is detectable from blood, which can be collected in a less invasive manner, and is capable of correctly determining a colorectal cancer patient as a colorectal cancer patient and a healthy subject as a healthy subject. The early detection and treatment of colorectal cancer can drastically improve survival rates. Furthermore, the early detection of colorectal cancer leads to the applicability of endoscopic surgery which permits treatment without abdominal resection. Therefore, a highly sensitive colorectal cancer marker that can detect colorectal cancer even at an early stage of progression is desired.

Solution to Problem

The present inventors have conducted diligent studies to attain the object and consequently completed the present invention by finding multiple genes usable as markers for the detection of colorectal cancer from blood, which can be collected with limited invasiveness, and finding that colorectal cancer can be significantly detected by using a nucleic acid capable of specifically binding to any of these markers.

<Summary of Invention>

Specifically, the present invention has the following features:

(1) A kit for the detection of colorectal cancer, comprising a nucleic acid capable of specifically binding to at least one or more polynucleotide(s) selected from the group consisting of colorectal cancer markers miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR- 6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p.

(2) The kit according to (1), wherein miR-6726-5p is hsa-miR-6726-5p, miR-4257 is hsa-miR-4257, miR-6787-5p is hsa-miR-6787-5p, miR-6780b-5p is hsa-miR-6780b-5p, miR-3131 is hsa-miR-3131, miR-7108-5p is hsa-miR-7108-5p, miR-1343-3p is hsa-miR-1343-3p, miR-1247-3p is hsa-miR-1247-3p, miR-4651 is hsa-miR-4651, miR-6757-5p is hsa-miR-6757-5p, miR-3679-5p is hsa-miR-3679-5p, miR-7641 is hsa-miR-7641, miR-6746-5p is hsa-miR-6746-5p, miR-8072 is hsa-miR-8072, miR-6741-5p is hsa-miR-6741-5p, miR-1908-5p is hsa-miR-1908-5p, miR-6857-5p is hsa-miR-6857-5p, miR-4746-3p is hsa-miR-4746-3p, miR-744-5p is hsa-miR-744-5p, miR-4792 is hsa-miR-4792, miR-564 is hsa-miR-564, miR-6791-5p is hsa-miR-6791-5p, miR-6825-5p is hsa-miR-6825-5p, miR-6826-5p is hsa-miR-6826-5p, miR-4665-3p is hsa-miR-4665-3p, miR-4467 is hsa-miR-4467, miR-3188 is hsa-miR-3188, miR-6125 is hsa-miR-6125, miR-6756-5p is hsa-miR-6756-5p, miR-1228-3p is hsa-miR-1228-3p, miR-8063 is hsa-miR-8063, miR-8069 is hsa-miR-8069, miR-6875-5p is hsa-miR-6875-5p, miR-3185 is hsa-miR-3185, miR-4433b-3p is hsa-miR-4433b-3p, miR-6887-5p is hsa-miR-6887-5p, miR-128-1-5p is hsa-miR-128-1-5p, miR-6724-5p is hsa-miR-6724-5p, miR-1914-3p is hsa-miR-1914-3p, miR-1225-5p is hsa-miR-1225-5p, miR-4419b is hsa-miR-4419b, miR-7110-5p is hsa-miR-7110-5p, miR-187-5p is hsa-miR-187-5p, miR-3184-5p is hsa-miR-3184-5p, miR-204-3p is hsa-miR-204-3p, miR-5572 is hsa-miR-5572, miR-6729-5p is hsa-miR-6729-5p, miR-615-5p is hsa-miR-615-5p, miR-6749-5p is hsa-miR-6749-5p, miR-6515-3p is hsa-miR-6515-3p, miR-3937 is hsa-miR-3937, miR-6840-3p is hsa-miR-6840-3p, miR-6893-5p is hsa-miR-6893-5p, miR-4728-5p is hsa-miR-4728-5p, miR-6717-5p is hsa-miR-6717-5p, miR-7113-3p is hsa-miR-7113-3p, miR-4665-5p is hsa-miR-4665-5p, miR-642b-3p is hsa-miR-642b-3p, miR-7109-5p is hsa-miR-7109-5p, miR-6842-5p is hsa-miR-6842-5p, miR-4442 is hsa-miR-4442, miR-4433-3p is hsa-miR-4433-3p, miR-4707-5p is hsa-miR-4707-5p, miR-6126 is hsa-miR-6126, miR-4449 is hsa-miR-4449, miR-4706 is hsa-miR-4706, miR-1913 is hsa-miR-1913, miR-602 is hsa-miR-602, miR-939-5p is hsa-miR-939-5p, miR-4695-5p is hsa-miR-4695-5p, miR-711 is hsa-miR-711, miR-6816-5p is hsa-miR-6816-5p, miR-4632-5p is hsa-miR-4632-5p, miR-6721-5p is hsa-miR-6721-5p, miR-7847-3p is hsa-miR-7847-3p, miR-6132 is hsa-miR-6132, miR-887-3p is hsa-miR-887-3p, miR-3679-3p is hsa-miR-3679-3p, miR-6784-5p is hsa-miR-6784-5p, miR-1249 is hsa-miR-1249, miR-937-5p is hsa-miR-937-5p, miR-5195-3p is hsa-miR-5195-3p, miR-6732-5p is hsa-miR-6732-5p, miR-4417 is hsa-miR-4417, miR-4281 is hsa-miR-4281, miR-4734 is hsa-miR-4734, miR-6766-3p is hsa-miR-6766-3p, miR-663a is hsa-miR-663a, miR-4513 is hsa-miR-4513, miR-6781-5p is hsa-miR-6781-5p, miR-1227-5p is hsa-miR-1227-5p, miR-6845-5p is hsa-miR-6845-5p, miR-6798-5p is hsa-miR-6798-5p, miR-3620-5p is hsa-miR-3620-5p, miR-1915-5p is hsa-miR-1915-5p, miR-4294 is hsa-miR-4294, miR-642a-3p is hsa-miR-642a-3p, miR-371a-5p is hsa-miR-371a-5p, miR-940 is hsa-miR-940, miR-4450 is hsa-miR-4450, miR-4723-5p is hsa-miR-4723-5p, miR-1469 is hsa-miR-1469, miR-6861-5p is hsa-miR-6861-5p, miR-7975 is hsa-miR-7975, miR-6879-5p is hsa-miR-6879-5p, miR-6802-5p is hsa-miR-6802-5p, miR-1268b is hsa-miR-1268b, miR-663b is hsa-miR-663b, miR-125a-3p is hsa-miR-125a-3p, miR-2861 is hsa-miR-2861, miR-6088 is hsa-miR-6088, miR-4758-5p is hsa-miR-4758-5p, miR-296-3p is hsa-miR-296-3p, miR-6738-5p is hsa-miR-6738-5p, miR-671-5p is hsa-miR-671-5p, miR-4454 is hsa-miR-4454, miR-4516 is hsa-miR-4516, miR-7845-5p is hsa-miR-7845-5p, miR-4741 is hsa-miR-4741, miR-92b-5p is hsa-miR-92b-5p, miR-6795-5p is hsa-miR-6795-5p, miR-6805-3p is hsa-miR-6805-3p, miR-4725-3p is hsa-miR-4725-3p, miR-6782-5p is hsa-miR-6782-5p, miR-4688 is hsa-miR-4688, miR-6850-5p is hsa-miR-6850-5p, miR-6777-5p is hsa-miR-6777-5p, miR-6785-5p is hsa-miR-6785-5p, miR-7106-5p is hsa-miR-7106-5p, miR-3663-3p is hsa-miR-3663-3p, miR-6131 is hsa-miR-6131, miR-1915-3p is hsa-miR-1915-3p, miR-4532 is hsa-miR-4532, miR-6820-5p is hsa-miR-6820-5p, miR-4689 is hsa-miR-4689, miR-4638-5p is hsa-miR-4638-5p, miR-3656 is hsa-miR-3656, miR-3621 is hsa-miR-3621, miR-6769b-5p is hsa-miR-6769b-5p, miR-149-3p is hsa-miR-149-3p, miR-23b-3p is hsa-miR-23b-3p, miR-3135b is hsa-miR-3135b, miR-6848-5p is hsa-miR-6848-5p, miR-6769a-5p is hsa-miR-6769a-5p, miR-4327 is hsa-miR-4327, miR-6765-3p is hsa-miR-6765-3p, miR-6716-5p is hsa-miR-6716-5p, miR-6877-5p is hsa-miR-6877-5p, miR-6727-5p is hsa-miR-6727-5p, miR-4534 is hsa-miR-4534, miR-614 is hsa-miR-614, miR-1202 is hsa-miR-1202, miR-575 is hsa-miR-575, miR-6870-5p is hsa-miR-6870-5p, miR-6722-3p is hsa-miR-6722-3p, miR-7977 is hsa-miR-7977, miR-4649-5p is hsa-miR-4649-5p, miR-4675 is hsa-miR-4675, miR-6075 is hsa-miR-6075, miR-6779-5p is hsa-miR-6779-5p, miR-4271 is hsa-miR-4271, miR-3196 is hsa-miR-3196, miR-6803-5p is hsa-miR-6803-5p, miR-6789-5p is hsa-miR-6789-5p, miR-4648 is hsa-miR-4648, miR-4508 is hsa-miR-4508, miR-4749-5p is hsa-miR-4749-5p, miR-4505 is hsa-miR-4505, miR-5698 is hsa-miR-5698, miR-1199-5p is hsa-miR-1199-5p, miR-4763-3p is hsa-miR-4763-3p, miR-6836-3p is hsa-miR-6836-3p, miR-3195 is hsa-miR-3195, miR-718 is hsa-miR-718, miR-3178 is hsa-miR-3178, miR-638 is hsa-miR-638, miR-4497 is hsa-miR-4497, miR-6085 is hsa-miR-6085, miR-6752-5p is hsa-miR-6752-5p, and miR-135a-3p is hsa-miR-135a-3p.

(3) The kit according to (1) or (2), wherein the nucleic acid is a polynucleotide selected from the group consisting of the following polynucleotides (a) to (e):
(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 171 and 606 to 614,
(c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to at least one or more polynucleotide(s) selected from the group consisting of other colorectal cancer markers miR-1231-5p, miR-1233-5p, miR-150-3p, miR-1225-3p, miR-92a-2-5p, miR-423-5p, miR-1268a, miR-128-2-5p and miR-24-3p.

(5) The kit according to (4), wherein miR-1231 is hsa-miR-1231, miR-1233-5p is hsa-miR-1233-5p, miR-150-3p is hsa-miR-150-3p, miR-1225-3p is hsa-miR-1225-3p, miR-92a-2-5p is hsa-miR-92a-2-5p, miR-423-5p is hsa-miR-423-5p, miR-1268a is hsa-miR-1268a, miR-128-2-5p is hsa-miR-128-2-5p, and miR-24-3p is hsa-miR-24-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180, (h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one or more polynucleotide(s) selected from the group consisting of other colorectal cancer markers miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476 and miR-6090.

(8) The kit according to (7), wherein miR-4697-5p is hsa-miR-4697-5p, miR-3197 is hsa-miR-3197, miR-675-5p is hsa-miR-675-5p, miR-4486 is hsa-miR-4486, miR-7107-5p is hsa-miR-7107-5p, miR-23a-3p is hsa-miR-23a-3p, miR-4667-5p is hsa-miR-4667-5p, miR-451a is hsa-miR-451a, miR-3940-5p is hsa-miR-3940-5p, miR-8059 is hsa-miR-8059, miR-6813-5p is hsa-miR-6813-5p, miR-4492 is hsa-miR-4492, miR-4476 is hsa-miR-4476, and miR-6090 is hsa-miR-6090.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 181 to 194, (m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 181 to 194 or a nucleotide sequence derived from the nucleotide sequence by the replacement of u with t, and (o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from the group consisting of all of the colorectal cancer markers according to (1) or (2).

(11) A device for the detection of colorectal cancer, comprising a nucleic acid capable of specifically binding to at least one or more polynucleotide(s) selected from the group consisting of colorectal cancer markers miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p.

(12) The device according to (11), wherein miR-6726-5p is hsa-miR-6726-5p, miR-4257 is hsa-miR-4257, miR-6787-5p is hsa-miR-6787-5p, miR-6780b-5p is hsa-miR-6780b-5p, miR-3131 is hsa-miR-3131, miR-7108-5p is hsa-miR-7108-5p, miR-1343-3p is hsa-miR-1343-3p, miR-1247-3p is hsa-miR-1247-3p, miR-4651 is hsa-miR-4651, miR-6757-5p is hsa-miR-6757-5p, miR-3679-5p is hsa-miR-3679-5p, miR-7641 is hsa-miR-7641, miR-6746-5p is hsa-miR-6746-5p, miR-8072 is hsa-miR-8072, miR-6741-5p is hsa-miR-6741-5p, miR-1908-5p is hsa-miR-1908-5p, miR-6857-5p is hsa-miR-6857-5p, miR-4746-3p is hsa-miR-4746-3p, miR-744-5p is hsa-miR-744-5p, miR-4792 is hsa-miR-4792, miR-564 is hsa-miR-564, miR-6791-5p is hsa-miR-6791-5p, miR-6825-5p is hsa-miR-6825-5p, miR-6826-5p is hsa-miR-6826-5p, miR-4665-3p is hsa-miR-4665-3p, miR-4467 is hsa-miR-4467, miR-3188 is hsa-miR-3188, miR-6125 is hsa-miR-6125, miR-6756-5p is hsa-miR-6756-5p, miR-1228-3p is hsa-miR-1228-3p, miR-8063 is hsa-miR-8063, miR-8069 is hsa-miR-8069, miR-6875-5p is hsa-miR-6875-5p, miR-3185 is hsa-miR-3185, miR-4433b-3p is hsa-miR-4433b-3p, miR-6887-5p is hsa-miR-6887-5p, miR-128-1-5p is hsa-miR-128-1-5p, miR-6724-5p is hsa-miR-6724-5p, miR-1914-3p is hsa-miR-1914-3p, miR-1225-5p is hsa-miR-1225-5p, miR-4419b is hsa-miR-4419b, miR-7110-5p is hsa-miR-7110-5p, miR-187-5p is hsa-miR-187-5p, miR-3184-5p is hsa-miR-3184-5p, miR-204-3p is hsa-miR-204-3p, miR-5572 is hsa-miR-5572, miR-6729-5p is hsa-miR-6729-5p, miR-615-5p is hsa-miR-615-5p, miR-6749-5p is hsa-miR-6749-5p, miR-6515-3p is hsa-miR-6515-3p, miR-3937 is hsa-miR-3937, miR-6840-3p is hsa-miR-6840-3p, miR-6893-5p is hsa-miR-6893-5p, miR-4728-5p is hsa-miR-4728-5p, miR-6717-5p is hsa-miR-6717-5p, miR-7113-3p is hsa-miR-7113-3p, miR-4665-5p is hsa-miR-4665-5p, miR-642b-3p is hsa-miR-642b-3p, miR-7109-5p is hsa-miR-7109-5p, miR-6842-5p is hsa-miR-6842-5p, miR-4442 is hsa-miR-4442, miR-4433-3p is hsa-miR-4433-3p, miR-4707-5p is hsa-miR-4707-5p, miR-6126 is hsa-miR-6126, miR-4449 is hsa-miR-4449, miR-4706 is hsa-miR-4706, miR-1913 is hsa-miR-1913, miR-602 is hsa-miR-602, miR-939-5p is hsa-miR-939-5p, miR-4695-5p is hsa-miR-4695-5p, miR-711 is hsa-miR-711, miR-6816-5p is hsa-miR-6816-5p, miR-4632-5p is hsa-miR-4632-5p, miR-6721-5p is hsa-miR-6721-5p, miR-7847-3p is hsa-miR-7847-3p, miR-6132 is hsa-miR-6132, miR-887-3p is hsa-miR-887-3p, miR-3679-3p is hsa-miR-3679-3p, miR-6784-5p is hsa-miR-6784-5p, miR-1249 is hsa-miR-1249, miR-937-5p is hsa-miR-937-5p, miR-5195-3p is hsa-miR-5195-3p, miR-6732-5p is hsa-miR-6732-5p, miR-4417 is hsa-miR-4417, miR-4281 is hsa-miR-4281, miR-4734 is hsa-miR-4734, miR-6766-3p is hsa-miR-6766-3p, miR-663a is hsa-miR-663a, miR-4513 is hsa-miR-4513, miR-6781-5p is hsa-miR-6781-5p, miR-1227-5p is hsa-miR-1227-5p, miR-6845-5p is hsa-miR-6845-5p, miR-6798-5p is hsa-miR-6798-5p, miR-3620-5p is hsa-miR-3620-5p, miR-1915-5p is hsa-miR-1915-5p, miR-4294 is hsa-miR-4294, miR-642a-3p is hsa-miR-642a-3p, miR-371a-5p is hsa-miR-371a-5p, miR-940 is hsa-miR-940, miR-4450 is hsa-miR-4450, miR-4723-5p is hsa-miR-4723-5p, miR-1469 is hsa-miR-1469, miR-6861-5p is hsa-miR-6861-5p, miR-7975 is hsa-miR-7975, miR-6879-5p is hsa-miR-6879-5p, miR-6802-5p is hsa-miR-6802-5p, miR-1268b is hsa-miR-1268b, miR-663b is hsa-miR-663b, miR-125a-3p is hsa-miR-125a-3p, miR-2861 is hsa-miR-2861, miR-6088 is hsa-miR-6088, miR-4758-5p is hsa-miR-4758-5p, miR-296-3p is hsa-miR-296-3p, miR-6738-5p is hsa-miR-6738-5p, miR-671-5p is hsa-miR-671-5p, miR-4454 is hsa-miR-4454, miR-4516 is hsa-miR-4516, miR-7845-5p is hsa-miR-7845-5p, miR-4741 is hsa-miR-4741, miR-92b-5p is hsa-miR-92b-5p, miR-6795-5p is hsa-miR-6795-5p, miR-6805-3p is hsa-miR-6805-3p, miR-4725-3p is hsa-miR-4725-3p, miR-6782-5p is hsa-miR-6782-5p, miR-4688 is hsa-miR-4688, miR-6850-5p is hsa-miR-6850-5p, miR-6777-5p is hsa-miR-6777-5p, miR-6785-5p is hsa-miR-6785-5p, miR-7106-5p is hsa-miR-7106-5p, miR-3663-3p is hsa-miR-3663-3p, miR-6131 is hsa-miR-6131, miR-1915-3p is hsa-miR-1915-3p, miR-4532 is hsa-miR-4532, miR-6820-5p is hsa-miR-6820-5p, miR-4689 is hsa-miR-4689, miR-4638-5p is hsa-miR-4638-5p, miR-3656 is hsa-miR-3656, miR-3621 is hsa-miR-3621, miR-6769b-5p is hsa-miR-6769b-5p, miR-149-3p is hsa-miR-149-3p, miR-23b-3p is hsa-miR-23b-3p, miR-3135b is hsa-miR-3135b, miR-6848-5p is hsa-miR-6848-5p, miR-6769a-5p is hsa-miR-6769a-5p, miR-4327 is hsa-miR-4327, miR-6765-3p is hsa-miR-6765-3p, miR-6716-5p is hsa-miR-6716-5p, miR-6877-5p is hsa-miR-6877-5p, miR-6727-5p is hsa-miR-6727-5p, miR-4534 is hsa-miR-4534, miR-614 is hsa-miR-614, miR-1202 is hsa-miR-1202, miR-575 is hsa-miR-575, miR-6870-5p is hsa-miR-6870-5p, miR-6722-3p is hsa-miR-6722-3p, miR-7977 is hsa-miR-7977, miR-4649-5p is hsa-miR-4649-5p, miR-4675 is hsa-miR-4675, miR-6075 is hsa-miR-6075, miR-6779-5p is hsa-miR-6779-5p, miR-4271 is hsa-miR-4271, miR-3196 is hsa-miR-3196, miR-6803-5p is hsa-miR-6803-5p, miR-6789-5p is hsa-miR-6789-5p, miR-4648 is hsa-miR-4648, miR-4508 is hsa-miR-4508, miR-4749-5p is hsa-miR-4749-5p, miR-4505 is hsa-miR-4505, miR-5698 is hsa-miR-5698, miR-1199-5p is hsa-miR-1199-5p, miR-4763-3p is hsa-miR-4763-3p, miR-6836-3p is hsa-miR-6836-3p, miR-3195 is hsa-miR-3195, miR-718 is hsa-miR-718, miR-3178 is hsa-miR-3178, miR-638 is hsa-miR-638, miR-4497 is hsa-miR-4497, miR-6085 is hsa-miR-6085, miR-6752-5p is hsa-miR-6752-5p, and miR-135a-3p is hsa-miR-135a-3p.

(13) The device according to (11) or (12), wherein the nucleic acid is a polynucleotide selected from the group consisting of the following polynucleotides (a) to (e):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises a nucleic acid capable of specifically binding to at least one or more polynucleotide(s)

selected from the group consisting of other colorectal cancer markers miR-1231, miR-1233-5p, miR-150-3p, miR-1225-3p, miR-92a-2-5p, miR-423-5p, miR-1268a, miR-128-2-5p and miR-24-3p.

(15) The device according to (14), wherein miR-1231 is hsa-miR-1231, miR-1233-5p is hsa-miR-1233-5p, miR-150-3p is hsa-miR-150-3p, miR-1225-3p is hsa-miR-1225-3p, miR-92a-2-5p is hsa-miR-92a-2-5p, miR-423-5p is hsa-miR-423-5p, miR-1268a is hsa-miR-1268a, miR-128-2-5p is hsa-miR-128-2-5p, and miR-24-3p is hsa-miR-24-3p.

(16) The device according to (14) or (15), wherein the nucleic acid is a polynucleotide selected from the group consisting of the following polynucleotides (f) to (j):
(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 172 to 180,
(h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 172 to 180 or a nucleotide sequence derived from the nucleotide sequence by the replacement of u with t, and
(j) a polynucleotide hybridizing under stringent conditions to any of the polynucleotides (f) to (i).

(17) The device according to any of (11) to (16), wherein the device further comprises a nucleic acid capable of specifically binding to at least one or more polynucleotide(s) selected from the group consisting of other colorectal cancer markers miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090.

(18) The device according to (17), wherein miR-4697-5p is hsa-miR-4697-5p, miR-3197 is hsa-miR-3197, miR-675-5p is hsa-miR-675-5p, miR-4486 is hsa-miR-4486, miR-7107-5p is hsa-miR-7107-5p, miR-23a-3p is hsa-miR-23a-3p, miR-4667-5p is hsa-miR-4667-5p, miR-451a is hsa-miR-451a, miR-3940-5p is hsa-miR-3940-5p, miR-8059 is hsa-miR-8059, miR-6813-5p is hsa-miR-6813-5p, miR-4492 is hsa-miR-4492, miR-4476 is hsa-miR-4476, and miR-6090 is hsa-miR-6090.

(19) The device according to (17) or (18), wherein the nucleic acid is a polynucleotide selected from the group consisting of the following polynucleotides (k) to (o):
(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 181 to 194,
(m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 181 to 194 or a nucleotide sequence derived from the nucleotide sequence by the replacement of u with t, and
(o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the colorectal cancer markers according to (11) or (12).

(23) A method for detecting colorectal cancer, comprising measuring an expression level of a target nucleic acid in a sample from a subject using a kit according to any one of (1) to (10) or a device according to any one of (11) to (22), and evaluating in vitro whether or not the subject has colorectal cancer using both of the measured expression level and a control expression level in a sample from a healthy subject measured in the same way.

(24) The method according to (23), wherein the subject is a human.

(25) The method according to (23) or (24), wherein the sample is blood, serum, or plasma.

Definition of Term

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein is used for a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here, the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. Here, the term "polynucleotide" is used interchangeably with the term "nucleic acid".

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but each single-stranded DNA such as a plus strand (or a sense strand) or a complementary strand (or an antisense strand) that constitutes a duplex. The gene is not particularly limited by its length.

Thus, the "gene" used herein includes any of double-stranded DNA including human genomic DNA, single-stranded DNA (plus strand) including cDNA, single-stranded DNA having a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 635 or a nucleotide sequence derived from the nucleotide sequence by the replacement of u with t. The "gene" is not particularly limited by its functional region and can contain, for example, an expression control region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is encapsulated by a lipid bilayer and secreted from a cell. The exosome is derived from a multivesicular endosome and may incorporate a biomaterial such as a "gene" (e.g., RNA or DNA) or a protein when released into an extracellular environment. The exosome is known to be contained in a body fluid such as blood, serum, plasma, or lymph.

The term "transcript" used herein refers to RNA synthesized with the DNA sequence of a gene as a template. RNA polymerase binds to a site called promoter which is located upstream of the gene and adds ribonucleotides complementary to the nucleotide sequence of the DNA to the 3' end to synthesize RNA. This RNA contains not only the gene itself but the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and is involved in the suppression of translation of mRNA, unless otherwise specified. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 635. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary base relationship of A:T (U) and G:C base pairs with the full-length sequence of a polynucleotide consisting of a nucleotide sequence defined by any of SEQ ID NOs: 1 to 635 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant that contains the deletion, substitution, addition, or insertion of 1 or 2 or more nucleotides in a nucleotide sequence represented by any of SEQ ID NOs: 1 to 194 and 606 to 614 or a nucleotide sequence derived from the nucleotide sequence by the replacement of u with t, or a partial sequence thereof; a variant that exhibits % identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative that is labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the colorectal cancer marker miRNAs described above is a synthesized or prepared nucleic acid and specifically includes a "nucleic acid probe" or a "primer". The "nucleic acid" is utilized directly or indirectly for detecting the presence or absence of colorectal cancer in a subject, for diagnosing the presence or absence of colorectal cancer, for diagnosing the severity of colorectal cancer, the presence or absence of amelioration or the degree of amelioration of colorectal cancer, or the sensitivity to treatment for colorectal cancer, or for screening for a candidate substance useful in the prevention, amelioration, or treatment of colorectal cancer. The "nucleic acid" includes a nucleotide, an oligonucleotide, and a polynucleotide capable of specifically recognizing and binding to a transcript represented by any of SEQ ID NOs: 1 to 635 or a synthetic cDNA nucleic acid thereof in vivo, particularly, in a sample such as a body fluid (e.g., blood or urine), in relation to the development of colorectal cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "capable of specifically binding" used herein means that the nucleic acid probe or the primer used in the present invention binds to a particular target nucleic acid and cannot substantially bind to other nucleic acids.

The term "detection" used herein is interchangeable with the term "examination", "measurement", "detection", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that is actually calculated from data under null hypothesis is observed in a statistical test. Thus, smaller "P" or "P value" means more significant difference between subjects to be compared.

The term "sensitivity" used herein means a value of (the number of true positives)/(the number of true positives+the number of false negatives). High sensitivity allows colorectal cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being colorectal cancer patients, leading to reduction in burden on patients and reduction in medical expense.

The term "accuracy" used herein means a value of (the number of true positives+the number of true negatives)/(the total number of cases). The accuracy indicates the ratio of samples that correctly identified in discriminant results to all samples, and serves as a primary index for evaluating detection performance.

As used herein, the "sample" that is subject to determination, detection, or diagnosis refers to a tissue and a biological material in which the expression of the gene of the present invention varies as colorectal cancer develops, colorectal cancer progresses, and therapeutic effects on colorectal cancer are exerted. Specifically, the "sample" refers to a large intestine tissue, a vascular channel around the large intestine, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6726-5p gene" or "hsa-miR-6726-5p" used herein includes the hsa-miR-6726-5p gene (miRBase Accession No. MIMAT0027353) described in SEQ ID NO: 1, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 195) having a hairpin-like structure is known as a precursor of "hsa-miR-6726-5p".

The term "hsa-miR-4257 gene" or "hsa-miR-4257" used herein includes the hsa-miR-4257 gene (miRBase Accession No. MIMAT0016878) described in SEQ ID NO: 2, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 196) having a hairpin-like structure is known as a precursor of "hsa-miR-4257".

The term "hsa-miR-6787-5p gene" or "hsa-miR-6787-5p" used herein includes the hsa-miR-6787-5p gene (miRBase Accession No. MIMAT0027474) described in SEQ ID NO: 3, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 197) having a hairpin-like structure is known as a precursor of "hsa-miR-6787-5p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 4, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 198) having a hairpin-like structure is known as a precursor of "hsa-miR-6780b-5p".

The term "hsa-miR-3131 gene" or "hsa-miR-3131" used herein includes the hsa-miR-3131 gene (miRBase Accession No. MIMAT0014996) described in SEQ ID NO: 5, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 199) having a hairpin-like structure is known as a precursor of "hsa-miR-3131".

The term "hsa-miR-7108-5p gene" or "hsa-miR-7108-5p" used herein includes the hsa-miR-7108-5p gene (miRBase Accession No. MIMAT0028113) described in SEQ ID NO: 6, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 200) having a hairpin-like structure is known as a precursor of "hsa-miR-7108-5p".

The term "hsa-miR-1343-3p gene" or "hsa-miR-1343-3p" used herein includes the hsa-miR-1343-3p gene (miRBase Accession No. MIMAT0019776) described in SEQ ID NO: 7, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 201) having a hairpin-like structure is known as a precursor of "hsa-miR-1343-3p".

The term "hsa-miR-1247-3p gene" or "hsa-miR-1247-3p" used herein includes the hsa-miR-1247-3p gene (miRBase Accession No. MIMAT0022721) described in SEQ ID NO: 8, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 202) having a hairpin-like structure is known as a precursor of "hsa-miR-1247-3p".

The term "hsa-miR-4651 gene" or "hsa-miR-4651" used herein includes the hsa-miR-4651 gene (miRBase Accession No. MIMAT0019715) described in SEQ ID NO: 9, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 203) having a hairpin-like structure is known as a precursor of "hsa-miR-4651".

The term "hsa-miR-6757-5p gene" or "hsa-miR-6757-5p" used herein includes the hsa-miR-6757-5p gene (miRBase Accession No. MIMAT0027414) described in SEQ ID NO: 10, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 204) having a hairpin-like structure is known as a precursor of "hsa-miR-6757-5p".

The term "hsa-miR-3679-5p gene" or "hsa-miR-3679-5p" used herein includes the hsa-miR-3679-5p gene (miRBase Accession No. MIMAT0018104) described in SEQ ID NO: 11, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 205) having a hairpin-like structure is known as a precursor of "hsa-miR-3679-5p".

The term "hsa-miR-7641 gene" or "hsa-miR-7641" used herein includes the hsa-miR-7641 gene (miRBase Accession No. MIMAT0029782) described in SEQ ID NO: 12, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1" and "hsa-mir-7641-2" (miRBase Accession Nos. MI0024975 and MI0024976, SEQ ID NOs: 206 and 207) having a hairpin-like structure are known as precursors of "hsa-miR-7641".

The term "hsa-miR-6746-5p gene" or "hsa-miR-6746-5p" used herein includes the hsa-miR-6746-5p gene (miRBase Accession No. MIMAT0027392) described in SEQ ID NO: 13, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 208) having a hairpin-like structure is known as a precursor of "hsa-miR-6746-5p".

The term "hsa-miR-8072 gene" or "hsa-miR-8072" used herein includes the hsa-miR-8072 gene (miRBase Accession No. MIMAT0030999) described in SEQ ID NO: 14, a homolog or an ortholog of a different organism species, and the like. The hsa-miR-8072 gene can be obtained by a method described in Wang R I et al., 2013, Shock, Vol. 39, p. 480-487. Also, "hsa-mir-8072" (miRBase Accession No. MI0025908, SEQ ID NO: 209) having a hairpin-like structure is known as a precursor of "hsa-miR-8072".

The term "hsa-miR-6741-5p gene" or "hsa-miR-6741-5p" used herein includes the hsa-miR-6741-5p gene (miRBase Accession No. MIMAT0027383) described in SEQ ID NO: 15, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 210) having a hairpin-like structure is known as a precursor of "hsa-miR-6741-5p".

The term "hsa-miR-1908-5p gene" or "hsa-miR-1908-5p" used herein includes the hsa-miR-1908-5p gene (miRBase Accession No. MIMAT0007881) described in SEQ ID NO: 16, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 211) having a hairpin-like structure is known as a precursor of "hsa-miR-1908-5p".

The term "hsa-miR-6857-5p gene" or "hsa-miR-6857-5p" used herein includes the hsa-miR-6857-5p gene (miRBase Accession No. MIMAT0027614) described in SEQ ID NO: 17, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 212) having a hairpin-like structure is known as a precursor of "hsa-miR-6857-5p".

The term "hsa-miR-4746-3p gene" or "hsa-miR-4746-3p" used herein includes the hsa-miR-4746-3p gene (miRBase Accession No. MIMAT0019881) described in SEQ ID NO: 18, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 213) having a hairpin-like structure is known as a precursor of "hsa-miR-4746-3p".

The term "hsa-miR-744-5p gene" or "hsa-miR-744-5p" used herein includes the hsa-miR-744-5p gene (miRBase Accession No. MIMAT0004945) described in SEQ ID NO: 19, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 214) having a hairpin-like structure is known as a precursor of "hsa-miR-744-5p".

The term "hsa-miR-4792 gene" or "hsa-miR-4792" used herein includes the hsa-miR-4792 gene (miRBase Accession No. MIMAT0019964) described in SEQ ID NO: 20, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 215) having a hairpin-like structure is known as a precursor of "hsa-miR-4792".

The term "hsa-miR-564 gene" or "hsa-miR-564" used herein includes the hsa-miR-564 gene (miRBase Accession No. MIMAT0003228) described in SEQ ID NO: 21, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 216) having a hairpin-like structure is known as a precursor of "hsa-miR-564".

The term "hsa-miR-6791-5p gene" or "hsa-miR-6791-5p" used herein includes the hsa-miR-6791-5p gene (miRBase Accession No. MIMAT0027482) described in SEQ ID NO: 22, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 217) having a hairpin-like structure is known as a precursor of "hsa-miR-6791-5p".

The term "hsa-miR-6825-5p gene" or "hsa-miR-6825-5p" used herein includes the hsa-miR-6825-5p gene (miRBase Accession No. MIMAT0027550) described in SEQ ID NO: 23, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 218) having a hairpin-like structure is known as a precursor of "hsa-miR-6825-5p".

The term "hsa-miR-6826-5p gene" or "hsa-miR-6826-5p" used herein includes the hsa-miR-6826-5p gene (miRBase Accession No. MIMAT0027552) described in SEQ ID NO: 24, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 219) having a hairpin-like structure is known as a precursor of "hsa-miR-6826-5p".

The term "hsa-miR-4665-3p gene" or "hsa-miR-4665-3p" used herein includes the hsa-miR-4665-3p gene (miRBase Accession No. MIMAT0019740) described in SEQ ID NO: 25, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 220) having a hairpin-like structure is known as a precursor of "hsa-miR-4665-3p".

The term "hsa-miR-4467 gene" or "hsa-miR-4467" used herein includes the hsa-miR-4467 gene (miRBase Accession No. MIMAT0018994) described in SEQ ID NO: 26, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 221) having a hairpin-like structure is known as a precursor of "hsa-miR-4467".

The term "hsa-miR-3188 gene" or "hsa-miR-3188" used herein includes the hsa-miR-3188 gene (miRBase Accession No. MIMAT0015070) described in SEQ ID NO: 27, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 222) having a hairpin-like structure is known as a precursor of "hsa-miR-3188".

The term "hsa-miR-6125 gene" or "hsa-miR-6125" used herein includes the hsa-miR-6125 gene (miRBase Accession No. MIMAT0024598) described in SEQ ID NO: 28, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 223) having a hairpin-like structure is known as a precursor of "hsa-miR-6125".

The term "hsa-miR-6756-5p gene" or "hsa-miR-6756-5p" used herein includes the hsa-miR-6756-5p gene (miRBase Accession No. MIMAT0027412) described in SEQ ID NO: 29, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 224) having a hairpin-like structure is known as a precursor of "hsa-miR-6756-5p".

The term "hsa-miR-1228-3p gene" or "hsa-miR-1228-3p" used herein includes the hsa-miR-1228-3p gene (miRBase Accession No. MIMAT0005583) described in SEQ ID NO: 30, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 225) having a hairpin-like structure is known as a precursor of "hsa-miR-1228-3p".

The term "hsa-miR-8063 gene" or "hsa-miR-8063" used herein includes the hsa-miR-8063 gene (miRBase Accession No. MIMAT0030990) described in SEQ ID NO: 31, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 226) having a hairpin-like structure is known as a precursor of "hsa-miR-8063".

The term "hsa-miR-8069 gene" or "hsa-miR-8069" used herein includes the hsa-miR-8069 gene (miRBase Accession No. MIMAT0030996) described in SEQ ID NO: 32, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No.

MI0025905, SEQ ID NO: 227) having a hairpin-like structure is known as a precursor of "hsa-miR-8069".

The term "hsa-miR-6875-5p gene" or "hsa-miR-6875-5p" used herein includes the hsa-miR-6875-5p gene (miRBase Accession No. MIMAT0027650) described in SEQ ID NO: 33, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 228) having a hairpin-like structure is known as a precursor of "hsa-miR-6875-5p".

The term "hsa-miR-3185 gene" or "hsa-miR-3185" used herein includes the hsa-miR-3185 gene (miRBase Accession No. MIMAT0015065) described in SEQ ID NO: 34, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 229) having a hairpin-like structure is known as a precursor of "hsa-miR-3185".

The term "hsa-miR-4433b-3p gene" or "hsa-miR-4433b-3p" used herein includes the hsa-miR-4433b-3p gene (miRBase Accession No. MIMAT0030414) described in SEQ ID NO: 35, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 230) having a hairpin-like structure is known as a precursor of "hsa-miR-4433b-3p".

The term "hsa-miR-6887-5p gene" or "hsa-miR-6887-5p" used herein includes the hsa-miR-6887-5p gene (miRBase Accession No. MIMAT0027674) described in SEQ ID NO: 36, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 231) having a hairpin-like structure is known as a precursor of "hsa-miR-6887-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 37, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 232) having a hairpin-like structure is known as a precursor of "hsa-miR-128-1-5p".

The term "hsa-miR-6724-5p gene" or "hsa-miR-6724-5p" used herein includes the hsa-miR-6724-5p gene (miRBase Accession No. MIMAT0025856) described in SEQ ID NO: 38, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 233) having a hairpin-like structure is known as a precursor of "hsa-miR-6724-5p".

The term "hsa-miR-1914-3p gene" or "hsa-miR-1914-3p" used herein includes the hsa-miR-1914-3p gene (miRBase Accession No. MIMAT0007890) described in SEQ ID NO: 39, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 234) having a hairpin-like structure is known as a precursor of "hsa-miR-1914-3p".

The term "hsa-miR-1225-5p gene" or "hsa-miR-1225-5p" used herein includes the hsa-miR-1225-5p gene (miRBase Accession No. MIMAT0005572) described in SEQ ID NO: 40, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 235) having a hairpin-like structure is known as a precursor of "hsa-miR-1225-5p".

The term "hsa-miR-4419b gene" or "hsa-miR-4419b" used herein includes the hsa-miR-4419b gene (miRBase Accession No. MIMAT0019034) described in SEQ ID NO: 41, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 236) having a hairpin-like structure is known as a precursor of "hsa-miR-4419b".

The term "hsa-miR-7110-5p gene" or "hsa-miR-7110-5p" used herein includes the hsa-miR-7110-5p gene (miRBase Accession No. MIMAT0028117) described in SEQ ID NO: 42, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 237) having a hairpin-like structure is known as a precursor of "hsa-miR-7110-5p".

The term "hsa-miR-187-5p gene" or "hsa-miR-187-5p" used herein includes the hsa-miR-187-5p gene (miRBase Accession No. MIMAT0004561) described in SEQ ID NO: 43, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 238) having a hairpin-like structure is known as a precursor of "hsa-miR-187-5p".

The term "hsa-miR-3184-5p gene" or "hsa-miR-3184-5p" used herein includes the hsa-miR-3184-5p gene (miRBase Accession No. MIMAT0015064) described in SEQ ID NO: 44, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 239) having a hairpin-like structure is known as a precursor of "hsa-miR-3184-5p".

The term "hsa-miR-204-3p gene" or "hsa-miR-204-3p" used herein includes the hsa-miR-204-3p gene (miRBase Accession No. MIMAT0022693) described in SEQ ID NO: 45, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 240) having a hairpin-like structure is known as a precursor of "hsa-miR-204-3p".

The term "hsa-miR-5572 gene" or "hsa-miR-5572" used herein includes the hsa-miR-5572 gene (miRBase Accession No. MIMAT0022260) described in SEQ ID NO: 46, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 241) having a hairpin-like structure is known as a precursor of "hsa-miR-5572".

The term "hsa-miR-6729-5p gene" or "hsa-miR-6729-5p" used herein includes the hsa-miR-6729-5p gene (miRBase Accession No. MIMAT0027359) described in SEQ ID NO: 47, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 242) having a hairpin-like structure is known as a precursor of "hsa-miR-6729-5p".

The term "hsa-miR-615-5p gene" or "hsa-miR-615-5p" used herein includes the hsa-miR-615-5p gene (miRBase Accession No. MIMAT0004804) described in SEQ ID NO: 48, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 243) having a hairpin-like structure is known as a precursor of "hsa-miR-615-5p".

The term "hsa-miR-6749-5p gene" or "hsa-miR-6749-5p" used herein includes the hsa-miR-6749-5p gene (miRBase Accession No. MIMAT0027398) described in SEQ ID NO: 49, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 244) having a hairpin-like structure is known as a precursor of "hsa-miR-6749-5p".

The term "hsa-miR-6515-3p gene" or "hsa-miR-6515-3p" used herein includes the hsa-miR-6515-3p gene (miRBase Accession No. MIMAT0025487) described in SEQ ID NO: 50, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 245) having a hairpin-like structure is known as a precursor of "hsa-miR-6515-3p".

The term "hsa-miR-3937 gene" or "hsa-miR-3937" used herein includes the hsa-miR-3937 gene (miRBase Accession No. MIMAT0018352) described in SEQ ID NO: 51, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 246) having a hairpin-like structure is known as a precursor of "hsa-miR-3937".

The term "hsa-miR-6840-3p gene" or "hsa-miR-6840-3p" used herein includes the hsa-miR-6840-3p gene (miRBase Accession No. MIMAT0027583) described in SEQ ID NO: 52, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 247) having a hairpin-like structure is known as a precursor of "hsa-miR-6840-3p".

The term "hsa-miR-6893-5p gene" or "hsa-miR-6893-5p" used herein includes the hsa-miR-6893-5p gene (miRBase Accession No. MIMAT0027686) described in SEQ ID NO: 53, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 248) having a hairpin-like structure is known as a precursor of "hsa-miR-6893-5p".

The term "hsa-miR-4728-5p gene" or "hsa-miR-4728-5p" used herein includes the hsa-miR-4728-5p gene (miRBase Accession No. MIMAT0019849) described in SEQ ID NO: 54, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 249) having a hairpin-like structure is known as a precursor of "hsa-miR-4728-5p".

The term "hsa-miR-6717-5p gene" or "hsa-miR-6717-5p" used herein includes the hsa-miR-6717-5p gene (miRBase Accession No. MIMAT0025846) described in SEQ ID NO: 55, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 250) having a hairpin-like structure is known as a precursor of "hsa-miR-6717-5p".

The term "hsa-miR-7113-3p gene" or "hsa-miR-7113-3p" used herein includes the hsa-miR-7113-3p gene (miRBase Accession No. MIMAT0028124) described in SEQ ID NO: 56, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 251) having a hairpin-like structure is known as a precursor of "hsa-miR-7113-3p".

The term "hsa-miR-4665-5p gene" or "hsa-miR-4665-5p" used herein includes the hsa-miR-4665-5p gene (miRBase Accession No. MIMAT0019739) described in SEQ ID NO: 57, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 220) having a hairpin-like structure is known as a precursor of "hsa-miR-4665-5p".

The term "hsa-miR-642b-3p gene" or "hsa-miR-642b-3p" used herein includes the hsa-miR-642b-3p gene (miRBase Accession No. MIMAT0018444) described in SEQ ID NO: 58, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 252) having a hairpin-like structure is known as a precursor of "hsa-miR-642b-3p".

The term "hsa-miR-7109-5p gene" or "hsa-miR-7109-5p" used herein includes the hsa-miR-7109-5p gene (miRBase Accession No. MIMAT0028115) described in SEQ ID NO: 59, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 253) having a hairpin-like structure is known as a precursor of "hsa-miR-7109-5p".

The term "hsa-miR-6842-5p gene" or "hsa-miR-6842-5p" used herein includes the hsa-miR-6842-5p gene (miRBase Accession No. MIMAT0027586) described in SEQ ID NO: 60, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 254) having a hairpin-like structure is known as a precursor of "hsa-miR-6842-5p".

The term "hsa-miR-4442 gene" or "hsa-miR-4442" used herein includes the hsa-miR-4442 gene (miRBase Accession No. MIMAT0018960) described in SEQ ID NO: 61, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 255) having a hairpin-like structure is known as a precursor of "hsa-miR-4442".

The term "hsa-miR-4433-3p gene" or "hsa-miR-4433-3p" used herein includes the hsa-miR-4433-3p gene (miRBase Accession No. MIMAT0018949) described in SEQ ID NO: 62, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 256) having a hairpin-like structure is known as a precursor of "hsa-miR-4433-3p".

The term "hsa-miR-4707-5p gene" or "hsa-miR-4707-5p" used herein includes the hsa-miR-4707-5p gene (miRBase Accession No. MIMAT0019807) described in SEQ ID NO: 63, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 257) having a hairpin-like structure is known as a precursor of "hsa-miR-4707-5p".

The term "hsa-miR-6126 gene" or "hsa-miR-6126" used herein includes the hsa-miR-6126 gene (miRBase Accession No. MIMAT0024599) described in SEQ ID NO: 64, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 258) having a hairpin-like structure is known as a precursor of "hsa-miR-6126".

The term "hsa-miR-4449 gene" or "hsa-miR-4449" used herein includes the hsa-miR-4449 gene (miRBase Accession No. MIMAT0018968) described in SEQ ID NO: 65, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 259) having a hairpin-like structure is known as a precursor of "hsa-miR-4449".

The term "hsa-miR-4706 gene" or "hsa-miR-4706" used herein includes the hsa-miR-4706 gene (miRBase Accession No. MIMAT0019806) described in SEQ ID NO: 66, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 260) having a hairpin-like structure is known as a precursor of "hsa-miR-4706".

The term "hsa-miR-1913 gene" or "hsa-miR-1913" used herein includes the hsa-miR-1913 gene (miRBase Accession No. MIMAT0007888) described in SEQ ID NO: 67, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 261) having a hairpin-like structure is known as a precursor of "hsa-miR-1913".

The term "hsa-miR-602 gene" or "hsa-miR-602" used herein includes the hsa-miR-602 gene (miRBase Accession No. MIMAT0003270) described in SEQ ID NO: 68, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 262) having a hairpin-like structure is known as a precursor of "hsa-miR-602".

The term "hsa-miR-939-5p gene" or "hsa-miR-939-5p" used herein includes the hsa-miR-939-5p gene (miRBase Accession No. MIMAT0004982) described in SEQ ID NO: 69, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 263) having a hairpin-like structure is known as a precursor of "hsa-miR-939-5p".

The term "hsa-miR-4695-5p gene" or "hsa-miR-4695-5p" used herein includes the hsa-miR-4695-5p gene (miRBase Accession No. MIMAT0019788) described in SEQ ID NO: 70, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 264) having a hairpin-like structure is known as a precursor of "hsa-miR-4695-5p".

The term "hsa-miR-711 gene" or "hsa-miR-711" used herein includes the hsa-miR-711 gene (miRBase Accession No. MIMAT0012734) described in SEQ ID NO: 71, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 265) having a hairpin-like structure is known as a precursor of "hsa-miR-711".

The term "hsa-miR-6816-5p gene" or "hsa-miR-6816-5p" used herein includes the hsa-miR-6816-5p gene (miRBase Accession No. MIMAT0027532) described in SEQ ID NO: 72, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 266) having a hairpin-like structure is known as a precursor of "hsa-miR-6816-5p".

The term "hsa-miR-4632-5p gene" or "hsa-miR-4632-5p" used herein includes the hsa-miR-4632-5p gene (miRBase Accession No. MIMAT0022977) described in SEQ ID NO: 73, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 267) having a hairpin-like structure is known as a precursor of "hsa-miR-4632-5p".

The term "hsa-miR-6721-5p gene" or "hsa-miR-6721-5p" used herein includes the hsa-miR-6721-5p gene (miRBase Accession No. MIMAT0025852) described in SEQ ID NO: 74, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 268) having a hairpin-like structure is known as a precursor of "hsa-miR-6721-5p".

The term "hsa-miR-7847-3p gene" or "hsa-miR-7847-3p" used herein includes the hsa-miR-7847-3p gene (miRBase Accession No. MIMAT0030422) described in SEQ ID NO: 75, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 269) having a hairpin-like structure is known as a precursor of "hsa-miR-7847-3p".

The term "hsa-miR-6132 gene" or "hsa-miR-6132" used herein includes the hsa-miR-6132 gene (miRBase Accession No. MIMAT0024616) described in SEQ ID NO: 76, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 270) having a hairpin-like structure is known as a precursor of "hsa-miR-6132".

The term "hsa-miR-887-3p gene" or "hsa-miR-887-3p" used herein includes the hsa-miR-887-3p gene (miRBase Accession No. MIMAT0004951) described in SEQ ID NO: 77, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 271) having a hairpin-like structure is known as a precursor of "hsa-miR-887-3p".

The term "hsa-miR-3679-3p gene" or "hsa-miR-3679-3p" used herein includes the hsa-miR-3679-3p gene (miRBase Accession No. MIMAT0018105) described in SEQ ID NO: 78, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 205) having a hairpin-like structure is known as a precursor of "hsa-miR-3679-3p".

The term "hsa-miR-6784-5p gene" or "hsa-miR-6784-5p" used herein includes the hsa-miR-6784-5p gene (miRBase Accession No. MIMAT0027468) described in SEQ ID NO: 79, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 272) having a hairpin-like structure is known as a precursor of "hsa-miR-6784-5p".

The term "hsa-miR-1249 gene" or "hsa-miR-1249" used herein includes the hsa-miR-1249 gene (miRBase Accession No. MIMAT0005901) described in SEQ ID NO: 80, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 273) having a hairpin-like structure is known as a precursor of "hsa-miR-1249".

The term "hsa-miR-937-5p gene" or "hsa-miR-937-5p" used herein includes the hsa-miR-937-5p gene (miRBase Accession No. MIMAT0022938) described in SEQ ID NO: 81, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 274) having a hairpin-like structure is known as a precursor of "hsa-miR-937-5p".

The term "hsa-miR-5195-3p gene" or "hsa-miR-5195-3p" used herein includes the hsa-miR-5195-3p gene (miRBase Accession No. MIMAT0021127) described in SEQ ID NO: 82, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 275) having a hairpin-like structure is known as a precursor of "hsa-miR-5195-3p".

The term "hsa-miR-6732-5p gene" or "hsa-miR-6732-5p" used herein includes the hsa-miR-6732-5p gene (miRBase Accession No. MIMAT0027365) described in SEQ ID NO: 83, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 276) having a hairpin-like structure is known as a precursor of "hsa-miR-6732-5p".

The term "hsa-miR-4417 gene" or "hsa-miR-4417" used herein includes the hsa-miR-4417 gene (miRBase Accession No. MIMAT0018929) described in SEQ ID NO: 84, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 277) having a hairpin-like structure is known as a precursor of "hsa-miR-4417".

The term "hsa-miR-4281 gene" or "hsa-miR-4281" used herein includes the hsa-miR-4281 gene (miRBase Accession No. MIMAT0016907) described in SEQ ID NO: 85, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 278) having a hairpin-like structure is known as a precursor of "hsa-miR-4281".

The term "hsa-miR-4734 gene" or "hsa-miR-4734" used herein includes the hsa-miR-4734 gene (miRBase Accession No. MIMAT0019859) described in SEQ ID NO: 86, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 279) having a hairpin-like structure is known as a precursor of "hsa-miR-4734".

The term "hsa-miR-6766-3p gene" or "hsa-miR-6766-3p" used herein includes the hsa-miR-6766-3p gene (miRBase Accession No. MIMAT0027433) described in SEQ ID NO: 87, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 280) having a hairpin-like structure is known as a precursor of "hsa-miR-6766-3p".

The term "hsa-miR-663a gene" or "hsa-miR-663a" used herein includes the hsa-miR-663a gene (miRBase Accession No. MIMAT0003326) described in SEQ ID NO: 88, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 281) having a hairpin-like structure is known as a precursor of "hsa-miR-663a".

The term "hsa-miR-4513 gene" or "hsa-miR-4513" used herein includes the hsa-miR-4513 gene (miRBase Accession No. MIMAT0019050) described in SEQ ID NO: 89, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 282) having a hairpin-like structure is known as a precursor of "hsa-miR-4513".

The term "hsa-miR-6781-5p gene" or "hsa-miR-6781-5p" used herein includes the hsa-miR-6781-5p gene (miRBase Accession No. MIMAT0027462) described in SEQ ID NO: 90, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 283) having a hairpin-like structure is known as a precursor of "hsa-miR-6781-5p".

The term "hsa-miR-1227-5p gene" or "hsa-miR-1227-5p" used herein includes the hsa-miR-1227-5p gene (miRBase Accession No. MIMAT0022941) described in SEQ ID NO: 91, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 284) having a hairpin-like structure is known as a precursor of "hsa-miR-1227-5p".

The term "hsa-miR-6845-5p gene" or "hsa-miR-6845-5p" used herein includes the hsa-miR-6845-5p gene (miRBase Accession No. MIMAT0027590) described in SEQ ID NO: 92, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 285) having a hairpin-like structure is known as a precursor of "hsa-miR-6845-5p".

The term "hsa-miR-6798-5p gene" or "hsa-miR-6798-5p" used herein includes the hsa-miR-6798-5p gene (miRBase Accession No. MIMAT0027496) described in SEQ ID NO: 93, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 286) having a hairpin-like structure is known as a precursor of "hsa-miR-6798-5p".

The term "hsa-miR-3620-5p gene" or "hsa-miR-3620-5p" used herein includes the hsa-miR-3620-5p gene (miRBase Accession No. MIMAT0022967) described in SEQ ID NO: 94, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 287) having a hairpin-like structure is known as a precursor of "hsa-miR-3620-5p".

The term "hsa-miR-1915-5p gene" or "hsa-miR-1915-5p" used herein includes the hsa-miR-1915-5p gene (miRBase Accession No. MIMAT0007891) described in SEQ ID NO: 95, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 288) having a hairpin-like structure is known as a precursor of "hsa-miR-1915-5p".

The term "hsa-miR-4294 gene" or "hsa-miR-4294" used herein includes the hsa-miR-4294 gene (miRBase Accession No. MIMAT0016849) described in SEQ ID NO: 96, a homolog or an ortholog of a different organism species, and the like. The hsa-miR-4294 gene can be obtained by a method described in Goff L A et al., 2009, PLoS One, Vol. 4, e7192.

Also, "hsa-mir-4294" (miRBase Accession No. MI0015827, SEQ ID NO: 289) having a hairpin-like structure is known as a precursor of "hsa-miR-4294".

The term "hsa-miR-642a-3p gene" or "hsa-miR-642a-3p" used herein includes the hsa-miR-642a-3p gene (miRBase Accession No. MIMAT0020924) described in SEQ ID NO: 97, a homolog or an ortholog of a different organism species, and the like. The hsa-miR-642a-3p gene can be obtained by a method described in Cummins J M et al., 2006, Proc Natl. Acad Sci USA, Vol. 103, p. 3687-3692. Also, "hsa-mir-642a" (miRBase Accession No. MI0003657, SEQ ID NO: 290) having a hairpin-like structure is known as a precursor of "hsa-miR-642a-3p".

The term "hsa-miR-371a-5p gene" or "hsa-miR-371a-5p" used herein includes the hsa-miR-371a-5p gene (miRBase Accession No. MIMAT0004687) described in SEQ ID NO: 98, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 291) having a hairpin-like structure is known as a precursor of "hsa-miR-371a-5p".

The term "hsa-miR-940 gene" or "hsa-miR-940" used herein includes the hsa-miR-940 gene (miRBase Accession No. MIMAT0004983) described in SEQ ID NO: 99, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 292) having a hairpin-like structure is known as a precursor of "hsa-miR-940".

The term "hsa-miR-4450 gene" or "hsa-miR-4450" used herein includes the hsa-miR-4450 gene (miRBase Accession No. MIMAT0018971) described in SEQ ID NO: 100, a homolog or an ortholog of a different organism species, and the like. The hsa-miR-4450 gene can be obtained by a method described in Jima D D et al., 2010, Blood, Vol. 116, e118-e127. Also, "hsa-mir-4450" (miRBase Accession No. MI0016795, SEQ ID NO: 293) having a hairpin-like structure is known as a precursor of "hsa-miR-4450".

The term "hsa-miR-4723-5p gene" or "hsa-miR-4723-5p" used herein includes the hsa-miR-4723-5p gene (miRBase Accession No. MIMAT0019838) described in SEQ ID NO: 101, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 294) having a hairpin-like structure is known as a precursor of "hsa-miR-4723-5p".

The term "hsa-miR-1469 gene" or "hsa-miR-1469" used herein includes the hsa-miR-1469 gene (miRBase Accession No. MIMAT0007347) described in SEQ ID NO: 102, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 295) having a hairpin-like structure is known as a precursor of "hsa-miR-1469".

The term "hsa-miR-6861-5p gene" or "hsa-miR-6861-5p" used herein includes the hsa-miR-6861-5p gene (miRBase Accession No. MIMAT0027623) described in SEQ ID NO:

103, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 296) having a hairpin-like structure is known as a precursor of "hsa-miR-6861-5p".

The term "hsa-miR-7975 gene" or "hsa-miR-7975" used herein includes the hsa-miR-7975 gene (miRBase Accession No. MIMAT0031178) described in SEQ ID NO: 104, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 297) having a hairpin-like structure is known as a precursor of "hsa-miR-7975".

The term "hsa-miR-6879-5p gene" or "hsa-miR-6879-5p" used herein includes the hsa-miR-6879-5p gene (miRBase Accession No. MIMAT0027658) described in SEQ ID NO: 105, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 298) having a hairpin-like structure is known as a precursor of "hsa-miR-6879-5p".

The term "hsa-miR-6802-5p gene" or "hsa-miR-6802-5p" used herein includes the hsa-miR-6802-5p gene (miRBase Accession No. MIMAT0027504) described in SEQ ID NO: 106, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 299) having a hairpin-like structure is known as a precursor of "hsa-miR-6802-5p".

The term "hsa-miR-1268b gene" or "hsa-miR-1268b" used herein includes the hsa-miR-1268b gene (miRBase Accession No. MIMAT0018925) described in SEQ ID NO: 107, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 300) having a hairpin-like structure is known as a precursor of "hsa-miR-1268b".

The term "hsa-miR-663b gene" or "hsa-miR-663b" used herein includes the hsa-miR-663b gene (miRBase Accession No. MIMAT0005867) described in SEQ ID NO: 108, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 301) having a hairpin-like structure is known as a precursor of "hsa-miR-663b".

The term "hsa-miR-125a-3p gene" or "hsa-miR-125a-3p" used herein includes the hsa-miR-125a-3p gene (miRBase Accession No. MIMAT0004602) described in SEQ ID NO: 109, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 302) having a hairpin-like structure is known as a precursor of "hsa-miR-125a-3p".

The term "hsa-miR-2861 gene" or "hsa-miR-2861" used herein includes the hsa-miR-2861 gene (miRBase Accession No. MIMAT0013802) described in SEQ ID NO: 110, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 303) having a hairpin-like structure is known as a precursor of "hsa-miR-2861".

The term "hsa-miR-6088 gene" or "hsa-miR-6088" used herein includes the hsa-miR-6088 gene (miRBase Accession No. MIMAT0023713) described in SEQ ID NO: 111, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 304) having a hairpin-like structure is known as a precursor of "hsa-miR-6088".

The term "hsa-miR-4758-5p gene" or "hsa-miR-4758-5p" used herein includes the hsa-miR-4758-5p gene (miRBase Accession No. MIMAT0019903) described in SEQ ID NO: 112, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 305) having a hairpin-like structure is known as a precursor of "hsa-miR-4758-5p".

The term "hsa-miR-296-3p gene" or "hsa-miR-296-3p" used herein includes the hsa-miR-296-3p gene (miRBase Accession No. MIMAT0004679) described in SEQ ID NO: 113, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 306) having a hairpin-like structure is known as a precursor of "hsa-miR-296-3p".

The term "hsa-miR-6738-5p gene" or "hsa-miR-6738-5p" used herein includes the hsa-miR-6738-5p gene (miRBase Accession No. MIMAT0027377) described in SEQ ID NO: 114, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 307) having a hairpin-like structure is known as a precursor of "hsa-miR-6738-5p".

The term "hsa-miR-671-5p gene" or "hsa-miR-671-5p" used herein includes the hsa-miR-671-5p gene (miRBase Accession No. MIMAT0003880) described in SEQ ID NO: 115, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 308) having a hairpin-like structure is known as a precursor of "hsa-miR-671-5p".

The term "hsa-miR-4454 gene" or "hsa-miR-4454" used herein includes the hsa-miR-4454 gene (miRBase Accession No. MIMAT0018976) described in SEQ ID NO: 116, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 309) having a hairpin-like structure is known as a precursor of "hsa-miR-4454".

The teen "hsa-miR-4516 gene" or "hsa-miR-4516" used herein includes the hsa-miR-4516 gene (miRBase Accession No. MIMAT0019053) described in SEQ ID NO: 117, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 310) having a hairpin-like structure is known as a precursor of "hsa-miR-4516".

The term "hsa-miR-7845-5p gene" or "hsa-miR-7845-5p" used herein includes the hsa-miR-7845-5p gene (miRBase Accession No. MIMAT0030420) described in SEQ ID NO: 118, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 311) having a hairpin-like structure is known as a precursor of "hsa-miR-7845-5p".

The term "hsa-miR-4741 gene" or "hsa-miR-4741" used herein includes the hsa-miR-4741 gene (miRBase Accession No. MIMAT0019871) described in SEQ ID NO: 119, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 312) having a hairpin-like structure is known as a precursor of "hsa-miR-4741".

The term "hsa-miR-92b-5p gene" or "hsa-miR-92b-5p" used herein includes the hsa-miR-92b-5p gene (miRBase Accession No. MIMAT0004792) described in SEQ ID NO: 120, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 313) having a hairpin-like structure is known as a precursor of "hsa-miR-92b-5p".

The term "hsa-miR-6795-5p gene" or "hsa-miR-6795-5p" used herein includes the hsa-miR-6795-5p gene (miRBase Accession No. MIMAT0027490) described in SEQ ID NO: 121, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795" (miRBase Accession No. MI0022640, SEQ ID NO: 314) having a hairpin-like structure is known as a precursor of "hsa-miR-6795-5p".

The term "hsa-miR-6805-3p gene" or "hsa-miR-6805-3p" used herein includes the hsa-miR-6805-3p gene (miRBase Accession No. MIMAT0027511) described in SEQ ID NO: 122, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 315) having a hairpin-like structure is known as a precursor of "hsa-miR-6805-3p".

The term "hsa-miR-4725-3p gene" or "hsa-miR-4725-3p" used herein includes the hsa-miR-4725-3p gene (miRBase Accession No. MIMAT0019844) described in SEQ ID NO: 123, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 316) having a hairpin-like structure is known as a precursor of "hsa-miR-4725-3p".

The term "hsa-miR-6782-5p gene" or "hsa-miR-6782-5p" used herein includes the hsa-miR-6782-5p gene (miRBase Accession No. MIMAT0027464) described in SEQ ID NO: 124, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 317) having a hairpin-like structure is known as a precursor of "hsa-miR-6782-5p".

The term "hsa-miR-4688 gene" or "hsa-miR-4688" used herein includes the hsa-miR-4688 gene (miRBase Accession No. MIMAT0019777) described in SEQ ID NO: 125, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 318) having a hairpin-like structure is known as a precursor of "hsa-miR-4688".

The term "hsa-miR-6850-5p gene" or "hsa-miR-6850-5p" used herein includes the hsa-miR-6850-5p gene (miRBase Accession No. MIMAT0027600) described in SEQ ID NO: 126, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 319) having a hairpin-like structure is known as a precursor of "hsa-miR-6850-5p".

The term "hsa-miR-6777-5p gene" or "hsa-miR-6777-5p" used herein includes the hsa-miR-6777-5p gene (miRBase Accession No. MIMAT0027454) described in SEQ ID NO: 127, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 320) having a hairpin-like structure is known as a precursor of "hsa-miR-6777-5p".

The term "hsa-miR-6785-5p gene" or "hsa-miR-6785-5p" used herein includes the hsa-miR-6785-5p gene (miRBase Accession No. MIMAT0027470) described in SEQ ID NO: 128, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 321) having a hairpin-like structure is known as a precursor of "hsa-miR-6785-5p".

The term "hsa-miR-7106-5p gene" or "hsa-miR-7106-5p" used herein includes the hsa-miR-7106-5p gene (miRBase Accession No. MIMAT0028109) described in SEQ ID NO: 129, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 322) having a hairpin-like structure is known as a precursor of "hsa-miR-7106-5p".

The term "hsa-miR-3663-3p gene" or "hsa-miR-3663-3p" used herein includes the hsa-miR-3663-3p gene (miRBase Accession No. MIMAT0018085) described in SEQ ID NO: 130, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 323) having a hairpin-like structure is known as a precursor of "hsa-miR-3663-3p".

The term "hsa-miR-6131 gene" or "hsa-miR-6131" used herein includes the hsa-miR-6131 gene (miRBase Accession No. MIMAT0024615) described in SEQ ID NO: 131, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 324) having a hairpin-like structure is known as a precursor of "hsa-miR-6131".

The term "hsa-miR-1915-3p gene" or "hsa-miR-1915-3p" used herein includes the hsa-miR-1915-3p gene (miRBase Accession No. MIMAT0007892) described in SEQ ID NO: 132, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 288) having a hairpin-like structure is known as a precursor of "hsa-miR-1915-3p".

The term "hsa-miR-4532 gene" or "hsa-miR-4532" used herein includes the hsa-miR-4532 gene (miRBase Accession No. MIMAT0019071) described in SEQ ID NO: 133, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 325) having a hairpin-like structure is known as a precursor of "hsa-miR-4532".

The term "hsa-miR-6820-5p gene" or "hsa-miR-6820-5p" used herein includes the hsa-miR-6820-5p gene (miRBase Accession No. MIMAT0027540) described in SEQ ID NO: 134, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 326) having a hairpin-like structure is known as a precursor of "hsa-miR-6820-5p".

The term "hsa-miR-4689 gene" or "hsa-miR-4689" used herein includes the hsa-miR-4689 gene (miRBase Accession No. MIMAT0019778) described in SEQ ID NO: 135, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 327) having a hairpin-like structure is known as a precursor of "hsa-miR-4689".

The term "hsa-miR-4638-5p gene" or "hsa-miR-4638-5p" used herein includes the hsa-miR-4638-5p gene (miRBase Accession No. MIMAT0019695) described in SEQ ID NO: 136, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 328) having a hairpin-like structure is known as a precursor of "hsa-miR-4638-5p".

The term "hsa-miR-3656 gene" or "hsa-miR-3656" used herein includes the hsa-miR-3656 gene (miRBase Accession No. MIMAT0018076) described in SEQ ID NO: 137, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 329) having a hairpin-like structure is known as a precursor of "hsa-miR-3656".

The term "hsa-miR-3621 gene" or "hsa-miR-3621" used herein includes the hsa-miR-3621 gene (miRBase Accession No. MIMAT0018002) described in SEQ ID NO: 138, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 330) having a hairpin-like structure is known as a precursor of "hsa-miR-3621".

The term "hsa-miR-6769b-5p gene" or "hsa-miR-6769b-5p" used herein includes the hsa-miR-6769b-5p gene (miRBase Accession No. MIMAT0027620) described in SEQ ID NO: 139, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 331) having a hairpin-like structure is known as a precursor of "hsa-miR-6769b-5p".

The term "hsa-miR-149-3p gene" or "hsa-miR-149-3p" used herein includes the hsa-miR-149-3p gene (miRBase Accession No. MIMAT0004609) described in SEQ ID NO: 140, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 332) having a hairpin-like structure is known as a precursor of "hsa-miR-149-3p".

The term "hsa-miR-23b-3p gene" or "hsa-miR-23b-3p" used herein includes the hsa-miR-23b-3p gene (miRBase Accession No. MIMAT0000418) described in SEQ ID NO: 141, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 333) having a hairpin-like structure is known as a precursor of "hsa-miR-23b-3p".

The term "hsa-miR-3135b gene" or "hsa-miR-3135b" used herein includes the hsa-miR-3135b gene (miRBase Accession No. MIMAT0018985) described in SEQ ID NO: 142, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 334) having a hairpin-like structure is known as a precursor of "hsa-miR-3135b".

The term "hsa-miR-6848-5p gene" or "hsa-miR-6848-5p" used herein includes the hsa-miR-6848-5p gene (miRBase Accession No. MIMAT0027596) described in SEQ ID NO: 143, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 335) having a hairpin-like structure is known as a precursor of "hsa-miR-6848-5p".

The term "hsa-miR-6769a-5p gene" or "hsa-miR-6769a-5p" used herein includes the hsa-miR-6769a-5p gene (miR- Base Accession No. MIMAT0027438) described in SEQ ID NO: 144, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 336) having a hairpin-like structure is known as a precursor of "hsa-miR-6769a-5p".

The term "hsa-miR-4327 gene" or "hsa-miR-4327" used herein includes the hsa-miR-4327 gene (miRBase Accession No. MIMAT0016889) described in SEQ ID NO: 145, a homolog or an ortholog of a different organism species, and the like. The hsa-miR-4327 gene can be obtained by a method described in Goff L A et al., 2009, PLoS One, Vol. 4, e7192. Also, "hsa-mir-4327" (miRBase Accession No. MI0015867, SEQ ID NO: 337) having a hairpin-like structure is known as a precursor of "hsa-miR-4327".

The term "hsa-miR-6765-3p gene" or "hsa-miR-6765-3p" used herein includes the hsa-miR-6765-3p gene (miRBase Accession No. MIMAT0027431) described in SEQ ID NO: 146, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 338) having a hairpin-like structure is known as a precursor of "hsa-miR-6765-3p".

The term "hsa-miR-6716-5p gene" or "hsa-miR-6716-5p" used herein includes the hsa-miR-6716-5p gene (miRBase Accession No. MIMAT0025844) described in SEQ ID NO: 147, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 339) having a hairpin-like structure is known as a precursor of "hsa-miR-6716-5p".

The term "hsa-miR-6877-5p gene" or "hsa-miR-6877-5p" used herein includes the hsa-miR-6877-5p gene (miRBase Accession No. MIMAT0027654) described in SEQ ID NO: 148, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 340) having a hairpin-like structure is known as a precursor of "hsa-miR-6877-5p".

The term "hsa-miR-6727-5p gene" or "hsa-miR-6727-5p" used herein includes the hsa-miR-6727-5p gene (miRBase Accession No. MIMAT0027355) described in SEQ ID NO: 149, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 341) having a hairpin-like structure is known as a precursor of "hsa-miR-6727-5p".

The term "hsa-miR-4534 gene" or "hsa-miR-4534" used herein includes the hsa-miR-4534 gene (miRBase Accession No. MIMAT0019073) described in SEQ ID NO: 150, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 342) having a hairpin-like structure is known as a precursor of "hsa-miR-4534".

The term "hsa-miR-614 gene" or "hsa-miR-614" used herein includes the hsa-miR-614 gene (miRBase Accession No. MIMAT0003282) described in SEQ ID NO: 151, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 343) having a hairpin-like structure is known as a precursor of "hsa-miR-614".

The term "hsa-miR-1202 gene" or "hsa-miR-1202" used herein includes the hsa-miR-1202 gene (miRBase Accession No. MIMAT0005865) described in SEQ ID NO: 152, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 344) having a hairpin-like structure is known as a precursor of "hsa-miR-1202".

The term "hsa-miR-575 gene" or "hsa-miR-575" used herein includes the hsa-miR-575 gene (miRBase Accession No. MIMAT0003240) described in SEQ ID NO: 153, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 345) having a hairpin-like structure is known as a precursor of "hsa-miR-575".

The term "hsa-miR-6870-5p gene" or "hsa-miR-6870-5p" used herein includes the hsa-miR-6870-5p gene (miRBase Accession No. MIMAT0027640) described in SEQ ID NO: 154, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 346) having a hairpin-like structure is known as a precursor of "hsa-miR-6870-5p".

The term "hsa-miR-6722-3p gene" or "hsa-miR-6722-3p" used herein includes the hsa-miR-6722-3p gene (miRBase Accession No. MIMAT0025854) described in SEQ ID NO: 155, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 347) having a hairpin-like structure is known as a precursor of "hsa-miR-6722-3p".

The term "hsa-miR-7977 gene" or "hsa-miR-7977" used herein includes the hsa-miR-7977 gene (miRBase Accession No. MIMAT0031180) described in SEQ ID NO: 156, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 348) having a hairpin-like structure is known as a precursor of "hsa-miR-7977".

The term "hsa-miR-4649-5p gene" or "hsa-miR-4649-5p" used herein includes the hsa-miR-4649-5p gene (miRBase Accession No. MIMAT0019711) described in SEQ ID NO: 157, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miR- Base Accession No. MI0017276, SEQ ID NO: 349) having a hairpin-like structure is known as a precursor of "hsa-miR-4649-5p".

The term "hsa-miR-4675 gene" or "hsa-miR-4675" used herein includes the hsa-miR-4675 gene (miRBase Accession No. MIMAT0019757) described in SEQ ID NO: 158, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 350) having a hairpin-like structure is known as a precursor of "hsa-miR-4675".

The term "hsa-miR-6075 gene" or "hsa-miR-6075" used herein includes the hsa-miR-6075 gene (miRBase Accession No. MIMAT0023700) described in SEQ ID NO: 159, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 351) having a hairpin-like structure is known as a precursor of "hsa-miR-6075".

The term "hsa-miR-6779-5p gene" or "hsa-miR-6779-5p" used herein includes the hsa-miR-6779-5p gene (miRBase Accession No. MIMAT0027458) described in SEQ ID NO: 160, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 352) having a hairpin-like structure is known as a precursor of "hsa-miR-6779-5p".

The term "hsa-miR-4271 gene" or "hsa-miR-4271" used herein includes the hsa-miR-4271 gene (miRBase Accession No. MIMAT0016901) described in SEQ ID NO: 161, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 353) having a hairpin-like structure is known as a precursor of "hsa-miR-4271".

The term "hsa-miR-3196 gene" or "hsa-miR-3196" used herein includes the hsa-miR-3196 gene (miRBase Accession No. MIMAT0015080) described in SEQ ID NO: 162, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 354) having a hairpin-like structure is known as a precursor of "hsa-miR-3196".

The term "hsa-miR-6803-5p gene" or "hsa-miR-6803-5p" used herein includes the hsa-miR-6803-5p gene (miRBase Accession No. MIMAT0027506) described in SEQ ID NO: 163, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 355) having a hairpin-like structure is known as a precursor of "hsa-miR-6803-5p".

The term "hsa-miR-6789-5p gene" or "hsa-miR-6789-5p" used herein includes the hsa-miR-6789-5p gene (miRBase Accession No. MIMAT0027478) described in SEQ ID NO: 164, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 356) having a hairpin-like structure is known as a precursor of "hsa-miR-6789-5p".

The term "hsa-miR-4648 gene" or "hsa-miR-4648" used herein includes the hsa-miR-4648 gene (miRBase Accession No. MIMAT0019710) described in SEQ ID NO: 165, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 357) having a hairpin-like structure is known as a precursor of "hsa-miR-4648".

The term "hsa-miR-4508 gene" or "hsa-miR-4508" used herein includes the hsa-miR-4508 gene (miRBase Accession No. MIMAT0019045) described in SEQ ID NO: 166, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 358) having a hairpin-like structure is known as a precursor of "hsa-miR-4508".

The term "hsa-miR-4749-5p gene" or "hsa-miR-4749-5p" used herein includes the hsa-miR-4749-5p gene (miRBase Accession No. MIMAT0019885) described in SEQ ID NO: 167, a homolog or an ortholog of a different organism species, and the like. The hsa-miR-4749-5p gene can be obtained by a method described in Persson H et al., 2011, Cancer Res, Vol. 71, p. 78-86. Also, "hsa-mir-4749" (miRBase Accession No. MI0017388, SEQ ID NO: 359) having a hairpin-like structure is known as a precursor of "hsa-miR-4749-5p".

The term "hsa-miR-4505 gene" or "hsa-miR-4505" used herein includes the hsa-miR-4505 gene (miRBase Accession No. MIMAT0019041) described in SEQ ID NO: 168, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 360) having a hairpin-like structure is known as a precursor of "hsa-miR-4505".

The term "hsa-miR-5698 gene" or "hsa-miR-5698" used herein includes the hsa-miR-5698 gene (miRBase Accession No. MIMAT0022491) described in SEQ ID NO: 169, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 361) having a hairpin-like structure is known as a precursor of "hsa-miR-5698".

The term "hsa-miR-1199-5p gene" or "hsa-miR-1199-5p" used herein includes the hsa-miR-1199-5p gene (miRBase Accession No. MIMAT0031119) described in SEQ ID NO: 170, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 362) having a hairpin-like structure is known as a precursor of "hsa-miR-1199-5p".

The term "hsa-miR-4763-3p gene" or "hsa-miR-4763-3p" used herein includes the hsa-miR-4763-3p gene (miRBase Accession No. MIMAT0019913) described in SEQ ID NO: 171, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miR- Base Accession No. MI0017404, SEQ ID NO: 363) having a hairpin-like structure is known as a precursor of "hsa-miR-4763-3p".

The term "hsa-miR-1231 gene" or "hsa-miR-1231" used herein includes the hsa-miR-1231 gene (miRBase Accession No. MIMAT0005586) described in SEQ ID NO: 172, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 364) having a hairpin-like structure is known as a precursor of "hsa-miR-1231".

The term "hsa-miR-1233-5p gene" or "hsa-miR-1233-5p" used herein includes the hsa-miR-1233-5p gene (miRBase Accession No. MIMAT0022943) described in SEQ ID NO: 173, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 365 and 366) having a hairpin-like structure are known as precursors of "hsa-miR-1233-5p".

The term "hsa-miR-150-3p gene" or "hsa-miR-150-3p" used herein includes the hsa-miR-150-3p gene (miRBase Accession No. MIMAT0004610) described in SEQ ID NO: 174, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 367) having a hairpin-like structure is known as a precursor of "hsa-miR-150-3p".

The term "hsa-miR-1225-3p gene" or "hsa-miR-1225-3p" used herein includes the hsa-miR-1225-3p gene (miRBase Accession No. MIMAT0005573) described in SEQ ID NO: 175, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 235) having a hairpin-like structure is known as a precursor of "hsa-miR-1225-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 176, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 368) having a hairpin-like structure is known as a precursor of "hsa-miR-92a-2-5p".

The term "hsa-miR-423-5p gene" or "hsa-miR-423-5p" used herein includes the hsa-miR-423-5p gene (miRBase Accession No. MIMAT0004748) described in SEQ ID NO: 177, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 369) having a hairpin-like structure is known as a precursor of "hsa-miR-423-5p".

The term "hsa-miR-1268a gene" or "hsa-miR-1268a" used herein includes the hsa-miR-1268a gene (miRBase Accession No. MIMAT0005922) described in SEQ ID NO: 178, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 370) having a hairpin-like structure is known as a precursor of "hsa-miR-1268a".

The term "hsa-miR-128-2-5p gene" or "hsa-miR-128-2-5p" used herein includes the hsa-miR-128-2-5p gene (miRBase Accession No. MIMAT0031095) described in SEQ ID NO: 179, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 371) having a hairpin-like structure is known as a precursor of "hsa-miR-128-2-5p".

The term "hsa-miR-24-3p gene" or "hsa-miR-24-3p" used herein includes the hsa-miR-24-3p gene (miRBase Accession No. MIMAT0000080) described in SEQ ID NO: 180, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 372 and 373) having a hairpin-like structure are known as precursors of "hsa-miR-24-3p".

The term "hsa-miR-4697-5p gene" or "hsa-miR-4697-5p" used herein includes the hsa-miR-4697-5p gene (miRBase Accession No. MIMAT0019791) described in SEQ ID NO: 181, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 374) having a hairpin-like structure is known as a precursor of "hsa-miR-4697-5p".

The term "hsa-miR-3197 gene" or "hsa-miR-3197" used herein includes the hsa-miR-3197 gene (miRBase Accession No. MIMAT0015082) described in SEQ ID NO: 182, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 375) having a hairpin-like structure is known as a precursor of "hsa-miR-3197".

The term "hsa-miR-675-5p gene" or "hsa-miR-675-5p" used herein includes the hsa-miR-675-5p gene (miRBase Accession No. MIMAT0004284) described in SEQ ID NO: 183, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 376) having a hairpin-like structure is known as a precursor of "hsa-miR-675-5p".

The term "hsa-miR-4486 gene" or "hsa-miR-4486" used herein includes the hsa-miR-4486 gene (miRBase Accession No. MIMAT0019020) described in SEQ ID NO: 184, a homolog or an ortholog of a different organism species, and the like. The hsa-miR-4486 gene can be obtained by a method described in Jima D D et al., 2010, Blood, Vol. 116, e118-e 127. Also, "hsa-mir-4486" (miRBase Accession No. MI0016847, SEQ ID NO: 377) having a hairpin-like structure is known as a precursor of "hsa-miR-4486".

The term "hsa-miR-7107-5p gene" or "hsa-miR-7107-5p" used herein includes the hsa-miR-7107-5p gene (miRBase Accession No. MIMAT0028111) described in SEQ ID NO:

185, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 378) having a hairpin-like structure is known as a precursor of "hsa-miR-7107-5p".

The term "hsa-miR-23a-3p gene" or "hsa-miR-23a-3p" used herein includes the hsa-miR-23a-3p gene (miRBase Accession No. MIMAT0000078) described in SEQ ID NO: 186, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 379) having a hairpin-like structure is known as a precursor of "hsa-miR-23a-3p".

The term "hsa-miR-4667-5p gene" or "hsa-miR-4667-5p" used herein includes the hsa-miR-4667-5p gene (miRBase Accession No. MIMAT0019743) described in SEQ ID NO: 187, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 380) having a hairpin-like structure is known as a precursor of "hsa-miR-4667-5p".

The term "hsa-miR-451a gene" or "hsa-miR-451a" used herein includes the hsa-miR-451a gene (miRBase Accession No. MIMAT0001631) described in SEQ ID NO: 188, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 381) having a hairpin-like structure is known as a precursor of "hsa-miR-451a".

The term "hsa-miR-3940-5p gene" or "hsa-miR-3940-5p" used herein includes the hsa-miR-3940-5p gene (miRBase Accession No. MIMAT0019229) described in SEQ ID NO: 189, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 382) having a hairpin-like structure is known as a precursor of "hsa-miR-3940-5p".

The term "hsa-miR-8059 gene" or "hsa-miR-8059" used herein includes the hsa-miR-8059 gene (miRBase Accession No. MIMAT0030986) described in SEQ ID NO: 190, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 383) having a hairpin-like structure is known as a precursor of "hsa-miR-8059".

The term "hsa-miR-6813-5p gene" or "hsa-miR-6813-5p" used herein includes the hsa-miR-6813-5p gene (miRBase Accession No. MIMAT0027526) described in SEQ ID NO: 191, a homolog or an ortholog of a different organism species, and the like. The hsa-miR-6813-5p gene can be obtained by a method described in Ladewig E et al., 2012, Genome Res, Vol. 22, p. 1634-1645. Also, "hsa-mir-6813" (miRBase Accession No. MI0022658, SEQ ID NO: 384) having a hairpin-like structure is known as a precursor of "hsa-miR-6813-5p".

The term "hsa-miR-4492 gene" or "hsa-miR-4492" used herein includes the hsa-miR-4492 gene (miRBase Accession No. MIMAT0019027) described in SEQ ID NO: 192, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 385) having a hairpin-like structure is known as a precursor of "hsa-miR-4492".

The term "hsa-miR-4476 gene" or "hsa-miR-4476" used herein includes the hsa-miR-4476 gene (miRBase Accession No. MIMAT0019003) described in SEQ ID NO: 193, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 386) having a hairpin-like structure is known as a precursor of "hsa-miR-4476".

The term "hsa-miR-6090 gene" or "hsa-miR-6090" used herein includes the hsa-miR-6090 gene (miRBase Accession No. MIMAT0023715) described in SEQ ID NO: 194, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 387) having a hairpin-like structure is known as a precursor of "hsa-miR-6090".

The term "hsa-miR-6836-3p gene" or "hsa-miR-6836-3p" used herein includes the hsa-miR-6836-3p gene (miRBase Accession No. MIMAT0027575) described in SEQ ID NO: 606, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 615) having a hairpin-like structure is known as a precursor of "hsa-miR-6836-3p".

The term "hsa-miR-3195 gene" or "hsa-miR-3195" used herein includes the hsa-miR-3195 gene (miRBase Accession No. MIMAT0015079) described in SEQ ID NO: 607, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 616) having a hairpin-like structure is known as a precursor of "hsa-miR-3195".

The term "hsa-miR-718 gene" or "hsa-miR-718" used herein includes the hsa-miR-718 gene (miRBase Accession No. MIMAT0012735) described in SEQ ID NO: 608, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 617) having a hairpin-like structure is known as a precursor of "hsa-miR-718".

The term "hsa-miR-3178 gene" or "hsa-miR-3178" used herein includes the hsa-miR-3178 gene (miRBase Accession No. MIMAT0015055) described in SEQ ID NO: 609, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 618) having a hairpin-like structure is known as a precursor of "hsa-miR-3178".

The term "hsa-miR-638 gene" or "hsa-miR-638" used herein includes the hsa-miR-638 gene (miRBase Accession No. MIMAT0003308) described in SEQ ID NO: 610, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 619) having a hairpin-like structure is known as a precursor of "hsa-miR-638".

The term "hsa-miR-4497 gene" or "hsa-miR-4497" used herein includes the hsa-miR-4497 gene (miRBase Accession No. MIMAT0019032) described in SEQ ID NO: 611, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 620) having a hairpin-like structure is known as a precursor of "hsa-miR-4497".

The term "hsa-miR-6085 gene" or "hsa-miR-6085" used herein includes the hsa-miR-6085 gene (miRBase Accession No. MIMAT0023710) described in SEQ ID NO: 612, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 621) having a hairpin-like structure is known as a precursor of "hsa-miR-6085".

The term "hsa-miR-6752-5p gene" or "hsa-miR-6752-5p" used herein includes the hsa-miR-6752-5p gene (miRBase Accession No. MIMAT0027404) described in SEQ ID NO: 613, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 622) having a hairpin-like structure is known as a precursor of "hsa-miR-6752-5p".

The term "hsa-miR-135a-3p gene" or "hsa-miR-135a-3p" used herein includes the hsa-miR-135a-3p gene (miRBase Accession No. MIMAT0004595) described in SEQ ID NO: 614, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a" (miRBase Accession No. MI0000452, SEQ ID NO: 623) having a hairpin-like structure is known as a precursor of "hsa-miR-135a-3p".

A mature miRNA may become a variant due to the sequence that is cleaved shorter or longer by one to several upstream or downstream nucleotides or nucleotide substitution when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 194 and 606 to 614 as well as a large number of the nucleotide sequence variants and fragments represented by SEQ ID NOs: 388 to 605 and 624 to 635, which are called isomiRs. These variants can also be obtained as miRNAs having a nucleotide sequence represented by any of SEQ ID NOs: 1 to 194 and 606 to 614. Specifically, among the variants of polynucleotides consisting of the nucleotide sequence represented by any of SEQ ID NOs: 5, 7, 8, 9, 11, 16, 19, 20, 21, 26, 27, 28, 30, 34, 37, 38, 39, 41, 43, 45, 46, 48, 50, 54, 55, 57, 58, 61, 62, 63, 64, 65, 66, 67, 69, 70, 71, 73, 74, 76, 77, 78, 80, 81, 82, 84, 85, 86, 88, 89, 94, 95, 97, 98, 99, 100, 101, 104, 107, 108, 109, 110, 111, 112, 113, 115, 116, 117, 119, 120, 123, 125, 131, 132, 133, 135, 136, 137, 140, 141, 142, 147, 151, 152, 157, 161, 162, 165, 166, 167, 168, 169, 171, 173, 174, 176, 177, 178, 179, 180, 182, 183, 184, 186, 187, 188, 189, 192, 193, 607, 608, 609, 610, 611 and 614, or a nucleotide sequence derived from the nucleotide sequence by the replacement of u with t according to the present invention, examples of the longest variants registered in the miRBase Release 20 include polynucleotides represented by SEQ ID NOs:388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 624, 626, 628, 630, 632 and 634, respectively. Also, among the variants of polynucleotides consisting of a nucleotide sequence represented by any of SEQ ID NOs: 5, 7, 8, 9, 11, 16, 19, 20, 21, 26, 27, 28, 30, 34, 37, 38, 39, 41, 43, 45, 46, 48, 50, 54, 55, 57, 58, 61, 62, 63, 64, 65, 66, 67, 69, 70, 71, 73, 74, 76, 77, 78, 80, 81, 82, 84, 85, 86, 88, 89, 94, 95, 97, 98, 99, 100, 101, 104, 107, 108, 109, 110, 111, 112, 113, 115, 116, 117, 119, 120, 123, 125, 131, 132, 133, 135, 136, 137, 140, 141, 142, 147, 151, 152, 157, 161, 162, 165, 166, 167, 168, 169, 171, 173, 174, 176, 177, 178, 179, 180, 182, 183, 184, 186, 187, 188, 189, 192, 193, 607, 608, 609, 610, 611 and 614, or a nucleotide sequence derived from the nucleotide sequence by the replacement of u with t according to the present invention, examples of the shortest variants registered in the miRBase Release 20 include polynucleotides having sequences represented by SEQ ID NOs: 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 625, 627, 629, 631, 633 and 635, respectively. In addition to these variants and fragments, examples thereof include a large number of isomiR polynucleotides of SEQ ID NOs: 1 to 194 and 606 to 614 registered in miRBase. Examples of the polynucleotide comprising a nucleotide sequence represented by any of SEQ ID NOs: 1 to 194 and 606 to 614 to 494 include a polynucleotide represented by any of SEQ ID NOs: 195 to 387 and 615 to 623, which are their respective precursors.

The names and miRBase Accession Nos. (registration numbers) of the genes represented by SEQ ID NOs: 1 to 635 are shown in Table 1.

TABLE 1

| SEQ ID NO: | Gene name | miRBase registration No. |
| --- | --- | --- |
| 1 | hsa-miR-6726-5p | MIMAT0027353 |
| 2 | hsa-miR-4257 | MIMAT0016878 |
| 3 | hsa-miR-6787-5p | MIMAT0027474 |
| 4 | hsa-miR-6780b-5p | MIMAT0027572 |
| 5 | hsa-miR-3131 | MIMAT0014996 |
| 6 | hsa-miR-7108-5p | MIMAT0028113 |
| 7 | hsa-miR-1343-3p | MIMAT0019776 |
| 8 | hsa-miR-1247-3p | MIMAT0022721 |
| 9 | hsa-miR-4651 | MIMAT0019715 |

TABLE 1-continued

| SEQ ID NO: | Gene name | miRBase registration No. |
|---|---|---|
| 10 | hsa-miR-6757-5p | MIMAT0027414 |
| 11 | hsa-miR-3679-5p | MIMAT0018104 |
| 12 | hsa-miR-7641 | MIMAT0029782 |
| 13 | hsa-miR-6746-5p | MIMAT0027392 |
| 14 | hsa-miR-8072 | MIMAT0030999 |
| 15 | hsa-miR-6741-5p | MIMAT0027383 |
| 16 | hsa-miR-1908-5p | MIMAT0007881 |
| 17 | hsa-miR-6857-5p | MIMAT0027614 |
| 18 | hsa-miR-4746-3p | MIMAT0019881 |
| 19 | hsa-miR-744-5p | MIMAT0004945 |
| 20 | hsa-miR-4792 | MIMAT0019964 |
| 21 | hsa-miR-564 | MIMAT0003228 |
| 22 | hsa-miR-6791-5p | MIMAT0027482 |
| 23 | hsa-miR-6825-5p | MIMAT0027550 |
| 24 | hsa-miR-6826-5p | MIMAT0027552 |
| 25 | hsa-miR-4665-3p | MIMAT0019740 |
| 26 | hsa-miR-4467 | MIMAT0018994 |
| 27 | hsa-miR-3188 | MIMAT0015070 |
| 28 | hsa-miR-6125 | MIMAT0024598 |
| 29 | hsa-miR-6756-5p | MIMAT0027412 |
| 30 | hsa-miR-1228-3p | MIMAT0005583 |
| 31 | hsa-miR-8063 | MIMAT0030990 |
| 32 | hsa-miR-8069 | MIMAT0030996 |
| 33 | hsa-miR-6875-5p | MIMAT0027650 |
| 34 | hsa-miR-3185 | MIMAT0015065 |
| 35 | hsa-miR-4433b-3p | MIMAT0030414 |
| 36 | hsa-miR-6887-5p | MIMAT0027674 |
| 37 | hsa-miR-128-1-5p | MIMAT0026477 |
| 38 | hsa-miR-6724-5p | MIMAT0025856 |
| 39 | hsa-miR-1914-3p | MIMAT0007890 |
| 40 | hsa-miR-1225-5p | MIMAT0005572 |
| 41 | hsa-miR-4419b | MIMAT0019034 |
| 42 | hsa-miR-7110-5p | MIMAT0028117 |
| 43 | hsa-miR-187-5p | MIMAT0004561 |
| 44 | hsa-miR-3184-5p | MIMAT0015064 |
| 45 | hsa-miR-204-3p | MIMAT0022693 |
| 46 | hsa-miR-5572 | MIMAT0022260 |
| 47 | hsa-miR-6729-5p | MIMAT0027359 |
| 48 | hsa-miR-615-5p | MIMAT0004804 |
| 49 | hsa-miR-6749-5p | MIMAT0027398 |
| 50 | hsa-miR-6515-3p | MIMAT0025487 |
| 51 | hsa-miR-3937 | MIMAT0018352 |
| 52 | hsa-miR-6840-3p | MIMAT0027583 |
| 53 | hsa-miR-6893-5p | MIMAT0027686 |
| 54 | hsa-miR-4728-5p | MIMAT0019849 |
| 55 | hsa-miR-6717-5p | MIMAT0025846 |
| 56 | hsa-miR-7113-3p | MIMAT0028124 |
| 57 | hsa-miR-4665-5p | MIMAT0019739 |
| 58 | hsa-miR-642b-3p | MIMAT0018444 |
| 59 | hsa-miR-7109-5p | MIMAT0028115 |
| 60 | hsa-miR-6842-5p | MIMAT0027586 |
| 61 | hsa-miR-4442 | MIMAT0018960 |
| 62 | hsa-miR-4433-3p | MIMAT0018949 |
| 63 | hsa-miR-4707-5p | MIMAT0019807 |
| 64 | hsa-miR-6126 | MIMAT0024599 |
| 65 | hsa-miR-4449 | MIMAT0018968 |
| 66 | hsa-miR-4706 | MIMAT0019806 |
| 67 | hsa-miR-1913 | MIMAT0007888 |
| 68 | hsa-miR-602 | MIMAT0003270 |
| 69 | hsa-miR-939-5p | MIMAT0004982 |
| 70 | hsa-miR-4695-5p | MIMAT0019788 |
| 71 | hsa-miR-711 | MIMAT0012734 |
| 72 | hsa-miR-6816-5p | MIMAT0027532 |
| 73 | hsa-miR-4632-5p | MIMAT0022977 |
| 74 | hsa-miR-6721-5p | MIMAT0025852 |
| 75 | hsa-miR-7847-3p | MIMAT0030422 |
| 76 | hsa-miR-6132 | MIMAT0024616 |
| 77 | hsa-miR-887-3p | MIMAT0004951 |
| 78 | hsa-miR-3679-3p | MIMAT0018105 |
| 79 | hsa-miR-6784-5p | MIMAT0027468 |
| 80 | hsa-miR-1249 | MIMAT0005901 |
| 81 | hsa-miR-937-5p | MIMAT0022938 |
| 82 | hsa-miR-5195-3p | MIMAT0021127 |
| 83 | hsa-miR-6732-5p | MIMAT0027365 |
| 84 | hsa-miR-4417 | MIMAT0018929 |
| 85 | hsa-miR-4281 | MIMAT0016907 |
| 86 | hsa-miR-4734 | MIMAT0019859 |
| 87 | hsa-miR-6766-3p | MIMAT0027433 |
| 88 | hsa-miR-663a | MIMAT0003326 |
| 89 | hsa-miR-4513 | MIMAT0019050 |
| 90 | hsa-miR-6781-5p | MIMAT0027462 |
| 91 | hsa-miR-1227-5p | MIMAT0022941 |
| 92 | hsa-miR-6845-5p | MIMAT0027590 |
| 93 | hsa-miR-6798-5p | MIMAT0027496 |
| 94 | hsa-miR-3620-5p | MIMAT0022967 |
| 95 | hsa-miR-1915-5p | MIMAT0007891 |
| 96 | hsa-miR-4294 | MIMAT0016849 |
| 97 | hsa-miR-642a-3p | MIMAT0020924 |
| 98 | hsa-miR-371a-5p | MIMAT0004687 |
| 99 | hsa-miR-940 | MIMAT0004983 |
| 100 | hsa-miR-4450 | MIMAT0018971 |
| 101 | hsa-miR-4723-5p | MIMAT0019838 |
| 102 | hsa-miR-1469 | MIMAT0007347 |
| 103 | hsa-miR-6861-5p | MIMAT0027623 |
| 104 | hsa-miR-7975 | MIMAT0031178 |
| 105 | hsa-miR-6879-5p | MIMAT0027658 |
| 106 | hsa-miR-6802-5p | MIMAT0027504 |
| 107 | hsa-miR-1268b | MIMAT0018925 |
| 108 | hsa-miR-663b | MIMAT0005867 |
| 109 | hsa-miR-125a-3p | MIMAT0004602 |
| 110 | hsa-miR-2861 | MIMAT0013802 |
| 111 | hsa-miR-6088 | MIMAT0023713 |
| 112 | hsa-miR-4758-5p | MIMAT0019903 |
| 113 | hsa-miR-296-3p | MIMAT0004679 |
| 114 | hsa-miR-6738-5p | MIMAT0027377 |
| 115 | hsa-miR-671-5p | MIMAT0003880 |
| 116 | hsa-miR-4454 | MIMAT0018976 |
| 117 | hsa-miR-4516 | MIMAT0019053 |
| 118 | hsa-miR-7845-5p | MIMAT0030420 |
| 119 | hsa-miR-4741 | MIMAT0019871 |
| 120 | hsa-miR-92b-5p | MIMAT0004792 |
| 121 | hsa-miR-6795-5p | MIMAT0027490 |
| 122 | hsa-miR-6805-3p | MIMAT0027511 |
| 123 | hsa-miR-4725-3p | MIMAT0019844 |
| 124 | hsa-miR-6782-5p | MIMAT0027464 |
| 125 | hsa-miR-4688 | MIMAT0019777 |
| 126 | hsa-miR-6850-5p | MIMAT0027600 |
| 127 | hsa-miR-6777-5p | MIMAT0027454 |
| 128 | hsa-miR-6785-5p | MIMAT0027470 |
| 129 | hsa-miR-7106-5p | MIMAT0028109 |
| 130 | hsa-miR-3663-3p | MIMAT0018085 |
| 131 | hsa-miR-6131 | MIMAT0024615 |
| 132 | hsa-miR-1915-3p | MIMAT0007892 |
| 133 | hsa-miR-4532 | MIMAT0019071 |
| 134 | hsa-miR-6820-5p | MIMAT0027540 |
| 135 | hsa-miR-4689 | MIMAT0019778 |
| 136 | hsa-miR-4638-5p | MIMAT0019695 |
| 137 | hsa-miR-3656 | MIMAT0018076 |
| 138 | hsa-miR-3621 | MIMAT0018002 |
| 139 | hsa-miR-6769b-5p | MIMAT0027620 |
| 140 | hsa-miR-149-3p | MIMAT0004609 |
| 141 | hsa-miR-23b-3p | MIMAT0000418 |
| 142 | hsa-miR-3135b | MIMAT0018985 |
| 143 | hsa-miR-6848-5p | MIMAT0027596 |
| 144 | hsa-miR-6769a-5p | MIMAT0027438 |
| 145 | hsa-miR-4327 | MIMAT0016889 |
| 146 | hsa-miR-6765-3p | MIMAT0027431 |
| 147 | hsa-miR-6716-5p | MIMAT0025844 |
| 148 | hsa-miR-6877-5p | MIMAT0027654 |
| 149 | hsa-miR-6727-5p | MIMAT0027355 |
| 150 | hsa-miR-4534 | MIMAT0019073 |
| 151 | hsa-miR-614 | MIMAT0003282 |
| 152 | hsa-miR-1202 | MIMAT0005865 |
| 153 | hsa-miR-575 | MIMAT0003240 |
| 154 | hsa-miR-6870-5p | MIMAT0027640 |
| 155 | hsa-miR-6722-3p | MIMAT0025854 |
| 156 | hsa-miR-7977 | MIMAT0031180 |
| 157 | hsa-miR-4649-5p | MIMAT0019711 |
| 158 | hsa-miR-4675 | MIMAT0019757 |
| 159 | hsa-miR-6075 | MIMAT0023700 |
| 160 | hsa-miR-6779-5p | MIMAT0027458 |
| 161 | hsa-miR-4271 | MIMAT0016901 |
| 162 | hsa-miR-3196 | MIMAT0015080 |
| 163 | hsa-miR-6803-5p | MIMAT0027506 |

TABLE 1-continued

| SEQ ID NO: | Gene name | miRBase registration No. |
|---|---|---|
| 164 | hsa-miR-6789-5p | MIMAT0027478 |
| 165 | hsa-miR-4648 | MIMAT0019710 |
| 166 | hsa-miR-4508 | MIMAT0019045 |
| 167 | hsa-miR-4749-5p | MIMAT0019885 |
| 168 | hsa-miR-4505 | MIMAT0019041 |
| 169 | hsa-miR-5698 | MIMAT0022491 |
| 170 | hsa-miR-1199-5p | MIMAT0031119 |
| 171 | hsa-miR-4763-3p | MIMAT0019913 |
| 172 | hsa-miR-1231 | MIMAT0005586 |
| 173 | hsa-miR-1233-5p | MIMAT0022943 |
| 174 | hsa-miR-150-3p | MIMAT0004610 |
| 175 | hsa-miR-1225-3p | MIMAT0005573 |
| 176 | hsa-miR-92a-2-5p | MIMAT0004508 |
| 177 | hsa-miR-423-5p | MIMAT0004748 |
| 178 | hsa-miR-1268a | MIMAT0005922 |
| 179 | hsa-miR-128-2-5p | MIMAT0031095 |
| 180 | hsa-miR-24-3p | MIMAT0000080 |
| 181 | hsa-miR-4697-5p | MIMAT0019791 |
| 182 | hsa-miR-3197 | MIMAT0015082 |
| 183 | hsa-miR-675-5p | MIMAT0004284 |
| 184 | hsa-miR-4486 | MIMAT0019020 |
| 185 | hsa-miR-7107-5p | MIMAT0028111 |
| 186 | hsa-miR-23a-3p | MIMAT0000078 |
| 187 | hsa-miR-4667-5p | MIMAT0019743 |
| 188 | hsa-miR-451a | MIMAT0001631 |
| 189 | hsa-miR-3940-5p | MIMAT0019229 |
| 190 | hsa-miR-8059 | MIMAT0030986 |
| 191 | hsa-miR-6813-5p | MIMAT0027526 |
| 192 | hsa-miR-4492 | MIMAT0019027 |
| 193 | hsa-miR-4476 | MIMAT0019003 |
| 194 | hsa-miR-6090 | MIMAT0023715 |
| 195 | hsa-mir-6726 | MI0022571 |
| 196 | hsa-mir-4257 | MI0015856 |
| 197 | hsa-mir-6787 | MI0022632 |
| 198 | hsa-mir-6780b | MI0022681 |
| 199 | hsa-mir-3131 | MI0014151 |
| 200 | hsa-mir-7108 | MI0022959 |
| 201 | hsa-mir-1343 | MI0017320 |
| 202 | hsa-mir-1247 | MI0006382 |
| 203 | hsa-mir-4651 | MI0017279 |
| 204 | hsa-mir-6757 | MI0022602 |
| 205 | hsa-mir-3679 | MI0016080 |
| 206 | hsa-mir-7641-1 | MI0024975 |
| 207 | hsa-mir-7641-2 | MI0024976 |
| 208 | hsa-mir-6746 | MI0022591 |
| 209 | hsa-mir-8072 | MI0025908 |
| 210 | hsa-mir-6741 | MI0022586 |
| 211 | hsa-mir-1908 | MI0008329 |
| 212 | hsa-mir-6857 | MI0022703 |
| 213 | hsa-mir-4746 | MI0017385 |
| 214 | hsa-mir-744 | MI0005559 |
| 215 | hsa-mir-4792 | MI0017439 |
| 216 | hsa-mir-564 | MI0003570 |
| 217 | hsa-mir-6791 | MI0022636 |
| 218 | hsa-mir-6825 | MI0022670 |
| 219 | hsa-mir-6826 | MI0022671 |
| 220 | hsa-mir-4665 | MI0017295 |
| 221 | hsa-mir-4467 | MI0016818 |
| 222 | hsa-mir-3188 | MI0014232 |
| 223 | hsa-mir-6125 | MI0021259 |
| 224 | hsa-mir-6756 | MI0022601 |
| 225 | hsa-mir-1228 | MI0006318 |
| 226 | hsa-mir-8063 | MI0025899 |
| 227 | hsa-mir-8069 | MI0025905 |
| 228 | hsa-mir-6875 | MI0022722 |
| 229 | hsa-mir-3185 | MI0014227 |
| 230 | hsa-mir-4433b | MI0025511 |
| 231 | hsa-mir-6887 | MI0022734 |
| 232 | hsa-mir-128-1 | MI0000447 |
| 233 | hsa-mir-6724 | MI0022559 |
| 234 | hsa-mir-1914 | MI0008335 |
| 235 | hsa-mir-1225 | MI0006311 |
| 236 | hsa-mir-4419b | MI0016861 |
| 237 | hsa-mir-7110 | MI0022961 |
| 238 | hsa-mir-187 | MI0000274 |
| 239 | hsa-mir-3184 | MI0014226 |
| 240 | hsa-mir-204 | MI0000284 |
| 241 | hsa-mir-5572 | MI0019117 |
| 242 | hsa-mir-6729 | MI0022574 |
| 243 | hsa-mir-615 | MI0003628 |
| 244 | hsa-mir-6749 | MI0022594 |
| 245 | hsa-mir-6515 | MI0022227 |
| 246 | hsa-mir-3937 | MI0016593 |
| 247 | hsa-mir-6840 | MI0022686 |
| 248 | hsa-mir-6893 | MI0022740 |
| 249 | hsa-mir-4728 | MI0017365 |
| 250 | hsa-mir-6717 | MI0022551 |
| 251 | hsa-mir-7113 | MI0022964 |
| 252 | hsa-mir-642b | MI0016685 |
| 253 | hsa-mir-7109 | MI0022960 |
| 254 | hsa-mir-6842 | MI0022688 |
| 255 | hsa-mir-4442 | MI0016785 |
| 256 | hsa-mir-4433 | MI0016773 |
| 257 | hsa-mir-4707 | MI0017340 |
| 258 | hsa-mir-6126 | MI0021260 |
| 259 | hsa-mir-4449 | MI0016792 |
| 260 | hsa-mir-4706 | MI0017339 |
| 261 | hsa-mir-1913 | MI0008334 |
| 262 | hsa-mir-602 | MI0003615 |
| 263 | hsa-mir-939 | MI0005761 |
| 264 | hsa-mir-4695 | MI0017328 |
| 265 | hsa-mir-711 | MI0012488 |
| 266 | hsa-mir-6816 | MI0022661 |
| 267 | hsa-mir-4632 | MI0017259 |
| 268 | hsa-mir-6721 | MI0022556 |
| 269 | hsa-mir-7847 | MI0025517 |
| 270 | hsa-mir-6132 | MI0021277 |
| 271 | hsa-mir-887 | MI0005562 |
| 272 | hsa-mir-6784 | MI0022629 |
| 273 | hsa-mir-1249 | MI0006384 |
| 274 | hsa-mir-937 | MI0005759 |
| 275 | hsa-mir-5195 | MI0018174 |
| 276 | hsa-mir-6732 | MI0022577 |
| 277 | hsa-mir-4417 | MI0016753 |
| 278 | hsa-mir-4281 | MI0015885 |
| 279 | hsa-mir-4734 | MI0017371 |
| 280 | hsa-mir-6766 | MI0022611 |
| 281 | hsa-mir-663a | MI0003672 |
| 282 | hsa-mir-4513 | MI0016879 |
| 283 | hsa-mir-6781 | MI0022626 |
| 284 | hsa-mir-1227 | MI0006316 |
| 285 | hsa-mir-6845 | MI0022691 |
| 286 | hsa-mir-6798 | MI0022643 |
| 287 | hsa-mir-3620 | MI0016011 |
| 288 | hsa-mir-1915 | MI0008336 |
| 289 | hsa-mir-4294 | MI0015827 |
| 290 | hsa-mir-642a | MI0003657 |
| 291 | hsa-mir-371a | MI0000779 |
| 292 | hsa-mir-940 | MI0005762 |
| 293 | hsa-mir-4450 | MI0016795 |
| 294 | hsa-mir-4723 | MI0017359 |
| 295 | hsa-mir-1469 | MI0007074 |
| 296 | hsa-mir-6861 | MI0022708 |
| 297 | hsa-mir-7975 | MI0025751 |
| 298 | hsa-mir-6879 | MI0022726 |
| 299 | hsa-mir-6802 | MI0022647 |
| 300 | hsa-mir-1268b | MI0016748 |
| 301 | hsa-mir-663b | MI0006336 |
| 302 | hsa-mir-125a | MI0000469 |
| 303 | hsa-mir-2861 | MI0013006 |
| 304 | hsa-mir-6088 | MI0020365 |
| 305 | hsa-mir-4758 | MI0017399 |
| 306 | hsa-mir-296 | MI0000747 |
| 307 | hsa-mir-6738 | MI0022583 |
| 308 | hsa-mir-671 | MI0003760 |
| 309 | hsa-mir-4454 | MI0016800 |
| 310 | hsa-mir-4516 | MI0016882 |
| 311 | hsa-mir-7845 | MI0025515 |
| 312 | hsa-mir-4741 | MI0017379 |
| 313 | hsa-mir-92b | MI0003560 |
| 314 | hsa-mir-6795 | MI0022640 |
| 315 | hsa-mir-6805 | MI0022650 |
| 316 | hsa-mir-4725 | MI0017362 |
| 317 | hsa-mir-6782 | MI0022627 |

TABLE 1-continued

| SEQ ID NO: | Gene name | miRBase registration No. |
|---|---|---|
| 318 | hsa-mir-4688 | MI0017321 |
| 319 | hsa-mir-6850 | MI0022696 |
| 320 | hsa-mir-6777 | MI0022622 |
| 321 | hsa-mir-6785 | MI0022630 |
| 322 | hsa-mir-7106 | MI0022957 |
| 323 | hsa-mir-3663 | MI0016064 |
| 324 | hsa-mir-6131 | MI0021276 |
| 325 | hsa-mir-4532 | MI0016899 |
| 326 | hsa-mir-6820 | MI0022665 |
| 327 | hsa-mir-4689 | MI0017322 |
| 328 | hsa-mir-4638 | MI0017265 |
| 329 | hsa-mir-3656 | MI0016056 |
| 330 | hsa-mir-3621 | MI0016012 |
| 331 | hsa-mir-6769b | MI0022706 |
| 332 | hsa-mir-149 | MI0000478 |
| 333 | hsa-mir-23b | MI0000439 |
| 334 | hsa-mir-3135b | MI0016809 |
| 335 | hsa-mir-6848 | MI0022694 |
| 336 | hsa-mir-6769a | MI0022614 |
| 337 | hsa-mir-4327 | MI0015867 |
| 338 | hsa-mir-6765 | MI0022610 |
| 339 | hsa-mir-6716 | MI0022550 |
| 340 | hsa-mir-6877 | MI0022724 |
| 341 | hsa-mir-6727 | MI0022572 |
| 342 | hsa-mir-4534 | MI0016901 |
| 343 | hsa-mir-614 | MI0003627 |
| 344 | hsa-mir-1202 | MI0006334 |
| 345 | hsa-mir-575 | MI0003582 |
| 346 | hsa-mir-6870 | MI0022717 |
| 347 | hsa-mir-6722 | MI0022557 |
| 348 | hsa-mir-7977 | MI0025753 |
| 349 | hsa-mir-4649 | MI0017276 |
| 350 | hsa-mir-4675 | MI0017306 |
| 351 | hsa-mir-6075 | MI0020352 |
| 352 | hsa-mir-6779 | MI0022624 |
| 353 | hsa-mir-4271 | MI0015879 |
| 354 | hsa-mir-3196 | MI0014241 |
| 355 | hsa-mir-6803 | MI0022648 |
| 356 | hsa-mir-6789 | MI0022634 |
| 357 | hsa-mir-4648 | MI0017275 |
| 358 | hsa-mir-4508 | MI0016872 |
| 359 | hsa-mir-4749 | MI0017388 |
| 360 | hsa-mir-4505 | MI0016868 |
| 361 | hsa-mir-5698 | MI0019305 |
| 362 | hsa-mir-1199 | MI0020340 |
| 363 | hsa-mir-4763 | MI0017404 |
| 364 | hsa-mir-1231 | MI0006321 |
| 365 | hsa-mir-1233-1 | MI0006323 |
| 366 | hsa-mir-1233-2 | MI0015973 |
| 367 | hsa-mir-150 | MI0000479 |
| 368 | hsa-mir-92a-2 | MI0000094 |
| 369 | hsa-mir-423 | MI0001445 |
| 370 | hsa-mir-1268a | MI0006405 |
| 371 | hsa-mir-128-2 | MI0000727 |
| 372 | hsa-mir-24-1 | MI0000080 |
| 373 | hsa-mir-24-2 | MI0000081 |
| 374 | hsa-mir-4697 | MI0017330 |
| 375 | hsa-mir-3197 | MI0014245 |
| 376 | hsa-mir-675 | MI0005416 |
| 377 | hsa-mir-4486 | MI0016847 |
| 378 | hsa-mir-7107 | MI0022958 |
| 379 | hsa-mir-23a | MI0000079 |
| 380 | hsa-mir-4667 | MI0017297 |
| 381 | hsa-mir-451a | MI0001729 |
| 382 | hsa-mir-3940 | MI0016597 |
| 383 | hsa-mir-8059 | MI0025895 |
| 384 | hsa-mir-6813 | MI0022658 |
| 385 | hsa-mir-4492 | MI0016854 |
| 386 | hsa-mir-4476 | MI0016828 |
| 387 | hsa-mir-6090 | MI0020367 |
| 388 | isomiR example 1 of SEQ ID NO: 5 | — |
| 389 | isomiR example 2 of SEQ ID NO: 5 | — |
| 390 | isomiR example 1 of SEQ ID NO: 7 | — |
| 391 | isomiR example 2 of SEQ ID NO: 7 | — |
| 392 | isomiR example 1 of SEQ ID NO: 8 | — |
| 393 | isomiR example 2 of SEQ ID NO: 8 | — |
| 394 | isomiR example 1 of SEQ ID NO: 9 | — |
| 395 | isomiR example 2 of SEQ ID NO: 9 | — |
| 396 | isomiR example 1 of SEQ ID NO: 11 | — |
| 397 | isomiR example 2 of SEQ ID NO: 11 | — |
| 398 | isomiR example 1 of SEQ ID NO: 16 | — |
| 399 | isomiR example 2 of SEQ ID NO: 16 | — |
| 400 | isomiR example 1 of SEQ ID NO: 19 | — |
| 401 | isomiR example 2 of SEQ ID NO: 19 | — |
| 402 | isomiR example 1 of SEQ ID NO: 20 | — |
| 403 | isomiR example 2 of SEQ ID NO: 20 | — |
| 404 | isomiR example 1 of SEQ ID NO: 21 | — |
| 405 | isomiR example 2 of SEQ ID NO: 21 | — |
| 406 | isomiR example 1 of SEQ ID NO: 26 | — |
| 407 | isomiR example 2 of SEQ ID NO: 26 | — |
| 408 | isomiR example 1 of SEQ ID NO: 27 | — |
| 409 | isomiR example 2 of SEQ ID NO: 27 | — |
| 410 | isomiR example 1 of SEQ ID NO: 28 | — |
| 411 | isomiR example 2 of SEQ ID NO: 28 | — |
| 412 | isomiR example 1 of SEQ ID NO: 30 | — |
| 413 | isomiR example 2 of SEQ ID NO: 30 | — |
| 414 | isomiR example 1 of SEQ ID NO: 34 | — |
| 415 | isomiR example 2 of SEQ ID NO: 34 | — |
| 416 | isomiR example 1 of SEQ ID NO: 37 | — |
| 417 | isomiR example 2 of SEQ ID NO: 37 | — |
| 418 | isomiR example 1 of SEQ ID NO: 38 | — |
| 419 | isomiR example 2 of SEQ ID NO: 38 | — |
| 420 | isomiR example 1 of SEQ ID NO: 39 | — |
| 421 | isomiR example 2 of SEQ ID NO: 39 | — |
| 422 | isomiR example 1 of SEQ ID NO: 41 | — |
| 423 | isomiR example 2 of SEQ ID NO: 41 | — |
| 424 | isomiR example 1 of SEQ ID NO: 43 | — |
| 425 | isomiR example 2 of SEQ ID NO: 43 | — |
| 426 | isomiR example 1 of SEQ ID NO: 45 | — |
| 427 | isomiR example 2 of SEQ ID NO: 45 | — |
| 428 | isomiR example 1 of SEQ ID NO: 46 | — |
| 429 | isomiR example 2 of SEQ ID NO: 46 | — |
| 430 | isomiR example 1 of SEQ ID NO: 48 | — |
| 431 | isomiR example 2 of SEQ ID NO: 48 | — |
| 432 | isomiR example 1 of SEQ ID NO: 50 | — |
| 433 | isomiR example 2 of SEQ ID NO: 50 | — |
| 434 | isomiR example 1 of SEQ ID NO: 54 | — |
| 435 | isomiR example 2 of SEQ ID NO: 54 | — |
| 436 | isomiR example 1 of SEQ ID NO: 55 | — |
| 437 | isomiR example 2 of SEQ ID NO: 55 | — |
| 438 | isomiR example 1 of SEQ ID NO: 57 | — |
| 439 | isomiR example 2 of SEQ ID NO: 57 | — |
| 440 | isomiR example 1 of SEQ ID NO: 58 | — |
| 441 | isomiR example 2 of SEQ ID NO: 58 | — |
| 442 | isomiR example 1 of SEQ ID NO: 61 | — |
| 443 | isomiR example 2 of SEQ ID NO: 61 | — |
| 444 | isomiR example 1 of SEQ ID NO: 62 | — |
| 445 | isomiR example 2 of SEQ ID NO: 62 | — |
| 446 | isomiR example 1 of SEQ ID NO: 63 | — |
| 447 | isomiR example 2 of SEQ ID NO: 63 | — |
| 448 | isomiR example 1 of SEQ ID NO: 64 | — |
| 449 | isomiR example 2 of SEQ ID NO: 64 | — |
| 450 | isomiR example 1 of SEQ ID NO: 65 | — |
| 451 | isomiR example 2 of SEQ ID NO: 65 | — |
| 452 | isomiR example 1 of SEQ ID NO: 66 | — |
| 453 | isomiR example 2 of SEQ ID NO: 66 | — |
| 454 | isomiR example 1 of SEQ ID NO: 67 | — |
| 455 | isomiR example 2 of SEQ ID NO: 67 | — |
| 456 | isomiR example 1 of SEQ ID NO: 69 | — |
| 457 | isomiR example 2 of SEQ ID NO: 69 | — |
| 458 | isomiR example 1 of SEQ ID NO: 70 | — |
| 459 | isomiR example 2 of SEQ ID NO: 70 | — |
| 460 | isomiR example 1 of SEQ ID NO: 71 | — |
| 461 | isomiR example 2 of SEQ ID NO: 71 | — |
| 462 | isomiR example 1 of SEQ ID NO: 73 | — |
| 463 | isomiR example 2 of SEQ ID NO: 73 | — |
| 464 | isomiR example 1 of SEQ ID NO: 74 | — |
| 465 | isomiR example 2 of SEQ ID NO: 74 | — |
| 466 | isomiR example 1 of SEQ ID NO: 76 | — |
| 467 | isomiR example 2 of SEQ ID NO: 76 | — |
| 468 | isomiR example 1 of SEQ ID NO: 77 | — |
| 469 | isomiR example 2 of SEQ ID NO: 77 | — |
| 470 | isomiR example 1 of SEQ ID NO: 78 | — |
| 471 | isomiR example 2 of SEQ ID NO: 78 | — |

TABLE 1-continued

| SEQ ID NO: | Gene name | miRBase registration No. |
|---|---|---|
| 472 | isomiR example 1 of SEQ ID NO: 80 | — |
| 473 | isomiR example 2 of SEQ ID NO: 80 | — |
| 474 | isomiR example 1 of SEQ ID NO: 81 | — |
| 475 | isomiR example 2 of SEQ ID NO: 81 | — |
| 476 | isomiR example 1 of SEQ ID NO: 82 | — |
| 477 | isomiR example 2 of SEQ ID NO: 82 | — |
| 478 | isomiR example 1 of SEQ ID NO: 84 | — |
| 479 | isomiR example 2 of SEQ ID NO: 84 | — |
| 480 | isomiR example 1 of SEQ ID NO: 85 | — |
| 481 | isomiR example 2 of SEQ ID NO: 85 | — |
| 482 | isomiR example 1 of SEQ ID NO: 86 | — |
| 483 | isomiR example 2 of SEQ ID NO: 86 | — |
| 484 | isomiR example 1 of SEQ ID NO: 88 | — |
| 485 | isomiR example 2 of SEQ ID NO: 88 | — |
| 486 | isomiR example 1 of SEQ ID NO: 89 | — |
| 487 | isomiR example 2 of SEQ ID NO: 89 | — |
| 488 | isomiR example 1 of SEQ ID NO: 94 | — |
| 489 | isomiR example 2 of SEQ ID NO: 94 | — |
| 490 | isomiR example 1 of SEQ ID NO: 95 | — |
| 491 | isomiR example 2 of SEQ ID NO: 95 | — |
| 492 | isomiR example 1 of SEQ ID NO: 97 | — |
| 493 | isomiR example 2 of SEQ ID NO: 97 | — |
| 494 | isomiR example 1 of SEQ ID NO: 98 | — |
| 495 | isomiR example 2 of SEQ ID NO: 98 | — |
| 496 | isomiR example 1 of SEQ ID NO: 99 | — |
| 497 | isomiR example 2 of SEQ ID NO: 99 | — |
| 498 | isomiR example 1 of SEQ ID NO: 100 | — |
| 499 | isomiR example 2 of SEQ ID NO: 100 | — |
| 500 | isomiR example 1 of SEQ ID NO: 101 | — |
| 501 | isomiR example 2 of SEQ ID NO: 101 | — |
| 502 | isomiR example 1 of SEQ ID NO: 104 | — |
| 503 | isomiR example 2 of SEQ ID NO: 104 | — |
| 504 | isomiR example 1 of SEQ ID NO: 107 | — |
| 505 | isomiR example 2 of SEQ ID NO: 107 | — |
| 506 | isomiR example 1 of SEQ ID NO: 108 | — |
| 507 | isomiR example 2 of SEQ ID NO: 108 | — |
| 508 | isomiR example 1 of SEQ ID NO: 109 | — |
| 509 | isomiR example 2 of SEQ ID NO: 109 | — |
| 510 | isomiR example 1 of SEQ ID NO: 110 | — |
| 511 | isomiR example 2 of SEQ ID NO: 110 | — |
| 512 | isomiR example 1 of SEQ ID NO: 111 | — |
| 513 | isomiR example 2 of SEQ ID NO: 111 | — |
| 514 | isomiR example 1 of SEQ ID NO: 112 | — |
| 515 | isomiR example 2 of SEQ ID NO: 112 | — |
| 516 | isomiR example 1 of SEQ ID NO: 113 | — |
| 517 | isomiR example 2 of SEQ ID NO: 113 | — |
| 518 | isomiR example 1 of SEQ ID NO: 115 | — |
| 519 | isomiR example 2 of SEQ ID NO: 115 | — |
| 520 | isomiR example 1 of SEQ ID NO: 116 | — |
| 521 | isomiR example 2 of SEQ ID NO: 116 | — |
| 522 | isomiR example 1 of SEQ ID NO: 117 | — |
| 523 | isomiR example 2 of SEQ ID NO: 117 | — |
| 524 | isomiR example 1 of SEQ ID NO: 119 | — |
| 525 | isomiR example 2 of SEQ ID NO: 119 | — |
| 526 | isomiR example 1 of SEQ ID NO: 120 | — |
| 527 | isomiR example 2 of SEQ ID NO: 120 | — |
| 528 | isomiR example 1 of SEQ ID NO: 123 | — |
| 529 | isomiR example 2 of SEQ ID NO: 123 | — |
| 530 | isomiR example 1 of SEQ ID NO: 125 | — |
| 531 | isomiR example 2 of SEQ ID NO: 125 | — |
| 532 | isomiR example 1 of SEQ ID NO: 131 | — |
| 533 | isomiR example 2 of SEQ ID NO: 131 | — |
| 534 | isomiR example 1 of SEQ ID NO: 132 | — |
| 535 | isomiR example 2 of SEQ ID NO: 132 | — |
| 536 | isomiR example 1 of SEQ ID NO: 133 | — |
| 537 | isomiR example 2 of SEQ ID NO: 133 | — |
| 538 | isomiR example 1 of SEQ ID NO: 135 | — |
| 539 | isomiR example 2 of SEQ ID NO: 135 | — |
| 540 | isomiR example 1 of SEQ ID NO: 136 | — |
| 541 | isomiR example 2 of SEQ ID NO: 136 | — |
| 542 | isomiR example 1 of SEQ ID NO: 137 | — |
| 543 | isomiR example 2 of SEQ ID NO: 137 | — |
| 544 | isomiR example 1 of SEQ ID NO: 140 | — |
| 545 | isomiR example 2 of SEQ ID NO: 140 | — |
| 546 | isomiR example 1 of SEQ ID NO: 141 | — |
| 547 | isomiR example 2 of SEQ ID NO: 141 | — |
| 548 | isomiR example 1 of SEQ ID NO: 142 | — |
| 549 | isomiR example 2 of SEQ ID NO: 142 | — |
| 550 | isomiR example 1 of SEQ ID NO: 147 | — |
| 551 | isomiR example 2 of SEQ ID NO: 147 | — |
| 552 | isomiR example 1 of SEQ ID NO: 151 | — |
| 553 | isomiR example 2 of SEQ ID NO: 151 | — |
| 554 | isomiR example 1 of SEQ ID NO: 152 | — |
| 555 | isomiR example 2 of SEQ ID NO: 152 | — |
| 556 | isomiR example 1 of SEQ ID NO: 157 | — |
| 557 | isomiR example 2 of SEQ ID NO: 157 | — |
| 558 | isomiR example 1 of SEQ ID NO: 161 | — |
| 559 | isomiR example 2 of SEQ ID NO: 161 | — |
| 560 | isomiR example 1 of SEQ ID NO: 162 | — |
| 561 | isomiR example 2 of SEQ ID NO: 162 | — |
| 562 | isomiR example 1 of SEQ ID NO: 165 | — |
| 563 | isomiR example 2 of SEQ ID NO: 165 | — |
| 564 | isomiR example 1 of SEQ ID NO: 166 | — |
| 565 | isomiR example 2 of SEQ ID NO: 166 | — |
| 566 | isomiR example 1 of SEQ ID NO: 167 | — |
| 567 | isomiR example 2 of SEQ ID NO: 167 | — |
| 568 | isomiR example 1 of SEQ ID NO: 168 | — |
| 569 | isomiR example 2 of SEQ ID NO: 168 | — |
| 570 | isomiR example 1 of SEQ ID NO: 169 | — |
| 571 | isomiR example 2 of SEQ ID NO: 169 | — |
| 572 | isomiR example 1 of SEQ ID NO: 171 | — |
| 573 | isomiR example 2 of SEQ ID NO: 171 | — |
| 574 | isomiR example 1 of SEQ ID NO: 173 | — |
| 575 | isomiR example 2 of SEQ ID NO: 173 | — |
| 576 | isomiR example 1 of SEQ ID NO: 174 | — |
| 577 | isomiR example 2 of SEQ ID NO: 174 | — |
| 578 | isomiR example 1 of SEQ ID NO: 176 | — |
| 579 | isomiR example 2 of SEQ ID NO: 176 | — |
| 580 | isomiR example 1 of SEQ ID NO: 177 | — |
| 581 | isomiR example 2 of SEQ ID NO: 177 | — |
| 582 | isomiR example 1 of SEQ ID NO: 178 | — |
| 583 | isomiR example 2 of SEQ ID NO: 178 | — |
| 584 | isomiR example 1 of SEQ ID NO: 179 | — |
| 585 | isomiR example 2 of SEQ ID NO: 179 | — |
| 586 | isomiR example 1 of SEQ ID NO: 180 | — |
| 587 | isomiR example 2 of SEQ ID NO: 180 | — |
| 588 | isomiR example 1 of SEQ ID NO: 182 | — |
| 589 | isomiR example 2 of SEQ ID NO: 182 | — |
| 590 | isomiR example 1 of SEQ ID NO: 183 | — |
| 591 | isomiR example 2 of SEQ ID NO: 183 | — |
| 592 | isomiR example 1 of SEQ ID NO: 184 | — |
| 593 | isomiR example 2 of SEQ ID NO: 184 | — |
| 594 | isomiR example 1 of SEQ ID NO: 186 | — |
| 595 | isomiR example 2 of SEQ ID NO: 186 | — |
| 596 | isomiR example 1 of SEQ ID NO: 187 | — |
| 597 | isomiR example 2 of SEQ ID NO: 187 | — |
| 598 | isomiR example 1 of SEQ ID NO: 188 | — |
| 599 | isomiR example 2 of SEQ ID NO: 188 | — |
| 600 | isomiR example 1 of SEQ ID NO: 189 | — |
| 601 | isomiR example 2 of SEQ ID NO: 189 | — |
| 602 | isomiR example 1 of SEQ ID NO: 192 | — |
| 603 | isomiR example 2 of SEQ ID NO: 192 | — |
| 604 | isomiR example 1 of SEQ ID NO: 193 | — |
| 605 | isomiR example 2 of SEQ ID NO: 193 | — |
| 606 | hsa-miR-6836-3p | MIMAT0027575 |
| 607 | hsa-miR-3195 | MIMAT0015079 |
| 608 | hsa-miR-718 | MIMAT0012735 |
| 609 | hsa-miR-3178 | MIMAT0015055 |
| 610 | hsa-miR-638 | MIMAT0003308 |
| 611 | hsa-miR-4497 | MIMAT0019032 |
| 612 | hsa-miR-6085 | MIMAT0023710 |
| 613 | hsa-miR-6752-5p | MIMAT0027404 |
| 614 | hsa-miR-135a-3p | MIMAT0004595 |
| 615 | hsa-mir-6836 | MI0022682 |
| 616 | hsa-mir-3195 | MI0014240 |
| 617 | hsa-mir-718 | MI0012489 |
| 618 | hsa-mir-3178 | MI0014212 |
| 619 | hsa-mir-638 | MI0003653 |
| 620 | hsa-mir-4497 | MI0016859 |
| 621 | hsa-mir-6085 | MI0020362 |
| 622 | hsa-mir-6752 | MI0022597 |
| 623 | hsa-mir-135a | MI0000452 |
| 624 | isomiR example 1 of SEQ ID NO: 607 | — |
| 625 | isomiR example 2 of SEQ ID NO: 607 | — |

TABLE 1-continued

| SEQ ID NO: | Gene name | miRBase registration No. |
|---|---|---|
| 626 | isomiR example 1 of SEQ ID NO: 608 | — |
| 627 | isomiR example 2 of SEQ ID NO: 608 | — |
| 628 | isomiR example 1 of SEQ ID NO: 609 | — |
| 629 | isomiR example 2 of SEQ ID NO: 609 | — |
| 630 | isomiR example 1 of SEQ ID NO: 610 | — |
| 631 | isomiR example 2 of SEQ ID NO: 610 | — |
| 632 | isomiR example 1 of SEQ ID NO: 611 | — |
| 633 | isomiR example 2 of SEQ ID NO: 611 | — |
| 634 | isomiR example 1 of SEQ ID NO: 614 | — |
| 635 | isomiR example 2 of SEQ ID NO: 614 | — |

The present specification encompasses the contents described in the specifications and/or drawings of Japanese Patent Application No. 2014-122686 and Japanese Patent Application No. 2015-070182 on which the priority of the present application is based.

Advantageous Effects of Invention

According to the present invention, colorectal cancer can be detected easily and highly accurately.

For example, the presence or absence of colorectal cancer in a patient can be easily detected by using, as an index, the expression level measurement values of several miRNAs in blood, serum, and/or plasma of the patient, which can be collected with limited invasiveness.

BRIEF DESCRIPTION OF DRAWINGS

FIG. 1 This figure shows the relationship between the nucleotide sequences of hsa-miR-3679-5p represented by SEQ ID NO: 11 and hsa-miR-3679-3p represented by SEQ ID NO: 78, which are produced from a precursor hsa-mir-3679 represented by SEQ ID NO: 205.

DESCRIPTION OF EMBODIMENTS

Figure 2:
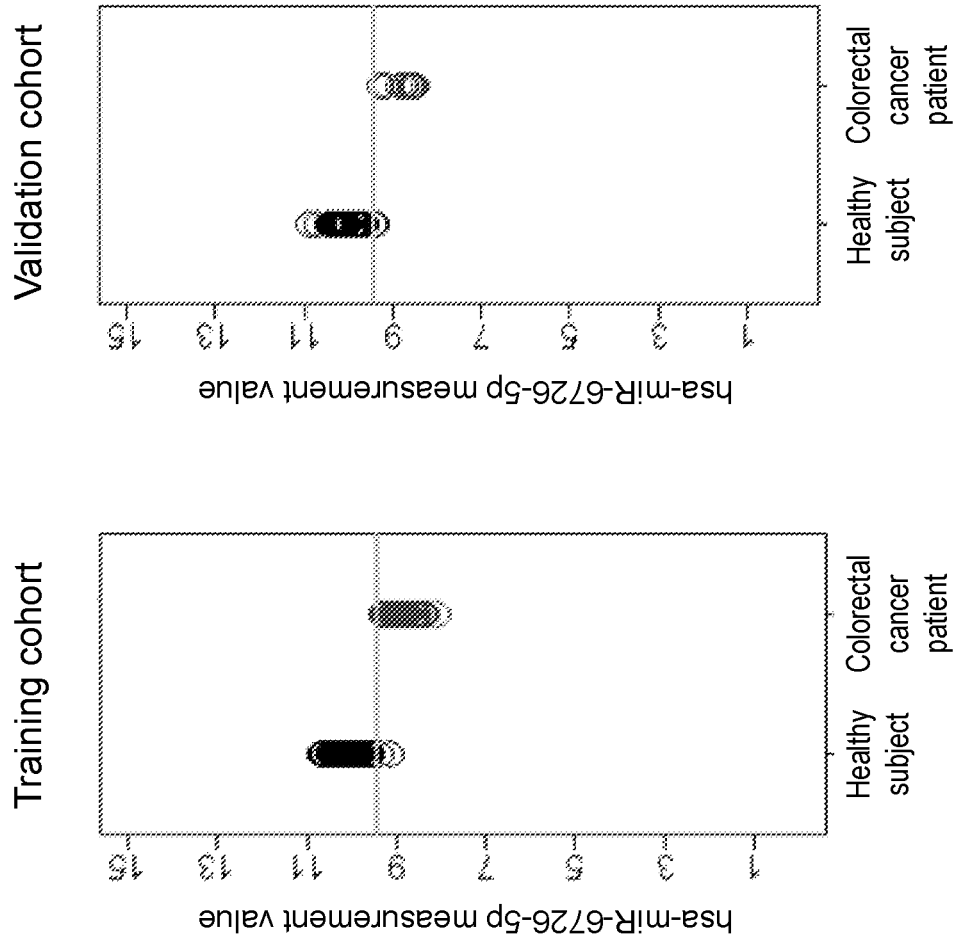
FIG. 2 Left diagram: the expression level measurement values of hsa-miR-6726-5p (SEQ ID NO: 1) in healthy subjects (100 persons) and colorectal cancer patients (34 persons) selected as a training cohort were each plotted on the ordinate. The horizontal line in the diagram depicts a threshold (9.43) that was optimized by Fisher's discriminant analysis and discriminated between the two groups. Right diagram: the expression level measurement values of hsa-miR-6726-5p (SEQ ID NO: 1) in healthy subjects (50 persons) and colorectal cancer patients (16 persons) selected as validation cohort were each plotted on the ordinate. The horizontal line in the diagram depicts the threshold (9.43) that was set for the training cohort and discriminated between the two groups.

Hereinafter, the present invention will be described further specifically.

1. Target Nucleic Acid for Colorectal Cancer

A primary target nucleic acid as a colorectal cancer marker for detecting the presence and/or absence of colorectal cancer or colorectal cancer cells using the nucleic acid probe or the primer for the detection of colorectal cancer defined above according to the present invention can use at least one or more miRNA(s) selected from the group consisting of hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR- 4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p. Furthermore, at least one or more miRNA(s) selected from the group consisting of other colorectal cancer markers that can be combined with these miRNAs, i.e., hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p and hsa-miR-24-3p can also be preferably used as a target nucleic acid. Moreover, at least one or more miRNA(s) selected from the group consisting of other colorectal cancer markers that can be combined with these miRNAs, i.e., hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-45a, hsa-miR-3940-5p, hsa-miR-8059, hsa-miR-6813-5p, hsa-miR-4492, hsa-miR-4476 and hsa-miR-6090 can also be preferably used as a target nucleic acid.

These miRNAs include, for example, a human gene comprising a nucleotide sequence represented by any of SEQ ID NOs: 1 to 194 and 606 to 614 (i.e., hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4'763-3p, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p, hsa-miR-24-3p, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476, hsa-miR-6090, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 635 or a transcript thereof, more preferably the transcript, i.e., a miRNA or its precursor RNA (pri-miRNA or pre-miRNA).

The first target gene is the hsa-miR-6726-5p gene, a congener thereof, a transcript thereof, or a variant or a derivative thereof. None of the previously known reports show that change in the expression of the gene or the transcript thereof can serve as a marker for colorectal cancer.

The second target gene is the hsa-miR-4257 gene, a congener thereof, a transcript thereof, or a variant or a derivative thereof. None of the previously known reports show that change in the expression of the gene or the transcript thereof can serve as a marker for colorectal cancer.

The third target gene is the hsa-miR-6787-5p gene, a congener thereof, a transcript thereof, or a variant or a derivative thereof. None of the previously known reports show that change in the expression of the gene or the transcript thereof can serve as a marker for colorectal cancer.

The fourth target gene is the hsa-miR-6780b-5p gene, a congener thereof, a transcript thereof, or a variant or a derivative thereof. None of the previously known reports show that change in the expression of the gene or the transcript thereof can serve as a marker for colorectal cancer.

The fifth target gene is the hsa-miR-3131 gene, a congener thereof, a transcript thereof, or a variant or a derivative thereof. None of the previously known reports show that change in the expression of the gene or the transcript thereof can serve as a marker for colorectal cancer.

The sixth target gene is the hsa-miR-7108-5p gene, a congener thereof, a transcript thereof, or a variant or a derivative thereof. None of the previously known reports show that change in the expression of the gene or the transcript thereof can serve as a marker for colorectal cancer.

The seventh target gene is the hsa-miR-1343-3p gene, a congener thereof, a transcript thereof, or a variant or a derivative thereof. None of the previously known reports show that change in the expression of the gene or the transcript thereof can serve as a marker for colorectal cancer.

The eighth target gene is the hsa-miR-1247-3p gene, a congener thereof, a transcript thereof, or a variant or a derivative thereof. None of the previously known reports show that change in the expression of the gene or the transcript thereof can serve as a marker for colorectal cancer.

The ninth target gene is the hsa-miR-4651 gene, a congener thereof, a transcript thereof, or a variant or a derivative thereof. None of the previously known reports show that change in the expression of the gene or the transcript thereof can serve as a marker for colorectal cancer.

The 10th target gene is the hsa-miR-6757-5p gene, a congener thereof, a transcript thereof, or a variant or a derivative thereof. None of the previously known reports show that change in the expression of the gene or the transcript thereof can serve as a marker for colorectal cancer.

The 11th target gene is the hsa-miR-3679-5p gene, a congener thereof, a transcript thereof, or a variant or a derivative thereof. None of the previously known reports show that change in the expression of the gene or the transcript thereof can serve as a marker for colorectal cancer.

The 12th target gene is the hsa-miR-7641 gene, a congener thereof, a transcript thereof, or a variant or a derivative thereof. None of the previously known reports show that change in the expression of the gene or the transcript thereof can serve as a marker for colorectal cancer.

The 13th target gene is the hsa-miR-6746-5p gene, a congener thereof, a transcript thereof, or a variant or a derivative thereof. None of the previously known reports show that change in the expression of the gene or the transcript thereof can serve as a marker for colorectal cancer.

The 14th target gene is the hsa-miR-8072 gene, a congener thereof, a transcript thereof, or a variant or a derivative thereof. None of the previously known reports show that change in the expression of the gene or the transcript thereof can serve as a marker for colorectal cancer.

The 15th target gene is the hsa-miR-6741-5p gene, a congener thereof, a transcript thereof, or a variant or a derivative thereof. None of the previously known reports show that change in the expression of the gene or the transcript thereof can serve as a marker for colorectal cancer.

The 16th target gene is the hsa-miR-1908-5p gene, a congener thereof, a transcript thereof, or a variant or a derivative thereof. None of the previously known reports show that change in the expression of the gene or the transcript thereof can serve as a marker for colorectal cancer.

The 17th target gene is the hsa-miR-6857-5p gene, a congener thereof, a transcript thereof, or a variant or a derivative thereof. None of the previously known reports show that change in the expression of the gene or the transcript thereof can serve as a marker for colorectal cancer.

The 18th target gene is the hsa-miR-4746-3p gene, a congener thereof, a transcript thereof, or a variant or a derivative thereof. None of the previously known reports show that change in the expression of the gene or the transcript thereof can serve as a marker for colorectal cancer.

The 19th target gene is the hsa-miR-744-5p gene, a congener thereof, a transcript thereof, or a variant or a derivative thereof. None of the previously known reports show that change in the expression of the gene or the transcript thereof can serve as a marker for colorectal cancer.

The 20th target gene is the hsa-miR-4792 gene, a congener thereof, a transcript thereof, or a variant or a derivative thereof. None of the previously known reports show that change in the expression of the gene or the transcript thereof can serve as a marker for colorectal cancer.

The 21st target gene is the hsa-miR-564 gene, a congener thereof, a transcript thereof, or a variant or a derivative thereof. None of the previously known reports show that change in the expression of the gene or the transcript thereof can serve as a marker for colorectal cancer.

The 22nd target gene is the hsa-miR-6791-5p gene, a congener thereof, a transcript thereof, or a variant or a derivative thereof. None of the previously known reports show that change in the expression of the gene or the transcript thereof can serve as a marker for colorectal cancer.

The 23rd target gene is the hsa-miR-6825-5p gene, a congener thereof, a transcript thereof, or a variant or a derivative thereof. None of the previously known reports show that change in the expression of the gene or the transcript thereof can serve as a marker for colorectal cancer.

The 24th target gene is the hsa-miR-6826-5p gene, a congener thereof, a transcript thereof, or a variant or a derivative thereof. None of the previously known reports show that change in the expression of the gene or the transcript thereof can serve as a marker for colorectal cancer.

The 25th target gene is the hsa-miR-4665-3p gene, a congener thereof, a transcript thereof, or a variant or a derivative thereof. None of the previously known reports show that change in the expression of the gene or the transcript thereof can serve as a marker for colorectal cancer.

The 26th target gene is the hsa-miR-4467 gene, a congener thereof, a transcript thereof, or a variant or a derivative thereof. None of the previously known reports show that change in the expression of the gene or the transcript thereof can serve as a marker for colorectal cancer.

The 27th target gene is the hsa-miR-3188 gene, a congener thereof, a transcript thereof, or a variant or a derivative thereof. None of the previously known reports show that change in the expression of the gene or the transcript thereof can serve as a marker for colorectal cancer.

The 28th target gene is the hsa-miR-6125 gene, a congener thereof, a transcript thereof, or a variant or a derivative thereof. None of the previously known reports show that change in the expression of the gene or the transcript thereof can serve as a marker for colorectal cancer.

The 29th target gene is the hsa-miR-6756-5p gene, a congener thereof, a transcript thereof, or a variant or a derivative thereof. None of the previously known reports show that change in the expression of the gene or the transcript thereof can serve as a marker for colorectal cancer.

The 30th target gene is the hsa-miR-1228-3p gene, a congener thereof, a transcript thereof, or a variant or a derivative thereof. None of the previously known reports show that change in the expression of the gene or the transcript thereof can serve as a marker for colorectal cancer.

The 31st target gene is the hsa-miR-8063 gene, a congener thereof, a transcript thereof, or a variant or a derivative thereof. None of the previously known reports show that change in the expression of the gene or the transcript thereof can serve as a marker for colorectal cancer.

The 32nd target gene is the hsa-miR-8069 gene, a congener thereof, a transcript thereof, or a variant or a derivative thereof. None of the previously known reports show that change in the expression of the gene or the transcript thereof can serve as a marker for colorectal cancer.

The 33rd target gene is the hsa-miR-6875-5p gene, a congener thereof, a transcript thereof, or a variant or a derivative thereof. None of the previously known reports show that change in the expression of the gene or the transcript thereof can serve as a marker for colorectal cancer.

The 34th target gene is the hsa-miR-3185 gene, a congener thereof, a transcript thereof, or a variant or a derivative thereof. None of the previously known reports show that change in the expression of the gene or the transcript thereof can serve as a marker for colorectal cancer.

The 35th target gene is the hsa-miR-4433b-3p gene, a congener thereof, a transcript thereof, or a variant or a derivative thereof. None of the previously known reports show that change in the expression of the gene or the transcript thereof can serve as a marker for colorectal cancer.

The 36th target gene is the hsa-miR-6887-5p gene, a congener thereof, a transcript thereof, or a variant or a derivative thereof. None of the previously known reports show that change in the expression of the gene or the transcript thereof can serve as a marker for colorectal cancer.

The 37th target gene is the hsa-miR-128-1-5p gene, a congener thereof, a transcript thereof, or a variant or a derivative thereof. None of the previously known reports show that change in the expression of the gene or the transcript thereof can serve as a marker for colorectal cancer.

The 38th target gene is the hsa-miR-6724-5p gene, a congener thereof, a transcript thereof, or a variant or a derivative thereof. None of the previously known reports show that change in the expression of the gene or the transcript thereof can serve as a marker for colorectal cancer.

The 39th target gene is the hsa-miR-1914-3p gene, a congener thereof, a transcript thereof, or a variant or a derivative thereof. None of the previously known reports show that change in the expression of the gene or the transcript thereof can serve as a marker for colorectal cancer.

The 40th target gene is the hsa-miR-1225-5p gene, a congener thereof, a transcript thereof, or a variant or a derivative thereof. None of the previously known reports show that change in the expression of the gene or the transcript thereof can serve as a marker for colorectal cancer.

The 41st target gene is the hsa-miR-4419b gene, a congener thereof, a transcript thereof, or a variant or a derivative thereof. None of the previously known reports show that change in the expression of the gene or the transcript thereof can serve as a marker for colorectal cancer.

The 42nd target gene is the hsa-miR-7110-5p gene, a congener thereof, a transcript thereof, or a variant or a derivative thereof. None of the previously known reports show that change in the expression of the gene or the transcript thereof can serve as a marker for colorectal cancer.

The 43rd target gene is the hsa-miR-187-5p gene, a congener thereof, a transcript thereof, or a variant or a derivative thereof. None of the previously known reports show that change in the expression of the gene or the transcript thereof can serve as a marker for colorectal cancer.

The 44th target gene is the hsa-miR-3184-5p gene, a congener thereof, a transcript thereof, or a variant or a derivative thereof. None of the previously known reports show that change in the expression of the gene or the transcript thereof can serve as a marker for colorectal cancer.

The 45th target gene is the hsa-miR-204-3p gene, a congener thereof, a transcript thereof, or a variant or a derivative thereof. None of the previously known reports show that change in the expression of the gene or the transcript thereof can serve as a marker for colorectal cancer.

The 46th target gene is the hsa-miR-5572 gene, a congener thereof, a transcript thereof, or a variant or a derivative thereof. None of the previously known reports show that change in the expression of the gene or the transcript thereof can serve as a marker for colorectal cancer.

The 47th target gene is the hsa-miR-6729-5p gene, a congener thereof, a transcript thereof, or a variant or a derivative thereof. None of the previously known reports show that change in the expression of the gene or the transcript thereof can serve as a marker for colorectal cancer.

The 48th target gene is the hsa-miR-615-5p gene, a congener thereof, a transcript thereof, or a variant or a derivative thereof. None of the previously known reports show that change in the expression of the gene or the transcript thereof can serve as a marker for colorectal cancer.

The 49th target gene is the hsa-miR-6749-5p gene, a congener thereof, a transcript thereof, or a variant or a derivative thereof. None of the previously known reports show that change in the expression of the gene or the transcript thereof can serve as a marker for colorectal cancer.

The 50th target gene is the hsa-miR-6515-3p gene, a congener thereof, a transcript thereof, or a variant or a derivative thereof. None of the previously known reports show that change in the expression of the gene or the transcript thereof can serve as a marker for colorectal cancer.

The 51st target gene is the hsa-miR-3937 gene, a congener thereof, a transcript thereof, or a variant or a derivative thereof. None of the previously known reports show that change in the expression of the gene or the transcript thereof can serve as a marker for colorectal cancer.

The 52nd target gene is the hsa-miR-6840-3p gene, a congener thereof, a transcript thereof, or a variant or a derivative thereof. None of the previously known reports show that change in the expression of the gene or the transcript thereof can serve as a marker for colorectal cancer.

The 53rd target gene is the hsa-miR-6893-5p gene, a congener thereof, a transcript thereof, or a variant or a derivative thereof. None of the previously known reports show that change in the expression of the gene or the transcript thereof can serve as a marker for colorectal cancer.

The 54th target gene is the hsa-miR-4728-5p gene, a congener thereof, a transcript thereof, or a variant or a derivative thereof. None of the previously known reports show that change in the expression of the gene or the transcript thereof can serve as a marker for colorectal cancer.

The 55th target gene is the hsa-miR-6717-5p gene, a congener thereof, a transcript thereof, or a variant or a derivative thereof. None of the previously known reports show that change in the expression of the gene or the transcript thereof can serve as a marker for colorectal cancer.

The 56th target gene is the hsa-miR-7113-3p gene, a congener thereof; a transcript thereof, or a variant or a derivative thereof. None of the previously known reports show that change in the expression of the gene or the transcript thereof can serve as a marker for colorectal cancer.

The 57th target gene is the hsa-miR-4665-5p gene, a congener thereof, a transcript thereof, or a variant or a derivative thereof. None of the previously known reports show that change in the expression of the gene or the transcript thereof can serve as a marker for colorectal cancer.

The 58th target gene is the hsa-miR-642b-3p gene, a congener thereof, a transcript thereof, or a variant or a derivative thereof. None of the previously known reports show that change in the expression of the gene or the transcript thereof can serve as a marker for colorectal cancer.

The 59th target gene is the hsa-miR-7109-5p gene, a congener thereof; a transcript thereof; or a variant or a derivative thereof. None of the previously known reports show that change in the expression of the gene or the transcript thereof can serve as a marker for colorectal cancer.

The 60th target gene is the hsa-miR-6842-5p gene, a congener thereof; a transcript thereof; or a variant or a derivative thereof. None of the previously known reports show that change in the expression of the gene or the transcript thereof can serve as a marker for colorectal cancer.

The 61st target gene is the hsa-miR-4442 gene, a congener thereof, a transcript thereof, or a variant or a derivative thereof. None of the previously known reports show that change in the expression of the gene or the transcript thereof can serve as a marker for colorectal cancer.

The 62nd target gene is the hsa-miR-4433-3p gene, a congener thereof, a transcript thereof, or a variant or a derivative thereof. None of the previously known reports show that change in the expression of the gene or the transcript thereof can serve as a marker for colorectal cancer.

The 63rd target gene is the hsa-miR-4707-5p gene, a congener thereof, a transcript thereof, or a variant or a derivative thereof. None of the previously known reports show that change in the expression of the gene or the transcript thereof can serve as a marker for colorectal cancer.

The 64th target gene is the hsa-miR-6126 gene, a congener thereof, a transcript thereof, or a variant or a derivative thereof. None of the previously known reports show that change in the expression of the gene or the transcript thereof can serve as a marker for colorectal cancer.

The 65th target gene is the hsa-miR-4449 gene, a congener thereof, a transcript thereof, or a variant or a derivative thereof. None of the previously known reports show that change in the expression of the gene or the transcript thereof can serve as a marker for colorectal cancer.

The 66th target gene is the hsa-miR-4706 gene, a congener thereof, a transcript thereof, or a variant or a derivative thereof. None of the previously known reports show that change in the expression of the gene or the transcript thereof can serve as a marker for colorectal cancer.

The 67th target gene is the hsa-miR-1913 gene, a congener thereof, a transcript thereof, or a variant or a derivative thereof. None of the previously known reports show that change in the expression of the gene or the transcript thereof can serve as a marker for colorectal cancer.

The 68th target gene is the hsa-miR-602 gene, a congener thereof, a transcript thereof, or a variant or a derivative thereof. None of the previously known reports show that change in the expression of the gene or the transcript thereof can serve as a marker for colorectal cancer.

The 69th target gene is the hsa-miR-939-5p gene, a congener thereof, a transcript thereof, or a variant or a derivative thereof. None of the previously known reports show that change in the expression of the gene or the transcript thereof can serve as a marker for colorectal cancer.

The 70th target gene is the hsa-miR-4695-5p gene, a congener thereof, a transcript thereof, or a variant or a derivative thereof. None of the previously known reports show that change in the expression of the gene or the transcript thereof can serve as a marker for colorectal cancer.

The 71st target gene is the hsa-miR-711 gene, a congener thereof, a transcript thereof, or a variant or a derivative thereof. None of the previously known reports show that change in the expression of the gene or the transcript thereof can serve as a marker for colorectal cancer.

The 72nd target gene is the hsa-miR-6816-5p gene, a congener thereof, a transcript thereof, or a variant or a derivative thereof. None of the previously known reports show that change in the expression of the gene or the transcript thereof can serve as a marker for colorectal cancer.

The 73rd target gene is the hsa-miR-4632-5p gene, a congener thereof, a transcript thereof, or a variant or a derivative thereof. None of the previously known reports show that change in the expression of the gene or the transcript thereof can serve as a marker for colorectal cancer.

The 74th target gene is the hsa-miR-6721-5p gene, a congener thereof, a transcript thereof, or a variant or a derivative thereof. None of the previously known reports show that change in the expression of the gene or the transcript thereof can serve as a marker for colorectal cancer.

The 75th target gene is the hsa-miR-7847-3p gene, a congener thereof, a transcript thereof, or a variant or a derivative thereof. None of the previously known reports show that change in the expression of the gene or the transcript thereof can serve as a marker for colorectal cancer.

The 76th target gene is the hsa-miR-6132 gene, a congener thereof, a transcript thereof, or a variant or a derivative thereof. None of the previously known reports show that change in the expression of the gene or the transcript thereof can serve as a marker for colorectal cancer.

The 77th target gene is the hsa-miR-887-3p gene, a congener thereof, a transcript thereof, or a variant or a derivative thereof. None of the previously known reports show that change in the expression of the gene or the transcript thereof can serve as a marker for colorectal cancer.

The 78th target gene is the hsa-miR-3679-3p gene, a congener thereof, a transcript thereof, or a variant or a derivative thereof. None of the previously known reports show that change in the expression of the gene or the transcript thereof can serve as a marker for colorectal cancer.

The 79th target gene is the hsa-miR-6784-5p gene, a congener thereof, a transcript thereof, or a variant or a derivative thereof. None of the previously known reports show that change in the expression of the gene or the transcript thereof can serve as a marker for colorectal cancer.

The 80th target gene is the hsa-miR-1249 gene, a congener thereof, a transcript thereof, or a variant or a derivative thereof. None of the previously known reports show that change in the expression of the gene or the transcript thereof can serve as a marker for colorectal cancer.

The 81st target gene is the hsa-miR-937-5p gene, a congener thereof, a transcript thereof, or a variant or a derivative thereof. None of the previously known reports show that change in the expression of the gene or the transcript thereof can serve as a marker for colorectal cancer.

The 82nd target gene is the hsa-miR-5195-3p gene, a congener thereof, a transcript thereof, or a variant or a derivative thereof. None of the previously known reports show that change in the expression of the gene or the transcript thereof can serve as a marker for colorectal cancer.

The 83rd target gene is the hsa-miR-6732-5p gene, a congener thereof, a transcript thereof, or a variant or a derivative thereof. None of the previously known reports show that change in the expression of the gene or the transcript thereof can serve as a marker for colorectal cancer.

The 84th target gene is the hsa-miR-4417 gene, a congener thereof, a transcript thereof, or a variant or a derivative thereof. None of the previously known reports show that change in the expression of the gene or the transcript thereof can serve as a marker for colorectal cancer.

The 85th target gene is the hsa-miR-4281 gene, a congener thereof, a transcript thereof, or a variant or a derivative thereof. None of the previously known reports show that change in the expression of the gene or the transcript thereof can serve as a marker for colorectal cancer.

The 86th target gene is the hsa-miR-4734 gene, a congener thereof, a transcript thereof, or a variant or a derivative thereof. None of the previously known reports show that change in the expression of the gene or the transcript thereof can serve as a marker for colorectal cancer.

The 87th target gene is the hsa-miR-6766-3p gene, a congener thereof, a transcript thereof, or a variant or a derivative thereof. None of the previously known reports show that change in the expression of the gene or the transcript thereof can serve as a marker for colorectal cancer.

The 88th target gene is the hsa-miR-663a gene, a congener thereof, a transcript thereof, or a variant or a derivative thereof. None of the previously known reports show that change in the expression of the gene or the transcript thereof can serve as a marker for colorectal cancer.

The 89th target gene is the hsa-miR-4513 gene, a congener thereof, a transcript thereof, or a variant or a derivative thereof. None of the previously known reports show that change in the expression of the gene or the transcript thereof can serve as a marker for colorectal cancer.

The 90th target gene is the hsa-miR-6781-5p gene, a congener thereof, a transcript thereof, or a variant or a derivative thereof. None of the previously known reports show that change in the expression of the gene or the transcript thereof can serve as a marker for colorectal cancer.

The 91st target gene is the hsa-miR-1227-5p gene, a congener thereof, a transcript thereof, or a variant or a derivative thereof. None of the previously known reports show that change in the expression of the gene or the transcript thereof can serve as a marker for colorectal cancer.

The 92nd target gene is the hsa-miR-6845-5p gene, a congener thereof, a transcript thereof, or a variant or a derivative thereof. None of the previously known reports show that change in the expression of the gene or the transcript thereof can serve as a marker for colorectal cancer.

The 93rd target gene is the hsa-miR-6798-5p gene, a congener thereof, a transcript thereof, or a variant or a derivative thereof. None of the previously known reports show that change in the expression of the gene or the transcript thereof can serve as a marker for colorectal cancer.

The 94th target gene is the hsa-miR-3620-5p gene, a congener thereof, a transcript thereof, or a variant or a derivative thereof. None of the previously known reports show that change in the expression of the gene or the transcript thereof can serve as a marker for colorectal cancer.

The 95th target gene is the hsa-miR-1915-5p gene, a congener thereof, a transcript thereof, or a variant or a derivative thereof. None of the previously known reports show that change in the expression of the gene or the transcript thereof can serve as a marker for colorectal cancer.

The 96th target gene is the hsa-miR-4294 gene, a congener thereof, a transcript thereof, or a variant or a derivative thereof. None of the previously known reports show that change in the expression of the gene or the transcript thereof can serve as a marker for colorectal cancer.

The 97th target gene is the hsa-miR-642a-3p gene, a congener thereof, a transcript thereof, or a variant or a derivative thereof. None of the previously known reports show that change in the expression of the gene or the transcript thereof can serve as a marker for colorectal cancer.

The 98th target gene is the hsa-miR-371a-5p gene, a congener thereof, a transcript thereof, or a variant or a derivative thereof. None of the previously known reports show that change in the expression of the gene or the transcript thereof can serve as a marker for colorectal cancer.

The 99th target gene is the hsa-miR-940 gene, a congener thereof, a transcript thereof, or a variant or a derivative thereof. None of the previously known reports show that change in the expression of the gene or the transcript thereof can serve as a marker for colorectal cancer.

The 100th target gene is the hsa-miR-4450 gene, a congener thereof, a transcript thereof, or a variant or a derivative thereof. None of the previously known reports show that change in the expression of the gene or the transcript thereof can serve as a marker for colorectal cancer.

The 101st target gene is the hsa-miR-4723-5p gene, a congener thereof, a transcript thereof, or a variant or a derivative thereof. None of the previously known reports show that change in the expression of the gene or the transcript thereof can serve as a marker for colorectal cancer.

The 102nd target gene is the hsa-miR-1469 gene, a congener thereof, a transcript thereof, or a variant or a derivative thereof. None of the previously known reports show that change in the expression of the gene or the transcript thereof can serve as a marker for colorectal cancer.

The 103rd target gene is the hsa-miR-6861-5p gene, a congener thereof, a transcript thereof, or a variant or a derivative thereof. None of the previously known reports show that change in the expression of the gene or the transcript thereof can serve as a marker for colorectal cancer.

The 104th target gene is the hsa-miR-7975 gene, a congener thereof, a transcript thereof, or a variant or a derivative thereof. None of the previously known reports show that change in the expression of the gene or the transcript thereof can serve as a marker for colorectal cancer.

The 105th target gene is the hsa-miR-6879-5p gene, a congener thereof, a transcript thereof, or a variant or a derivative thereof. None of the previously known reports show that change in the expression of the gene or the transcript thereof can serve as a marker for colorectal cancer.

The 106th target gene is the hsa-miR-6802-5p gene, a congener thereof, a transcript thereof, or a variant or a derivative thereof. None of the previously known reports show that change in the expression of the gene or the transcript thereof can serve as a marker for colorectal cancer.

The 107th target gene is the hsa-miR-1268b gene, a congener thereof, a transcript thereof, or a variant or a derivative thereof. None of the previously known reports show that change in the expression of the gene or the transcript thereof can serve as a marker for colorectal cancer.

The 108th target gene is the hsa-miR-663b gene, a congener thereof, a transcript thereof, or a variant or a derivative thereof. None of the previously known reports show that change in the expression of the gene or the transcript thereof can serve as a marker for colorectal cancer.

The 109th target gene is the hsa-miR-125a-3p gene, a congener thereof, a transcript thereof, or a variant or a derivative thereof. None of the previously known reports show that change in the expression of the gene or the transcript thereof can serve as a marker for colorectal cancer.

The 110th target gene is the hsa-miR-2861 gene, a congener thereof, a transcript thereof, or a variant or a derivative thereof. None of the previously known reports show that change in the expression of the gene or the transcript thereof can serve as a marker for colorectal cancer.

The 111th target gene is the hsa-miR-6088 gene, a congener thereof, a transcript thereof, or a variant or a derivative thereof. None of the previously known reports show that change in the expression of the gene or the transcript thereof can serve as a marker for colorectal cancer.

The 112th target gene is the hsa-miR-4758-5p gene, a congener thereof, a transcript thereof, or a variant or a derivative thereof. None of the previously known reports show that change in the expression of the gene or the transcript thereof can serve as a marker for colorectal cancer.

The 113th target gene is the hsa-miR-296-3p gene, a congener thereof, a transcript thereof, or a variant or a derivative thereof. None of the previously known reports show that change in the expression of the gene or the transcript thereof can serve as a marker for colorectal cancer.

The 114th target gene is the hsa-miR-6738-5p gene, a congener thereof, a transcript thereof, or a variant or a derivative thereof. None of the previously known reports show that change in the expression of the gene or the transcript thereof can serve as a marker for colorectal cancer.

The 115th target gene is the hsa-miR-671-5p gene, a congener thereof, a transcript thereof, or a variant or a derivative thereof. None of the previously known reports show that change in the expression of the gene or the transcript thereof can serve as a marker for colorectal cancer.

The 116th target gene is the hsa-miR-4454 gene, a congener thereof, a transcript thereof, or a variant or a derivative thereof. None of the previously known reports show that change in the expression of the gene or the transcript thereof can serve as a marker for colorectal cancer.

The 117th target gene is the hsa-miR-4516 gene, a congener thereof, a transcript thereof, or a variant or a derivative thereof. None of the previously known reports show that change in the expression of the gene or the transcript thereof can serve as a marker for colorectal cancer.

The 118th target gene is the hsa-miR-7845-5p gene, a congener thereof, a transcript thereof, or a variant or a derivative thereof. None of the previously known reports show that change in the expression of the gene or the transcript thereof can serve as a marker for colorectal cancer.

The 119th target gene is the hsa-miR-4741 gene, a congener thereof, a transcript thereof, or a variant or a derivative thereof. None of the previously known reports show that change in the expression of the gene or the transcript thereof can serve as a marker for colorectal cancer.

The 120th target gene is the hsa-miR-92b-5p gene, a congener thereof, a transcript thereof, or a variant or a derivative thereof. None of the previously known reports show that change in the expression of the gene or the transcript thereof can serve as a marker for colorectal cancer.

The 121st target gene is the hsa-miR-6795-5p gene, a congener thereof, a transcript thereof, or a variant or a derivative thereof. None of the previously known reports show that change in the expression of the gene or the transcript thereof can serve as a marker for colorectal cancer.

The 122nd target gene is the hsa-miR-6805-3p gene, a congener thereof, a transcript thereof, or a variant or a derivative thereof. None of the previously known reports show that change in the expression of the gene or the transcript thereof can serve as a marker for colorectal cancer.

The 123rd target gene is the hsa-miR-4725-3p gene, a congener thereof, a transcript thereof, or a variant or a derivative thereof. None of the previously known reports show that change in the expression of the gene or the transcript thereof can serve as a marker for colorectal cancer.

The 124th target gene is the hsa-miR-6782-5p gene, a congener thereof, a transcript thereof, or a variant or a derivative thereof. None of the previously known reports show that change in the expression of the gene or the transcript thereof can serve as a marker for colorectal cancer.

The 125th target gene is the hsa-miR-4688 gene, a congener thereof, a transcript thereof, or a variant or a derivative thereof. None of the previously known reports show that change in the expression of the gene or the transcript thereof can serve as a marker for colorectal cancer.

The 126th target gene is the hsa-miR-6850-5p gene, a congener thereof, a transcript thereof, or a variant or a derivative thereof. None of the previously known reports show that change in the expression of the gene or the transcript thereof can serve as a marker for colorectal cancer.

The 127th target gene is the hsa-miR-6777-5p gene, a congener thereof, a transcript thereof, or a variant or a derivative thereof. None of the previously known reports show that change in the expression of the gene or the transcript thereof can serve as a marker for colorectal cancer.

The 128th target gene is the hsa-miR-6785-5p gene, a congener thereof, a transcript thereof, or a variant or a derivative thereof. None of the previously known reports show that change in the expression of the gene or the transcript thereof can serve as a marker for colorectal cancer.

The 129th target gene is the hsa-miR-7106-5p gene, a congener thereof, a transcript thereof, or a variant or a derivative thereof. None of the previously known reports show that change in the expression of the gene or the transcript thereof can serve as a marker for colorectal cancer.

The 130th target gene is the hsa-miR-3663-3p gene, a congener thereof, a transcript thereof, or a variant or a derivative thereof. None of the previously known reports show that change in the expression of the gene or the transcript thereof can serve as a marker for colorectal cancer.

The 131st target gene is the hsa-miR-6131 gene, a congener thereof, a transcript thereof, or a variant or a derivative thereof. None of the previously known reports show that change in the expression of the gene or the transcript thereof can serve as a marker for colorectal cancer.

The 132nd target gene is the hsa-miR-1915-3p gene, a congener thereof, a transcript thereof, or a variant or a derivative thereof. None of the previously known reports show that change in the expression of the gene or the transcript thereof can serve as a marker for colorectal cancer.

The 133rd target gene is the hsa-miR-4532 gene, a congener thereof, a transcript thereof, or a variant or a derivative thereof. None of the previously known reports show that change in the expression of the gene or the transcript thereof can serve as a marker for colorectal cancer.

The 134th target gene is the hsa-miR-6820-5p gene, a congener thereof, a transcript thereof, or a variant or a derivative thereof. None of the previously known reports show that change in the expression of the gene or the transcript thereof can serve as a marker for colorectal cancer.

The 135th target gene is the hsa-miR-4689 gene, a congener thereof, a transcript thereof, or a variant or a derivative thereof. None of the previously known reports show that change in the expression of the gene or the transcript thereof can serve as a marker for colorectal cancer.

The 136th target gene is the hsa-miR-4638-5p gene, a congener thereof, a transcript thereof, or a variant or a derivative thereof. None of the previously known reports show that change in the expression of the gene or the transcript thereof can serve as a marker for colorectal cancer.

The 137th target gene is the hsa-miR-3656 gene, a congener thereof, a transcript thereof, or a variant or a derivative thereof. None of the previously known reports show that change in the expression of the gene or the transcript thereof can serve as a marker for colorectal cancer.

The 138th target gene is the hsa-miR-3621 gene, a congener thereof, a transcript thereof, or a variant or a derivative thereof. None of the previously known reports show that change in the expression of the gene or the transcript thereof can serve as a marker for colorectal cancer.

The 139th target gene is the hsa-miR-6769b-5p gene, a congener thereof, a transcript thereof, or a variant or a derivative thereof. None of the previously known reports show that change in the expression of the gene or the transcript thereof can serve as a marker for colorectal cancer.

The 140th target gene is the hsa-miR-149-3p gene, a congener thereof, a transcript thereof, or a variant or a derivative thereof. None of the previously known reports show that change in the expression of the gene or the transcript thereof can serve as a marker for colorectal cancer.

The 141st target gene is the hsa-miR-23b-3p gene, a congener thereof, a transcript thereof, or a variant or a derivative thereof. None of the previously known reports show that change in the expression of the gene or the transcript thereof can serve as a marker for colorectal cancer.

The 142nd target gene is the hsa-miR-3135b gene, a congener thereof, a transcript thereof, or a variant or a derivative thereof. None of the previously known reports show that change in the expression of the gene or the transcript thereof can serve as a marker for colorectal cancer.

The 143rd target gene is the hsa-miR-6848-5p gene, a congener thereof, a transcript thereof, or a variant or a derivative thereof. None of the previously known reports show that change in the expression of the gene or the transcript thereof can serve as a marker for colorectal cancer.

The 144th target gene is the hsa-miR-6769a-5p gene, a congener thereof, a transcript thereof, or a variant or a derivative thereof. None of the previously known reports show that change in the expression of the gene or the transcript thereof can serve as a marker for colorectal cancer.

The 145th target gene is the hsa-miR-4327 gene, a congener thereof, a transcript thereof, or a variant or a derivative thereof. None of the previously known reports show that change in the expression of the gene or the transcript thereof can serve as a marker for colorectal cancer.

The 146th target gene is the hsa-miR-6765-3p gene, a congener thereof, a transcript thereof, or a variant or a derivative thereof. None of the previously known reports show that change in the expression of the gene or the transcript thereof can serve as a marker for colorectal cancer.

The 147th target gene is the hsa-miR-6716-5p gene, a congener thereof, a transcript thereof, or a variant or a derivative thereof. None of the previously known reports show that change in the expression of the gene or the transcript thereof can serve as a marker for colorectal cancer.

The 148th target gene is the hsa-miR-6877-5p gene, a congener thereof, a transcript thereof, or a variant or a derivative thereof. None of the previously known reports show that change in the expression of the gene or the transcript thereof can serve as a marker for colorectal cancer.

The 149th target gene is the hsa-miR-6727-5p gene, a congener thereof, a transcript thereof, or a variant or a derivative thereof. None of the previously known reports show that change in the expression of the gene or the transcript thereof can serve as a marker for colorectal cancer.

The 150th target gene is the hsa-miR-4534 gene, a congener thereof, a transcript thereof, or a variant or a derivative thereof. None of the previously known reports show that change in the expression of the gene or the transcript thereof can serve as a marker for colorectal cancer.

The 151st target gene is the hsa-miR-614 gene, a congener thereof, a transcript thereof, or a variant or a derivative thereof. None of the previously known reports show that change in the expression of the gene or the transcript thereof can serve as a marker for colorectal cancer.

The 152nd target gene is the hsa-miR-1202 gene, a congener thereof, a transcript thereof, or a variant or a derivative thereof. None of the previously known reports show that change in the expression of the gene or the transcript thereof can serve as a marker for colorectal cancer.

The 153rd target gene is the hsa-miR-575 gene, a congener thereof, a transcript thereof, or a variant or a derivative thereof. None of the previously known reports show that change in the expression of the gene or the transcript thereof can serve as a marker for colorectal cancer.

The 154th target gene is the hsa-miR-6870-5p gene, a congener thereof, a transcript thereof, or a variant or a derivative thereof. None of the previously known reports show that change in the expression of the gene or the transcript thereof can serve as a marker for colorectal cancer.

The 155th target gene is the hsa-miR-6722-3p gene, a congener thereof, a transcript thereof, or a variant or a derivative thereof. None of the previously known reports show that change in the expression of the gene or the transcript thereof can serve as a marker for colorectal cancer.

The 156th target gene is the hsa-miR-7977 gene, a congener thereof, a transcript thereof, or a variant or a derivative thereof. None of the previously known reports show that change in the expression of the gene or the transcript thereof can serve as a marker for colorectal cancer.

The 157th target gene is the hsa-miR-4649-5p gene, a congener thereof, a transcript thereof, or a variant or a derivative thereof. None of the previously known reports show that change in the expression of the gene or the transcript thereof can serve as a marker for colorectal cancer.

The 158th target gene is the hsa-miR-4675 gene, a congener thereof, a transcript thereof, or a variant or a derivative thereof. None of the previously known reports show that change in the expression of the gene or the transcript thereof can serve as a marker for colorectal cancer.

The 159th target gene is the hsa-miR-6075 gene, a congener thereof, a transcript thereof, or a variant or a derivative thereof. None of the previously known reports show that change in the expression of the gene or the transcript thereof can serve as a marker for colorectal cancer.

The 160th target gene is the hsa-miR-6779-5p gene, a congener thereof, a transcript thereof, or a variant or a derivative thereof. None of the previously known reports show that change in the expression of the gene or the transcript thereof can serve as a marker for colorectal cancer.

The 161st target gene is the hsa-miR-4271 gene, a congener thereof, a transcript thereof, or a variant or a derivative thereof. None of the previously known reports show that change in the expression of the gene or the transcript thereof can serve as a marker for colorectal cancer.

The 162nd target gene is the hsa-miR-3196 gene, a congener thereof, a transcript thereof, or a variant or a derivative thereof. None of the previously known reports show that change in the expression of the gene or the transcript thereof can serve as a marker for colorectal cancer.

The 163rd target gene is the hsa-miR-6803-5p gene, a congener thereof, a transcript thereof, or a variant or a derivative thereof. None of the previously known reports show that change in the expression of the gene or the transcript thereof can serve as a marker for colorectal cancer.

The 164th target gene is the hsa-miR-6789-5p gene, a congener thereof, a transcript thereof, or a variant or a derivative thereof. None of the previously known reports show that change in the expression of the gene or the transcript thereof can serve as a marker for colorectal cancer.

The 165th target gene is the hsa-miR-4648 gene, a congener thereof, a transcript thereof, or a variant or a derivative thereof. None of the previously known reports show that change in the expression of the gene or the transcript thereof can serve as a marker for colorectal cancer.

The 166th target gene is the hsa-miR-4508 gene, a congener thereof, a transcript thereof, or a variant or a derivative thereof. None of the previously known reports show that change in the expression of the gene or the transcript thereof can serve as a marker for colorectal cancer.

The 167th target gene is the hsa-miR-4749-5p gene, a congener thereof, a transcript thereof, or a variant or a derivative thereof. None of the previously known reports show that change in the expression of the gene or the transcript thereof can serve as a marker for colorectal cancer.

The 168th target gene is the hsa-miR-4505 gene, a congener thereof, a transcript thereof, or a variant or a derivative thereof. None of the previously known reports show that change in the expression of the gene or the transcript thereof can serve as a marker for colorectal cancer.

The 169th target gene is the hsa-miR-5698 gene, a congener thereof, a transcript thereof, or a variant or a derivative thereof. None of the previously known reports show that change in the expression of the gene or the transcript thereof can serve as a marker for colorectal cancer.

The 170th target gene is the hsa-miR-1199-5p gene, a congener thereof, a transcript thereof, or a variant or a derivative thereof. None of the previously known reports show that change in the expression of the gene or the transcript thereof can serve as a marker for colorectal cancer.

The 171st target gene is the hsa-miR-4763-3p gene, a congener thereof, a transcript thereof, or a variant or a derivative thereof. None of the previously known reports show that change in the expression of the gene or the transcript thereof can serve as a marker for colorectal cancer.

The 172nd target gene is the hsa-miR-1231 gene, a congener thereof, a transcript thereof, or a variant or a derivative thereof. The previously known report shows that change in the expression of the gene or the transcript thereof can serve as a marker for colorectal cancer (Patent Literature 3).

The 173rd target gene is the hsa-miR-1233-5p gene, a congener thereof, a transcript thereof, or a variant or a derivative thereof. The previously known report shows that change in the expression of the gene or the transcript thereof can serve as a marker for colorectal cancer (Patent Literature 2).

The 174th target gene is the hsa-miR-150-3p gene, a congener thereof, a transcript thereof, or a variant or a derivative thereof. The previously known report shows that change in the expression of the gene or the transcript thereof can serve as a marker for colorectal cancer (Patent Literature 4).

The 175th target gene is the hsa-miR-1225-3p gene, a congener thereof, a transcript thereof, or a variant or a derivative thereof. The previously known report shows that change in the expression of the gene or the transcript thereof can serve as a marker for colorectal cancer (Patent Literature 2).

The 176th target gene is the hsa-miR-92a-2-5p gene, a congener thereof, a transcript thereof, or a variant or a derivative thereof. The previously known report shows that change in the expression of the gene or the transcript thereof can serve as a marker for colorectal cancer (Patent Literatures 1 and 4).

The 177th target gene is the hsa-miR-423-5p gene, a congener thereof, a transcript thereof, or a variant or a derivative thereof. The previously known report shows that change in the expression of the gene or the transcript thereof can serve as a marker for colorectal cancer (Patent Literature 3).

The 178th target gene is the hsa-miR-1268a gene, a congener thereof, a transcript thereof, or a variant or a derivative thereof. The previously known report shows that change in the expression of the gene or the transcript thereof can serve as a marker for colorectal cancer (Patent Literature 3).

The 179th target gene is the hsa-miR-128-2-5p gene, a congener thereof, a transcript thereof, or a variant or a derivative thereof. The previously known report shows that change in the expression of the gene or the transcript thereof can serve as a marker for colorectal cancer (Patent Literature 1).

The 180th target gene is the hsa-miR-24-3p gene, a congener thereof, a transcript thereof, or a variant or a derivative thereof. The previously known report shows that change in the expression of the gene or the transcript thereof can serve as a marker for colorectal cancer (Patent Literature 1).

The 181st target gene is the hsa-miR-4697-5p gene, a congener thereof, a transcript thereof, or a variant or a derivative thereof. None of the previously known reports show that change in the expression of the gene or the transcript thereof can serve as a marker for colorectal cancer.

The 182nd target gene is the hsa-miR-3197 gene, a congener thereof, a transcript thereof, or a variant or a derivative thereof. None of the previously known reports show that change in the expression of the gene or the transcript thereof can serve as a marker for colorectal cancer.

The 183rd target gene is the hsa-miR-675-5p gene, a congener thereof, a transcript thereof, or a variant or a derivative thereof. None of the previously known reports show that change in the expression of the gene or the transcript thereof can serve as a marker for colorectal cancer.

The 184th target gene is the hsa-miR-4486 gene, a congener thereof, a transcript thereof, or a variant or a derivative thereof. None of the previously known reports show that change in the expression of the gene or the transcript thereof can serve as a marker for colorectal cancer.

The 185th target gene is the hsa-miR-7107-5p gene, a congener thereof, a transcript thereof, or a variant or a derivative thereof. None of the previously known reports show that change in the expression of the gene or the transcript thereof can serve as a marker for colorectal cancer.

The 186th target gene is the hsa-miR-23a-3p gene, a congener thereof, a transcript thereof, or a variant or a derivative thereof. The previously known report shows that change in the expression of the gene or the transcript thereof can serve as a marker for colorectal cancer (Patent Literature 2).

The 187th target gene is the hsa-miR-4667-5p gene, a congener thereof, a transcript thereof, or a variant or a derivative thereof. None of the previously known reports show that change in the expression of the gene or the transcript thereof can serve as a marker for colorectal cancer.

The 188th target gene is the hsa-miR-451a gene, a congener thereof, a transcript thereof, or a variant or a derivative thereof. None of the previously known reports show that change in the expression of the gene or the transcript thereof can serve as a marker for colorectal cancer.

The 189th target gene is the hsa-miR-3940-5p gene, a congener thereof, a transcript thereof, or a variant or a derivative thereof. None of the previously known reports show that change in the expression of the gene or the transcript thereof can serve as a marker for colorectal cancer.

The 190th target gene is the hsa-miR-8059 gene, a congener thereof, a transcript thereof, or a variant or a derivative thereof. None of the previously known reports show that change in the expression of the gene or the transcript thereof can serve as a marker for colorectal cancer.

The 191st target gene is the hsa-miR-6813-5p gene, a congener thereof, a transcript thereof, or a variant or a derivative thereof. None of the previously known reports show that change in the expression of the gene or the transcript thereof can serve as a marker for colorectal cancer.

The 192nd target gene is the hsa-miR-4492 gene, a congener thereof, a transcript thereof, or a variant or a derivative thereof. None of the previously known reports show that change in the expression of the gene or the transcript thereof can serve as a marker for colorectal cancer.

The 193rd target gene is the hsa-miR-4476 gene, a congener thereof, a transcript thereof, or a variant or a derivative thereof. None of the previously known reports show that change in the expression of the gene or the transcript thereof can serve as a marker for colorectal cancer.

The 194th target gene is the hsa-miR-6090 gene, a congener thereof, a transcript thereof, or a variant or a derivative thereof. None of the previously known reports show that change in the expression of the gene or the transcript thereof can serve as a marker for colorectal cancer.

The 195th target gene is the hsa-miR-6836-3p gene, a congener thereof, a transcript thereof, or a variant or a derivative thereof. None of the previously known reports show that change in the expression of the gene or the transcript thereof can serve as a marker for colorectal cancer.

The 196th target gene is the hsa-miR-3195 gene, a congener thereof, a transcript thereof, or a variant or a derivative thereof. None of the previously known reports show that change in the expression of the gene or the transcript thereof can serve as a marker for colorectal cancer.

The 197th target gene is the hsa-miR-718 gene, a congener thereof, a transcript thereof, or a variant or a derivative thereof. None of the previously known reports show that change in the expression of the gene or the transcript thereof can serve as a marker for colorectal cancer.

The 198th target gene is the hsa-miR-3178 gene, a congener thereof, a transcript thereof, or a variant or a derivative thereof. None of the previously known reports show that change in the expression of the gene or the transcript thereof can serve as a marker for colorectal cancer.

The 199th target gene is the hsa-miR-638 gene, a congener thereof, a transcript thereof, or a variant or a derivative thereof. None of the previously known reports show that change in the expression of the gene or the transcript thereof can serve as a marker for colorectal cancer.

The 200th target gene is the hsa-miR-4497 gene, a congener thereof, a transcript thereof, or a variant or a derivative thereof. None of the previously known reports show that change in the expression of the gene or the transcript thereof can serve as a marker for colorectal cancer.

The 201st target gene is the hsa-miR-6085 gene, a congener thereof, a transcript thereof, or a variant or a derivative thereof. None of the previously known reports show that change in the expression of the gene or the transcript thereof can serve as a marker for colorectal cancer.

The 202nd target gene is the hsa-miR-6752-5p gene, a congener thereof, a transcript thereof, or a variant or a derivative thereof. None of the previously known reports show that change in the expression of the gene or the transcript thereof can serve as a marker for colorectal cancer.

The 203rd target gene is the hsa-miR-135a-3p gene, a congener thereof, a transcript thereof, or a variant or a derivative thereof. None of the previously known reports show that change in the expression of the gene or the transcript thereof can serve as a marker for colorectal cancer.

2. Nucleic Acid Probe or Primer for Detection of Colorectal Cancer

In the present invention, a nucleic acid capable of specifically binding to any of the target nucleic acids as the colorectal cancer markers described above can be used as a nucleic acid, for example, a nucleic acid probe or a primer, for the detection or diagnosis of colorectal cancer.

In the present invention, the nucleic acid probe or the primer that can be used for detecting colorectal cancer or for diagnosing colorectal cancer permits qualitative and/or quantitative measurement of the presence, expression level, or abundance of any of the target nucleic acids as the colorectal cancer markers described above, for example, human-derived hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-

5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p, or a combination thereof, congeners thereof, transcripts thereof, or variants or derivatives thereof: and, optionally in combination therewith, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p and hsa-miR-24-3p or a combination thereof, congeners thereof, transcripts thereof, or variants or derivatives thereof: and, optionally in combination therewith, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476 and hsa-miR-6090 or a combination thereof, congeners thereof, transcripts thereof, or variants or derivatives thereof.

The expression level of each target nucleic acid described above is increased or decreased (hereinafter, referred to as "increased/decreased") according to the type of the target nucleic acid in a subject who has colorectal cancer as compared with a healthy subject. Hence, the nucleic acid of the present invention can be effectively used for measuring the expression level of the target nucleic acid described above in a body fluid derived from a subject (e.g., a human) suspected of having colorectal cancer and a body fluid derived from a healthy subject and detecting colorectal cancer by the comparison thereof.

The nucleic acid probe or the primer that can be used in the present invention is a nucleic acid probe capable of specifically binding to a polynucleotide that consists of a nucleotide sequence represented by at least one of SEQ ID NOs: 1 to 171 and 606 to 614, or a primer for amplifying a polynucleotide that consists of a nucleotide sequence represented by at least one of SEQ ID NOs: 1 to 171 and 606 to 614.

The nucleic acid probe or the primer that can be further used in the present invention can comprise a nucleic acid probe capable of specifically binding to a polynucleotide consisting of a nucleotide sequence represented by at least one of SEQ ID NOs: 172 to 180, or a primer for amplifying a polynucleotide consisting of a nucleotide sequence represented by at least one of SEQ ID NOs: 172 to 180.

The nucleic acid probe or the primer that can be further used in the present invention can comprise a nucleic acid probe capable of specifically binding to a polynucleotide consisting of a nucleotide sequence represented by at least one of SEQ ID NOs: 181 to 194, or a primer for amplifying a polynucleotide consisting of a nucleotide sequence represented by at least one of SEQ ID NOs: 181 to 194.

Specifically, these nucleic acid probes or primers comprise a combination of one or more polynucleotides selected from a polynucleotide group comprising nucleotide sequences represented by any of SEQ ID NOs: 1 to 635 or nucleotide sequences derived from the nucleotide sequences by the replacement of u with t, and a complementary polynucleotide group thereof, a polynucleotide group respectively hybridizing under stringent conditions (mentioned later) to DNAs consisting of nucleotide sequences complementary to these nucleotide sequences, and a complementary polynucleotide group thereof, and a polynucleotide group comprising 15 or more, preferably 17 or more consecutive nucleotides in the nucleotide sequences of these polynucleotide groups. These polynucleotides can be used as nucleic acid probes and primers for detecting the colorectal cancer markers as target nucleic acids.

More specifically, examples of the nucleic acid probe or the primer that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the polynucleotides (a) to (e), the nucleic acid probe or the primer that can be further used in the present invention can comprise polynucleotides selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180, (h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

In addition to at least one or more polynucleotide(s) selected from the polynucleotides (a) to (j), the nucleic acid probe or the primer that can be further used in the present invention can comprise polynucleotides selected from the group consisting of the following polynucleotides (k) to (o):
(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs:181 to 194,
(m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 181 to 194 or a nucleotide sequence derived from the nucleotide sequence by the replacement of u with t, and
(o) a polynucleotide hybridizing under stringent conditions to any of the polynucleotides (k) to (n).

For these polynucleotides, the "fragment thereof comprising 15 or more consecutive nucleotides" can contain the number of nucleotides in the range of, for example, from 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide, though the fragment is not limited thereto.

These polynucleotides or the fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p, hsa-miR-24-3p, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476, hsa-miR-6090, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p represented by SEQ ID NOs: 1 to 194 and 606 to 614 are known in the art, and their acquisition methods are also known as mentioned above. Therefore, each polynucleotide that can be used as a nucleic acid probe or a primer in the present invention can be prepared by cloning the gene.

Such a nucleic acid probe or a primer can be chemically synthesized using an automatic DNA synthesis apparatus. In general, a phosphoramidite method is used in this synthesis, and single-stranded DNA up to approximately 100 nucleotides can be automatically synthesized by this method. The automatic DNA synthesis apparatus is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide consisting of a nucleotide sequence represented by any of SEQ ID NOs: 1 to 194 and 606 to 614 do not exist as miRNAs or precursors thereof in vivo. For example, the nucleotide sequences represented by SEQ ID NO: 11 and SEQ ID NO: 78 are produced from the precursor represented by SEQ ID NO: 205. This precursor has a hairpin-like structure as shown in FIG. 1, and the nucleotide sequences represented by SEQ ID NO: 11 and SEQ ID NO: 78 have mismatch sequences with each other. Likewise, a nucleotide sequence completely complementary to the nucleotide sequence represented by SEQ ID NO: 11 or SEQ ID NO: 78 is not naturally produced in vivo. Therefore, the nucleic acid probe and the primer for detecting the nucleotide sequence represented by any of SEQ ID NOs: 1 to 194 and 606 to 614 each have an artificial nucleotide sequence that does not exist in vivo.

3. Kit or Device for Detection of Colorectal Cancer

The present invention also provides a kit or a device for the detection of colorectal cancer, comprising one or more polynucleotide(s) (which can include a variant, a fragment, and a derivative; hereinafter, also referred to as a polynucleotide for detection) that can be used as a nucleic acid probe or a primer in the present invention for measuring a target nucleic acid as a colorectal cancer marker.

The target nucleic acid as a colorectal cancer marker according to the present invention is preferably selected from the following group 1:
miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p.

An additional target nucleic acid that can be optionally used in the measurement is selected from the following group 2: miR-1231, miR-1233-5p, miR-150-3p, miR-1225-3p, miR-92a-2-5p, miR-423-5p, miR-1268a, miR-128-2-5p and miR-24-3p.

An additional target nucleic acid that can be optionally further used in the measurement is selected from the following group 3: miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090.

The kit or the device of the present invention comprises one or more nucleic acid(s) capable of specifically binding to any of the target nucleic acids as the colorectal cancer markers described above, preferably one or more polynucleotide(s) selected from the nucleic acid probes or the primers described in the preceding Section 2, specifically, the polynucleotides described in the preceding Section 2, or variant(s) thereof.

Specifically, the kit or the device of the present invention can comprise at least one or more polynucleotide(s) comprising (or consisting of) a nucleotide sequence represented by any of SEQ ID NOs: 1 to 171 and 606 to 614 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 172 to 180 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 181 to 194 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that can be contained in the kit or the device of the present invention is, for example, one or more, preferably two or more polynucleotides selected from the group consisting of the following polynucleotides (1) to (3):
(1) a polynucleotide comprising 15 or more consecutive nucleotides in a nucleotide sequence derived from a nucleotide sequence represented by any of SEQ ID NOs: 1 to 171 and 606 to 614 by the replacement of u with t, or a complementary sequence thereof;
(2) a polynucleotide comprising 15 or more consecutive nucleotides in a nucleotide sequence derived from a nucleotide sequence represented by any of SEQ ID NOs: 172 to 180 by the replacement of u with t, or a complementary sequence thereof; and
(3) a polynucleotide comprising 15 or more consecutive nucleotides in a nucleotide sequence derived from a nucleotide sequence represented by any of SEQ ID NOs: 181 to 194 by the replacement of u with t, or a complementary sequence thereof.

In a preferred embodiment, the polynucleotide is a polynucleotide consisting of a nucleotide sequence represented by any of SEQ ID NOs: 1 to 171 and 606 to 614 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 172 to 180 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 181 to 194 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of bases in the range of, for example, from 15 consecutive nucleotides to less than the total number of bases of the sequence, from 17 consecutive nucleotides to less than the total number of bases of the sequence, or from 19 consecutive nucleotides to less than the total number of nucleotides of the sequence, in the nucleotide sequence of each polynucleotide.

Specific examples of the aforementioned polynucleotide combination constituting the kit or the device of the present invention can include combinations of 1, 2, 3, 4, 5, 6, 7, 8, 9, 10 or more of the polynucleotides consisting of nucleotide sequences represented by SEQ ID NOs shown in Table 1 (SEQ ID NOs: 1 to 194 and 606 to 614 corresponding to the miRNA markers in the table). However, these are given merely for illustrative purposes, and various other possible combinations are included in the present invention.

The combination constituting the kit or the device for discriminating a colorectal cancer patient from a healthy subject according to the present invention is desirably, for example, a combination of two or more of the polynucleotides consisting of nucleotide sequences represented by SEQ ID NOs shown in Table 1. Usually, a combination of two of these polynucleotides can produce adequate performance.

The specific combination of two polynucleotides consisting of the nucleotide sequences or the complementary sequences thereof for discriminating a colorectal cancer patient from a healthy subject is preferably a combination comprising at least one or more of newly found polynucleotides consisting of the nucleotide sequences represented by SEQ ID NOs: 1 to 171, among the combinations constituted by two of the aforementioned polynucleotides consisting of the nucleotide sequences represented by SEQ ID NOs: 1 to 194 and 606 to 614. More specifically, a combination comprising at least one of polynucleotides consisting of the nucleotide sequences represented by SEQ ID NOs: 5, 15, 24, 32, 38, 45, 55, 64, 96, 97, and 162, among the combinations of the polynucleotides consisting of the nucleotide sequences represented by SEQ ID NOs: 1 to 194 and 606 to 614, is more preferred.

The combination of polynucleotides with cancer type specificity capable of discriminating a colorectal cancer patient not only from a healthy subject but also from other cancer patients is preferably, for example, a combination of multiple polynucleotides comprising at least one polynucleotide selected from the group consisting of polynucleotides of SEQ ID NOs: 5, 13, 15, 24, 32, 38, 41, 45, 55, 57, 64, 72, 75, 77, 96, 97, 115, 162, 163, 173, 189, 606, 607, 608, 609, 610, 611, 612, 613 and 614 (hereinafter, this group is referred to as "cancer type-specific polynucleotide group 1"), with any of the polynucleotides of the other SEQ ID NOs.

The combination of polynucleotides with cancer type specificity capable of discriminating a colorectal cancer patient not only from a healthy subject but also from other cancer patients is more preferably a combination of multiple polynucleotides selected from the cancer type-specific polynucleotide group 1.

The combination of polynucleotides with cancer type specificity capable of discriminating a colorectal cancer patient not only from a healthy subject but also from other cancer patients is more preferably a combination comprising at least one or more polynucleotide(s) selected from the group consisting of polynucleotides of SEQ ID NOs: 5, 45, 57, 96, and 606 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the aforementioned polynucleotides with cancer type specificity in the combination can be 1, 2, 3, 4, 5, 6, 7, 8, 9, 10 or more for the combination and is more preferably 6 or more for the combination. Usually, the combination of 5 or 6 of these polynucleotides can produce adequate performance.

Non-limiting examples of the combination of the polynucleotide consisting of the nucleotide sequence represented by SEQ ID NO: 5 or a complementary sequence thereof with polynucleotides consisting of nucleotide sequences represented by SEQ ID NOs of four or five polynucleotides selected from the cancer type-specific polynucleotide group 1 or complementary sequences thereof will be listed.

(1) a combination of SEQ ID NOs: 5, 45, 57, 75, and 607 (markers: hsa-miR-3131, hsa-miR-204-3p, hsa-miR-4665-5p, hsa-miR-7847-3p, and hsa-miR-3195);

(2) a combination of SEQ ID NOs: 5, 45, 96, 606, and 607 (markers: hsa-miR-3131, hsa-miR-204-3p, hsa-miR-4294, hsa-miR-6836-3p, and hsa-miR-3195);

(3) a combination of SEQ ID NOs: 5, 45, 57, 97, 115, and 607 (markers: hsa-miR-3131, hsa-miR-204-3p, hsa-miR-4665-5p, hsa-miR-642a-3p, hsa-miR-671-5p, and hsa-miR-3195);

(4) a combination of SEQ ID NOs: 5, 45, 57, 97, 162, and 607 (markers: hsa-miR-3131, hsa-miR-204-3p, hsa-miR-4665-5p, hsa-miR-642a-3p, hsa-miR-3196, and hsa-miR-3195);

(5) a combination of SEQ ID NOs: 5, 45, 57, 162, 607, and 613 (markers: hsa-miR-3131, hsa-miR-204-3p, hsa-miR-4665-5p, hsa-miR-3196, hsa-miR-3195, and hsa-miR-6752-5p);

(6) a combination of SEQ ID NOs: 5, 45, 57, 97, 607, and 612 (markers: hsa-miR-3131, hsa-miR-204-3p, hsa-miR-4665-5p, hsa-miR-642a-3p, hsa-miR-3195, and hsa-miR-6085);

(7) a combination of SEQ ID NOs: 5, 13, 45, 57, 606, and 607 (markers: hsa-miR-3131, hsa-miR-6746-5p, hsa-miR-204-3p, hsa-miR-4665-5p, hsa-miR-6836-3p, and hsa-miR-3195);

(8) a combination of SEQ ID NOs: 5, 45, 96, 189, 606, and 608 (markers: hsa-miR-3131, hsa-miR-204-3p, hsa-miR-4294, hsa-miR-3940-5p, hsa-miR-6836-3p, and hsa-miR-718);

(9) a combination of SEQ ID NOs: 5, 45, 57, 96, 189, and 606 (markers: hsa-miR-3131, hsa-miR-204-3p, hsa-miR-4665-5p, hsa-miR-4294, hsa-miR-3940-5p, and hsa-miR-6836-3p);

(10) a combination of SEQ ID NOs: 5, 24, 45, 57, 96, and 608 (markers: hsa-miR-3131, hsa-miR-6826-5p, hsa-miR-204-3p, hsa-miR-4665-5p, hsa-miR-4294, and hsa-miR-718);

(11) a combination of SEQ ID NOs: 5, 45, 57, 162, 607, and 610 (markers: hsa-miR-3131, hsa-miR-204-3p, hsa-miR-4665-5p, hsa-miR-3196, hsa-miR-3195, and hsa-miR-638); and

(12) a combination of SEQ ID NOs: 5, 45, 57, 189, 606, and 607 (markers: hsa-miR-3131, hsa-miR-204-3p, hsa-miR-4665-5p, hsa-miR-3940-5p, hsa-miR-6836-3p, and hsa-miR-3195).

Non-limiting examples of the combination of the polynucleotide consisting of the nucleotide sequence represented by SEQ ID NO: 45 or a complementary sequence thereof with polynucleotides consisting of nucleotide sequences represented by SEQ ID NOs of four or five polynucleotides selected from the cancer type-specific polynucleotide group 1 or complementary sequences thereof will be further listed.

(1) a combination of SEQ ID NOs: 5, 45, 96, 606, and 607 (markers: hsa-miR-3131, hsa-miR-204-3p, hsa-miR-4294, hsa-miR-6836-3p, and hsa-miR-3195);

(2) a combination of SEQ ID NOs: 5, 45, 57, 75, and 607 (markers: hsa-miR-3131, hsa-miR-204-3p, hsa-miR-4665-5p, hsa-miR-7847-3p, and hsa-miR-3195);

(3) a combination of SEQ ID NOs: 5, 45, 57, 75, 606, and 607 (markers: hsa-miR-3131, hsa-miR-204-3p, hsa-miR-4665-5p, hsa-miR-7847-3p, hsa-miR-6836-3p, and hsa-miR-3195);

(4) a combination of SEQ ID NOs: 5, 45, 57, 77, 607, and 613 (markers: hsa-miR-3131, hsa-miR-204-3p, hsa-miR-4665-5p, hsa-miR-887-3p, hsa-miR-3195, and hsa-miR-6752-5p);

(5) a combination of SEQ ID NOs: 5, 45, 57, 97, 606, and 607 (markers: hsa-miR-3131, hsa-miR-204-3p, hsa-miR-4665-5p, hsa-miR-642a-3p, hsa-miR-6836-3p, and hsa-miR-3195);

(6) a combination of SEQ ID NOs: 5, 45, 57, 75, 77, and 607 (markers: hsa-miR-3131, hsa-miR-204-3p, hsa-miR-4665-5p, hsa-miR-7847-3p, hsa-miR-887-3p, and hsa-miR-3195);

(7) a combination of SEQ ID NOs: 5, 32, 45, 57, 96, and 606 (markers: hsa-miR-3131, hsa-miR-8069, hsa-miR-204-3p, hsa-miR-4665-5p, hsa-miR-4294, and hsa-miR-6836-3p);

(8) a combination of SEQ ID NOs: 5, 24, 45, 57, 96, and 606 (markers: hsa-miR-3131, hsa-miR-6826-5p, hsa-miR-204-3p, hsa-miR-4665-5p, hsa-miR-4294, and hsa-miR-6836-3p);

(9) a combination of SEQ ID NOs: 5, 45, 57, 96, 162, and 606 (markers: hsa-miR-3131, hsa-miR-204-3p, hsa-miR-4665-5p, hsa-miR-4294, hsa-miR-3196, and hsa-miR-6836-3p);

(10) a combination of SEQ ID NOs: 5, 15, 45, 75, 96, and 606 (markers: hsa-miR-3131, hsa-miR-6741-5p, hsa-miR-204-3p, hsa-miR-7847-3p, hsa-miR-4294, and hsa-miR-6836-3p);

(11) a combination of SEQ ID NOs: 5, 32, 45, 57, 162, and 607 (markers: hsa-miR-3131, hsa-miR-8069, hsa-miR-204-3p, hsa-miR-4665-5p, hsa-miR-3196, and hsa-miR-3195); and

(12) a combination of SEQ ID NOs: 38, 45, 96, 606, 608, and 611 (markers: hsa-miR-6724-5p, hsa-miR-204-3p, hsa-miR-4294, hsa-miR-6836-3p, hsa-miR-718, and hsa-miR-4497).

Non-limiting examples of the combination of the polynucleotide consisting of the nucleotide sequence represented by SEQ ID NO: 57 or a complementary sequence thereof with polynucleotides consisting of nucleotide sequences represented by SEQ ID NOs of four or five polynucleotides selected from the cancer type-specific polynucleotide group 1 or complementary sequences thereof will be further listed.

(1) a combination of SEQ ID NOs: 24, 41, 57, 45, and 96 (markers: hsa-miR-6826-5p, hsa-miR-4419b, hsa-miR-4665-5p, hsa-miR-204-3p, and hsa-miR-4294);

(2) a combination of SEQ ID NOs: 5, 45, 57, 607, and 612 (markers: hsa-miR-3131, hsa-miR-204-3p, hsa-miR-4665-5p, hsa-miR-3195, and hsa-miR-6085);

(3) a combination of SEQ ID NOs: 5, 45, 57, 606, 607, and 608 (markers: hsa-miR-3131, hsa-miR-204-3p, hsa-miR-4665-5p, hsa-miR-6836-3p, hsa-miR-3195, and hsa-miR-718);

(4) a combination of SEQ ID NOs: 5, 13, 45, 57, 75, and 607 (markers: hsa-miR-3131, hsa-miR-6746-5p, hsa-miR-204-3p, hsa-miR-4665-5p, hsa-miR-7847-3p, and hsa-miR-3195);

(5) a combination of SEQ ID NOs: 5, 45, 57, 64, 75, and 607 (markers: hsa-miR-3131, hsa-miR-204-3p, hsa-miR-4665-5p, hsa-miR-6126, hsa-miR-7847-3p, and hsa-miR-3195);

(6) a combination of SEQ ID NOs: 5, 45, 55, 57, 607, and 613 (markers: hsa-miR-3131, hsa-miR-204-3p, hsa-miR-6717-5p, hsa-miR-4665-5p, hsa-miR-3195, and hsa-miR-6752-5p);

(7) a combination of SEQ ID NOs: 5, 45, 55, 57, 75, and 607 (markers: hsa-miR-3131, hsa-miR-204-3p, hsa-miR-6717-5p, hsa-miR-4665-5p, hsa-miR-7847-3p, and hsa-miR-3195);

(8) a combination of SEQ ID NOs: 5, 38, 45, 57, 96, and 607 (markers: hsa-miR-3131, hsa-miR-6724-5p, hsa-miR-204-3p, hsa-miR-4665-5p, hsa-miR-4294, and hsa-miR-3195);

(9) a combination of SEQ ID NOs: 5, 45, 57, 75, 162, and 607 (markers: hsa-miR-3131, hsa-miR-204-3p, hsa-miR-4665-5p, hsa-miR-7847-3p, hsa-miR-3196, and hsa-miR-3195);

(10) a combination of SEQ ID NOs: 5, 45, 57, 75, 162, and 609 (markers: hsa-miR-3131, hsa-miR-204-3p, hsa-miR-4665-5p, hsa-miR-7847-3p, hsa-miR-3196, and hsa-miR-3178);

(11) a combination of SEQ ID NOs: 5, 45, 57, 64, 96, and 607 (markers: hsa-miR-3131, hsa-miR-204-3p, hsa-miR-4665-5p, hsa-miR-6126, hsa-miR-4294, and hsa-miR-3195); and

(12) a combination of SEQ ID NOs: 57, 64, 96, 606, 608, and 611 (markers: hsa-miR-4665-5p, hsa-miR-6126, hsa-miR-4294, hsa-miR-6836-3p, hsa-miR-718, and hsa-miR-4497).

Non-limiting examples of the combination of the polynucleotide consisting of the nucleotide sequence represented by SEQ ID NO: 96 or a complementary sequence thereof with polynucleotides consisting of nucleotide sequences represented by SEQ ID NOs of four or five polynucleotides selected from the cancer type-specific polynucleotide group 1 or complementary sequences thereof will be further listed below.

(1) a combination of SEQ ID NOs: 38, 96, 606, 608, and 611 (markers: hsa-miR-6724-5p, hsa-miR-4294, hsa-miR-6836-3p, hsa-miR-718, and hsa-miR-4497);

(2) a combination of SEQ ID NOs: 5, 45, 57, 96, and 607 (markers: hsa-miR-3131, hsa-miR-204-3p, hsa-miR-4665-5p, hsa-miR-4294, and hsa-miR-3195);

(3) a combination of SEQ ID NOs: 38, 72, 96, 606, 608, and 611 (markers: hsa-miR-6724-5p, hsa-miR-6816-5p, hsa-miR-4294, hsa-miR-6836-3p, hsa-miR-718, and hsa-miR-4497);

(4) a combination of SEQ ID NOs: 32, 38, 96, 606, 608, and 611 (markers: hsa-miR-8069, hsa-miR-6724-5p, hsa-miR-4294, hsa-miR-6836-3p, hsa-miR-718, and hsa-miR-4497);

(5) a combination of SEQ ID NOs: 38, 96, 163, 606, 608, and 611 (markers: hsa-miR-6724-5p, hsa-miR-4294, hsa-miR-6803-5p, hsa-miR-6836-3p, hsa-miR-718, and hsa-miR-4497);

(6) a combination of SEQ ID NOs: 64, 72, 96, 162, 609, and 611 (markers: hsa-miR-6126, hsa-miR-6816-5p, hsa-miR-4294, hsa-miR-3196, hsa-miR-3178, and hsa-miR-4497);

(7) a combination of SEQ ID NOs: 38, 64, 96, 163, 606, and 608 (markers: hsa-miR-6724-5p, hsa-miR-6126, hsa-miR-4294, hsa-miR-6803-5p, hsa-miR-6836-3p, and hsa-miR-718);

(8) a combination of SEQ ID NOs: 5, 45, 57, 75, 96, and 606 (markers: hsa-miR-3131, hsa-miR-204-3p, hsa-miR-4665-5p, hsa-miR-7847-3p, hsa-miR-4294, and hsa-miR-6836-3p);

(9) a combination of SEQ ID NOs: 5, 15, 45, 57, 96, and 606 (markers: hsa-miR-3131, hsa-miR-6741-5p, hsa-miR-204-3p, hsa-miR-4665-5p, hsa-miR-4294, and hsa-miR-6836-3p);

(10) a combination of SEQ ID NOs: 5, 41, 45, 57, 96, and 606 (markers: hsa-miR-3131, hsa-miR-4419b, hsa-miR-204-3p, hsa-miR-4665-5p, hsa-miR-4294, and hsa-miR-6836-3p);

(11) a combination of SEQ ID NOs: 5, 41, 45, 96, 189, and 606 (markers: hsa-miR-3131, hsa-miR-4419b, hsa-miR-204-3p, hsa-miR-4294, hsa-miR-3940-5p, and hsa-miR-6836-3p); and

(12) a combination of SEQ ID NOs: 5, 45, 75, 96, 189, and 606 (markers: hsa-miR-3131, hsa-miR-204-3p, hsa-miR-7847-3p, hsa-miR-4294, hsa-miR-3940-5p, and hsa-miR-6836-3p).

Non-limiting examples of the combination of the polynucleotide consisting of the nucleotide sequence represented by SEQ ID NO: 606 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 5, 24, 45, 96, 189, and 606 (markers: hsa-miR-3131, hsa-miR-6826-5p, hsa-miR-204-3p, hsa-miR-4294, hsa-miR-3940-5p, and hsa-miR-6836-3p);

(2) a combination of SEQ ID NOs: 5, 15, 45, 96, 189, and 606 (markers: hsa-miR-3131, hsa-miR-6741-5p, hsa-miR-204-3p, hsa-miR-4294, hsa-miR-3940-5p, and hsa-miR-6836-3p);

(3) a combination of SEQ ID NOs: 5, 45, 96, 189, 606, and 613 (markers: hsa-miR-3131, hsa-miR-204-3p, hsa-miR-4294, hsa-miR-3940-5p, hsa-miR-6836-3p, and hsa-miR-6752-5p);

(4) a combination of SEQ ID NOs: 5, 45, 72, 96, 189, and 606 (markers: hsa-miR-3131, hsa-miR-204-3p, hsa-miR-6816-5p, hsa-miR-4294, hsa-miR-3940-5p, and hsa-miR-6836-3p); and (5) a combination of SEQ ID NOs: 5, 15, 32, 45, 96, and 606 (markers: hsa-miR-3131, hsa-miR-6741-5p, hsa-miR-8069, hsa-miR-204-3p, hsa-miR-4294, and hsa-miR-6836-3p).

The kit or the device of the present invention can also contain a polynucleotide that is already known or that will be found in the future, to enable detection of colorectal cancer, in addition to the polynucleotide(s) (which can include a variant, a fragment, and a derivative) according to the present invention described above.

The kit of the present invention can also contain an antibody for measuring a marker for colorectal cancer examination known in the art, such as CEA or CA19-9, in addition to the polynucleotide(s) according to the present invention described above.

These polynucleotides contained in the kit of the present invention can be packaged in different containers either individually or in any combination.

The kit of the present invention can contain a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves binding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one or more, preferably at least two or more, more preferably at least three or more, most preferably at least five or more to all of the colorectal cancer marker miRNAs, respectively, of group 1 described above. The kit or the device of the present invention can optionally further comprise nucleic acids capable of specifically binding to the polynucleotides of at least one or more, preferably at least two or more, more preferably at least three or more, most preferably at least five or more to all of the colorectal cancer marker miRNAs, respectively, of group 2 described above. The kit or the device of the present invention can optionally further comprise nucleic acids capable of specifically binding to the polynucleotides of at least one or more, preferably at least two or more, more preferably at least three or more, most preferably at least five or more to all of the colorectal cancer marker miRNAs, respectively, of group 3 described above.

The kit or the device of the present invention can be used for detecting colorectal cancer as described in the Section 4 below.

4. Method for Detecting Colorectal Cancer

The present invention further provides a method for detecting colorectal cancer, comprising using the kit or the device of the present invention (including the nucleic acid(s) that can be used in the present invention) described in the preceding Section 3 above to measure an expression level of one or more colorectal cancer-derived gene(s) represented by an expression level of colorectal cancer-derived gene(s) selected from the following group: miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p, optionally an expression level of colorectal cancer-derived gene(s) selected from the following group: miR-1231, miR-1233-5p, miR-150-3p, miR-1225-3p, miR-92a-2-5p, miR-423-5p, miR-1268a, miR-128-2-5p and miR-24-3p, and optionally an expression level of colorectal cancer-derived gene(s) selected from the following group: miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090 in a sample in vitro, further comparing, for example, the expression level of the aforementioned gene in the sample (e.g., blood, serum, or plasma) collected from a subject suspected of having colorectal cancer with a control expression level in the sample collected from a healthy subject (including a non-colorectal cancer patient), and evaluating the subject as having colorectal cancer when the expression level of the target nucleic acid is statistically significantly different between the samples.

This method of the present invention permits lowly-invasive early diagnosis of cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the colorectal cancer-derived gene from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The colorectal cancer-derived gene may be prepared by the addition of a reagent for RNA extraction containing acidic phenol, such as Trizol (Life Technologies Corp.) or Isogen (Nippon Gene Co., Ltd.). Alternatively, a kit such as miRNeasy™ Mini Kit (Qiagen N.V.) can be used, though the method is not limited thereto.

The present invention also provides use of the kit or the device of the present invention for detecting in vitro an expression product of a colorectal cancer-derived miRNA gene in a sample derived from a subject.

In the method of the present invention, a kit or a device comprising, each alone or in every possible composition, the polynucleotides that can be used in the present invention as described above is used as the kit or the device.

In the detection or (genetic) diagnosis of colorectal cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of colorectal cancer or the detection of the presence or absence of colorectal cancer. Specifically, the detection of colorectal cancer using the kit or the device can be performed by detecting in vitro an expression level of a gene using the nucleic acid probe or the primer contained in the kit or the device in a sample such as blood, serum, plasma, or urine from a subject suspected of having colorectal cancer. The subject suspected of having colorectal cancer can be evaluated as having colorectal cancer when the expression level of a target miRNA marker measured using polynucleotide(s) (including a variant, a fragment, and a derivative thereof) consisting of a nucleotide sequence represented by at least one or more of SEQ ID NOs: 1 to 171 and 606 to 614 or a complementary sequence thereof, optionally a nucleotide sequence represented by one or more of SEQ ID NOs: 172 to 180 or a complementary sequence thereof, and optionally a nucleotide sequence represented by one or more of SEQ ID NOs: 181 to 194 or a complementary sequence thereof in the sample such as blood, serum, plasma, or urine of the subject is statistically significantly different from the expression level thereof in the sample such as blood, serum, or plasma, or urine of a healthy subject.

The method of the present invention can be combined with fecal occult blood, rectal examination, and colonoscopy as well as a diagnostic imaging method such as barium enema, CT, MRI, or bone scintigraphy. The method of the present invention is capable of specifically detecting colorectal cancer and can substantially discriminate colorectal cancer from other cancers.

The method for detecting the absence of an expression product of a colorectal cancer-derived gene or the presence of the expression product of a colorectal cancer-derived gene in a sample using the kit or the device of the present invention comprises; collecting a body fluid such as blood, serum, plasma, or urine from a subject, measuring the expression level of the target gene that contains therein using one or more polynucleotide(s) (including a variant, a fragment, and a derivative) selected from the polynucleotide group of the present invention, and evaluating the presence or absence of colorectal cancer or detecting colorectal cancer. Using the method for detecting colorectal cancer according to the present invention, for example, the presence or absence of amelioration of the disease or the degree of amelioration thereof in a colorectal cancer patient given a therapeutic drug for the amelioration of the disease can be also evaluated or diagnosed.

The method of the present invention can comprise, for example, the following steps (a), (b), and (c):

(a) a step of contacting a sample derived from a subject with a polynucleotide in the kit or the device of the present invention in vitro;

(b) a step of measuring an expression level of the target nucleic acid in the sample using the polynucleotide as a nucleic acid probe or a primer; and (c) a step of evaluating the presence or absence of colorectal cancer (cells) in the subject on the basis of the step (b).

Specifically, the present invention provides a method for detecting colorectal cancer, comprising measuring an expression level of a target nucleic acid in a sample of a subject using a nucleic acid capable of specifically binding to at least one or more (preferably at least two or more) polynucleotide(s) selected from the group consisting of miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p and miR-4763-3p, miR-6836-3p, miR-3195, miR-718, miR-3178, miR-638, miR-4497, miR-6085, miR-6752-5p and miR-135a-3p and evaluating in vitro whether or not the subject has colorectal cancer using the measured expression level and a control expression level of a healthy subject measured in the same way as above.

As used herein, the term "evaluation" is evaluation support based on results of in vitro examination, not physician's judgment.

As described above, as for the target nucleic acids in a preferred embodiment of the method of the present invention, specifically, miR-6726-5p is hsa-miR-6726-5p, miR-4257 is hsa-miR-4257, miR-6787-5p is hsa-miR-6787-5p, miR-6780b-5p is hsa-miR-6780b-5p, miR-3131 is hsa-miR-3131, miR-7108-5p is hsa-miR-7108-5p, miR-1343-3p is hsa-miR-1343-3p, miR-1247-3p is hsa-miR-1247-3p, miR-4651 is hsa-miR-4651, miR-6757-5p is hsa-miR-6757-5p, miR-3679-5p is hsa-miR-3679-5p, miR-7641 is hsa-miR-7641, miR-6746-5p is hsa-miR-6746-5p, miR-8072 is hsa-miR-8072, miR-6741-5p is hsa-miR-6741-5p, miR-1908-5p is hsa-miR-1908-5p, miR-6857-5p is hsa-miR-6857-5p, miR-4746-3p is hsa-miR-4746-3p, miR-744-5p is hsa-miR-744-5p, miR-4792 is hsa-miR-4792, miR-564 is hsa-miR-564, miR-6791-5p is hsa-miR-6791-5p, miR-6825-5p is hsa-miR-6825-5p, miR-6826-5p is hsa-miR-6826-5p, miR-4665-3p is hsa-miR-4665-3p, miR-4467 is hsa-miR-4467, miR-3188 is hsa-miR-3188, miR-6125 is hsa-miR-6125, miR-6756-5p is hsa-miR-6756-5p, miR-1228-3p is hsa-miR-1228-3p, miR-8063 is hsa-miR-8063, miR-8069 is hsa-miR-8069, miR-6875-5p is hsa-miR-6875-5p, miR-3185 is hsa-miR-3185, miR-4433b-3p is hsa-miR-4433b-3p, miR-6887-5p is hsa-miR-6887-5p, miR-128-1-5p is hsa-miR-128-1-5p, miR-6724-5p is hsa-miR-6724-5p, miR- 1914-3p is hsa-miR-1914-3p, miR-1225-5p is hsa-miR-1225-5p, miR-4419b is hsa-miR-4419b, miR-7110-5p is hsa-miR-7110-5p, miR-187-5p is hsa-miR-187-5p, miR-3184-5p is hsa-miR-3184-5p, miR-204-3p is hsa-miR-204-3p, miR-5572 is hsa-miR-5572, miR-6729-5p is hsa-miR-6729-5p, miR-615-5p is hsa-miR-615-5p, miR-6749-5p is hsa-miR-6749-5p, miR-6515-3p is hsa-miR-6515-3p, miR-3937 is hsa-miR-3937, miR-6840-3p is hsa-miR-6840-3p, miR-6893-5p is hsa-miR-6893-5p, miR-4728-5p is hsa-miR-4728-5p, miR-6717-5p is hsa-miR-6717-5p, miR-7113-3p is hsa-miR-7113-3p, miR-4665-5p is hsa-miR-4665-5p, miR-642b-3p is hsa-miR-642b-3p, miR-7109-5p is hsa-miR-7109-5p, miR-6842-5p is hsa-miR-6842-5p, miR-4442 is hsa-miR-4442, miR-4433-3p is hsa-miR-4433-3p, miR-4707-5p is hsa-miR-4707-5p, miR-6126 is hsa-miR-6126, miR-4449 is hsa-miR-4449, miR-4706 is hsa-miR-4706, miR-1913 is hsa-miR-1913, miR-602 is hsa-miR-602, miR-939-5p is hsa-miR-939-5p, miR-4695-5p is hsa-miR-4695-5p, miR-711 is hsa-miR-711, miR-6816-5p is hsa-miR-6816-5p, miR-4632-5p is hsa-miR-4632-5p, miR-6721-5p is hsa-miR-6721-5p, miR-7847-3p is hsa-miR-7847-3p, miR-6132 is hsa-miR-6132, miR-887-3p is hsa-miR-887-3p, miR-3679-3p is hsa-miR-3679-3p, miR-6784-5p is hsa-miR-6784-5p, miR-1249 is hsa-miR-1249, miR-937-5p is hsa-miR-937-5p, miR-5195-3p is hsa-miR-5195-3p, miR-6732-5p is hsa-miR-6732-5p, miR-4417 is hsa-miR-4417, miR-4281 is hsa-miR-4281, miR-4734 is hsa-miR-4734, miR-6766-3p is hsa-miR-6766-3p, miR-663a is hsa-miR-663a, miR-4513 is hsa-miR-4513, miR-6781-5p is hsa-miR-6781-5p, miR-1227-5p is hsa-miR-1227-5p, miR-6845-5p is hsa-miR-6845-5p, miR-6798-5p is hsa-miR-6798-5p, miR-3620-5p is hsa-miR-3620-5p, miR-1915-5p is hsa-miR-1915-5p, miR-4294 is hsa-miR-4294, miR-642a-3p is hsa-miR-642a-3p, miR-371a-5p is hsa-miR-371a-5p, miR-940 is hsa-miR-940, miR-4450 is hsa-miR-4450, miR-4723-5p is hsa-miR-4723-5p, miR-1469 is hsa-miR-1469, miR-6861-5p is hsa-miR-6861-5p, miR-7975 is hsa-miR-7975, miR-6879-5p is hsa-miR-6879-5p, miR-6802-5p is hsa-miR-6802-5p, miR-1268b is hsa-miR-1268b, miR-663b is hsa-miR-663b, miR-125a-3p is hsa-miR-125a-3p, miR-2861 is hsa-miR-2861, miR-6088 is hsa-miR-6088, miR-4758-5p is hsa-miR-4758-5p, miR-296-3p is hsa-miR-296-3p, miR-6738-5p is hsa-miR-6738-5p, miR-671-5p is hsa-miR-671-5p, miR-4454 is hsa-miR-4454, miR-4516 is hsa-miR-4516, miR-7845-5p is hsa-miR-7845-5p, miR-4741 is hsa-miR-4741, miR-92b-5p is hsa-miR-92b-5p, miR-6795-5p is hsa-miR-6795-5p, miR-6805-3p is hsa-miR-6805-3p, miR-4725-3p is hsa-miR-4725-3p, miR-6782-5p is hsa-miR-6782-5p, miR-4688 is hsa-miR-4688, miR-6850-5p is hsa-miR-6850-5p, miR-6777-5p is hsa-miR-6777-5p, miR-6785-5p is hsa-miR-6785-5p, miR-7106-5p is hsa-miR-7106-5p, miR-3663-3p is hsa-miR-3663-3p, miR-6131 is hsa-miR-6131, miR-1915-3p is hsa-miR-1915-3p, miR-4532 is hsa-miR-4532, miR-6820-5p is hsa-miR-6820-5p, miR-4689 is hsa-miR-4689, miR-4638-5p is hsa-miR-4638-5p, miR-3656 is hsa-miR-3656, miR-3621 is hsa-miR-3621, miR-6769b-5p is hsa-miR-6769b-5p, miR-149-3p is hsa-miR-149-3p, miR-23b-3p is hsa-miR-23b-3p, miR-3135b is hsa-miR-3135b, miR-6848-5p is hsa-miR-6848-5p, miR-6769a-5p is hsa-miR-6769a-5p, miR-4327 is hsa-miR-4327, miR-6765-3p is hsa-miR-6765-3p, miR-6716-5p is hsa-miR-6716-5p, miR-6877-5p is hsa-miR-6877-5p, miR-6727-5p is hsa-miR-6727-5p, miR-4534 is hsa-miR-4534, miR-614 is hsa-miR-614, miR-1202 is hsa-miR-1202, miR-575 is hsa-miR-575, miR-6870-5p is hsa-miR-6870-5p, miR-6722-3p is hsa-miR-6722-3p, miR-7977 is hsa-miR-7977, miR-4649-5p is hsa-miR-4649-5p, miR-4675 is hsa-miR-4675, miR-6075 is hsa-miR-6075, miR-6779-5p is hsa-miR-6779-5p, miR-4271 is hsa-miR-4271, miR-3196 is hsa-miR-3196, miR-6803-5p is hsa-miR-6803-5p, miR-6789-5p is hsa-miR-6789-5p, miR-4648 is hsa-miR-4648, miR-4508 is hsa-miR-4508, miR-4749-5p is hsa-miR-4749-5p, miR-4505 is hsa-miR-4505, miR-5698 is hsa-miR-5698, miR-1199-5p is hsa-miR-1199-5p, miR-4763-3p is hsa-miR-4763-3p, miR-6836-3p is hsa-miR-6836-3p, miR-3195 is hsa-miR-3195, miR-718 is hsa-miR-718, miR-3178 is hsa-miR-3178, miR-638 is hsa-miR-638, miR-4497 is hsa-miR-4497, miR-6085 is hsa-miR-6085, miR-6752-5p is hsa-miR-6752-5p, and miR-135a-3p is hsa-miR-135a-3p.

In a preferred embodiment of the method of the present invention, specifically, the nucleic acid (specifically, probe or primer) is selected from the group consisting of the following polynucleotides (a) to (e):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

The method of the present invention can further employ a nucleic acid capable of specifically binding to at least one or more polynucleotide(s) selected from the group consisting of miR-1231, miR-1233-5p, miR-150-3p, miR-1225-3p, miR-92a-2-5p, miR-423-5p, miR-1268a, miR-128-2-5p and miR-24-3p.

As for such a nucleic acid, specifically, miR-1231 is hsa-miR-1231, miR-1233-5p is hsa-miR-1233-5p, miR-150-3p is hsa-miR-150-3p, miR-1225-3p is hsa-miR-1225-3p, miR-92a-2-5p is hsa-miR-92a-2-5p, miR-423-5p is hsa-miR-423-5p, miR-1268a is hsa-miR-1268a, miR-128-2-5p is hsa-miR-128-2-5p, and miR-24-3p is hsa-miR-24-3p.

In a preferred embodiment, such a nucleic acid is specifically selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180, (h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

The nucleic acid further used in the method of the present invention can comprise a nucleic acid capable of specifically binding to at least one or more polynucleotide(s) selected from the group consisting of miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476 and miR-6090.

As for such a nucleic acid, specifically, miR-4697-5p is hsa-miR-4697-5p, miR-3197 is hsa-miR-3197, miR-675-5p is hsa-miR-675-5p, miR-4486 is hsa-miR-4486, miR-7107-5p is hsa-miR-7107-5p, miR-23a-3p is hsa-miR-23a-3p, miR-4667-5p is hsa-miR-4667-5p, miR-451a is hsa-miR-451a, miR-3940-5p is hsa-miR-3940-5p, miR-8059 is hsa-miR-8059, miR-6813-5p is hsa-miR-6813-5p, miR-4492 is hsa-miR-4492, miR-4476 is hsa-miR-4476, and miR-6090 is hsa-miR-6090.

In a preferred embodiment, such a nucleic acid is specifically a polynucleotide selected from the group consisting of the following polynucleotides (k) to (o):

(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 181 to 194, (m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 181 to 194 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a colorectal tissue) or a body fluid such as blood, serum, plasma, or urine from the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse and a rat without any limitation, and is preferably a human.

The steps of the method of the present invention can be changed according to the type of the sample to be assayed.

In the case of using RNA as an analyte, the detection of colorectal cancer (cells) can comprise, for example, the following steps (a), (b), and (c):

(a) a step of binding RNA prepared from the sample of the subject or a complementary polynucleotide (cDNA) transcribed therefrom to a polynucleotide in the kit or the device of the present invention;

(b) a step of measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) a step of evaluating the presence or absence of colorectal cancer (or colorectal cancer-derived gene expression) on the basis of the measurement results of the step (b).

For example, various hybridization methods can be used for detecting, examining, evaluating, or diagnosing colorectal cancer (or colorectal cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which involves labeling the nucleic acid probe (or its complementary strand) with a radioisotope ($^{32}$P, $^{33}$P, $^{35}$S, etc.), a fluorescent material, or the like, that hybridizes the labeled product with the living tissue-derived RNA from a subject transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which involves; preparing cDNA from the living tissue-derived RNA of a subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions that have the attached nucleic acid probes are referred to as probe spots, and regions that have no attached nucleic acid probe are referred to as blank spots. A gene group immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probes using an image detector (examples thereof can include Typhoon 9410 (GE Healthcare Japan Corp.) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent washing conditions. The hybridization conditions involve, for example, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the conditions of the washing, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by the washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.); LNA™-based MicroRNA PCR (Exiqon); or Ncode™ miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger, in 20% or more, preferably 5-0% 50% or more, more preferably 80% or more of the number of measurement samples can be selected as the analyte. Examples of the normalization of the gene expression level include, but are not limited to, global nomialization and quantile nomialization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a colorectal cancer patient and a sample derived from a healthy subject as supervising samples, and determining or evaluating the presence and/or absence of the colorectal cancer-derived gene in the sample.

Specifically, the present invention further provides the method comprising: a first step of measuring in vitro an expression level of a target gene (target nucleic acid) in multiple samples known to determine or evaluate the presence and/or absence of the colorectal cancer-derived gene in the samples, using the polynucleotide, the kit, or the device (e.g., chip) for detection of the present invention, or a combination thereof; a second step of preparing a discriminant with the measurement values of the expression level of the target gene obtained in the first step as supervising samples; a third step of measuring in vitro an expression level of the target gene in a sample derived from a subject in the same way as in the first step; and a fourth step of assigning the measurement value of the expression level of the target gene obtained in the third step into the discriminant obtained in the second step, and determining or evaluating the presence or absence of the colorectal cancer-derived gene in the sample on the basis of the results obtained from the discriminant, wherein the target gene can be detected using the polynucleotide or using a polynucleotide for detection contained in the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and w0 represents a constant term.

$$f(x) = w_0 + \sum_{i=1}^{n} w_i x_i \quad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs synthetic variable with highly discriminant performance by focusing on the variance of synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this Formula, µ represents an average input, ng represents the number of data associated to class g, and µg represents an average input of the data associated to class g. The numerator and the denominator are the inter-classe variance and the intra-classe variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)} \quad \text{Formula 2}$$

$$\text{subject to } \mu = \sum_{i=1}^{n} \frac{x_i}{n}, \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining a cluster having a closer Mahalanobis' distance from each cluster as an associated cluster. In this Formula 3, µ represents a central vector of each cluster, and S-1 represents an inverse matrix of the variance-covariance matrix of the cluster. The central vector is calculated from explanatory variable x, and an average vector, a median value vector, or the like can be used.

$$D(x,\mu) = \{(x-\mu)^t S^{-1} (x-\mu)\}^{1/2} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, involves preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a colorectal cancer patient group and a healthy subject group. For example, colorectal tissue examination can be used for each subject to be confirmed either as a colorectal cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using explanatory variables that are genes found to differ clearly in their gene expression levels between the two groups, and objective variables (e.g., −1 and +1) that are the grouping. An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \quad \text{Formula 4}$$

subject to $y^T a = 0$, $0 \le a_i \le C$, $i = 1, \ldots, l,$

Formula 5 is a finally obtained discriminant, and an associated group can be determined on the basis of the sign of a value obtained according to the discriminant. In this Formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this Formula, x represents a support vector, and y represents a kernel parameter for adjusting the complexity of the hyperplane.

$$K(x_i,x_j)=\exp(-r\|x_i-x_j\|^2), r<0 \qquad \text{Formula 6}$$

In addition, an approach such as neural network, k-nearest neighbor algorithms, decision trees, or logistic regression analysis can be selected as a method for determining or evaluating the presence and/or absence of expression of a colorectal cancer-derived target gene in a sample derived from a subject, or for evaluating the expression level thereof by comparison with a control derived from a healthy subject.

The method of the present invention can comprise, for example, the following steps (a), (b), and (c):

(a) a step of measuring an expression level of a target gene in tissues containing colorectal cancer-derived genes derived from colorectal cancer patients and/or samples already known to be tissues containing no colorectal cancer-derived gene derived from healthy subjects, using the polynucleotide, the kit, or the device (e.g., DNA chip) for detection according to the present invention;

(b) a step of preparing the discriminants of Formulas 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, assigning the obtained measurement value to the discriminants prepared in the step (b), and determining or evaluating the presence and/or absence of the colorectal cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described in Section 2 above, or a fragment thereof, etc. Specifically, the explanatory variable for discriminating a colorectal cancer patient from a healthy subject according to the present invention is a gene expression level selected from, for example, the following expression levels (1) to (3):

(1) a gene expression level in the serum of a colorectal cancer patient or a healthy subject measured by any DNA comprising 15 or more consecutive nucleotides in a nucleotide sequence represented by any of SEQ ID NOs: 1 to 171 and 606 to 614 or a complementary sequence thereof, (2) a gene expression level in the serum of a colorectal cancer patient or a healthy subject measured by any DNA comprising 15 or more consecutive nucleotides in a nucleotide sequence represented by any of SEQ ID NOs: 172 to 180 or a complementary sequence thereof, and (3) a gene expression level in the serum of a colorectal cancer patient or a healthy subject measured by any DNA comprising 15 or more consecutive nucleotides in a nucleotide sequence represented by any of SEQ ID NOs: 181 to 194 or a complementary sequence thereof.

As described above, for the method for determining or evaluating the presence and/or absence of a colorectal cancer-derived gene in a sample derived from a subject, the preparation of a discriminant requires a discriminant constructed from a training cohort. For enhancing the discriminant accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a colorectal cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a colorectal cancer patient group and gene expression levels of a healthy subject group may be calculated to select a gene that is used for an explanatory variable in a discriminant. Alternatively, ROC curves may be prepared using gene expression levels of a colorectal cancer patient group and a healthy subject group, and a gene that is used for an explanatory variable in a discriminant can be selected on the basis of an AUROC value.

Next, a discriminant that can be calculated by various methods described above is constructed using any number of genes that show large difference in their gene expression levels determined here. Examples of the method for constructing a discriminant that produces the largest discriminant accuracy include a method of constructing a discriminant in every combination of genes that satisfy the significance level of P value, and a method of repetitively evaluating the genes for use in the construction of a discriminant while increasing the number of genes one by one in a descending order of the difference in gene expression level (Furey T S. et al., 2000, Bioinformatics., Vol. 16, p. 906-14). A gene expression level of another independent colorectal cancer patient or healthy subject is assigned as an explanatory variable to this discriminant, and a result of the discriminant analysis regarding the group to which this independent colorectal cancer patient or healthy subject associated, is calculated. Specifically, the found gene set for diagnosis and the discriminant constructed using the gene set for diagnosis can be evaluated in an independent sample group to find a more universal gene set for diagnosis capable of detecting colorectal cancer and a more universal method for discriminating colorectal cancer.

Split-sample method is preferably used for evaluating the discriminant performance (generality) of the discriminant. Specifically, a data set is divided into a training cohort and a validation cohort, and gene selection by a statistical test and discriminant construction are performed in the training cohort. Accuracy, sensitivity, and specificity are calculated using results of discriminating a validation cohort according to the discriminant and a true group to which the validation cohort associated, to evaluate the discriminant performance. On the other hand, instead of dividing a data set, gene selection by a statistical test and discriminant preparation may be performed using all of samples, and accuracy, sensitivity, and specificity can be calculated by the discriminant of newly prepared samples according to the discriminant to evaluate the discriminant performance.

The present invention provides a polynucleotide for detection or for disease diagnosis useful in the diagnosis and treatment of colorectal cancer, a method for detecting colorectal cancer using the polynucleotide, and a kit and a device for the detection of colorectal cancer, comprising the polynucleotide. Particularly, in order to select a gene for diagnosis and prepare a discriminant so as to exhibit accuracy beyond a colorectal cancer diagnosis method using existing tumor markers CEA, a gene set for diagnosis and a discriminant for the method of the present invention can be constructed, which exhibit accuracy beyond CEA, for example, by comparing genes expressed in serum derived from a patient confirmed to be negative using CEA but finally found to have colorectal cancer by detailed examination such as computed tomography using a contrast medium, with genes expressed in serum derived from a patient who has no colorectal cancer.

For example, the gene set for diagnosis is set to any combination selected from one or two or more of the polynucleotides based on a nucleotide sequence represented by any of SEQ ID NOs: 1 to 171 and 606 to 614 or a complementary sequence thereof as described above, optionally one or two or more of the polynucleotides based on a nucleotide sequence represented by any of SEQ ID NOs: 172 to 180 or a complementary sequence thereof, and optionally one or two or more of the polynucleotides based on a nucleotide sequence represented by any of SEQ ID NOs: 181 to 194 or a complementary sequence thereof. Further, a discriminant is constructed using expression levels of the gene set for diagnosis in samples derived from class I colorectal cancer patients and samples derived from class II healthy subjects as a result of tissue diagnosis. As a result, the presence or absence of colorectal cancer-derived genes in an unknown sample can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples from Colorectal Cancer Patients and Healthy Subjects>
Serum was collected using VENOJECT II vacuum blood collecting tube VP-AS109K60 (Terumo Corp.) from each of 100 healthy subjects and 34 colorectal cancer patients (15 cases with stage I, 6 cases with stage IIA, 4 cases with stage IIIA, 6 cases with stage IIIB, 2 cases with stage IIIC, and 1 case with stage IV) who were confirmed to have no primary cancer other than colorectal cancer after acquisition of informed consent, and used as a training cohort. Likewise, serum was collected using VENOJECT II vacuum blood collecting tube VP-AS109K60 (Terumo Corp.) from each of 50 healthy subjects and 16 colorectal cancer patients (3 cases with stage I, 4 cases with stage IIA, 1 case with stage IIB, 2 cases with stage IIIB, 2 cases with stage MC, and 4 cases with stage IV) who were confirmed to have no primary cancer other than colorectal cancer after acquisition of informed consent, and used as a validation cohort.

<Extraction of Total RNA>
Total RNA was obtained from 300 µL of the serum sample obtained from each of 200 persons in total of 150 healthy subjects and 50 colorectal cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level>
miRNAs in the total RNA obtained from the serum sample of each of 200 persons in total of 150 healthy subjects and 50 colorectal cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value with a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the serum were obtained for the 50 colorectal cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancer Other than Colorectal Cancer>
Serum was collected using VENOJECT II vacuum blood collecting tube VP-AS109K60 (Terumo Corp.) from each of 69 pancreatic cancer patients, 66 biliary tract cancer patients, 30 stomach cancer patients, 33 esophageal cancer patients, 32 liver cancer patients, and 15 benign pancreaticobiliary disease patients who were confirmed to have no cancer in other organs after acquisition of informed consent, and used as a training cohort together with the samples of 34 colorectal cancer patients and 103 healthy subjects of Reference Example 1. Likewise, serum was collected using VENOJECT II vacuum blood collecting tube VP-AS109K60 (Terumo Corp.) from each of 30 pancreatic cancer patients, 33 bile duct cancer patients, 20 stomach cancer patients, 17 esophageal cancer patients, 20 liver cancer patients, and 6 benign pancreaticobiliary disease patients who were confirmed to have no cancer in other organs after acquisition of informed consent, and used as a validation cohort together with the samples of 16 colorectal cancer patients confirmed to have no cancer in organs other than the large intestine and 47 healthy subjects of Reference Example 1. Subsequent operations were conducted in the same way as in Reference Example 1.

Example 1

<Selection of Gene Marker Using Samples in the Training Cohort, and Method for Evaluating Colorectal Cancer Discriminant Performance of Single Gene Marker Using Samples of in the Validation Cohort>

In this Example, a gene marker for discriminating a colorectal cancer patient from a healthy subject was selected in the training cohort and studied in samples in the validation cohort independent of the training cohort, for a method for evaluating the colorectal cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes that show a gene expression level of $2^6$ or higher in 50% or more of the samples in either of the colorectal cancer patient group in the training cohort or the healthy subject group in the training cohort were selected. In order to further acquire statistically significant genes for discriminating a colorectal cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The obtained genes are described in Table 2.

In this way, hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p and hsa-miR-4763-3p, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p and hsa-miR-24-3p genes, and polynucleotides consisting of the nucleotide sequences of SEQ ID NOs: 1 to 180 related thereto were found.

Among them, genes newly found as markers for examining the presence or absence of colorectal cancer are polynucleotides consisting of the nucleotide sequences represented by SEQ ID NOs: 1 to 171.

A discriminant for determining the presence or absence of colorectal cancer was further prepared by Fisher's discriminant analysis with the expression levels of these genes as an index. Specifically, any polynucleotide consisting of a nucleotide sequence represented by any of SEQ ID NOs: 1 to 180 found in the training cohort was applied to Formula 2 above to construct a discriminant. Calculated accuracy, sensitivity, and specificity are shown in Table 3. In this respect, a discriminant coefficient and a constant term are shown in Table 4.

Accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (100 persons) and the colorectal cancer patients (34 persons) in the training cohort. As a result, the gene expression level measurement values were found to be significantly lower in the colorectal cancer patient group than in the healthy subject group (see the left diagram of FIG. 2). These results were also reproducible for the healthy subjects (50 persons) and the colorectal cancer patients (16 persons) in the validation cohort (see the right diagram of FIG. 2). Likewise, the results obtained about the other polynucleotides shown in SEQ ID NOs: 2 to 180 showed that the gene expression level measurement values were significantly lower (−) or higher (+) in the colorectal cancer patient group than in the healthy subject group (Table 2). These results were able to be validated in the validation cohort. For example, as for this nucleotide sequence represented by SEQ ID NO: 1, the number of samples that correctly identified in the detection of colorectal cancer in the validation cohort was calculated using the threshold (9.43) that was set in the training cohort and discriminated between the two groups. As a result, 16 true positives, 50 true negatives, 0 false positives, and 0 false negatives were obtained. From these values, 100% accuracy, 100% sensitivity, and 100% specificity were obtained as detection performance. In this way, the detection performance was calculated as to all of the polynucleotides shown in SEQ ID NOs: 1 to 180, and described in Table 3.

For example, 110 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 55, 56, 57, 58, 59, 60, 61, 62, 63, 65, 66, 67, 68, 69, 71, 72, 73, 74, 76, 77, 78, 79, 80, 81, 83, 84, 86, 87, 88, 90, 92, 93, 95, 96, 97, 99, 100, 101, 102, 107, 109, 110, 111, 113, 114, 115, 118, 120, 122, 124, 126, 134, 136, 142, 153, 172, 173 and 175 exhibited sensitivity of 100%, 100%, 100%, 75%, 93.8%, 75%, 87.5%, 75%, 93.8%, 68.8%, 81.2%, 100%, 75%, 50%, 75%, 75%, 68.8%, 75%, 81.2%, 81.2%, 75%, 62.5%, 75%, 56.2%, 75%, 68.8%, 56.2%, 62.5%, 68.8%, 75%, 68.8%, 68.8%, 56.2%, 68.8%, 62.5%, 68.8%, 62.5%, 50%, 56.2%, 56.2%, 56.2%, 75%, 50%, 68.8%, 68.8%, 68.8%, 50%, 56.2%, 62.5%, 62.5%, 50%, 62.5%, 68.8%, 56.2%, 56.2%, 43.8%, 75%, 62.5%, 62.5%, 56.2%, 62.5%, 62.5%, 56.2%, 62.5%, 56.2%, 56.2%, 56.2%, 56.2%, 56.2%, 43.8%, 43.8%, 50%, 68.8%, 56.2%, 62.5%, 62.5%, 43.8%, 62.5%, 56.2%, 62.5%, 62.5%, 50%, 56.2%, 43.8%, 50%, 43.8%, 50%, 43.8%, 56.2%, 43.8%, 50%, 50%, 50%, 50%, 50%, 50%, 43.8%, 50%, 43.8%, 50%, 50%, 50%, 43.8%, 43.8%, 50%, 43.8%, 43.8%, 50%, 81.2%, 68.8% and 56.2%, respectively in the validation cohort (Table 3). As seen from Comparative Example mentioned later, the existing markers CEA had sensitivity of 43.75% in the validation cohort (Tables 5-1 and 5-2), demonstrating that the 110 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 55, 56, 57, 58, 59, 60, 61, 62, 63, 65, 66, 67, 68, 69, 71, 72, 73, 74, 76, 77, 78, 79, 80, 81, 83, 84, 86, 87, 88, 90, 92, 93, 95, 96, 97, 99, 100, 101, 102, 107, 109, 110, 111, 113, 114, 115, 118, 120, 122, 124, 126, 134, 136, 142, 153, 172, 173 and 175 can discriminate, each alone, colorectal cancer in the validation cohort with sensitivity beyond CEA.

For example, 14 polynucleotides consisting of the nucleotide sequences represented by SEQ ID NOs: 1, 2, 3, 10, 14, 17, 21, 23, 32, 36, 47, 59, 65, and 101 were able to correctly determine colorectal cancer as to all of three stage 1 colorectal cancer samples that were contained in the validation cohort. Thus, these polynucleotides can detect even early colorectal cancer and contribute to the early diagnosis of colorectal cancer.

For example, 12 polynucleotides consisting of the nucleotide sequences represented by SEQ ID NOs: 1, 2, 3, 5, 7, 10, 14, 39, 46, 73, 81, and 148 were able to correctly determine colorectal cancer as to all of one cecal cancer case and 3 ascending colon cancer cases, which were cancer cases in the upper large intestine that are reportedly difficult to detect by the fecal occult blood test, in the validation cohort. Thus, these polynucleotides can detect colorectal cancer regardless of where colorectal cancer develops.

Example 2

<Method for Evaluating Colorectal Cancer Discriminant Performance by Combination of Multiple Gene Markers Using Samples in the Validation Cohort>

In this Example, a method for evaluating colorectal cancer discriminant performance by a combination of the gene markers selected in Example 1 was studied. Specifically, Fisher's discriminant analysis was conducted as to 16,074 combinations of two polynucleotides comprising at least one or more of the expression level measurement values of the newly found polynucleotides consisting of the nucleotide sequences represented by SEQ ID NOs: 1 to 171 among the polynucleotides consisting of the nucleotide sequences represented by SEQ ID NOs: 1 to 180 selected in Example 1, to construct a discriminant for determining the presence or absence of colorectal cancer. Next, accuracy, sensitivity, and specificity in the validation cohort were calculated using the discriminant thus prepared, and the discriminant performance of the selected polynucleotides was validated using independent samples.

Figure 3:
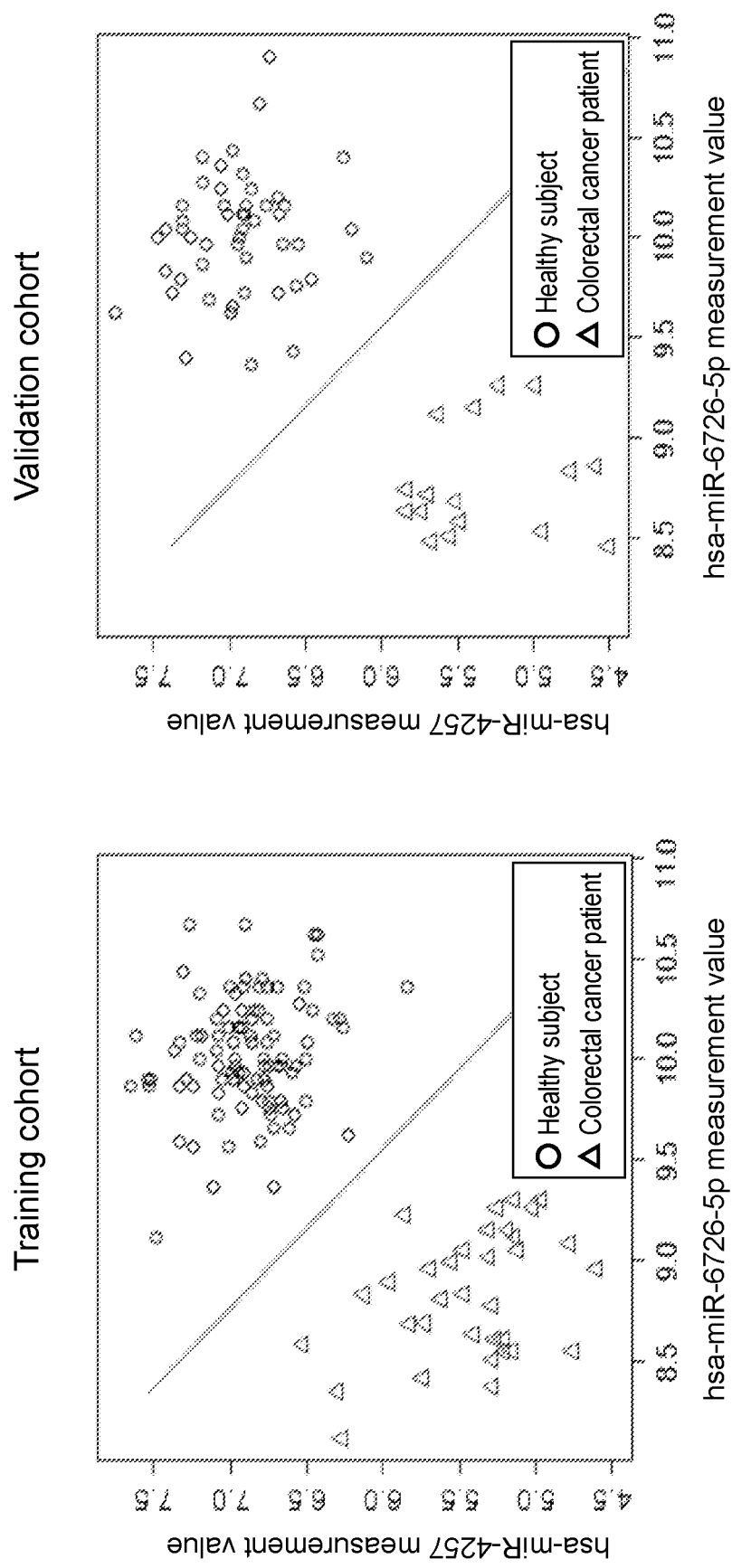
FIG. 3 Left diagram: the expression level measurement values of hsa-miR-6726-5p (SEQ ID NO: 1) in healthy subjects (100 persons, circles) and colorectal cancer patients (34 persons, triangles) selected as a training cohort were each plotted on the abscissa against their expression level measurement values of hsa-miR-4257 (SEQ ID NO: 2) on the ordinate. The line in the diagram depicts a discriminant function (0=1.26x+y−18.06) that was optimized by Fisher's discriminant analysis and discriminated between the two groups. Right diagram: the expression level measurement values of hsa-miR-6726-5p (SEQ ID NO: 1) in healthy subjects (50 persons, circles) and colorectal cancer patients (16 persons, triangles) selected as a validation cohort were each plotted on the abscissa against their expression level measurement values of hsa-miR-4257 (SEQ ID NO: 2) on the ordinate. The line in the diagram depicts the threshold (0=1.26x+y−18.06) that was set in the training cohort and discriminated between the two groups.

For example, the expression level measurement values of the nucleotide sequences represented by SEQ ID NO: 1 and SEQ ID NO: 2 were compared between the healthy subjects (100 persons) and the colorectal cancer patients (34 persons) in the training cohort. As a result, a scatter diagram that significantly separated the gene expression level measurement values of the colorectal cancer patient group from those of the healthy subject group was obtained (see the left diagram of FIG. 3). These results were also reproducible for the healthy subjects (50 persons) and the colorectal cancer patients (16 persons) in the validation cohort (see the right diagram of FIG. 3). Likewise, a scatter diagram that significantly separated the gene expression level measurement values of the colorectal cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 171 among the polynucleotides consisting of the nucleotide sequences represented by SEQ ID NOs: 1 to 180. These results were able to be validated in the validation cohort. For example, as for these nucleotide sequences represented by SEQ ID NO: 1 and SEQ ID NO: 2, the number of samples that correctly identified in the detection of colorectal cancer was calculated using the function (0=1.26x+y−18.06) that was set in the training cohort and discriminated between the two groups. As a result, 16 true positives, 50 true negatives, 0 false positives, and 0 false negatives were obtained. From these values, 100% accuracy, 100% sensitivity, and 100% specificity were obtained as detection performance. In this way, the detection performance was calculated as to all of the combinations of two expression level measurement values comprising at least one or more of the expression level measurement values of the newly found polynucleotides consisting of the nucleotide sequences represented by SEQ ID NOs: 1 to 171 among the polynucleotides consisting of the nucleotide sequences represented by SEQ ID NOs: 1 to 180. Among them, 179 combinations comprising the expression level measurement value of the polynucleotide consisting of the nucleotide sequence represented by SEQ ID NO: 1 and the detection performance thereof were described in Table 6 as an example. For example, all of combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 100% in the validation cohort (Table 6). Further, combinations of two polynucleotides consisting of nucleotide sequences other than SEQ ID NO: 1 were described in Table 7 as an example.

As specific combinations of two polynucleotides, for example, combinations represented by SEQ ID NOs: 5 and 6, SEQ ID NOs: 5 and 11, SEQ ID NOs: 5 and 38, SEQ ID NOs: 15 and 16, SEQ ID NOs: 15 and 21, SEQ ID NOs: 15 and 64, SEQ ID NOs: 24 and 25, SEQ ID NOs: 24 and 30, SEQ ID NOs: 24 and 32, SEQ ID NOs: 2 and 32, SEQ ID NOs: 32 and 36, SEQ ID NOs: 15 and 32, SEQ ID NOs: 3 and 38, SEQ ID NOs: 38 and 39, SEQ ID NOs: 38 and 64, SEQ ID NOs: 3 and 45, SEQ ID NOs: 45 and 58, SEQ ID NOs: 45 and 64, SEQ ID NOs: 2 and 55, SEQ ID NOs: 6 and 55, SEQ ID NOs: 55 and 64, SEQ ID NOs: 2 and 64, SEQ ID NOs: 4 and 64, SEQ ID NOs: 2 and 96, SEQ ID NOs: 7 and 96, SEQ ID NOs: 96 and 97, SEQ ID NOs: 2 and 97, SEQ ID NOs: 3 and 97, SEQ ID NOs: 5 and 97, SEQ ID NOs: 2 and 162, SEQ ID NOs: 3 and 162, and SEQ ID NOs: 5 and 162, exhibited accuracy of 75% or higher for discriminating the colorectal cancer patients from the healthy subjects in both of the training cohort and the validation cohort. In this way, 14,598 combinations of the expression level measurement values of two polynucleotides that have sensitivity beyond the existing marker CEA (43.8% in Table 5-2) were obtained in the validation cohort. All of the nucleotide sequences 1 to 180 described in Table 2 obtained in Example 1 were employed at least once in these combinations. These results demonstrated that the combined use of two of the polynucleotides consisting of the nucleotide sequences represented by SEQ ID NOs: 1 to 180 can also discriminate colorectal cancer with excellent, performance beyond the existing marker.

Markers for the detection of colorectal cancer with better sensitivity are obtained by combining 3, 4, 5, 6, 7, 8, 9, 10 or more of the expression level measurement values of the polynucleotides consisting of the nucleotide sequences represented by SEQ ID NOs: 1 to 180. For example, the newly found polynucleotides consisting of the nucleotide sequences represented by SEQ ID NOs: 1 to 171 among the polynucleotides consisting of the nucleotide sequences represented by SEQ ID NOs: 1 to 180 selected in Example 1 were measured to obtain their expression levels between the healthy subject group and the colorectal cancer group in the validation cohort. All of the polynucleotides were ranked in the descending order of their P values obtained by the Student's t-test, which indicates statistical significance of difference between groups (i.e., one having the lowest P value was ranked in the first place), and colorectal cancer detection sensitivity was evaluated using combinations of one or more polynucleotides to which the polynucleotides were added to the combination one by one from the top to the bottom according to the rank. In short, the order in which the polynucleotides were combined in this evaluation is in reverse in terms of SEQ ID NOs, from SEQ ID NO: 171 to SEQ ID NOs: 170, 169, . . . as shown in Table 2. As a result, the sensitivity in the validation cohort was 12.5% for 1 polynucleotide (SEQ ID NO: 171), 18.8% for 2 polynucleotides (SEQ ID NOs: 170 and 171), 25.0% for 4 polynucleotides (SEQ ID NOs: 168 to 171), 31.2% for 5 polynucleotides (SEQ ID NOs: 167 to 171), 37.5% for 7 polynucleotides (SEQ ID NOs: 165 to 171), 87.5% for 10 polynucleotides (SEQ ID NOs: 162 to 171), 100% for 20 polynucleotides (SEQ ID NOs: 152 to 171), 100% for 30 polynucleotides (SEQ ID NOs: 142 to 171), 100% for 80 polynucleotides (SEQ ID NOs: 92 to 171), 100% for 170 polynucleotides (SEQ ID NOs: 2 to 171), and 100% for 171 polynucleotides (SEQ ID NOs: 1 to 171).

These results demonstrated that a combination of multiple polynucleotides can produce higher colorectal cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of colorectal cancer.

From these results, it can be concluded that all of the polynucleotides consisting of the nucleotide sequences represented by SEQ ID NOs: 1 to 180 serve as excellent markers for the detection of colorectal cancer.

TABLE 2

| SEQ ID NO: | Gene name | P value after Bonferroni correction | Expression level in colorectal cancer patient with respect to healthy subject |
|---|---|---|---|
| 1 | hsa-miR-6726-5p | 5.20.E−41 | − |
| 2 | hsa-miR-4257 | 7.54.E−40 | − |
| 3 | hsa-miR-6787-5p | 1.72.E−30 | − |
| 4 | hsa-miR-6780b-5p | 3.42.E−30 | + |
| 5 | hsa-miR-3131 | 1.62.E−27 | − |
| 6 | hsa-miR-7108-5p | 5.42.E−27 | + |
| 7 | hsa-miR-1343-3p | 2.12.E−26 | − |
| 8 | hsa-miR-1247-3p | 9.98.E−26 | + |
| 9 | hsa-miR-4651 | 3.90.E−24 | − |
| 10 | hsa-miR-6757-5p | 2.25.E−23 | − |
| 11 | hsa-miR-3679-5p | 2.55.E−23 | + |
| 12 | hsa-miR-7641 | 9.71.E−22 | − |
| 13 | hsa-miR-6746-5p | 1.64.E−21 | − |
| 14 | hsa-miR-8072 | 4.09.E−21 | + |
| 15 | hsa-miR-6741-5p | 7.23.E−21 | − |
| 16 | hsa-miR-1908-5p | 2.12.E−20 | + |
| 17 | hsa-miR-6857-5p | 2.70.E−20 | + |
| 18 | hsa-miR-4746-3p | 3.58.E−20 | + |
| 19 | hsa-miR-744-5p | 4.23.E−20 | + |
| 20 | hsa-miR-4792 | 8.25.E−20 | + |
| 21 | hsa-miR-564 | 1.78.E−19 | − |
| 22 | hsa-miR-6791-5p | 3.80.E−19 | + |
| 23 | hsa-miR-6825-5p | 5.93.E−19 | + |
| 24 | hsa-miR-6826-5p | 8.67.E−19 | − |
| 25 | hsa-miR-4665-3p | 1.92.E−18 | + |
| 26 | hsa-miR-4467 | 5.55.E−18 | + |
| 27 | hsa-miR-3188 | 8.48.E−18 | + |
| 28 | hsa-miR-6125 | 1.09.E−17 | + |
| 29 | hsa-miR-6756-5p | 1.24.E−17 | − |
| 30 | hsa-miR-1228-3p | 1.68.E−17 | + |
| 31 | hsa-miR-8063 | 2.70.E−17 | − |
| 32 | hsa-miR-8069 | 3.58.E−17 | + |
| 33 | hsa-miR-6875-5p | 6.07.E−17 | + |
| 34 | hsa-miR-3185 | 5.07.E−16 | + |
| 35 | hsa-miR-4433b-3p | 1.22.E−15 | + |
| 36 | hsa-miR-6887-5p | 1.30.E−15 | − |
| 37 | hsa-miR-128-1-5p | 3.61.E−15 | + |
| 38 | hsa-miR-6724-5p | 3.81.E−15 | + |
| 39 | hsa-miR-1914-3p | 1.05.E−14 | − |
| 40 | hsa-miR-1225-5p | 3.93.E−14 | + |
| 41 | hsa-miR-4419b | 5.90.E−14 | − |
| 42 | hsa-miR-7110-5p | 6.01.E−14 | + |
| 43 | hsa-miR-187-5p | 8.57.E−14 | − |
| 44 | hsa-miR-3184-5p | 1.40.E−13 | + |
| 45 | hsa-miR-204-3p | 2.23.E−13 | − |
| 46 | hsa-miR-5572 | 2.34.E−13 | + |
| 47 | hsa-miR-6729-5p | 3.33.E−13 | + |
| 48 | hsa-miR-615-5p | 4.27.E−13 | − |
| 49 | hsa-miR-6749-5p | 5.30.E−13 | − |
| 50 | hsa-miR-6515-3p | 7.31.E−13 | + |
| 51 | hsa-miR-3937 | 8.10.E−13 | + |
| 52 | hsa-miR-6840-3p | 1.15.E−12 | − |
| 53 | hsa-miR-6893-5p | 1.34.E−12 | − |
| 54 | hsa-miR-4728-5p | 2.48.E−12 | − |
| 55 | hsa-miR-6717-5p | 4.45.E−12 | − |
| 56 | hsa-miR-7113-3p | 5.11.E−12 | + |
| 57 | hsa-miR-4665-5p | 5.33.E−12 | − |
| 58 | hsa-miR-642b-3p | 6.74.E−12 | − |
| 59 | hsa-miR-7109-5p | 6.88.E−12 | − |
| 60 | hsa-miR-6842-5p | 6.91.E−12 | + |

TABLE 2-continued

| SEQ ID NO: | Gene name | P value after Bonferroni correction | Expression level in colorectal cancer patient with respect to healthy subject |
|---|---|---|---|
| 61 | hsa-miR-4442 | 8.87.E−12 | − |
| 62 | hsa-miR-4433-3p | 9.88.E−12 | + |
| 63 | hsa-miR-4707-5p | 1.19.E−11 | + |
| 64 | hsa-miR-6126 | 1.27.E−11 | + |
| 65 | hsa-miR-4449 | 1.32.E−11 | + |
| 66 | hsa-miR-4706 | 2.85.E−11 | − |
| 67 | hsa-miR-1913 | 3.15.E−11 | + |
| 68 | hsa-miR-602 | 4.98.E−11 | + |
| 69 | hsa-miR-939-5p | 6.08.E−11 | + |
| 70 | hsa-miR-4695-5p | 8.15.E−11 | + |
| 71 | hsa-miR-711 | 1.23.E−10 | + |
| 72 | hsa-miR-6816-5p | 1.29.E−10 | + |
| 73 | hsa-miR-4632-5p | 1.50.E−10 | + |
| 74 | hsa-miR-6721-5p | 1.98.E−10 | + |
| 75 | hsa-miR-7847-3p | 2.14.E−10 | − |
| 76 | hsa-miR-6132 | 2.68.E−10 | + |
| 77 | hsa-miR-887-3p | 2.81.E−10 | + |
| 78 | hsa-miR-3679-3p | 3.07.E−10 | + |
| 79 | hsa-miR-6784-5p | 3.20.E−10 | + |
| 80 | hsa-miR-1249 | 3.40.E−10 | + |
| 81 | hsa-miR-937-5p | 5.57.E−10 | − |
| 82 | hsa-miR-5195-3p | 6.88.E−10 | − |
| 83 | hsa-miR-6732-5p | 7.27.E−10 | + |
| 84 | hsa-miR-4417 | 7.95.E−10 | + |
| 85 | hsa-miR-4281 | 9.35.E−10 | − |
| 86 | hsa-miR-4734 | 1.04.E−09 | + |
| 87 | hsa-miR-6766-3p | 1.07.E−09 | + |
| 88 | hsa-miR-663a | 2.19.E−09 | + |
| 89 | hsa-miR-4513 | 3.03.E−09 | − |
| 90 | hsa-miR-6781-5p | 5.11.E−09 | + |
| 91 | hsa-miR-1227-5p | 6.16.E−09 | + |
| 92 | hsa-miR-6845-5p | 6.49.E−09 | + |
| 93 | hsa-miR-6798-5p | 8.99.E−09 | + |
| 94 | hsa-miR-3620-5p | 1.09.E−08 | + |
| 95 | hsa-miR-1915-5p | 1.78.E−08 | − |
| 96 | hsa-miR-4294 | 2.30.E−08 | − |
| 97 | hsa-miR-642a-3p | 2.61.E−08 | − |
| 98 | hsa-miR-371a-5p | 3.15.E−08 | − |
| 99 | hsa-miR-940 | 3.18.E−08 | + |
| 100 | hsa-miR-4450 | 3.25.E−08 | − |
| 101 | hsa-miR-4723-5p | 4.21.E−08 | − |
| 102 | hsa-miR-1469 | 4.26.E−08 | + |
| 103 | hsa-miR-6861-5p | 4.71.E−08 | − |
| 104 | hsa-miR-7975 | 7.28.E−08 | − |
| 105 | hsa-miR-6879-5p | 7.64.E−08 | + |
| 106 | hsa-miR-6802-5p | 9.22.E−08 | + |
| 107 | hsa-miR-1268b | 1.08.E−07 | + |
| 108 | hsa-miR-663b | 1.12.E−07 | − |
| 109 | hsa-miR-125a-3p | 1.16.E−07 | − |
| 110 | hsa-miR-2861 | 1.87.E−07 | − |
| 111 | hsa-miR-6088 | 2.97.E−07 | − |
| 112 | hsa-miR-4758-5p | 3.12.E−07 | − |
| 113 | hsa-miR-296-3p | 3.43.E−07 | − |
| 114 | hsa-miR-6738-5p | 4.05.E−07 | − |
| 115 | hsa-miR-671-5p | 5.76.E−07 | − |
| 116 | hsa-miR-4454 | 6.68.E−07 | − |
| 117 | hsa-miR-4516 | 1.04.E−06 | − |
| 118 | hsa-miR-7845-5p | 1.10.E−06 | + |
| 119 | hsa-miR-4741 | 1.52.E−06 | − |
| 120 | hsa-miR-92b-5p | 1.63.E−06 | + |
| 121 | hsa-miR-6795-5p | 2.31.E−06 | − |
| 122 | hsa-miR-6805-3p | 3.95.E−06 | + |
| 123 | hsa-miR-4725-3p | 5.35.E−06 | − |
| 124 | hsa-miR-6782-5p | 5.69.E−06 | + |
| 125 | hsa-miR-4688 | 8.95.E−06 | − |
| 126 | hsa-miR-6850-5p | 1.66.E−05 | + |
| 127 | hsa-miR-6777-5p | 1.74.E−05 | − |
| 128 | hsa-miR-6785-5p | 1.89.E−05 | − |
| 129 | hsa-miR-7106-5p | 1.94.E−05 | − |
| 130 | hsa-miR-3663-3p | 2.08.E−05 | − |
| 131 | hsa-miR-6131 | 2.29.E−05 | − |
| 132 | hsa-miR-1915-3p | 3.16.E−05 | + |
| 133 | hsa-miR-4532 | 3.46.E−05 | − |
| 134 | hsa-miR-6820-5p | 3.81.E−05 | − |
| 135 | hsa-miR-4689 | 4.54.E−05 | − |
| 136 | hsa-miR-4638-5p | 4.70.E−05 | − |
| 137 | hsa-miR-3656 | 5.75.E−05 | + |
| 138 | hsa-miR-3621 | 6.34.E−05 | − |
| 139 | hsa-miR-6769b-5p | 6.63.E−05 | − |
| 140 | hsa-miR-149-3p | 1.01.E−04 | − |
| 141 | hsa-miR-23b-3p | 1.11.E−04 | − |
| 142 | hsa-miR-3135b | 1.16.E−04 | − |
| 143 | hsa-miR-6848-5p | 1.17.E−04 | + |
| 144 | hsa-miR-6769a-5p | 1.23.E−04 | − |
| 145 | hsa-miR-4327 | 1.40.E−04 | + |
| 146 | hsa-miR-6765-3p | 1.50.E−04 | − |
| 147 | hsa-miR-6716-5p | 1.51.E−04 | + |
| 148 | hsa-miR-6877-5p | 1.52.E−04 | − |
| 149 | hsa-miR-6727-5p | 2.04.E−04 | − |
| 150 | hsa-miR-4534 | 2.10.E−04 | − |
| 151 | hsa-miR-614 | 3.18.E−04 | − |
| 152 | hsa-miR-1202 | 4.86.E−04 | − |
| 153 | hsa-miR-575 | 4.92.E−04 | − |
| 154 | hsa-miR-6870-5p | 5.55.E−04 | + |
| 155 | hsa-miR-6722-3p | 7.07.E−04 | + |
| 156 | hsa-miR-7977 | 7.17.E−04 | − |
| 157 | hsa-miR-4649-5p | 7.70.E−04 | − |
| 158 | hsa-miR-4675 | 9.21.E−04 | − |
| 159 | hsa-miR-6075 | 1.03.E−03 | + |
| 160 | hsa-miR-6779-5p | 1.04.E−03 | − |
| 161 | hsa-miR-4271 | 1.43.E−03 | − |
| 162 | hsa-miR-3196 | 1.45.E−03 | + |
| 163 | hsa-miR-6803-5p | 1.46.E−03 | + |
| 164 | hsa-miR-6789-5p | 1.71.E−03 | + |
| 165 | hsa-miR-4648 | 1.90.E−03 | + |
| 166 | hsa-miR-4508 | 3.41.E−03 | + |
| 167 | hsa-miR-4749-5p | 3.52.E−03 | + |
| 168 | hsa-miR-4505 | 4.01.E−03 | + |
| 169 | hsa-miR-5698 | 4.99.E−03 | − |
| 170 | hsa-miR-1199-5p | 5.88.E−03 | − |
| 171 | hsa-miR-4763-3p | 8.40.E−03 | + |
| 172 | hsa-miR-1231 | 7.36.E−25 | + |
| 173 | hsa-miR-1233-5p | 1.21.E−22 | − |
| 174 | hsa-miR-150-3p | 5.76.E−07 | − |
| 175 | hsa-miR-1225-3p | 1.44.E−06 | + |
| 176 | hsa-miR-92a-2-5p | 2.36.E−05 | + |
| 177 | hsa-miR-423-5p | 4.62.E−05 | − |
| 178 | hsa-miR-1268a | 4.30.E−04 | + |
| 179 | hsa-miR-128-2-5p | 6.64.E−04 | − |
| 180 | hsa-miR-24-3p | 1.31.E−03 | − |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 99.3 | 100 | 99 | 100 | 100 | 100 |
| 2 | 96.3 | 88.2 | 99 | 100 | 100 | 100 |
| 3 | 96.3 | 91.2 | 98 | 98.5 | 100 | 98 |
| 4 | 93.3 | 85.3 | 96 | 93.9 | 75 | 100 |
| 5 | 97 | 91.2 | 99 | 97 | 93.8 | 98 |
| 6 | 94 | 82.4 | 98 | 90.9 | 75 | 96 |
| 7 | 96.3 | 88.2 | 99 | 95.5 | 87.5 | 98 |
| 8 | 92.5 | 82.4 | 96 | 89.4 | 75 | 94 |
| 9 | 93.3 | 85.3 | 96 | 97 | 93.8 | 98 |
| 10 | 91.8 | 79.4 | 96 | 92.4 | 68.8 | 100 |
| 11 | 94.8 | 91.2 | 96 | 95.5 | 81.2 | 100 |
| 12 | 90.3 | 82.4 | 93 | 97 | 100 | 96 |
| 13 | 89.6 | 79.4 | 93 | 90.9 | 75 | 96 |
| 14 | 91 | 73.5 | 97 | 80.3 | 50 | 90 |
| 15 | 94 | 79.4 | 99 | 89.4 | 75 | 94 |
| 16 | 88.1 | 73.5 | 93 | 89.4 | 75 | 94 |
| 17 | 91 | 85.3 | 93 | 87.9 | 68.8 | 94 |
| 18 | 91 | 79.4 | 95 | 92.4 | 75 | 98 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 19 | 90.3 | 76.5 | 95 | 93.9 | 81.2 | 98 |
| 20 | 91.8 | 88.2 | 93 | 92.4 | 81.2 | 96 |
| 21 | 87.3 | 58.8 | 97 | 92.4 | 75 | 98 |
| 22 | 88.1 | 73.5 | 93 | 89.4 | 62.5 | 98 |
| 23 | 87.3 | 79.4 | 90 | 87.9 | 75 | 92 |
| 24 | 90.3 | 67.6 | 98 | 89.4 | 56.2 | 100 |
| 25 | 89.6 | 67.6 | 97 | 84.8 | 75 | 88 |
| 26 | 83.6 | 70.6 | 88 | 89.4 | 68.8 | 96 |
| 27 | 91.8 | 76.5 | 97 | 87.9 | 56.2 | 98 |
| 28 | 91 | 82.4 | 94 | 87.9 | 62.5 | 96 |
| 29 | 88.8 | 67.6 | 96 | 83.3 | 68.8 | 88 |
| 30 | 91.8 | 85.3 | 94 | 86.4 | 75 | 90 |
| 31 | 87.3 | 79.4 | 90 | 87.9 | 68.8 | 94 |
| 32 | 87.3 | 64.7 | 95 | 89.4 | 68.8 | 96 |
| 33 | 91 | 79.4 | 95 | 80.3 | 56.2 | 88 |
| 34 | 89.6 | 76.5 | 94 | 89.4 | 68.8 | 96 |
| 35 | 89.6 | 79.4 | 93 | 78.8 | 62.5 | 84 |
| 36 | 88.1 | 55.9 | 99 | 92.4 | 68.8 | 100 |
| 37 | 85.1 | 61.8 | 93 | 80.3 | 62.5 | 86 |
| 38 | 86.6 | 70.6 | 92 | 78.8 | 50 | 88 |
| 39 | 88.1 | 70.6 | 94 | 81.8 | 56.2 | 90 |
| 40 | 91 | 76.5 | 96 | 84.8 | 56.2 | 94 |
| 41 | 86.6 | 58.8 | 96 | 87.9 | 56.2 | 98 |
| 42 | 84.3 | 64.7 | 91 | 86.4 | 75 | 90 |
| 43 | 84.3 | 52.9 | 95 | 86.4 | 50 | 98 |
| 44 | 87.3 | 70.6 | 93 | 87.9 | 68.8 | 94 |
| 45 | 87.3 | 61.8 | 96 | 77.3 | 68.8 | 80 |
| 46 | 83.6 | 70.6 | 88 | 84.8 | 68.8 | 90 |
| 47 | 86.6 | 52.9 | 98 | 86.4 | 50 | 98 |
| 48 | 88.8 | 58.8 | 99 | 81.8 | 31.2 | 98 |
| 49 | 87.3 | 61.8 | 96 | 87.9 | 56.2 | 98 |
| 50 | 86.6 | 73.5 | 91 | 77.3 | 62.5 | 82 |
| 51 | 86.6 | 64.7 | 94 | 87.9 | 62.5 | 96 |
| 52 | 84.3 | 52.9 | 95 | 84.8 | 50 | 96 |
| 53 | 88.8 | 64.7 | 97 | 87.9 | 62.5 | 96 |
| 54 | 81.3 | 50 | 92 | 77.3 | 31.2 | 92 |
| 55 | 88.8 | 58.8 | 99 | 90.9 | 68.8 | 98 |
| 56 | 84.2 | 66.7 | 90 | 83.3 | 56.2 | 92 |
| 57 | 84.3 | 58.8 | 93 | 80.3 | 56.2 | 88 |
| 58 | 85.1 | 50 | 97 | 86.4 | 43.8 | 100 |
| 59 | 82.8 | 55.9 | 92 | 89.4 | 75 | 94 |
| 60 | 87.3 | 64.7 | 95 | 87.9 | 62.5 | 96 |
| 61 | 81.3 | 52.9 | 91 | 84.8 | 62.5 | 92 |
| 62 | 82.8 | 67.6 | 88 | 80.3 | 56.2 | 88 |
| 63 | 82.1 | 55.9 | 91 | 84.8 | 62.5 | 92 |
| 64 | 78.4 | 38.2 | 92 | 83.3 | 37.5 | 98 |
| 65 | 86.6 | 61.8 | 95 | 87.9 | 62.5 | 96 |
| 66 | 85.1 | 58.8 | 94 | 84.8 | 56.2 | 94 |
| 67 | 83.6 | 61.8 | 91 | 80 | 62.5 | 85.7 |
| 68 | 85.1 | 61.8 | 93 | 84.8 | 56.2 | 94 |
| 69 | 80.6 | 64.7 | 86 | 80.3 | 56.2 | 88 |
| 70 | 81.3 | 52.9 | 91 | 78.8 | 31.2 | 94 |
| 71 | 85.1 | 58.8 | 94 | 87.9 | 56.2 | 98 |
| 72 | 83.6 | 64.7 | 90 | 83.3 | 56.2 | 92 |
| 73 | 87.3 | 55.9 | 98 | 84.8 | 43.8 | 98 |
| 74 | 83.6 | 64.7 | 90 | 77.3 | 43.8 | 88 |
| 75 | 82.7 | 33.3 | 99 | 84.8 | 37.5 | 100 |
| 76 | 83.6 | 44.1 | 97 | 86.4 | 50 | 98 |
| 77 | 85.8 | 73.5 | 90 | 83.3 | 68.8 | 88 |
| 78 | 83.6 | 52.9 | 94 | 81.8 | 56.2 | 90 |
| 79 | 83.6 | 67.6 | 89 | 81.8 | 62.5 | 88 |
| 80 | 85 | 58.8 | 93.9 | 83.3 | 62.5 | 90 |
| 81 | 84.3 | 50 | 96 | 83.3 | 43.8 | 96 |
| 82 | 81.3 | 44.1 | 94 | 81.8 | 37.5 | 96 |
| 83 | 82.1 | 61.8 | 89 | 78.8 | 62.5 | 84 |
| 84 | 90.3 | 70.6 | 97 | 84.8 | 56.2 | 94 |
| 85 | 83.6 | 55.9 | 93 | 80.3 | 31.2 | 96 |
| 86 | 80.6 | 41.2 | 94 | 86.4 | 62.5 | 94 |
| 87 | 83.6 | 50 | 95 | 83.3 | 62.5 | 90 |
| 88 | 84.3 | 52.9 | 95 | 83.3 | 50 | 94 |
| 89 | 84.3 | 44.1 | 98 | 77.3 | 12.5 | 98 |
| 90 | 82.8 | 50 | 94 | 81.8 | 56.2 | 90 |
| 91 | 79.9 | 38.2 | 94 | 75.8 | 31.2 | 90 |
| 92 | 84.3 | 50 | 96 | 78.8 | 43.8 | 90 |
| 93 | 82.8 | 61.8 | 90 | 75.8 | 50 | 84 |
| 94 | 84.3 | 55.9 | 94 | 77.3 | 31.2 | 92 |
| 95 | 82.1 | 41.2 | 96 | 83.3 | 43.8 | 96 |
| 96 | 85.1 | 55.9 | 95 | 81.8 | 50 | 92 |
| 97 | 78.4 | 38.2 | 92 | 78.8 | 43.8 | 90 |
| 98 | 82.8 | 50 | 94 | 75.8 | 37.5 | 88 |
| 99 | 81.3 | 47.1 | 93 | 86.4 | 56.2 | 96 |
| 100 | 85.1 | 47.1 | 98 | 83.3 | 43.8 | 96 |
| 101 | 87.3 | 58.8 | 97 | 83.3 | 50 | 94 |
| 102 | 80.6 | 38.2 | 95 | 80.3 | 50 | 90 |
| 103 | 83.6 | 47.1 | 96 | 80.3 | 37.5 | 94 |
| 104 | 79.1 | 35.3 | 94 | 78.8 | 37.5 | 92 |
| 105 | 82.8 | 38.2 | 98 | 84.8 | 37.5 | 100 |
| 106 | 82.8 | 44.1 | 96 | 81.8 | 37.5 | 96 |
| 107 | 74.6 | 32.4 | 89 | 75.8 | 50 | 84 |
| 108 | 83.6 | 47.1 | 96 | 83.3 | 31.2 | 100 |
| 109 | 85.1 | 44.1 | 99 | 87.9 | 50 | 100 |
| 110 | 82.8 | 52.9 | 93 | 84.8 | 50 | 96 |
| 111 | 78.4 | 44.1 | 90 | 81.8 | 50 | 92 |
| 112 | 84.3 | 44.1 | 98 | 80.3 | 25 | 98 |
| 113 | 82.8 | 50 | 94 | 80.3 | 43.8 | 92 |
| 114 | 82.8 | 52.9 | 93 | 83.3 | 50 | 94 |
| 115 | 82.1 | 44.1 | 95 | 84.8 | 43.8 | 98 |
| 116 | 79.9 | 41.2 | 93 | 77.3 | 31.2 | 92 |
| 117 | 87.3 | 50 | 100 | 84.8 | 37.5 | 100 |
| 118 | 88.1 | 58.8 | 98 | 81.8 | 50 | 92 |
| 119 | 78.4 | 29.4 | 95 | 77.3 | 25 | 94 |
| 120 | 78.4 | 41.2 | 91 | 84.8 | 50 | 96 |
| 121 | 80.6 | 26.5 | 99 | 80.3 | 18.8 | 100 |
| 122 | 77.6 | 38.2 | 91 | 83.3 | 50 | 94 |
| 123 | 76.1 | 26.5 | 93 | 74.2 | 12.5 | 94 |
| 124 | 83.6 | 44.1 | 97 | 83.3 | 43.8 | 96 |
| 125 | 77.6 | 35.3 | 92 | 74.2 | 18.8 | 92 |
| 126 | 80.6 | 41.2 | 94 | 78.8 | 43.8 | 90 |
| 127 | 79.1 | 23.5 | 98 | 83.3 | 31.2 | 100 |
| 128 | 80.6 | 38.2 | 95 | 80.3 | 31.2 | 96 |
| 129 | 78.4 | 23.5 | 97 | 80.3 | 25 | 98 |
| 130 | 78.4 | 29.4 | 95 | 80.3 | 31.2 | 96 |
| 131 | 81.3 | 35.3 | 97 | 83.3 | 37.5 | 98 |
| 132 | 80.6 | 35.3 | 96 | 80.3 | 25 | 98 |
| 133 | 82.8 | 44.1 | 96 | 80.3 | 37.5 | 94 |
| 134 | 83.6 | 41.2 | 98 | 83.3 | 50 | 94 |
| 135 | 79.9 | 29.4 | 97 | 81.8 | 25 | 100 |
| 136 | 83.6 | 41.2 | 98 | 86.4 | 43.8 | 100 |
| 137 | 79.9 | 38.2 | 94 | 77.3 | 12.5 | 98 |
| 138 | 76.1 | 26.5 | 93 | 77.3 | 25 | 94 |
| 139 | 79.1 | 26.5 | 97 | 78.8 | 18.8 | 98 |
| 140 | 76.9 | 23.5 | 95 | 77.3 | 25 | 94 |
| 141 | 79.1 | 26.5 | 97 | 75.8 | 18.8 | 94 |
| 142 | 83.6 | 38.2 | 99 | 86.4 | 43.8 | 100 |
| 143 | 77.6 | 26.5 | 95 | 78.8 | 25 | 96 |
| 144 | 74.6 | 17.6 | 94 | 80.3 | 31.2 | 96 |
| 145 | 79.1 | 41.2 | 92 | 75.8 | 25 | 92 |
| 146 | 78.4 | 32.4 | 94 | 80.3 | 31.2 | 96 |
| 147 | 79.1 | 29.4 | 96 | 77.3 | 31.2 | 92 |
| 148 | 73.9 | 20.6 | 92 | 71.2 | 6.2 | 92 |
| 149 | 79.1 | 38.2 | 93 | 81.8 | 31.2 | 98 |
| 150 | 78.4 | 23.5 | 97 | 74.2 | 25 | 90 |
| 151 | 76.1 | 32.4 | 91 | 77.3 | 25 | 94 |
| 152 | 81.3 | 29.4 | 99 | 81.8 | 25 | 100 |
| 153 | 82.1 | 29.4 | 100 | 87.9 | 50 | 100 |
| 154 | 81.3 | 35.3 | 97 | 84.8 | 37.5 | 100 |
| 155 | 79.1 | 29.4 | 96 | 78.8 | 31.2 | 94 |
| 156 | 78.9 | 24.2 | 97 | 77.3 | 25 | 94 |
| 157 | 79.9 | 29.4 | 97 | 83.3 | 31.2 | 100 |
| 158 | 80.6 | 35.3 | 96 | 84.8 | 37.5 | 100 |
| 159 | 82.1 | 35.3 | 98 | 81.8 | 31.2 | 98 |
| 160 | 78.4 | 20.6 | 98 | 81.8 | 31.2 | 98 |
| 161 | 78.4 | 26.5 | 96 | 81.8 | 25 | 100 |
| 162 | 79.1 | 29.4 | 96 | 77.3 | 18.8 | 96 |
| 163 | 74.6 | 26.5 | 91 | 63.6 | 0 | 84 |
| 164 | 76.1 | 20.6 | 95 | 71.2 | 12.5 | 90 |
| 165 | 77.6 | 23.5 | 96 | 81.8 | 25 | 100 |
| 166 | 78.4 | 29.4 | 95 | 69.7 | 6.2 | 90 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 167 | 78.4 | 14.7 | 100 | 75.8 | 0 | 100 |
| 168 | 78.2 | 21.2 | 97 | 78.8 | 12.5 | 100 |
| 169 | 78.4 | 23.5 | 97 | 77.3 | 6.2 | 100 |
| 170 | 73.9 | 2.9 | 98 | 77.3 | 6.2 | 100 |
| 171 | 80.6 | 26.5 | 99 | 78.8 | 12.5 | 100 |
| 172 | 93.3 | 85.3 | 96 | 90.9 | 81.2 | 94 |
| 173 | 91 | 76.5 | 96 | 90.9 | 68.8 | 98 |
| 174 | 82.1 | 35.3 | 98 | 77.3 | 31.2 | 92 |
| 175 | 87.3 | 52.9 | 99 | 89.4 | 56.2 | 100 |
| 176 | 74.6 | 29.4 | 90 | 78.8 | 37.5 | 92 |
| 177 | 79.9 | 35.3 | 95 | 69.7 | 12.5 | 88 |
| 178 | 73.9 | 17.6 | 93 | 71.2 | 6.2 | 92 |
| 179 | 81.3 | 32.4 | 98 | 84.8 | 37.5 | 100 |
| 180 | 76.9 | 11.8 | 99 | 81.8 | 25 | 100 |

TABLE 4

| SEQ ID NO: | Discriminant coefficient | Constant term |
|---|---|---|
| 1 | 3.451 | 32.537 |
| 2 | 2.778 | 17.111 |
| 3 | 3.893 | 32.032 |
| 4 | 3.208 | 29.340 |
| 5 | 2.408 | 15.716 |
| 6 | 4.760 | 44.132 |
| 7 | 1.872 | 13.040 |
| 8 | 4.189 | 26.554 |
| 9 | 5.692 | 61.192 |
| 10 | 2.915 | 20.140 |
| 11 | 2.801 | 19.585 |
| 12 | 1.247 | 8.323 |
| 13 | 3.434 | 21.316 |
| 14 | 5.315 | 65.956 |
| 15 | 3.971 | 26.352 |
| 16 | 4.335 | 50.272 |
| 17 | 1.843 | 9.956 |
| 18 | 2.796 | 18.550 |
| 19 | 2.726 | 19.273 |
| 20 | 2.151 | 14.586 |
| 21 | 1.432 | 7.567 |
| 22 | 4.810 | 44.500 |
| 23 | 2.202 | 14.554 |
| 24 | 1.787 | 9.999 |
| 25 | 4.048 | 23.773 |
| 26 | 2.353 | 23.473 |
| 27 | 3.139 | 19.203 |
| 28 | 5.364 | 64.417 |
| 29 | 5.274 | 42.891 |
| 30 | 4.406 | 27.813 |
| 31 | 2.590 | 20.814 |
| 32 | 6.586 | 84.911 |
| 33 | 3.426 | 31.099 |
| 34 | 2.365 | 16.821 |
| 35 | 3.810 | 30.817 |
| 36 | 2.245 | 13.547 |
| 37 | 2.667 | 20.060 |
| 38 | 4.817 | 48.162 |
| 39 | 4.582 | 33.609 |
| 40 | 3.409 | 25.092 |
| 41 | 2.180 | 12.620 |
| 42 | 1.846 | 14.493 |
| 43 | 2.092 | 20.352 |
| 44 | 2.237 | 18.151 |
| 45 | 1.808 | 22.979 |
| 46 | 2.361 | 15.747 |
| 47 | 8.658 | 108.735 |
| 48 | 1.910 | 11.860 |
| 49 | 4.384 | 43.382 |
| 50 | 4.476 | 30.075 |
| 51 | 4.069 | 35.285 |
| 52 | 2.888 | 24.905 |
| 53 | 2.016 | 16.544 |
| 54 | 4.690 | 32.139 |
| 55 | 2.207 | 13.044 |
| 56 | 3.152 | 18.319 |
| 57 | 3.384 | 31.679 |
| 58 | 2.167 | 19.956 |
| 59 | 5.078 | 36.907 |
| 60 | 3.628 | 21.525 |
| 61 | 3.373 | 31.520 |
| 62 | 3.836 | 28.118 |
| 63 | 4.332 | 31.744 |
| 64 | 2.949 | 32.215 |
| 65 | 3.709 | 24.031 |
| 66 | 3.738 | 28.272 |
| 67 | 3.638 | 22.448 |
| 68 | 3.013 | 19.232 |
| 69 | 2.461 | 18.582 |
| 70 | 4.311 | 32.255 |
| 71 | 3.548 | 29.298 |
| 72 | 4.499 | 45.352 |
| 73 | 4.079 | 32.445 |
| 74 | 3.995 | 30.128 |
| 75 | 2.483 | 15.148 |
| 76 | 3.479 | 27.463 |
| 77 | 2.342 | 16.975 |
| 78 | 3.352 | 20.098 |
| 79 | 3.684 | 46.309 |
| 80 | 3.835 | 22.808 |
| 81 | 3.983 | 32.779 |
| 82 | 2.904 | 19.401 |
| 83 | 3.426 | 29.138 |
| 84 | 5.296 | 43.216 |
| 85 | 3.793 | 43.429 |
| 86 | 5.582 | 66.478 |
| 87 | 3.815 | 22.562 |
| 88 | 4.509 | 45.905 |
| 89 | 2.269 | 12.804 |
| 90 | 5.547 | 57.838 |
| 91 | 6.325 | 60.270 |
| 92 | 3.946 | 37.787 |
| 93 | 2.967 | 30.962 |
| 94 | 3.865 | 30.606 |
| 95 | 1.266 | 7.550 |
| 96 | 2.410 | 24.206 |
| 97 | 2.733 | 20.281 |
| 98 | 3.561 | 25.772 |
| 99 | 3.064 | 19.551 |
| 100 | 1.188 | 6.373 |
| 101 | 2.565 | 22.283 |
| 102 | 5.084 | 51.748 |
| 103 | 3.700 | 26.315 |
| 104 | 2.224 | 21.832 |
| 105 | 3.135 | 25.894 |
| 106 | 4.526 | 37.574 |
| 107 | 3.166 | 31.384 |
| 108 | 2.839 | 24.460 |
| 109 | 1.007 | 6.029 |
| 110 | 5.545 | 68.155 |
| 111 | 3.299 | 33.145 |
| 112 | 6.271 | 53.263 |
| 113 | 2.148 | 12.402 |
| 114 | 3.608 | 25.322 |
| 115 | 2.758 | 17.059 |
| 116 | 2.175 | 25.025 |
| 117 | 3.823 | 49.903 |
| 118 | 2.725 | 18.024 |
| 119 | 3.890 | 38.378 |
| 120 | 3.506 | 27.825 |
| 121 | 2.582 | 15.075 |
| 122 | 2.476 | 18.382 |
| 123 | 4.084 | 39.823 |
| 124 | 2.978 | 18.190 |
| 125 | 3.980 | 27.914 |
| 126 | 5.916 | 67.040 |
| 127 | 2.075 | 13.104 |
| 128 | 2.317 | 20.667 |

TABLE 4-continued

| SEQ ID NO: | Discriminant coefficient | Constant term |
|---|---|---|
| 129 | 2.093 | 12.035 |
| 130 | 4.219 | 50.899 |
| 131 | 1.841 | 19.246 |
| 132 | 3.960 | 43.646 |
| 133 | 3.277 | 38.660 |
| 134 | 2.733 | 19.515 |
| 135 | 3.239 | 30.244 |
| 136 | 1.482 | 8.655 |
| 137 | 4.554 | 52.325 |
| 138 | 5.175 | 61.317 |
| 139 | 3.430 | 21.115 |
| 140 | 5.430 | 50.527 |
| 141 | 1.168 | 6.718 |
| 142 | 2.311 | 17.824 |
| 143 | 4.599 | 33.779 |
| 144 | 3.921 | 24.668 |
| 145 | 4.968 | 43.118 |
| 146 | 1.700 | 14.753 |
| 147 | 3.593 | 23.332 |
| 148 | 4.307 | 30.486 |
| 149 | 6.087 | 77.329 |
| 150 | 2.704 | 17.759 |
| 151 | 1.757 | 11.661 |
| 152 | 2.635 | 16.886 |
| 153 | 1.214 | 6.968 |
| 154 | 3.201 | 23.463 |
| 155 | 6.593 | 55.857 |
| 156 | 2.177 | 21.212 |
| 157 | 2.411 | 24.700 |
| 158 | 2.636 | 19.709 |
| 159 | 3.045 | 25.772 |
| 160 | 5.593 | 39.283 |
| 161 | 3.606 | 29.381 |
| 162 | 6.360 | 76.890 |
| 163 | 6.727 | 74.567 |
| 164 | 4.350 | 42.883 |
| 165 | 1.256 | 7.389 |
| 166 | 6.503 | 84.138 |
| 167 | 3.665 | 29.142 |
| 168 | 4.233 | 35.592 |
| 169 | 1.766 | 10.169 |
| 170 | 1.955 | 12.693 |
| 171 | 3.328 | 27.665 |
| 172 | 3.674 | 24.498 |
| 173 | 2.869 | 31.161 |
| 174 | 1.758 | 11.388 |
| 175 | 2.132 | 11.850 |
| 176 | 2.148 | 20.104 |
| 177 | 2.169 | 15.443 |
| 178 | 3.124 | 34.907 |
| 179 | 2.552 | 27.422 |
| 180 | 1.417 | 8.536 |

TABLE 5-1

| Training cohort | | | |
|---|---|---|---|
| Sample name | Cancer stage | CEA(ng/mL) | CA19-9(U/mL) |
| CC03 | I | 1.6 | 13.5 |
| CC04 | I | 2 | 30.6 |
| CC05 | I | 1.3 | 3.2 |
| CC06 | I | 1.7 | 13.5 |
| CC07 | IIIA | 4.4 | 0.1 |
| CC09 | IIIB | 0.9 | 4.4 |
| CC10 | I | 1.5 | 13.2 |
| CC12 | I | 0.9 | 13.2 |
| CC13 | I | 0.8 | 3.1 |
| CC15 | I | 1.6 | 5.6 |
| CC17 | IIIA | 2.7 | 21.7 |
| CC18 | I | 3.2 | 16.4 |
| CC19 | IVL | 6.2 | 45.9 |
| CC20 | IIIC | 9.4 | 5.4 |
| CC23 | I | 2.3 | 7.9 |
| CC24 | IIA | 8.8 | 106.7 |
| CC25 | IIA | 6.2 | 29.6 |
| CC26 | I | 4.5 | 18.6 |
| CC27 | IIIC | 17.3 | 14.4 |
| CC29 | IIA | 2.1 | 6.9 |
| CC30 | IIIA | 3.2 | 13.2 |
| CC31 | IIIB | 6 | 5.7 |
| CC32 | IIIA | 2.4 | 26.7 |
| CC34 | I | 0.6 | 9.3 |
| CC36 | I | 6.7 | 0.1 |
| CC38 | IIA | 1.2 | 6.1 |
| CC40 | IIIB | 2.1 | 7.6 |
| CC41 | I | 2.8 | 10.6 |
| CC42 | IIIB | 46.7 | 3524 |
| CC45 | I | 2.2 | 38.4 |
| CC47 | IIIB | 1.7 | 7.1 |
| CC48 | IIA | 2 | 19.1 |
| CC49 | IIIB | 0.9 | 8.1 |
| CC50 | IIA | 7.6 | 12.2 |
| Sensitivity | | 26.5% | 12% |

TABLE 5-2

| Validation cohort | | | |
|---|---|---|---|
| Sample name | Cancer stage | CEA(ng/mL) | CA19-9(U/mL) |
| CC01 | I | 2.2 | 13.9 |
| CC02 | I | 3.9 | 16 |
| CC08 | IVH | 15.4 | 9.5 |
| CC11 | IIIC | 7.2 | 8 |
| CC14 | I | 0.6 | 14 |
| CC16 | IVL | 10.1 | 106.7 |
| CC21 | IIIB | 6.7 | 23.6 |
| CC22 | IIIC | 2.9 | 42.4 |
| CC28 | IIIB | 35.5 | 71 |
| CC33 | IIB | 5 | — |
| CC35 | IVH | 20.3 | 552 |
| CC37 | IIA | 0.1 | 8.1 |
| CC39 | IVHLu | 267.7 | 269.6 |
| CC43 | IIA | 2 | 10.3 |
| CC44 | IIA | 3.7 | 14 |
| CC46 | IIA | 1.7 | 4.2 |
| Sensitivity | | 43.8% | 31% |

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 100 | 100 | 100 | 100 | 100 | 100 |
| 1_3 | 99.3 | 97.1 | 100 | 100 | 100 | 100 |
| 1_4 | 100 | 100 | 100 | 100 | 100 | 100 |
| 1_5 | 100 | 100 | 100 | 100 | 100 | 100 |
| 1_6 | 100 | 100 | 100 | 100 | 100 | 100 |
| 1_7 | 100 | 100 | 100 | 100 | 100 | 100 |
| 1_8 | 100 | 100 | 100 | 100 | 100 | 100 |
| 1_9 | 98.5 | 100 | 98 | 98.5 | 100 | 98 |
| 1_10 | 100 | 100 | 100 | 100 | 100 | 100 |
| 1_11 | 99.3 | 100 | 99 | 100 | 100 | 100 |
| 1_12 | 99.3 | 100 | 99 | 98.5 | 100 | 98 |
| 1_13 | 99.3 | 100 | 99 | 100 | 100 | 100 |
| 1_14 | 100 | 100 | 100 | 98.5 | 100 | 98 |
| 1_15 | 99.3 | 97.1 | 100 | 97 | 100 | 96 |
| 1_16 | 100 | 100 | 100 | 100 | 100 | 100 |
| 1_17 | 97.8 | 94.1 | 99 | 100 | 100 | 100 |
| 1_18 | 99.3 | 100 | 99 | 100 | 100 | 100 |
| 1_19 | 98.5 | 100 | 98 | 100 | 100 | 100 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_20 | 100 | 100 | 100 | 100 | 100 | 100 |
| 1_21 | 99.3 | 100 | 99 | 100 | 100 | 100 |
| 1_22 | 98.5 | 97.1 | 99 | 100 | 100 | 100 |
| 1_23 | 99.3 | 100 | 99 | 100 | 100 | 100 |
| 1_24 | 98.5 | 94.1 | 100 | 100 | 100 | 100 |
| 1_25 | 99.3 | 100 | 99 | 98.5 | 100 | 98 |
| 1_26 | 99.3 | 100 | 99 | 100 | 100 | 100 |
| 1_27 | 98.5 | 94.1 | 100 | 100 | 100 | 100 |
| 1_28 | 100 | 100 | 100 | 98.5 | 100 | 98 |
| 1_29 | 98.5 | 97.1 | 99 | 100 | 100 | 100 |
| 1_30 | 100 | 100 | 100 | 100 | 100 | 100 |
| 1_31 | 98.5 | 97.1 | 99 | 100 | 100 | 100 |
| 1_32 | 99.3 | 100 | 99 | 98.5 | 100 | 98 |
| 1_33 | 98.5 | 97.1 | 99 | 100 | 100 | 100 |
| 1_34 | 97.8 | 97.1 | 98 | 100 | 100 | 100 |
| 1_35 | 98.5 | 97.1 | 99 | 98.5 | 100 | 98 |
| 1_36 | 100 | 100 | 100 | 100 | 100 | 100 |
| 1_37 | 97.8 | 97.1 | 98 | 98.5 | 100 | 98 |
| 1_38 | 98.5 | 97.1 | 99 | 100 | 100 | 100 |
| 1_39 | 99.3 | 97.1 | 100 | 100 | 100 | 100 |
| 1_40 | 97.8 | 97.1 | 98 | 100 | 100 | 100 |
| 1_41 | 99.3 | 100 | 99 | 100 | 100 | 100 |
| 1_42 | 98.5 | 100 | 98 | 98.5 | 100 | 98 |
| 1_43 | 100 | 100 | 100 | 100 | 100 | 100 |
| 1_44 | 97.8 | 97.1 | 98 | 100 | 100 | 100 |
| 1_45 | 98.5 | 100 | 98 | 100 | 100 | 100 |
| 1_46 | 98.5 | 100 | 98 | 100 | 100 | 100 |
| 1_47 | 100 | 100 | 100 | 98.5 | 100 | 98 |
| 1_48 | 99.3 | 100 | 99 | 100 | 100 | 100 |
| 1_49 | 97.8 | 97.1 | 98 | 98.5 | 100 | 98 |
| 1_50 | 100 | 100 | 100 | 98.5 | 100 | 98 |
| 1_51 | 98.5 | 97.1 | 99 | 100 | 100 | 100 |
| 1_52 | 97.8 | 94.1 | 99 | 98.5 | 100 | 98 |
| 1_53 | 98.5 | 100 | 98 | 100 | 100 | 100 |
| 1_54 | 100 | 100 | 100 | 98.5 | 93.8 | 100 |
| 1_55 | 99.3 | 97.1 | 100 | 100 | 100 | 100 |
| 1_56 | 100 | 100 | 100 | 98.5 | 100 | 98 |
| 1_57 | 99.3 | 100 | 99 | 100 | 100 | 100 |
| 1_58 | 98.5 | 97.1 | 99 | 100 | 100 | 100 |
| 1_59 | 99.3 | 100 | 99 | 100 | 100 | 100 |
| 1_60 | 99.3 | 100 | 99 | 100 | 100 | 100 |
| 1_61 | 99.3 | 100 | 99 | 98.5 | 100 | 98 |
| 1_62 | 99.3 | 100 | 99 | 100 | 100 | 100 |
| 1_63 | 99.3 | 100 | 99 | 100 | 100 | 100 |
| 1_64 | 100 | 100 | 100 | 98.5 | 100 | 98 |
| 1_65 | 99.3 | 100 | 99 | 98.5 | 100 | 98 |
| 1_66 | 99.3 | 97.1 | 100 | 100 | 100 | 100 |
| 1_67 | 99.3 | 100 | 99 | 98.5 | 100 | 98 |
| 1_68 | 100 | 100 | 100 | 98.5 | 100 | 98 |
| 1_69 | 98.5 | 100 | 98 | 98.5 | 100 | 98 |
| 1_70 | 99.3 | 100 | 99 | 100 | 100 | 100 |
| 1_71 | 99.3 | 100 | 99 | 100 | 100 | 100 |
| 1_72 | 99.3 | 100 | 99 | 100 | 100 | 100 |
| 1_73 | 97.8 | 97.1 | 98 | 100 | 100 | 100 |
| 1_74 | 98.5 | 97.1 | 99 | 98.5 | 100 | 98 |
| 1_75 | 99.2 | 100 | 99 | 98.5 | 100 | 98 |
| 1_76 | 98.5 | 100 | 98 | 100 | 100 | 100 |
| 1_77 | 99.3 | 100 | 99 | 98.5 | 100 | 98 |
| 1_78 | 99.3 | 100 | 99 | 98.5 | 100 | 98 |
| 1_79 | 99.3 | 100 | 99 | 98.5 | 100 | 98 |
| 1_80 | 98.5 | 100 | 98 | 98.5 | 100 | 98 |
| 1_81 | 98.5 | 97.1 | 99 | 98.5 | 100 | 98 |
| 1_82 | 99.3 | 100 | 99 | 100 | 100 | 100 |
| 1_83 | 99.3 | 100 | 99 | 98.5 | 100 | 98 |
| 1_84 | 98.5 | 97.1 | 99 | 100 | 100 | 100 |
| 1_85 | 98.5 | 97.1 | 99 | 100 | 100 | 100 |
| 1_86 | 99.3 | 100 | 99 | 100 | 100 | 100 |
| 1_87 | 99.3 | 97.1 | 100 | 100 | 100 | 100 |
| 1_88 | 98.5 | 100 | 98 | 100 | 100 | 100 |
| 1_89 | 99.3 | 100 | 99 | 100 | 100 | 100 |
| 1_90 | 100 | 100 | 100 | 100 | 100 | 100 |
| 1_91 | 99.3 | 100 | 99 | 100 | 100 | 100 |
| 1_92 | 99.3 | 100 | 99 | 100 | 100 | 100 |
| 1_93 | 99.3 | 100 | 99 | 98.5 | 100 | 98 |
| 1_94 | 98.5 | 97.1 | 99 | 100 | 100 | 100 |
| 1_95 | 99.3 | 100 | 99 | 100 | 100 | 100 |
| 1_96 | 99.3 | 100 | 99 | 100 | 100 | 100 |
| 1_97 | 99.3 | 100 | 99 | 98.5 | 100 | 98 |
| 1_98 | 99.3 | 100 | 99 | 98.5 | 100 | 98 |
| 1_99 | 98.5 | 100 | 98 | 100 | 100 | 100 |
| 1_100 | 97 | 97.1 | 97 | 100 | 100 | 100 |
| 1_101 | 98.5 | 97.1 | 99 | 100 | 100 | 100 |
| 1_102 | 99.3 | 100 | 99 | 98.5 | 100 | 98 |
| 1_103 | 97.8 | 97.1 | 98 | 98.5 | 100 | 98 |
| 1_104 | 100 | 100 | 100 | 100 | 100 | 100 |
| 1_105 | 98.5 | 100 | 98 | 100 | 100 | 100 |
| 1_106 | 98.5 | 97.1 | 99 | 98.5 | 100 | 98 |
| 1_107 | 99.3 | 100 | 99 | 100 | 100 | 100 |
| 1_108 | 97.8 | 97.1 | 98 | 100 | 100 | 100 |
| 1_109 | 98.5 | 97.1 | 99 | 100 | 100 | 100 |
| 1_110 | 98.5 | 97.1 | 99 | 100 | 100 | 100 |
| 1_111 | 98.5 | 100 | 98 | 100 | 100 | 100 |
| 1_112 | 98.5 | 97.1 | 99 | 100 | 100 | 100 |
| 1_113 | 99.3 | 97.1 | 100 | 98.5 | 93.8 | 100 |
| 1_114 | 97.8 | 97.1 | 98 | 98.5 | 100 | 98 |
| 1_115 | 99.3 | 100 | 99 | 100 | 100 | 100 |
| 1_116 | 100 | 100 | 100 | 100 | 100 | 100 |
| 1_117 | 97.8 | 94.1 | 99 | 98.5 | 100 | 98 |
| 1_118 | 99.3 | 100 | 99 | 98.5 | 100 | 98 |
| 1_119 | 99.3 | 100 | 99 | 100 | 100 | 100 |
| 1_120 | 98.5 | 100 | 98 | 97 | 93.8 | 98 |
| 1_121 | 99.3 | 97.1 | 100 | 100 | 100 | 100 |
| 1_122 | 98.5 | 100 | 98 | 98.5 | 100 | 98 |
| 1_123 | 97.8 | 97.1 | 98 | 100 | 100 | 100 |
| 1_124 | 98.5 | 100 | 98 | 100 | 100 | 100 |
| 1_125 | 98.5 | 97.1 | 99 | 98.5 | 93.8 | 100 |
| 1_126 | 99.3 | 100 | 99 | 100 | 100 | 100 |
| 1_127 | 99.3 | 100 | 99 | 100 | 100 | 100 |
| 1_128 | 99.3 | 100 | 99 | 98.5 | 100 | 98 |
| 1_129 | 99.3 | 100 | 99 | 100 | 100 | 100 |
| 1_130 | 97.8 | 97.1 | 98 | 100 | 100 | 100 |
| 1_131 | 97 | 94.1 | 98 | 100 | 100 | 100 |
| 1_132 | 97.8 | 97.1 | 98 | 98.5 | 100 | 98 |
| 1_133 | 99.3 | 100 | 99 | 100 | 100 | 100 |
| 1_134 | 99.3 | 100 | 99 | 100 | 100 | 100 |
| 1_135 | 98.5 | 97.1 | 99 | 100 | 100 | 100 |
| 1_136 | 97.8 | 100 | 97 | 100 | 100 | 100 |
| 1_137 | 99.3 | 100 | 99 | 100 | 100 | 100 |
| 1_138 | 99.3 | 100 | 99 | 100 | 100 | 100 |
| 1_139 | 98.5 | 97.1 | 99 | 97 | 100 | 96 |
| 1_140 | 98.5 | 94.1 | 100 | 100 | 100 | 100 |
| 1_141 | 99.3 | 100 | 99 | 100 | 100 | 100 |
| 1_142 | 98.5 | 100 | 98 | 100 | 100 | 100 |
| 1_143 | 98.5 | 97.1 | 99 | 100 | 100 | 100 |
| 1_144 | 99.3 | 100 | 99 | 100 | 100 | 100 |
| 1_145 | 97.8 | 97.1 | 98 | 100 | 100 | 100 |
| 1_146 | 100 | 100 | 100 | 100 | 100 | 100 |
| 1_147 | 99.3 | 100 | 99 | 100 | 100 | 100 |
| 1_148 | 99.3 | 100 | 99 | 100 | 100 | 100 |
| 1_149 | 98.5 | 97.1 | 99 | 98.5 | 100 | 98 |
| 1_150 | 99.3 | 100 | 99 | 100 | 100 | 100 |
| 1_151 | 99.3 | 100 | 99 | 100 | 100 | 100 |
| 1_152 | 98.5 | 97.1 | 99 | 100 | 100 | 100 |
| 1_153 | 99.3 | 100 | 99 | 100 | 100 | 100 |
| 1_154 | 99.3 | 100 | 99 | 100 | 100 | 100 |
| 1_155 | 98.5 | 100 | 98 | 100 | 100 | 100 |
| 1_156 | 100 | 100 | 100 | 100 | 100 | 100 |
| 1_157 | 97.8 | 97.1 | 98 | 98.5 | 100 | 98 |
| 1_158 | 98.5 | 97.1 | 99 | 100 | 100 | 100 |
| 1_159 | 97.8 | 97.1 | 98 | 100 | 100 | 100 |
| 1_160 | 99.3 | 100 | 99 | 98.5 | 100 | 98 |
| 1_161 | 98.5 | 100 | 98 | 100 | 100 | 100 |
| 1_162 | 99.3 | 100 | 99 | 100 | 100 | 100 |
| 1_163 | 97.8 | 100 | 97 | 100 | 100 | 100 |
| 1_164 | 99.3 | 100 | 99 | 100 | 100 | 100 |
| 1_165 | 98.5 | 97.1 | 99 | 100 | 100 | 100 |
| 1_166 | 99.3 | 100 | 99 | 98.5 | 100 | 98 |
| 1_167 | 99.3 | 100 | 99 | 100 | 100 | 100 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_168 | 99.2 | 100 | 99 | 100 | 100 | 100 |
| 1_169 | 99.3 | 100 | 99 | 100 | 100 | 100 |
| 1_170 | 99.3 | 100 | 99 | 100 | 100 | 100 |
| 1_171 | 97.8 | 100 | 97 | 100 | 100 | 100 |
| 1_172 | 98.5 | 97.1 | 99 | 98.5 | 100 | 98 |
| 1_173 | 99.3 | 100 | 99 | 100 | 100 | 100 |
| 1_174 | 99.3 | 100 | 99 | 100 | 100 | 100 |
| 1_175 | 98.5 | 97.1 | 99 | 100 | 100 | 100 |
| 1_176 | 100 | 100 | 100 | 98.5 | 100 | 98 |
| 1_177 | 98.5 | 97.1 | 99 | 100 | 100 | 100 |
| 1_178 | 99.3 | 100 | 99 | 98.5 | 93.8 | 100 |
| 1_179 | 99.3 | 100 | 99 | 98.5 | 100 | 98 |
| 1_180 | 99.3 | 100 | 99 | 100 | 100 | 100 |

TABLE 7

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 5_6 | 98.5 | 97.1 | 99.0 | 93.9 | 87.5 | 96.0 |
| 5_11 | 98.5 | 97.1 | 99.0 | 97.0 | 87.5 | 100 |
| 5_38 | 97.0 | 97.1 | 97.0 | 95.5 | 87.5 | 98.0 |
| 15_16 | 93.3 | 82.4 | 97.0 | 92.4 | 75.0 | 98.0 |
| 15_21 | 97.8 | 97.1 | 98.0 | 95.5 | 93.8 | 96.0 |
| 15_64 | 91.0 | 70.6 | 98.0 | 90.9 | 68.8 | 98.0 |
| 24_25 | 97.8 | 94.1 | 99.0 | 95.5 | 81.2 | 100 |
| 24_30 | 96.3 | 91.2 | 98.0 | 89.4 | 75.0 | 94.0 |
| 24_32 | 90.3 | 70.6 | 97.0 | 90.9 | 68.8 | 98.0 |
| 2_32 | 97.0 | 88.2 | 100 | 100 | 100 | 100 |
| 32_36 | 94.8 | 82.4 | 99.0 | 89.4 | 68.8 | 96.0 |
| 15_32 | 92.5 | 76.5 | 98.0 | 95.5 | 87.5 | 98.0 |
| 3_38 | 97.0 | 97.1 | 97.0 | 97.0 | 100 | 96.0 |
| 38_39 | 93.3 | 82.4 | 97.0 | 87.9 | 75.0 | 92.0 |
| 38_64 | 87.3 | 61.8 | 96.0 | 87.9 | 62.5 | 96.0 |
| 3_45 | 96.3 | 85.3 | 100 | 97.0 | 100 | 96.0 |
| 45_58 | 96.3 | 91.2 | 98.0 | 83.3 | 75.0 | 86.0 |
| 45_64 | 95.5 | 94.1 | 96.0 | 95.5 | 87.5 | 98.0 |
| 2_55 | 96.3 | 88.2 | 99.0 | 100 | 100 | 100 |
| 6_55 | 95.5 | 85.3 | 99.0 | 90.9 | 81.2 | 94.0 |
| 55_64 | 88.1 | 61.8 | 97.0 | 84.8 | 56.2 | 94.0 |
| 2_64 | 97.0 | 91.2 | 99.0 | 100 | 100 | 100 |
| 4_64 | 94.8 | 85.3 | 98.0 | 97.0 | 87.5 | 100 |
| 2_96 | 97.8 | 94.1 | 99.0 | 98.5 | 100 | 98.0 |
| 7_96 | 98.5 | 100 | 98.0 | 93.9 | 93.8 | 94.0 |
| 96_97 | 85.1 | 61.8 | 93.0 | 77.3 | 31.2 | 92.0 |
| 2_97 | 96.3 | 88.2 | 99.0 | 100 | 100 | 100 |
| 3_97 | 98.5 | 97.1 | 99.0 | 98.5 | 100 | 98.0 |
| 5_97 | 96.3 | 91.2 | 98.0 | 97.0 | 93.8 | 98.0 |
| 2_162 | 96.3 | 88.2 | 99.0 | 98.5 | 100 | 98.0 |
| 3_162 | 97.8 | 94.1 | 99.0 | 100 | 100 | 100 |
| 5_162 | 97.8 | 94.1 | 99.0 | 98.5 | 93.8 | 100 |

Example 3

<Selection of Gene Marker Using all Samples and Method for Evaluating Colorectal Cancer Discriminant Performance of Acquired Gene Marker>

In this Example, the samples in the training cohort and the validation cohort used in Examples 1 and 2 were integrated, and selection of a gene marker and evaluation of its colorectal cancer discriminant performance were conducted using all of the samples.

Specifically, the miRNA expression levels in the serum of the 50 colorectal cancer patients and the 150 healthy subjects obtained in the preceding Reference Examples were normalized by quantile normalization. In order to acquire diagnostic markers with higher reliability, only genes having a gene expression level of $2^6$ or higher in 50% or more of the samples in either of the colorectal cancer patient group or the healthy subject group were selected in the gene marker selection. In order to further acquire statistical significance for discriminating a colorectal cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant, and the obtained genes are described in Table 8. In this way, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476 and hsa-miR-6090 genes, and the nucleotide sequences of SEQ ID NOs: 181 to 194 related thereto were found in addition to the genes described in Table 2. As with the nucleotide sequences of SEQ ID NOs: 1 to 180, the results obtained about the polynucleotides shown in SEQ ID NOs: 181 to 194 also showed that the gene measurement values were significantly lower (−) or higher (+) in the colorectal cancer patient group than in the healthy subject group (Table 8). These results were able to be validated in the validation cohort. Thus, the presence or absence of colorectal cancer in the newly obtained samples can be determined by the methods described in Examples 1 and 2 by using the gene expression level measurement values described in Table 8 either alone or in combination with the gene expression level measurement values described in Table 2.

TABLE 8

| SEQ ID NO: | Gene name | P value after Bonferroni correction | Expression level in colorectal cancer patient with respect to healthy subject |
|---|---|---|---|
| 1 | hsa-miR-6726-5p | 5.31.E−62 | − |
| 2 | hsa-miR-4257 | 1.09.E−61 | − |
| 3 | hsa-miR-6787-5p | 2.44.E−47 | − |
| 4 | hsa-miR-6780b-5p | 2.11.E−42 | + |
| 5 | hsa-miR-3131 | 4.30.E−42 | − |
| 6 | hsa-miR-7108-5p | 3.00.E−35 | + |
| 7 | hsa-miR-1343-3p | 4.27.E−43 | − |
| 8 | hsa-miR-1247-3p | 9.79.E−35 | + |
| 9 | hsa-miR-4651 | 9.99.E−39 | − |
| 10 | hsa-miR-6757-5p | 2.24.E−34 | − |
| 11 | hsa-miR-3679-5p | 3.50.E−37 | + |
| 12 | hsa-miR-7641 | 5.56.E−34 | − |
| 13 | hsa-miR-6746-5p | 1.02.E−31 | − |
| 14 | hsa-miR-8072 | 1.54.E−27 | + |
| 15 | hsa-miR-6741-5p | 2.21.E−31 | − |
| 16 | hsa-miR-1908-5p | 4.52.E−29 | + |
| 17 | hsa-miR-6857-5p | 3.92.E−22 | + |
| 18 | hsa-miR-4746-3p | 3.57.E−31 | + |
| 19 | hsa-miR-744-5p | 7.34.E−32 | + |
| 20 | hsa-miR-4792 | 1.24.E−27 | + |
| 21 | hsa-miR-564 | 2.13.E−30 | − |
| 22 | hsa-miR-6791-5p | 2.90.E−27 | + |
| 23 | hsa-miR-6825-5p | 4.61.E−29 | + |
| 24 | hsa-miR-6826-5p | 2.05.E−29 | − |
| 25 | hsa-miR-4665-3p | 7.74.E−29 | + |
| 26 | hsa-miR-4467 | 5.07.E−27 | + |
| 27 | hsa-miR-3188 | 5.96.E−29 | + |
| 28 | hsa-miR-6125 | 2.14.E−23 | + |
| 29 | hsa-miR-6756-5p | 2.14.E−22 | − |
| 30 | hsa-miR-1228-3p | 7.24.E−25 | + |
| 31 | hsa-miR-8063 | 1.63.E−24 | − |
| 32 | hsa-miR-8069 | 9.97.E−22 | + |
| 33 | hsa-miR-6875-5p | 6.41.E−21 | + |
| 34 | hsa-miR-3185 | 1.30.E−24 | + |

TABLE 8-continued

| SEQ ID NO: | Gene name | P value after Bonferroni correction | Expression level in colorectal cancer patient with respect to healthy subject |
|---|---|---|---|
| 35 | hsa-miR-4433b-3p | 2.47.E−20 | + |
| 36 | hsa-miR-6887-5p | 5.17.E−26 | − |
| 37 | hsa-miR-128-1-5p | 3.06.E−18 | + |
| 38 | hsa-miR-6724-5p | 4.44.E−21 | + |
| 39 | hsa-miR-1914-3p | 2.19.E−16 | − |
| 40 | hsa-miR-1225-5p | 9.96.E−22 | + |
| 41 | hsa-miR-4419b | 2.99.E−22 | − |
| 42 | hsa-miR-7110-5p | 1.00.E−22 | + |
| 43 | hsa-miR-187-5p | 1.62.E−19 | − |
| 44 | hsa-miR-3184-5p | 2.98.E−20 | + |
| 45 | hsa-miR-204-3p | 1.12.E−17 | − |
| 46 | hsa-miR-5572 | 5.88.E−21 | + |
| 47 | hsa-miR-6729-5p | 6.07.E−18 | + |
| 48 | hsa-miR-615-5p | 3.71.E−19 | − |
| 49 | hsa-miR-6749-5p | 1.52.E−19 | − |
| 50 | hsa-miR-6515-3p | 1.14.E−15 | + |
| 51 | hsa-miR-3937 | 1.06.E−20 | + |
| 52 | hsa-miR-6840-3p | 3.27.E−16 | − |
| 53 | hsa-miR-6893-5p | 3.70.E−20 | − |
| 54 | hsa-miR-4728-5p | 1.49.E−16 | − |
| 55 | hsa-miR-6717-5p | 5.86.E−21 | − |
| 56 | hsa-miR-7113-3p | 1.99.E−19 | + |
| 57 | hsa-miR-4665-5p | 4.71.E−16 | − |
| 58 | hsa-miR-642b-3p | 1.28.E−15 | − |
| 59 | hsa-miR-7109-5p | 6.89.E−19 | − |
| 60 | hsa-miR-6842-5p | 5.06.E−19 | + |
| 61 | hsa-miR-4442 | 9.22.E−16 | − |
| 62 | hsa-miR-4433-3p | 2.94.E−16 | + |
| 63 | hsa-miR-4707-5p | 1.21.E−17 | + |
| 64 | hsa-miR-6126 | 3.89.E−16 | + |
| 65 | hsa-miR-4449 | 3.16.E−20 | + |
| 66 | hsa-miR-4706 | 1.73.E−16 | − |
| 67 | hsa-miR-1913 | 3.48.E−16 | + |
| 68 | hsa-miR-602 | 1.60.E−16 | + |
| 69 | hsa-miR-939-5p | 4.02.E−16 | + |
| 70 | hsa-miR-4695-5p | 2.61.E−14 | + |
| 71 | hsa-miR-711 | 1.79.E−16 | + |
| 72 | hsa-miR-6816-5p | 5.98.E−14 | + |
| 73 | hsa-miR-4632-5p | 4.56.E−14 | + |
| 74 | hsa-miR-6721-5p | 5.64.E−13 | + |
| 75 | hsa-miR-7847-3p | 7.52.E−17 | − |
| 76 | hsa-miR-6132 | 6.77.E−16 | + |
| 77 | hsa-miR-887-3p | 3.26.E−14 | + |
| 78 | hsa-miR-3679-3p | 5.22.E−14 | + |
| 79 | hsa-miR-6784-5p | 6.38.E−13 | + |
| 80 | hsa-miR-1249 | 1.62.E−14 | + |
| 81 | hsa-miR-937-5p | 8.71.E−13 | − |
| 82 | hsa-miR-5195-3p | 2.51.E−14 | − |
| 83 | hsa-miR-6732-5p | 2.71.E−13 | + |
| 84 | hsa-miR-4417 | 4.13.E−15 | + |
| 85 | hsa-miR-4281 | 1.09.E−13 | − |
| 86 | hsa-miR-4734 | 7.65.E−15 | + |
| 87 | hsa-miR-6766-3p | 1.32.E−13 | + |
| 88 | hsa-miR-663a | 1.12.E−14 | + |
| 90 | hsa-miR-6781-5p | 1.88.E−11 | + |
| 91 | hsa-miR-1227-5p | 6.26.E−12 | + |
| 92 | hsa-miR-6845-5p | 1.06.E−14 | + |
| 93 | hsa-miR-6798-5p | 2.72.E−08 | + |
| 94 | hsa-miR-3620-5p | 7.80.E−10 | + |
| 95 | hsa-miR-1915-5p | 1.02.E−11 | − |
| 96 | hsa-miR-4294 | 1.22.E−12 | − |
| 97 | hsa-miR-642a-3p | 5.69.E−12 | − |
| 98 | hsa-miR-371a-5p | 2.55.E−09 | − |
| 99 | hsa-miR-940 | 2.85.E−14 | + |
| 100 | hsa-miR-4450 | 2.15.E−13 | − |
| 101 | hsa-miR-4723-5p | 8.73.E−13 | − |
| 102 | hsa-miR-1469 | 5.67.E−12 | + |
| 103 | hsa-miR-6861-5p | 2.03.E−12 | − |
| 104 | hsa-miR-7975 | 1.02.E−09 | − |
| 105 | hsa-miR-6879-5p | 6.99.E−11 | + |
| 106 | hsa-miR-6802-5p | 1.21.E−10 | − |
| 107 | hsa-miR-1268b | 8.63.E−11 | + |
| 108 | hsa-miR-663b | 1.02.E−10 | − |
| 109 | hsa-miR-125a-3p | 1.21.E−12 | − |
| 110 | hsa-miR-2861 | 4.18.E−13 | − |
| 111 | hsa-miR-6088 | 6.31.E−12 | − |
| 112 | hsa-miR-4758-5p | 1.17.E−10 | − |
| 113 | hsa-miR-296-3p | 1.20.E−08 | − |
| 114 | hsa-miR-6738-5p | 1.29.E−09 | − |
| 115 | hsa-miR-671-5p | 8.62.E−11 | − |
| 116 | hsa-miR-4454 | 4.34.E−10 | − |
| 117 | hsa-miR-4516 | 3.61.E−10 | − |
| 118 | hsa-miR-7845-5p | 7.69.E−09 | + |
| 119 | hsa-miR-4741 | 2.27.E−09 | + |
| 120 | hsa-miR-92b-5p | 2.68.E−09 | + |
| 121 | hsa-miR-6795-5p | 1.14.E−09 | − |
| 122 | hsa-miR-6805-3p | 1.59.E−11 | + |
| 123 | hsa-miR-4725-3p | 6.13.E−07 | + |
| 124 | hsa-miR-6782-5p | 1.59.E−08 | + |
| 125 | hsa-miR-4688 | 5.22.E−07 | − |
| 126 | hsa-miR-6850-5p | 7.32.E−08 | + |
| 127 | hsa-miR-6777-5p | 7.19.E−11 | − |
| 128 | hsa-miR-6785-5p | 1.41.E−07 | − |
| 129 | hsa-miR-7106-5p | 6.63.E−09 | − |
| 130 | hsa-miR-3663-3p | 3.69.E−09 | − |
| 131 | hsa-miR-6131 | 1.40.E−09 | − |
| 132 | hsa-miR-1915-3p | 6.80.E−08 | + |
| 133 | hsa-miR-4532 | 2.71.E−07 | − |
| 134 | hsa-miR-6820-5p | 1.32.E−07 | − |
| 135 | hsa-miR-4689 | 3.51.E−09 | − |
| 136 | hsa-miR-4638-5p | 2.60.E−07 | − |
| 137 | hsa-miR-3656 | 1.23.E−07 | + |
| 138 | hsa-miR-3621 | 6.72.E−07 | − |
| 139 | hsa-miR-6769b-5p | 7.12.E−08 | − |
| 140 | hsa-miR-149-3p | 1.99.E−07 | − |
| 141 | hsa-miR-23b-3p | 1.65.E−07 | − |
| 142 | hsa-miR-3135b | 1.27.E−07 | − |
| 143 | hsa-miR-6848-5p | 3.54.E−06 | + |
| 144 | hsa-miR-6769a-5p | 5.27.E−08 | − |
| 145 | hsa-miR-4327 | 4.27.E−06 | + |
| 146 | hsa-miR-6765-3p | 2.60.E−07 | − |
| 147 | hsa-miR-6716-5p | 1.00.E−06 | + |
| 148 | hsa-miR-6877-5p | 1.64.E−06 | − |
| 149 | hsa-miR-6727-5p | 3.79.E−06 | − |
| 150 | hsa-miR-4534 | 4.38.E−06 | − |
| 151 | hsa-miR-614 | 2.94.E−06 | − |
| 152 | hsa-miR-1202 | 3.36.E−07 | − |
| 153 | hsa-miR-575 | 5.28.E−08 | − |
| 154 | hsa-miR-6870-5p | 3.19.E−08 | + |
| 155 | hsa-miR-6722-3p | 8.34.E−06 | + |
| 156 | hsa-miR-7977 | 6.56.E−05 | − |
| 157 | hsa-miR-4649-5p | 1.23.E−05 | − |
| 158 | hsa-miR-4675 | 3.15.E−07 | − |
| 159 | hsa-miR-6075 | 6.53.E−05 | + |
| 160 | hsa-miR-6779-5p | 5.68.E−07 | − |
| 161 | hsa-miR-4271 | 1.02.E−05 | − |
| 162 | hsa-miR-3196 | 2.40.E−06 | + |
| 163 | hsa-miR-6803-5p | 3.32.E−03 | + |
| 164 | hsa-miR-6789-5p | 1.02.E−06 | + |
| 165 | hsa-miR-4648 | 7.63.E−08 | + |
| 167 | hsa-miR-4749-5p | 3.78.E−05 | + |
| 168 | hsa-miR-4505 | 7.82.E−05 | + |
| 169 | hsa-miR-5698 | 2.28.E−04 | − |
| 170 | hsa-miR-1199-5p | 2.58.E−04 | − |
| 171 | hsa-miR-4763-3p | 1.20.E−03 | + |
| 172 | hsa-miR-1231 | 2.42.E−35 | + |
| 173 | hsa-miR-1233-5p | 4.01.E−32 | − |
| 174 | hsa-miR-150-3p | 4.05.E−09 | − |
| 175 | hsa-miR-1225-3p | 3.42.E−13 | + |
| 176 | hsa-miR-92a-2-5p | 3.89.E−08 | + |
| 177 | hsa-miR-423-5p | 1.73.E−06 | − |
| 178 | hsa-miR-1268a | 2.52.E−05 | + |
| 179 | hsa-miR-128-2-5p | 5.33.E−06 | − |
| 180 | hsa-miR-24-3p | 1.01.E−07 | − |
| 181 | hsa-miR-4697-5p | 4.79.E−05 | − |
| 182 | hsa-miR-3197 | 1.62.E−04 | + |
| 183 | hsa-miR-675-5p | 2.19.E−04 | − |
| 184 | hsa-miR-4486 | 4.27.E−04 | + |
| 185 | hsa-miR-7107-5p | 4.72.E−04 | − |
| 186 | hsa-miR-23a-3p | 1.53.E−03 | − |

TABLE 8-continued

| SEQ ID NO: | Gene name | P value after Bonferroni correction | Expression level in colorectal cancer patient with respect to healthy subject |
|---|---|---|---|
| 187 | hsa-miR-4667-5p | 2.51.E−03 | + |
| 188 | hsa-miR-451a | 3.74.E−03 | − |
| 189 | hsa-miR-3940-5p | 4.95.E−03 | + |
| 190 | hsa-miR-8059 | 5.22.E−03 | − |
| 191 | hsa-miR-6813-5p | 5.33.E−03 | + |
| 192 | hsa-miR-4492 | 9.03.E−03 | + |
| 193 | hsa-miR-4476 | 9.04.E−03 | − |
| 194 | hsa-miR-6090 | 9.46.E−03 | + |

Example 4

<Method for Evaluating Colorectal Cancer-Specific Discriminant Performance by Combination of Multiple Gene Markers Using Samples in the Validation Cohort>

In this Example, a gene for diagnosis is selected by comparing gene expression levels of miRNAs in serum between colorectal cancer patients and a control group that consist of healthy subjects, pancreatic cancer patients, bile duct cancer patients, stomach cancer patients, esophageal cancer patients, liver cancer patients, and benign pancreaticobiliary disease patients in the same way as the method described in Example 1, using the gene markers selected in Example 1, and targeting the training cohort as the sample group described in Reference Example 2. The polynucleotides consisting of the nucleotide sequences represented by SEQ ID NOs: 606 to 614 thus selected were further combined therewith to study a method for evaluating colorectal cancer-specific discriminant performance.

Specifically, first, the miRNA expression levels in the training cohort and the validation cohort obtained in Reference Example 2 were combined and normalized by quantile normalization. Next, Fisher's discriminant analysis was conducted as to combinations of 1 to 6 expression level measurement values comprising at least one or more of the expression level measurement values of the polynucleotides consisting of the nucleotide sequences represented by SEQ ID NOs: 1 to 171 and 606 to 614, to construct a discriminant for determining the presence or absence of colorectal cancer. Next, accuracy, sensitivity, and specificity in the validation cohort were calculated using the discriminant thus prepared, with the colorectal cancer patient group as a positive sample group and, on the other hand, the healthy subject group, the pancreatic cancer patient group, the bile duct cancer patient group, the stomach cancer patient group, the esophageal cancer patient group, the liver cancer patient group, and the benign pancreaticobiliary disease patient group as a negative sample group. The discriminant performance of the selected polynucleotides was validated using independent samples.

Most of polynucleotides consisting of the nucleotide sequences represented by these SEQ ID NOs (SEQ ID NOs: 1 to 194 and 606 to 614 corresponding to the miRNA markers of Table 1) or complementary sequences thereof were able to provide relatively high accuracy, sensitivity, and specificity in the determination of the presence or absence of colorectal cancer, and furthermore, were able to specifically discriminate colorectal cancer from the other cancers. For example, among the combinations of multiple polynucleotides selected from the group consisting of polynucleotides consisting of the nucleotide sequences represented by SEQ ID NOs: 5, 13, 15, 24, 32, 38, 41, 45, 55, 57, 64, 72, 75, 77, 96, 97, 115, 162, 163, 173, 189, 606, 607, 608, 609, 610, 611, 612, 613 and 614, or complementary sequences thereof (the cancer type-specific polynucleotide group 1) as polynucleotides capable of specifically binding to target markers, combinations comprising at least one or more polynucleotide(s) selected from the group consisting of polynucleotides consisting of the nucleotide sequences represented by SEQ ID NOs: 5, 45, 57, 96, and 606, or complementary sequences thereof (the cancer type-specific polynucleotide group 2) included in the cancer type-specific polynucleotide group 1 were able to specifically discriminate colorectal cancer from the other cancers with high accuracy.

The number of the aforementioned polynucleotides with cancer type specificity in the combination can be 1, 2, 3, 4, 5, 6, 7, 8, 9, 10 or more for the combination. The combinations of 6 or more of these polynucleotides were able to exhibit discriminant accuracy of 90% or higher.

Specifically, the discriminant accuracy of the measurement using the polynucleotide that consists of the nucleotide sequence represented by SEQ ID NO: 5 or a complementary sequence thereof is shown in Table 9-1. The measurement using the combination of one polynucleotide comprising at least one polynucleotide consisting of the nucleotide sequence represented by SEQ ID NO: 5 or a complementary sequence thereof exhibited the highest accuracy of 90.1% in the training cohort and accuracy of 87.6% in the validation cohort. Also, for example, the measurement using the combinations of two polynucleotides comprising at least one polynucleotide consisting of the nucleotide sequence represented by SEQ ID NO: 5 or a complementary sequence thereof exhibited the highest accuracy of 91.7% in the training cohort and accuracy of 88.8% in the validation cohort. Furthermore, for example, the measurement using the combinations of three polynucleotides comprising at least one polynucleotide consisting of the nucleotide sequence represented by SEQ ID NO: 5 or a complementary sequence thereof exhibited the highest accuracy of 94.0% in the training cohort and accuracy of 91.2% in the validation cohort. Furthermore, for example, the measurement using the combinations of four polynucleotides comprising at least one polynucleotide consisting of the nucleotide sequence represented by SEQ ID NO: 5 or a complementary sequence thereof exhibited the highest accuracy of 95.6% in the training cohort and accuracy of 93.6% in the validation cohort. Furthermore, for example, the measurement using the combinations of five polynucleotides comprising at least one polynucleotide consisting of the nucleotide sequence represented by SEQ ID NO: 5 or a complementary sequence thereof exhibited the highest accuracy of 96.4% in the training cohort and accuracy of 94.8% in the validation cohort. Furthermore, for example, the measurement using the combinations of six polynucleotides comprising at least one polynucleotide consisting of the nucleotide sequence represented by SEQ ID NO: 5 or a complementary sequence thereof exhibited the highest accuracy of 96.9% in the training cohort and accuracy of 94.7% in the validation cohort.

The discriminant accuracy of the measurement using the polynucleotide consisting of the nucleotide sequence represented by SEQ ID NO: 45 or a complementary sequence thereof is shown in Table 9-2. The measurement using the combination of one polynucleotide comprising at least one polynucleotide consisting of the nucleotide sequence represented by SEQ ID NO: 45 or a complementary sequence thereof exhibited the highest accuracy of 56.7% in the training cohort and accuracy of 55.4% in the validation cohort. Also, for example, the measurement using the combinations of two polynucleotides comprising at least one polynucleotide consisting of the nucleotide sequence represented by SEQ ID NO: 45 or a complementary sequence thereof exhibited the highest accuracy of 90.7% in the training cohort and accuracy of 88.4% in the validation cohort. Furthermore, for example, the measurement using the combinations of three polynucleotides comprising at least one polynucleotide consisting of the nucleotide sequence represented by SEQ ID NO: 45 or a complementary sequence thereof exhibited the highest accuracy of 94.0% in the training cohort and accuracy of 89.6% in the validation cohort. Furthermore, for example, the measurement using the combinations of four polynucleotides comprising at least one polynucleotide consisting of the nucleotide sequence represented by SEQ ID NO: 45 or a complementary sequence thereof exhibited the highest accuracy of 95.2% in the training cohort and accuracy of 91.6% in the validation cohort. Furthermore, for example, the measurement using the combinations of five polynucleotides comprising at least one polynucleotide consisting of the nucleotide sequence represented by SEQ ID NO: 45 or a complementary sequence thereof exhibited the highest accuracy of 96.4% in the training cohort and accuracy of 94.4% in the validation cohort. Furthermore, for example, the measurement using the combinations of six polynucleotides comprising at least one polynucleotide consisting of the nucleotide sequence represented by SEQ ID NO: 45 or a complementary sequence thereof exhibited the highest accuracy of 97.6% in the training cohort and accuracy of 92.6% in the validation cohort.

The discriminant accuracy of the measurement using the polynucleotide consisting of the nucleotide sequence represented by SEQ ID NO: 57 or a complementary sequence thereof is shown in Table 9-3. The measurement using the combination of one polynucleotide comprising at least one polynucleotide consisting of the nucleotide sequence represented by SEQ ID NO: 57 or a complementary sequence thereof exhibited the highest accuracy of 60.2% in the training cohort and accuracy of 60.6% in the validation cohort. Also, for example, the measurement using the combinations of two polynucleotides comprising at least one polynucleotide consisting of the nucleotide sequence represented by SEQ ID NO: 57 or a complementary sequence thereof exhibited the highest accuracy of 86.7% in the training cohort and accuracy of 83.7% in the validation cohort. Furthermore, for example, the measurement using the combinations of three polynucleotides comprising at least one polynucleotide consisting of the nucleotide sequence represented by SEQ ID NO: 57 or a complementary sequence thereof exhibited the highest accuracy of 92.4% in the training cohort and accuracy of 90.0% in the validation cohort. Furthermore, for example, the measurement using the combinations of four polynucleotides comprising at least one polynucleotide consisting of the nucleotide sequence represented by SEQ ID NO: 57 or a complementary sequence thereof exhibited the highest accuracy of 95.2% in the training cohort and accuracy of 91.2% in the validation cohort. Furthermore, for example, the measurement using the combinations of five polynucleotides comprising at least one polynucleotide consisting of the nucleotide sequence represented by SEQ ID NO: 57 or a complementary sequence thereof exhibited the highest accuracy of 96.2% in the training cohort and accuracy of 94.8% in the validation cohort. Furthermore, for example, the measurement using the combinations of six polynucleotides comprising at least one polynucleotide consisting of the nucleotide sequence represented by SEQ ID NO: 57 or a complementary sequence thereof exhibited the highest accuracy of 96.9% in the training cohort and accuracy of 93.6% in the validation cohort.

The discriminant accuracy of the measurement using the polynucleotide consisting of the nucleotide sequence represented by SEQ ID NO: 96 or a complementary sequence thereof is shown in Table 9-4. The measurement using the combination of one polynucleotide comprising at least one polynucleotide consisting of the nucleotide sequence represented by SEQ ID NO: 96 or a complementary sequence thereof exhibited the highest accuracy of 57.9% in the training cohort and accuracy of 59.4% in the validation cohort. Also, for example, the measurement using the combinations of two polynucleotides comprising at least one polynucleotide consisting of the nucleotide sequence represented by SEQ ID NO: 96 or a complementary sequence thereof exhibited the highest accuracy of 85.9% in the training cohort and accuracy of 83.7% in the validation cohort. Furthermore, for example, the measurement using the combinations of three polynucleotides comprising at least one polynucleotide consisting of the nucleotide sequence represented by SEQ ID NO: 96 or a complementary sequence thereof exhibited the highest accuracy of 92.6% in the training cohort and accuracy of 90.4% in the validation cohort. Furthermore, for example, the measurement using the combinations of four polynucleotides comprising at least one polynucleotide consisting of the nucleotide sequence represented by SEQ ID NO: 96 or a complementary sequence thereof exhibited the highest accuracy of 94.4% in the training cohort and accuracy of 91.2% in the validation cohort. Furthermore, for example, the measurement using the combinations of five polynucleotides comprising at least one polynucleotide consisting of the nucleotide sequence represented by SEQ ID NO: 96 or a complementary sequence thereof exhibited the highest accuracy of 96.0% in the training cohort and accuracy of 94.0% in the validation cohort. Furthermore, for example, the measurement using the combinations of six polynucleotides comprising at least one polynucleotide consisting of the nucleotide sequence represented by SEQ ID NO: 96 or a complementary sequence thereof exhibited the highest accuracy of 96.3% in the training cohort and accuracy of 93.6% in the validation cohort.

The discriminant accuracy of the measurement using the polynucleotide consisting of the nucleotide sequence represented by SEQ ID NO: 606 or a complementary sequence thereof is shown in Table 9-5. The measurement using the combination of one polynucleotide comprising at least one polynucleotide consisting of the nucleotide sequence represented by SEQ ID NO: 606 or a complementary sequence thereof exhibited the highest accuracy of 59.4% in the training cohort and accuracy of 58.6% in the validation cohort. Also, for example, the measurement using the combinations of two polynucleotides comprising at least one polynucleotide consisting of the nucleotide sequence represented by SEQ ID NO: 606 or a complementary sequence thereof exhibited the highest accuracy of 86.6% in the training cohort and accuracy of 82.9% in the validation cohort. Furthermore, for example, the measurement using the combinations of three polynucleotides comprising at least one polynucleotide consisting of the nucleotide sequence represented by SEQ ID NO: 606 or a complementary sequence thereof exhibited the highest accuracy of 92.6% in the training cohort and accuracy of 91.2% in the validation cohort. Furthermore, for example, the measurement using the combinations of four polynucleotides comprising at least one polynucleotide consisting of the nucleotide sequence represented by SEQ ID NO: 606 or a complementary sequence thereof exhibited the highest accuracy of 94.8% in the training cohort and accuracy of 90.0% in the validation cohort. Furthermore, for example, the measurement using the combinations of five polynucleotides comprising at least one polynucleotide consisting of the nucleotide sequence represented by SEQ ID NO: 606 or a complementary sequence thereof exhibited the highest accuracy of 96.0% in the training cohort and accuracy of 93.6% in the validation cohort. Furthermore, for example, the measurement using the combinations of six polynucleotides comprising at least one polynucleotide consisting of the nucleotide sequence represented by SEQ ID NO: 606 or a complementary sequence thereof exhibited the highest accuracy of 95.3% in the training cohort and accuracy of 93.6% in the validation cohort.

Figure 4:
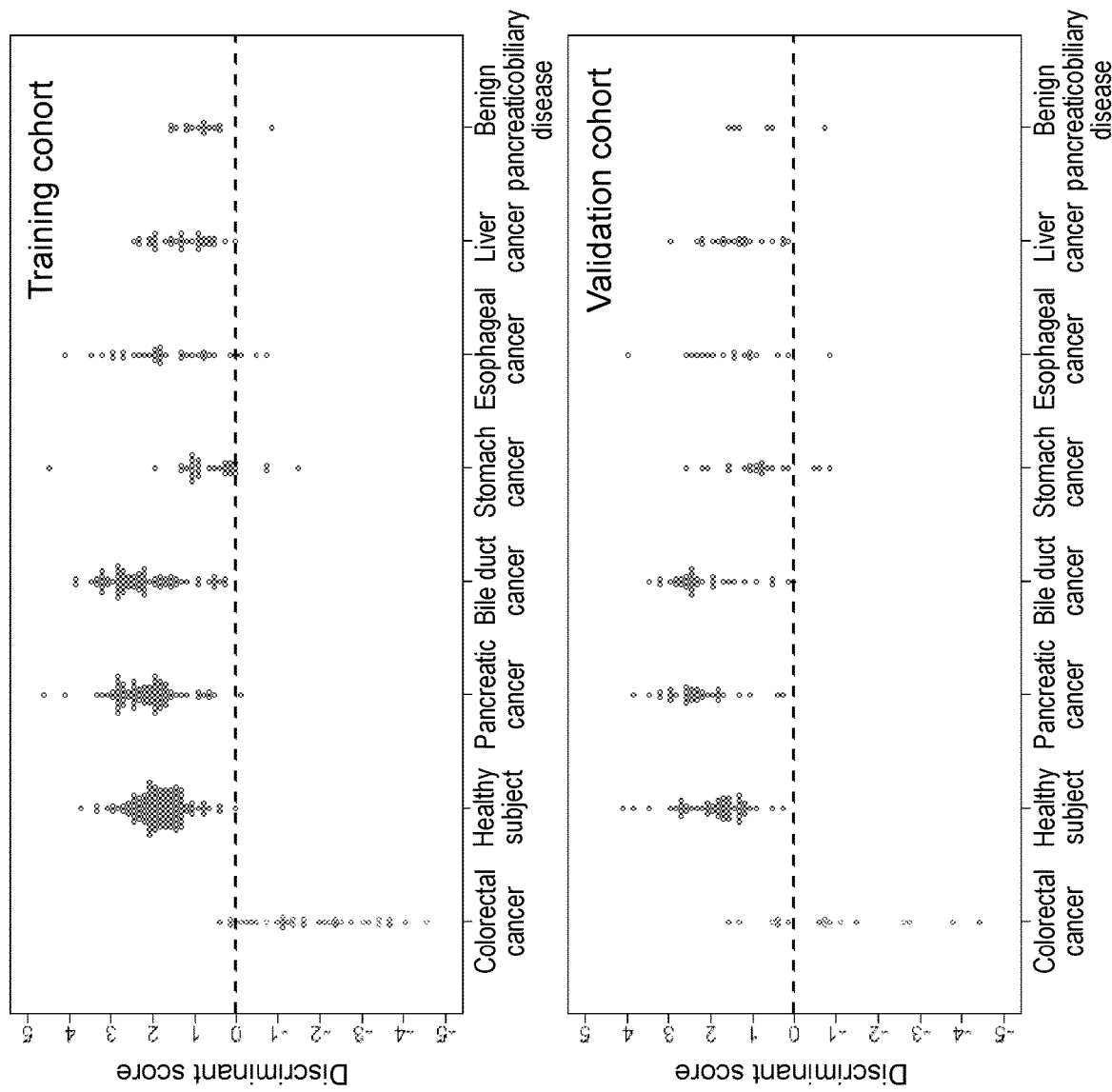
FIG. 4 Upper diagram: a discriminant (1.49×hsa-miR-3131−0.23×hsa-miR-7847-3p−1.13×hsa-miR-3196+1.11×hsa-miR-3195+2.25×hsa-miR-4665-5p−1.00×hsa-miR-204-3p−11.16) was prepared by use of Fisher's discriminant analysis from the expression level measurement values of hsa-miR-3131 (SEQ ID NO: 5), hsa-miR-204-3p (SEQ ID NO: 45), hsa-miR-4665-5p (SEQ ID NO: 57), hsa-miR-7847-3p (SEQ ID NO: 75), hsa-miR-3196 (SEQ ID NO: 162), and hsa-miR-3195 (SEQ ID NO: 607) in 34 colorectal cancer patients, 103 healthy subjects, 69 pancreatic cancer patients, 66 bile duct cancer patients, 30 stomach cancer patients, 33 esophageal cancer patients, 32 liver cancer patients, and 15 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared in the training cohort as to the expression level measurement values of hsa-miR-3131 (SEQ ID NO: 5), hsa-miR-204-3p (SEQ ID NO: 45), hsa-miR-4665-5p (SEQ ID NO: 57), hsa-miR-7847-3p (SEQ ID NO: 75), hsa-miR-3196 (SEQ ID NO: 162), and hsa-miR-3195 (SEQ ID NO: 607) in 16 colorectal cancer patients, 47 healthy subjects, 30 pancreatic cancer patients, 33 bile duct cancer patients, 20 stomach cancer patients, 17 esophageal cancer patients, 20 liver cancer patients, and 6 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 5, 45, 57, 75, 162, and 607 were compared among 34 colorectal cancer patients, 103 healthy subject, 69 pancreatic cancer patients, 66 bile duct cancer patients, 30 stomach cancer patients, 33 esophageal cancer patients, 32 liver cancer patients, and 15 benign pancreaticobiliary disease patients in the training cohort. As a result, a scatter diagram that significantly separated the discriminant score of the colorectal cancer patient group from the discriminant scores of the other groups was obtained in the training cohort (see the upper diagram of FIG. 4). These results were also reproducible in the validation cohort (see the lower diagram of FIG. 4).

TABLE 9-1

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 5 | 90.1 | 100 | 89.3 | 87.6 | 87.5 | 87.7 |
| 5_608 | 91.7 | 91.2 | 91.7 | 88.8 | 62.5 | 90.6 |
| 5_45_607 | 94 | 91.2 | 94.2 | 91.2 | 75 | 92.3 |
| 5_45_57_607 | 95.6 | 88.2 | 96.2 | 93.6 | 62.5 | 95.7 |
| 5_45_57_75_607 | 96.3 | 84.8 | 97.4 | 93.1 | 62.5 | 95.9 |
| 5_45_96_606_607 | 96.4 | 97.1 | 96.4 | 94.8 | 87.5 | 95.3 |
| 5_45_57_97_115_607 | 96.9 | 88.2 | 97.7 | 94.7 | 75.0 | 96.5 |
| 5_45_57_97_162_607 | 96.9 | 88.2 | 97.7 | 94.1 | 68.8 | 96.5 |
| 5_45_57_162_607_613 | 96.9 | 88.2 | 97.7 | 94.1 | 62.5 | 97.1 |
| 5_45_57_97_607_612 | 96.9 | 94.1 | 97.1 | 94.1 | 81.2 | 95.3 |
| 5_13_45_57_606_607 | 96.9 | 91.2 | 97.4 | 93.6 | 68.8 | 95.9 |
| 5_45_96_189_606_608 | 95.3 | 94.1 | 95.4 | 94.7 | 75 | 96.5 |
| 5_45_57_96_189_606 | 96.3 | 97.1 | 96.3 | 93.6 | 75 | 95.3 |
| 5_24_45_57_96_608 | 95.3 | 94.1 | 95.4 | 92.6 | 56.2 | 95.9 |
| 5_45_57_162_607_610 | 95.8 | 85.3 | 96.8 | 93.6 | 62.5 | 96.5 |
| 5_45_57_189_606_607 | 96.1 | 91.2 | 96.6 | 93.6 | 75 | 95.3 |

TABLE 9-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 45 | 56.7 | 61.8 | 56.3 | 55.4 | 56.2 | 55.3 |
| 5_45 | 90.7 | 100 | 90 | 88.4 | 87.5 | 88.5 |
| 5_45_57 | 94 | 94.1 | 94 | 89.6 | 81.2 | 90.2 |
| 5_45_57_97 | 95.2 | 94.1 | 95.3 | 91.6 | 81.2 | 92.3 |
| 5_45_96_606_607 | 95.5 | 91.2 | 96.0 | 95.2 | 87.5 | 95.9 |
| 5_45_57_75_607 | 96.4 | 87.9 | 97 | 94.4 | 62.5 | 96.6 |
| 5_45_57_75_606_607 | 97.6 | 87.9 | 98.6 | 92.6 | 62.5 | 95.3 |
| 5_45_57_77_607_613 | 97.4 | 94.1 | 97.7 | 94.1 | 75.0 | 95.9 |
| 5_45_57_97_606_607 | 97.1 | 94.1 | 97.4 | 94.1 | 81.2 | 95.3 |
| 5_45_57_75_77_607 | 97.1 | 90.9 | 97.7 | 93.1 | 68.8 | 95.3 |
| 5_32_45_57_96_606 | 96.3 | 97.1 | 96.3 | 93.6 | 68.8 | 95.9 |
| 5_24_45_57_96_606 | 96.1 | 97.1 | 96 | 93.1 | 68.8 | 95.3 |
| 5_45_57_96_162_606 | 95.5 | 91.2 | 96 | 94.7 | 81.2 | 95.9 |
| 5_15_45_75_96_606 | 95.5 | 100 | 95.1 | 93.6 | 81.2 | 94.8 |
| 5_32_45_57_162_607 | 95.8 | 85.3 | 96.8 | 93.6 | 62.5 | 96.5 |
| 38_45_96_606_608_611 | 87.1 | 88.2 | 87.0 | 86.2 | 68.8 | 87.8 |

TABLE 9-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 57 | 60.2 | 70.6 | 59.5 | 60.6 | 56.2 | 60.9 |
| 24_57 | 86.7 | 91.2 | 86.4 | 83.7 | 62.5 | 85.1 |

TABLE 9-3-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 5_57_608 | 92.4 | 88.2 | 92.8 | 90 | 68.8 | 91.5 |
| 5_45_57_608 | 95.2 | 91.2 | 95.5 | 91.2 | 62.5 | 93.2 |
| 24_41_57_45_96 | 94.5 | 94.1 | 94.5 | 88.8 | 56.2 | 91.9 |
| 5_45_57_607_612 | 96.2 | 94.1 | 96.4 | 94.8 | 68.8 | 96.6 |
| 5_45_57_606_607_608 | 96.9 | 91.2 | 97.4 | 93.6 | 68.8 | 95.9 |
| 5_13_45_57_75_607 | 96.9 | 90.9 | 97.4 | 93.1 | 68.8 | 95.3 |
| 5_45_57_64_75_607 | 96.9 | 90.9 | 97.4 | 92.6 | 68.8 | 94.8 |
| 5_45_55_57_607_613 | 96.9 | 91.2 | 97.4 | 92.6 | 68.8 | 94.8 |
| 5_45_55_57_75_607 | 96.6 | 87.9 | 97.4 | 92.6 | 68.8 | 94.8 |
| 5_38_45_57_96_607 | 96.3 | 88.2 | 97.1 | 94.1 | 68.8 | 96.5 |
| 5_45_57_75_162_607 | 96.6 | 87.9 | 97.4 | 94.1 | 62.5 | 97.1 |
| 5_45_57_75_162_609 | 94.2 | 97 | 94 | 91.5 | 62.5 | 94.2 |
| 5_45_57_64_96_607 | 95.5 | 88.2 | 96.3 | 94.7 | 75 | 96.5 |
| 57_64_96_606_608_611 | 90.6 | 91.2 | 90.5 | 88.3 | 75.0 | 89.5 |

TABLE 9-4

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 96 | 57.9 | 58.8 | 57.8 | 59.4 | 62.5 | 59.1 |
| 41_96 | 85.9 | 88.2 | 85.7 | 83.7 | 62.5 | 85.1 |
| 5_96_606 | 92.6 | 100 | 92.1 | 90.4 | 87.5 | 90.6 |
| 5_45_57_96 | 94.4 | 91.2 | 94.7 | 91.2 | 75 | 92.3 |
| 38_96_606_608_611 | 86.4 | 91.2 | 85.9 | 85.6 | 75 | 86.6 |
| 5_45_57_96_607 | 96 | 91.2 | 96.4 | 94 | 68.8 | 95.7 |
| 38_72_96_606_608_611 | 89.0 | 88.2 | 89.0 | 87.7 | 75.0 | 88.9 |
| 32_38_96_606_608_611 | 89.8 | 88.2 | 89.9 | 86.7 | 68.8 | 88.4 |
| 38_96_163_606_608_611 | 87.4 | 85.3 | 87.6 | 85.1 | 68.8 | 86.6 |
| 64_72_96_162_609_611 | 81.9 | 85.3 | 81.6 | 81.8 | 81.2 | 81.9 |
| 38_64_96_163_606_608 | 87.4 | 91.2 | 87.1 | 86.7 | 68.8 | 88.4 |
| 5_45_57_75_96_606 | 96.3 | 93.9 | 96.6 | 93.6 | 81.2 | 94.8 |
| 5_15_45_57_96_606 | 95.5 | 91.2 | 96 | 94.1 | 87.5 | 94.8 |
| 5_41_45_57_96_606 | 94.8 | 91.2 | 95.1 | 94.1 | 87.5 | 94.8 |
| 5_41_45_96_189_606 | 94.5 | 100 | 94 | 93.1 | 75 | 94.8 |
| 5_45_75_96_189_606 | 94.8 | 97 | 94.5 | 94.7 | 75 | 96.5 |

TABLE 9-5

|  | Training cohort | | | Validation cohort | | |
| --- | --- | --- | --- | --- | --- | --- |
| 606 SEQ ID NO: | Accuracy (%) | Sensitivity (%) | Specificity (%) | Accuracy (%) | Sensitivity (%) | Specificity (%) |
| 606 | 59.4 | 61.8 | 59.3 | 58.6 | 50 | 59.1 |
| 75_606 | 86.6 | 84.8 | 86.8 | 82.9 | 62.5 | 84.3 |
| 5_606_610 | 92.6 | 97.1 | 92.3 | 91.2 | 81.2 | 91.9 |
| 5_45_96_606 | 94.8 | 100 | 94.5 | 90 | 87.5 | 90.2 |
| 64_96_606_608_611 | 86.4 | 91.2 | 85.9 | 85.6 | 75.0 | 86.6 |
| 5_45_57_606_610 | 96 | 94.1 | 96.2 | 93.6 | 68.8 | 95.3 |
| 64_96_162_609_610_611 | 81.9 | 85.3 | 81.6 | 81.4 | 81.2 | 81.4 |
| 38_64_96_606_608_611 | 88.7 | 88.2 | 88.8 | 87.8 | 75.0 | 89.0 |
| 64_72_96_606_608_611 | 89.0 | 88.2 | 89.0 | 88.2 | 75.0 | 89.5 |
| 64_96_97_606_608_611 | 89.7 | 88.2 | 89.9 | 89.4 | 75.0 | 90.7 |
| 45_64_96_606_608_611 | 89.8 | 88.2 | 89.9 | 88.8 | 75.0 | 90.1 |
| 5_24_45_96_189_606 | 95.3 | 100 | 94.8 | 93.6 | 62.5 | 96.5 |
| 5_15_45_96_189_606 | 94 | 94.1 | 94 | 94.1 | 75 | 95.9 |
| 5_45_96_189_606_613 | 95 | 97.1 | 94.8 | 94.7 | 81.2 | 95.9 |
| 5_45_72_96_189_606 | 95 | 97.1 | 94.8 | 94.7 | 81.2 | 95.9 |
| 5_15_32_45_96_606 | 95.3 | 97.1 | 95.1 | 93.6 | 68.8 | 95.9 |

Comparative Example 1

<Colorectal Cancer Discriminant Performance of an Existing Tumor Marker in Blood>

The concentration of the existing tumor marker CEA in blood was measured in the training cohort and the validation cohort obtained in the preceding Reference Examples. When the concentration of the tumor marker in blood is higher than the reference value described in Non Patent Literature 4 (CEA: 5 ng/mL), subjects are generally suspected of having cancer. Thus, whether or not the concentration of CEA in blood exceeded its reference value was confirmed for each sample, and the results were assessed for the ability of the tumor marker to detect cancer in colorectal cancer patients. The sensitivity of the existing marker in the training cohort and the validation cohort was calculated. The results are shown in Tables 5-1 and 5-2. The sensitivity of CEA was as low as 26.5% in the training cohort and was as low as 43.8% in the validation cohort, demonstrating that the marker is not useful in the detection of colorectal cancer (Tables 5-1 and 5-2).

On the other hand, as shown above in Tables 3 and 6 of Examples 1 and 2, it can be concluded that in all of the polynucleotides consisting of the nucleotide sequences represented by SEQ ID NOs: 1 to 180, combinations of 1 or 2 polynucleotides exhibiting sensitivity beyond the existing colorectal cancer marker are present, and thus such polynucleotides serve as excellent diagnosis markers.

As shown in these Examples and Comparative Example, the kit, etc., and the method of the present invention can detect colorectal cancer more sensitively than the existing tumor marker and therefore permit early detection and treatment of colorectal cancer. As a result, improvement in survival rate and a therapeutic option of endoscopic operation, which places less burden on patients, can also be provided.

INDUSTRIAL APPLICABILITY

According to the present invention, colorectal cancer can be effectively detected by a simple and inexpensive method. This enables early detection, diagnosis and treatment of colorectal cancer. The method of the present invention can detect colorectal cancer with limited invasiveness using the blood of a patient and therefore allows colorectal cancer to be detected conveniently and rapidly.

All publications, patents, and patent applications cited herein are incorporated herein by reference in their entirety.

The invention claimed is:

1. A method for detecting colorectal cancer in vitro, comprising
   determining an expression level of hsa-miR-6726-5p in a sample comprising blood, serum, or plasma from a human subject using a kit comprising a nucleic acid(s), as a primer(s) for PCR, or a probe(s) for Northern blot, Southern blot, or in situ hybridization, capable of specifically binding to hsa-miR-6726-5p, wherein the determining comprises the following steps of:
   (a) contacting hsa-miR-6726-5p in the sample or complementary polynucleotide(s) thereof prepared from hsa-miR-6726-5p with the nucleic acid(s);
   (b) measuring an expression level of hsa-miR-6726-5p by quantitative RT-PCR using the nucleic acid(s) as the primer(s), or Northern blot, Southern blot, or in situ hybridization using the nucleic acids as the probe(s); and
   (c) comparing the expression level of hsa-miR-6726-5p measured in the step (b) with a control expression level of hsa-miR-6726-5p in a control sample from a healthy subject measured in the same way as in the step (b), wherein a lower expression level of hsa-miR-6726-5p in the sample comprising blood, serum, or plasma from the subject as compared to the control expression level is detected and is indicative that the subject has colorectal cancer; and treating the subject for colorectal cancer or performing a diagnostic procedure on the subject, wherein the treatment comprises surgery, radiotherapy, chemotherapy or a combination thereof, and wherein the diagnostic procedure comprises a fecal occult blood test, rectal examination, colonoscopy or imaging of the colon.

2. A method for detecting colorectal cancer in vitro, comprising: determining an expression level of hsa-miR-6726-5p in a sample comprising blood, serum, or plasma from a human subject using a device comprising a nucleic acid(s), as a probe(s), capable of specifically binding to hsa-miR-6726-5p, wherein the determining comprises the following steps of:
   (a) binding hsa-miR-6726-5p in the sample or cDNA thereof prepared from hsa-miR-6726-5p to the nucleic acid(s) to measure an expression level of hsa-miR-6726-5p by hybridization using the nucleic acid(s); and
   (b) comparing the expression level of hsa-miR-6726-5p measured in the step (a) with a control expression level of hsa-miR-6726-5p in a control sample from a healthy subject measured in the same way as in the step (b), wherein a lower expression level of hsa-miR-6726-5p in the sample comprising blood, serum, or plasma from the subject as compared to the control expression level is detected and is indicative that the subject has colorectal cancer; and treating the subject for colorectal cancer or performing a diagnostic procedure on the subject, wherein the treatment comprises surgery, radiotherapy, chemotherapy or a combination thereof, and wherein the diagnostic procedure comprises a fecal occult blood test, rectal examination, colonoscopy or imaging of the colon.

3. The method according to claim 1, wherein step (c) further comprises preparing a discriminant based on a formula.

4. The method according to claim 3, wherein the discriminant is compared to a threshold.

5. The method according to claim 2, wherein step (b) further comprises preparing a discriminant based on a formula.

6. The method according to claim 5, wherein the discriminant is compared to a threshold.

\* \* \* \* \*

SEQUENCE LISTING

```
<160> NUMBER OF SEQ ID NOS: 635

<210> SEQ ID NO 1
<211> LENGTH: 21
<212> TYPE: RNA
<213> ORGANISM: Homo sapiens

<400> SEQUENCE: 1
cgggagcugg ggucugcagg u                                         21

<210> SEQ ID NO 2
<211> LENGTH: 18
<212> TYPE: RNA
<213> ORGANISM: Homo sapiens

<400> SEQUENCE: 2
ccagaggugg ggacugag                                             18

<210> SEQ ID NO 3
<211> LENGTH: 22
<212> TYPE: RNA
<213> ORGANISM: Homo sapiens

<400> SEQUENCE: 3
uggcgggggu agagcuggcu gc                                        22

<210> SEQ ID NO 4
<211> LENGTH: 23
<212> TYPE: RNA
<213> ORGANISM: Homo sapiens

<400> SEQUENCE: 4
uggggaaggc uuggcaggga aga                                       23

<210> SEQ ID NO 5
<211> LENGTH: 23
<212> TYPE: RNA
<213> ORGANISM: Homo sapiens
```

```
<400> SEQUENCE: 5
ucgaggacug guggaagggc cuu                                          23

<210> SEQ ID NO 6
<211> LENGTH: 21
<212> TYPE: RNA
<213> ORGANISM: Homo sapiens

<400> SEQUENCE: 6
guguggccgg caggcgggug g                                            21

<210> SEQ ID NO 7
<211> LENGTH: 22
<212> TYPE: RNA
<213> ORGANISM: Homo sapiens

<400> SEQUENCE: 7
cuccuggggc ccgcacucuc gc                                           22

<210> SEQ ID NO 8
<211> LENGTH: 24
<212> TYPE: RNA
<213> ORGANISM: Homo sapiens

<400> SEQUENCE: 8
ccccgggaac gucgagacug gagc                                         24

<210> SEQ ID NO 9
<211> LENGTH: 20
<212> TYPE: RNA
<213> ORGANISM: Homo sapiens

<400> SEQUENCE: 9
cggggugggu gaggucgggc                                              20

<210> SEQ ID NO 10
<211> LENGTH: 22
<212> TYPE: RNA
<213> ORGANISM: Homo sapiens

<400> SEQUENCE: 10 uagggaugggg aggccaggau ga                                          22

<210> SEQ ID NO 11
<211> LENGTH: 23
<212> TYPE: RNA
<213> ORGANISM: Homo sapiens

<400> SEQUENCE: 11
ugaggauaug gcagggaagg gga                                          23

<210> SEQ ID NO 12
<211> LENGTH: 19
<212> TYPE: RNA
<213> ORGANISM: Homo sapiens

<400> SEQUENCE: 12
uugaucucgg aagcuaagc                                               19

<210> SEQ ID NO 13
<211> LENGTH: 22
<212> TYPE: RNA
<213> ORGANISM: Homo sapiens
```

```
<400> SEQUENCE: 13
ccgggagaag gagguggccu gg                                              22

<210> SEQ ID NO 14
<211> LENGTH: 20
<212> TYPE: RNA
<213> ORGANISM: Homo sapiens

<400> SEQUENCE: 14
ggcggcgggg agguaggcag                                                 20

<210> SEQ ID NO 15
<211> LENGTH: 22
<212> TYPE: RNA
<213> ORGANISM: Homo sapiens

<400> SEQUENCE: 15
gugggugcug gugggagccg ug                                              22

<210> SEQ ID NO 16
<211> LENGTH: 21
<212> TYPE: RNA
<213> ORGANISM: Homo sapiens

<400> SEQUENCE: 16
cggcggggac ggcgauuggu c                                               21

<210> SEQ ID NO 17
<211> LENGTH: 22
<212> TYPE: RNA
<213> ORGANISM: Homo sapiens

<400> SEQUENCE: 17
uuggggauug ggucaggcca gu                                              22

<210> SEQ ID NO 18
<211> LENGTH: 21
<212> TYPE: RNA
<213> ORGANISM: Homo sapiens

<400> SEQUENCE: 18
agcggugcuc cugcgggccg a                                               21

<210> SEQ ID NO 19
<211> LENGTH: 22
<212> TYPE: RNA
<213> ORGANISM: Homo sapiens

<400> SEQUENCE: 19
ugcggggcua gggcuaacag ca                                              22

<210> SEQ ID NO 20
<211> LENGTH: 18
<212> TYPE: RNA
<213> ORGANISM: Homo sapiens

<400> SEQUENCE: 20
cggugagcgc ucgcuggc                                                   18

<210> SEQ ID NO 21
<211> LENGTH: 19
<212> TYPE: RNA
```

```
<213> ORGANISM: Homo sapiens

<400> SEQUENCE: 21
aggcacggug ucagcaggc                                                    19

<210> SEQ ID NO 22
<211> LENGTH: 22
<212> TYPE: RNA
<213> ORGANISM: Homo sapiens

<400> SEQUENCE: 22
ccccuggggc ugggcaggcg ga                                                22

<210> SEQ ID NO 23
<211> LENGTH: 22
<212> TYPE: RNA
<213> ORGANISM: Homo sapiens

<400> SEQUENCE: 23
ugggagggug uggagucagc au                                                22

<210> SEQ ID NO 24
<211> LENGTH: 23
<212> TYPE: RNA
<213> ORGANISM: Homo sapiens

<400> SEQUENCE: 24
ucaauaggaa agagguggga ccu                                               23

<210> SEQ ID NO 25
<211> LENGTH: 26
<212> TYPE: RNA
<213> ORGANISM: Homo sapiens

<400> SEQUENCE: 25
cucggccgcg gcgcguagcc cccgcc                                            26

<210> SEQ ID NO 26
<211> LENGTH: 22
<212> TYPE: RNA
<213> ORGANISM: Homo sapiens

<400> SEQUENCE: 26
uggcggcggu aguuaugggc uu                                                22

<210> SEQ ID NO 27
<211> LENGTH: 23
<212> TYPE: RNA
<213> ORGANISM: Homo sapiens

<400> SEQUENCE: 27
agaggcuuug ugcggauacg ggg                                               23

<210> SEQ ID NO 28
<211> LENGTH: 20
<212> TYPE: RNA
<213> ORGANISM: Homo sapiens

<400> SEQUENCE: 28
gcggaaggcg gagcggcgga                                                   20

<210> SEQ ID NO 29
<211> LENGTH: 23
```

```
<212> TYPE: RNA
<213> ORGANISM: Homo sapiens

<400> SEQUENCE: 29 agggugggc uggaggugggg gcu                                              23

<210> SEQ ID NO 30
<211> LENGTH: 20
<212> TYPE: RNA
<213> ORGANISM: Homo sapiens

<400> SEQUENCE: 30
ucacaccugc cucgccccc                                                   20

<210> SEQ ID NO 31
<211> LENGTH: 22
<212> TYPE: RNA
<213> ORGANISM: Homo sapiens

<400> SEQUENCE: 31
ucaaaaucag gagucggggc uu                                               22

<210> SEQ ID NO 32
<211> LENGTH: 23
<212> TYPE: RNA
<213> ORGANISM: Homo sapiens

<400> SEQUENCE: 32
ggaugguugg gggcggucgg cgu                                              23

<210> SEQ ID NO 33
<211> LENGTH: 21
<212> TYPE: RNA
<213> ORGANISM: Homo sapiens

<400> SEQUENCE: 33
ugagggaccc aggacaggag a                                                21

<210> SEQ ID NO 34
<211> LENGTH: 23
<212> TYPE: RNA
<213> ORGANISM: Homo sapiens

<400> SEQUENCE: 34
agaagaaggc ggucggucug cgg                                              23

<210> SEQ ID NO 35
<211> LENGTH: 21
<212> TYPE: RNA
<213> ORGANISM: Homo sapiens

<400> SEQUENCE: 35
caggaguggg ggugggacg u                                                 21

<210> SEQ ID NO 36
<211> LENGTH: 23
<212> TYPE: RNA
<213> ORGANISM: Homo sapiens

<400> SEQUENCE: 36
uggggggaca gauggagagg aca                                              23

<210> SEQ ID NO 37
```

-continued

```
<211> LENGTH: 23
<212> TYPE: RNA
<213> ORGANISM: Homo sapiens

<400> SEQUENCE: 37
cggggccgua gcacugucug aga                                           23

<210> SEQ ID NO 38
<211> LENGTH: 23
<212> TYPE: RNA
<213> ORGANISM: Homo sapiens

<400> SEQUENCE: 38
cugggcccgc ggcgggcgug ggg                                           23

<210> SEQ ID NO 39
<211> LENGTH: 22
<212> TYPE: RNA
<213> ORGANISM: Homo sapiens

<400> SEQUENCE: 39
ggaggggucc cgcacuggga gg                                            22

<210> SEQ ID NO 40
<211> LENGTH: 22
<212> TYPE: RNA
<213> ORGANISM: Homo sapiens

<400> SEQUENCE: 40
guggguacgg cccagugggg gg                                            22

<210> SEQ ID NO 41
<211> LENGTH: 18
<212> TYPE: RNA
<213> ORGANISM: Homo sapiens

<400> SEQUENCE: 41
gaggcugaag gaagaugg                                                 18

<210> SEQ ID NO 42
<211> LENGTH: 21
<212> TYPE: RNA
<213> ORGANISM: Homo sapiens

<400> SEQUENCE: 42 uggggugug gggagagaga g                                              21

<210> SEQ ID NO 43
<211> LENGTH: 22
<212> TYPE: RNA
<213> ORGANISM: Homo sapiens

<400> SEQUENCE: 43
ggcuacaaca caggacccgg gc                                            22

<210> SEQ ID NO 44
<211> LENGTH: 24
<212> TYPE: RNA
<213> ORGANISM: Homo sapiens

<400> SEQUENCE: 44
ugaggggccu cagaccgagc uuuu                                          24
```

```
<210> SEQ ID NO 45
<211> LENGTH: 21
<212> TYPE: RNA
<213> ORGANISM: Homo sapiens

<400> SEQUENCE: 45
gcugggaagg caaagggacg u                                              21

<210> SEQ ID NO 46
<211> LENGTH: 21
<212> TYPE: RNA
<213> ORGANISM: Homo sapiens

<400> SEQUENCE: 46
guuggggugc aggggucugc u                                              21

<210> SEQ ID NO 47
<211> LENGTH: 22
<212> TYPE: RNA
<213> ORGANISM: Homo sapiens

<400> SEQUENCE: 47
ugggcgaggg cggcugagcg gc                                             22

<210> SEQ ID NO 48
<211> LENGTH: 22
<212> TYPE: RNA
<213> ORGANISM: Homo sapiens

<400> SEQUENCE: 48
gggggucccc ggugcucgga uc                                             22

<210> SEQ ID NO 49
<211> LENGTH: 22
<212> TYPE: RNA
<213> ORGANISM: Homo sapiens

<400> SEQUENCE: 49
ucgggccugg gguuggggga gc                                             22

<210> SEQ ID NO 50
<211> LENGTH: 20
<212> TYPE: RNA
<213> ORGANISM: Homo sapiens

<400> SEQUENCE: 50
ucucuucauc uaccccccag                                                20

<210> SEQ ID NO 51
<211> LENGTH: 23
<212> TYPE: RNA
<213> ORGANISM: Homo sapiens

<400> SEQUENCE: 51
acaggcggcu guagcaaugg ggg                                            23

<210> SEQ ID NO 52
<211> LENGTH: 22
<212> TYPE: RNA
<213> ORGANISM: Homo sapiens

<400> SEQUENCE: 52
gcccaggacu uugugcgggg ug                                             22
```

```
<210> SEQ ID NO 53
<211> LENGTH: 21
<212> TYPE: RNA
<213> ORGANISM: Homo sapiens

<400> SEQUENCE: 53
caggcaggug uaggguggag c                                              21

<210> SEQ ID NO 54
<211> LENGTH: 23
<212> TYPE: RNA
<213> ORGANISM: Homo sapiens

<400> SEQUENCE: 54 ugggaggggga gaggcagcaa gca                                           23

<210> SEQ ID NO 55
<211> LENGTH: 22
<212> TYPE: RNA
<213> ORGANISM: Homo sapiens

<400> SEQUENCE: 55
aggcgaugug gggauguaga ga                                             22

<210> SEQ ID NO 56
<211> LENGTH: 23
<212> TYPE: RNA
<213> ORGANISM: Homo sapiens

<400> SEQUENCE: 56
ccucccugcc cgccucucug cag                                            23

<210> SEQ ID NO 57
<211> LENGTH: 23
<212> TYPE: RNA
<213> ORGANISM: Homo sapiens

<400> SEQUENCE: 57 cuggggggacg cgugagcgcg agc                                           23

<210> SEQ ID NO 58
<211> LENGTH: 22
<212> TYPE: RNA
<213> ORGANISM: Homo sapiens

<400> SEQUENCE: 58
agacacauuu ggagagggac cc                                             22

<210> SEQ ID NO 59
<211> LENGTH: 21
<212> TYPE: RNA
<213> ORGANISM: Homo sapiens

<400> SEQUENCE: 59
cuggggggag gagacccugc u                                              21

<210> SEQ ID NO 60
<211> LENGTH: 22
<212> TYPE: RNA
<213> ORGANISM: Homo sapiens

<400> SEQUENCE: 60
uggggguggu cucuagccaa gg                                             22
```

<210> SEQ ID NO 61
<211> LENGTH: 17
<212> TYPE: RNA
<213> ORGANISM: Homo sapiens

<400> SEQUENCE: 61
gccggacaag agggagg                                                  17

<210> SEQ ID NO 62
<211> LENGTH: 21
<212> TYPE: RNA
<213> ORGANISM: Homo sapiens

<400> SEQUENCE: 62
acaggagugg ggugggaca u                                              21

<210> SEQ ID NO 63
<211> LENGTH: 23
<212> TYPE: RNA
<213> ORGANISM: Homo sapiens

<400> SEQUENCE: 63
gccccggcgc gggcgdgguuc ugg                                          23

<210> SEQ ID NO 64
<211> LENGTH: 18
<212> TYPE: RNA
<213> ORGANISM: Homo sapiens

<400> SEQUENCE: 64
gugaaggccc ggcggaga                                                 18

<210> SEQ ID NO 65
<211> LENGTH: 22
<212> TYPE: RNA
<213> ORGANISM: Homo sapiens

<400> SEQUENCE: 65
cgucccgggg cugcgcgagg ca                                            22

<210> SEQ ID NO 66
<211> LENGTH: 25
<212> TYPE: RNA
<213> ORGANISM: Homo sapiens

<400> SEQUENCE: 66
agcggggagg aagugggcgc ugcuu                                         25

<210> SEQ ID NO 67
<211> LENGTH: 22
<212> TYPE: RNA
<213> ORGANISM: Homo sapiens

<400> SEQUENCE: 67 ucugccccu ccgcugcugc ca                                             22

<210> SEQ ID NO 68
<211> LENGTH: 23
<212> TYPE: RNA
<213> ORGANISM: Homo sapiens

<400> SEQUENCE: 68

```
gacacgggcg acagcugcgg ccc                                          23

<210> SEQ ID NO 69
<211> LENGTH: 24
<212> TYPE: RNA
<213> ORGANISM: Homo sapiens

<400> SEQUENCE: 69 ugggagcug aggcucuggg ggug                                          24

<210> SEQ ID NO 70
<211> LENGTH: 22
<212> TYPE: RNA
<213> ORGANISM: Homo sapiens

<400> SEQUENCE: 70
caggaggcag ugggcgagca gg                                           22

<210> SEQ ID NO 71
<211> LENGTH: 22
<212> TYPE: RNA
<213> ORGANISM: Homo sapiens

<400> SEQUENCE: 71
gggacccagg gagagacgua ag                                           22

<210> SEQ ID NO 72
<211> LENGTH: 21
<212> TYPE: RNA
<213> ORGANISM: Homo sapiens

<400> SEQUENCE: 72
uggggcgggg caggucccug c                                            21

<210> SEQ ID NO 73
<211> LENGTH: 23
<212> TYPE: RNA
<213> ORGANISM: Homo sapiens

<400> SEQUENCE: 73
gagggcagcg ugggugugc gga                                           23

<210> SEQ ID NO 74
<211> LENGTH: 23
<212> TYPE: RNA
<213> ORGANISM: Homo sapiens

<400> SEQUENCE: 74
ugggcagggg cuuauuguag gag                                          23

<210> SEQ ID NO 75
<211> LENGTH: 21
<212> TYPE: RNA
<213> ORGANISM: Homo sapiens

<400> SEQUENCE: 75
cguggaggac gaggaggagg c                                            21

<210> SEQ ID NO 76
<211> LENGTH: 19
<212> TYPE: RNA
<213> ORGANISM: Homo sapiens

<400> SEQUENCE: 76
```

```
agcagggcug gggauugca                                              19

<210> SEQ ID NO 77
<211> LENGTH: 22
<212> TYPE: RNA
<213> ORGANISM: Homo sapiens

<400> SEQUENCE: 77
gugaacgggc gccaucccga gg                                          22

<210> SEQ ID NO 78
<211> LENGTH: 22
<212> TYPE: RNA
<213> ORGANISM: Homo sapiens

<400> SEQUENCE: 78 cuuccccca guaaucuuca uc                                           22

<210> SEQ ID NO 79
<211> LENGTH: 20
<212> TYPE: RNA
<213> ORGANISM: Homo sapiens

<400> SEQUENCE: 79
gccggggcuu ugggugaggg                                             20

<210> SEQ ID NO 80
<211> LENGTH: 22
<212> TYPE: RNA
<213> ORGANISM: Homo sapiens

<400> SEQUENCE: 80
acgcccuucc cccccuucuu ca                                          22

<210> SEQ ID NO 81
<211> LENGTH: 20
<212> TYPE: RNA
<213> ORGANISM: Homo sapiens

<400> SEQUENCE: 81
gugagucagg gugggggcugg                                            20

<210> SEQ ID NO 82
<211> LENGTH: 21
<212> TYPE: RNA
<213> ORGANISM: Homo sapiens

<400> SEQUENCE: 82
auccaguucu cugaggggc u                                            21

<210> SEQ ID NO 83
<211> LENGTH: 20
<212> TYPE: RNA
<213> ORGANISM: Homo sapiens

<400> SEQUENCE: 83 uaggggugg caggcuggcc                                              20

<210> SEQ ID NO 84
<211> LENGTH: 18
<212> TYPE: RNA
<213> ORGANISM: Homo sapiens
```

-continued

```
<400> SEQUENCE: 84 gugggcuuc ccggaggg                                                    18

<210> SEQ ID NO 85
<211> LENGTH: 18
<212> TYPE: RNA
<213> ORGANISM: Homo sapiens

<400> SEQUENCE: 85 ggguccoggg gagggggg                                                   18

<210> SEQ ID NO 86
<211> LENGTH: 22
<212> TYPE: RNA
<213> ORGANISM: Homo sapiens

<400> SEQUENCE: 86
gcugcgggcu gcggucaggg cg                                              22

<210> SEQ ID NO 87
<211> LENGTH: 22
<212> TYPE: RNA
<213> ORGANISM: Homo sapiens

<400> SEQUENCE: 87
ugauugucuu cccccacccu ca                                              22

<210> SEQ ID NO 88
<211> LENGTH: 22
<212> TYPE: RNA
<213> ORGANISM: Homo sapiens

<400> SEQUENCE: 88
aggcggggcg ccgcgggacc gc                                              22

<210> SEQ ID NO 89
<211> LENGTH: 22
<212> TYPE: RNA
<213> ORGANISM: Homo sapiens

<400> SEQUENCE: 89
agacugacgg cuggaggccc au                                              22

<210> SEQ ID NO 90
<211> LENGTH: 21
<212> TYPE: RNA
<213> ORGANISM: Homo sapiens

<400> SEQUENCE: 90
cgggccggag gucaagggcg u                                               21

<210> SEQ ID NO 91
<211> LENGTH: 17
<212> TYPE: RNA
<213> ORGANISM: Homo sapiens

<400> SEQUENCE: 91 gugggggccag gcggugg                                                   17

<210> SEQ ID NO 92
<211> LENGTH: 19
<212> TYPE: RNA
<213> ORGANISM: Homo sapiens
```

```
<400> SEQUENCE: 92
cggggccaga gcagagagc                                                    19

<210> SEQ ID NO 93
<211> LENGTH: 23
<212> TYPE: RNA
<213> ORGANISM: Homo sapiens

<400> SEQUENCE: 93 ccaggggau gggcgagcuu ggg                                                23

<210> SEQ ID NO 94
<211> LENGTH: 22
<212> TYPE: RNA
<213> ORGANISM: Homo sapiens

<400> SEQUENCE: 94
gugggcuggg cugggcuggg cc                                                22

<210> SEQ ID NO 95
<211> LENGTH: 22
<212> TYPE: RNA
<213> ORGANISM: Homo sapiens

<400> SEQUENCE: 95
accuugccuu gcugcccggg cc                                                22

<210> SEQ ID NO 96
<211> LENGTH: 17
<212> TYPE: RNA
<213> ORGANISM: Homo sapiens

<400> SEQUENCE: 96
gggagucuac agcaggg                                                      17

<210> SEQ ID NO 97
<211> LENGTH: 22
<212> TYPE: RNA
<213> ORGANISM: Homo sapiens

<400> SEQUENCE: 97
agacacauuu ggagagggaa cc                                                22

<210> SEQ ID NO 98
<211> LENGTH: 20
<212> TYPE: RNA
<213> ORGANISM: Homo sapiens

<400> SEQUENCE: 98
acucaaacug uggggcacu                                                    20

<210> SEQ ID NO 99
<211> LENGTH: 21
<212> TYPE: RNA
<213> ORGANISM: Homo sapiens

<400> SEQUENCE: 99
aaggcagggc ccccgcuccc c                                                 21

<210> SEQ ID NO 100
<211> LENGTH: 22
<212> TYPE: RNA
```

-continued

```
<213> ORGANISM: Homo sapiens

<400> SEQUENCE: 100 ugggauuug gagaaguggu ga                                              22

<210> SEQ ID NO 101
<211> LENGTH: 24
<212> TYPE: RNA
<213> ORGANISM: Homo sapiens

<400> SEQUENCE: 101 uggggagcc augagauaag agca                                            24

<210> SEQ ID NO 102
<211> LENGTH: 22
<212> TYPE: RNA
<213> ORGANISM: Homo sapiens

<400> SEQUENCE: 102
cucggcgcgg ggcgcgggcu cc                                             22

<210> SEQ ID NO 103
<211> LENGTH: 22
<212> TYPE: RNA
<213> ORGANISM: Homo sapiens

<400> SEQUENCE: 103 acugguagg uggggcucca gg                                              22

<210> SEQ ID NO 104
<211> LENGTH: 18
<212> TYPE: RNA
<213> ORGANISM: Homo sapiens

<400> SEQUENCE: 104
auccuaguca cggcacca                                                  18

<210> SEQ ID NO 105
<211> LENGTH: 22
<212> TYPE: RNA
<213> ORGANISM: Homo sapiens

<400> SEQUENCE: 105
cagggcaggg aaggugggag ag                                             22

<210> SEQ ID NO 106
<211> LENGTH: 20
<212> TYPE: RNA
<213> ORGANISM: Homo sapiens

<400> SEQUENCE: 106
cuaggugggg ggcuugaagc                                                20

<210> SEQ ID NO 107
<211> LENGTH: 20
<212> TYPE: RNA
<213> ORGANISM: Homo sapiens

<400> SEQUENCE: 107
cgggcguggu gguggggug                                                 20

<210> SEQ ID NO 108
<211> LENGTH: 22
```

```
<212> TYPE: RNA
<213> ORGANISM: Homo sapiens

<400> SEQUENCE: 108
gguggcccgg ccgugccuga gg                                         22

<210> SEQ ID NO 109
<211> LENGTH: 22
<212> TYPE: RNA
<213> ORGANISM: Homo sapiens

<400> SEQUENCE: 109
acaggugagg uucuugggag cc                                         22

<210> SEQ ID NO 110
<211> LENGTH: 19
<212> TYPE: RNA
<213> ORGANISM: Homo sapiens

<400> SEQUENCE: 110
ggggccuggc ggugggcgg                                             19

<210> SEQ ID NO 111
<211> LENGTH: 20
<212> TYPE: RNA
<213> ORGANISM: Homo sapiens

<400> SEQUENCE: 111
agagaugaag cgggggggcg                                            20

<210> SEQ ID NO 112
<211> LENGTH: 23
<212> TYPE: RNA
<213> ORGANISM: Homo sapiens

<400> SEQUENCE: 112
gugaguggga gccgguggggg cug                                       23

<210> SEQ ID NO 113
<211> LENGTH: 22
<212> TYPE: RNA
<213> ORGANISM: Homo sapiens

<400> SEQUENCE: 113
gaggguuggg uggaggcucu cc                                         22

<210> SEQ ID NO 114
<211> LENGTH: 23
<212> TYPE: RNA
<213> ORGANISM: Homo sapiens

<400> SEQUENCE: 114 cgaggggguag aagagcacag ggg                                       23

<210> SEQ ID NO 115
<211> LENGTH: 23
<212> TYPE: RNA
<213> ORGANISM: Homo sapiens

<400> SEQUENCE: 115
aggaagcccu ggaggggcug gag                                        23

<210> SEQ ID NO 116
```

```
<211> LENGTH: 20
<212> TYPE: RNA
<213> ORGANISM: Homo sapiens

<400> SEQUENCE: 116
ggauccgagu cacggcacca                                                    20

<210> SEQ ID NO 117
<211> LENGTH: 17
<212> TYPE: RNA
<213> ORGANISM: Homo sapiens

<400> SEQUENCE: 117
gggagaaggg ucggggc                                                       17

<210> SEQ ID NO 118
<211> LENGTH: 21
<212> TYPE: RNA
<213> ORGANISM: Homo sapiens

<400> SEQUENCE: 118
aagggacagg gagggucgug g                                                  21

<210> SEQ ID NO 119
<211> LENGTH: 23
<212> TYPE: RNA
<213> ORGANISM: Homo sapiens

<400> SEQUENCE: 119
cgggcugucc ggaggggucg gcu                                                23

<210> SEQ ID NO 120
<211> LENGTH: 22
<212> TYPE: RNA
<213> ORGANISM: Homo sapiens

<400> SEQUENCE: 120
agggacggga cgcggugcag ug                                                 22

<210> SEQ ID NO 121
<211> LENGTH: 24
<212> TYPE: RNA
<213> ORGANISM: Homo sapiens

<400> SEQUENCE: 121
uggggggaca ggaugagagg cugu                                               24

<210> SEQ ID NO 122
<211> LENGTH: 23
<212> TYPE: RNA
<213> ORGANISM: Homo sapiens

<400> SEQUENCE: 122
uugcucugcu cccccgcccc cag                                                23

<210> SEQ ID NO 123
<211> LENGTH: 22
<212> TYPE: RNA
<213> ORGANISM: Homo sapiens

<400> SEQUENCE: 123
uggggaaggc gucagugucg gg                                                 22
```

```
<210> SEQ ID NO 124
<211> LENGTH: 25
<212> TYPE: RNA
<213> ORGANISM: Homo sapiens

<400> SEQUENCE: 124
uagggguggg ggaauucagg ggugu                                  25

<210> SEQ ID NO 125
<211> LENGTH: 22
<212> TYPE: RNA
<213> ORGANISM: Homo sapiens

<400> SEQUENCE: 125
uaggggcagc agaggaccug gg                                     22

<210> SEQ ID NO 126
<211> LENGTH: 22
<212> TYPE: RNA
<213> ORGANISM: Homo sapiens

<400> SEQUENCE: 126
gugcggaacg cuggccgggg cg                                     22

<210> SEQ ID NO 127
<211> LENGTH: 23
<212> TYPE: RNA
<213> ORGANISM: Homo sapiens

<400> SEQUENCE: 127
acggggaguc aggcaguggu gga                                    23

<210> SEQ ID NO 128
<211> LENGTH: 22
<212> TYPE: RNA
<213> ORGANISM: Homo sapiens

<400> SEQUENCE: 128
ugggagggcg uggaugaugg ug                                     22

<210> SEQ ID NO 129
<211> LENGTH: 20
<212> TYPE: RNA
<213> ORGANISM: Homo sapiens

<400> SEQUENCE: 129
ugggaggagg ggaucuuggg                                        20

<210> SEQ ID NO 130
<211> LENGTH: 23
<212> TYPE: RNA
<213> ORGANISM: Homo sapiens

<400> SEQUENCE: 130
ugagcaccac acaggccggg cgc                                    23

<210> SEQ ID NO 131
<211> LENGTH: 19
<212> TYPE: RNA
<213> ORGANISM: Homo sapiens

<400> SEQUENCE: 131
ggcuggucag augggagug                                         19
```

-continued

```
<210> SEQ ID NO 132
<211> LENGTH: 20
<212> TYPE: RNA
<213> ORGANISM: Homo sapiens

<400> SEQUENCE: 132
ccccagggcg acgcggcggg                                              20

<210> SEQ ID NO 133
<211> LENGTH: 17
<212> TYPE: RNA
<213> ORGANISM: Homo sapiens

<400> SEQUENCE: 133
ccccggggag cccggcg                                                 17

<210> SEQ ID NO 134
<211> LENGTH: 19
<212> TYPE: RNA
<213> ORGANISM: Homo sapiens

<400> SEQUENCE: 134
ugcggcagag cugggguca                                               19

<210> SEQ ID NO 135
<211> LENGTH: 22
<212> TYPE: RNA
<213> ORGANISM: Homo sapiens

<400> SEQUENCE: 135
uugaggagac auguggggg cc                                            22

<210> SEQ ID NO 136
<211> LENGTH: 21
<212> TYPE: RNA
<213> ORGANISM: Homo sapiens

<400> SEQUENCE: 136
acucggcugc gguggacaag u                                            21

<210> SEQ ID NO 137
<211> LENGTH: 17
<212> TYPE: RNA
<213> ORGANISM: Homo sapiens

<400> SEQUENCE: 137
ggcgggugcg ggggugg                                                 17

<210> SEQ ID NO 138
<211> LENGTH: 20
<212> TYPE: RNA
<213> ORGANISM: Homo sapiens

<400> SEQUENCE: 138
cgcgggucgg ggucugcagg                                              20

<210> SEQ ID NO 139
<211> LENGTH: 23
<212> TYPE: RNA
<213> ORGANISM: Homo sapiens

<400> SEQUENCE: 139
uggugggugg ggaggagaag ugc                                          23
```

```
<210> SEQ ID NO 140
<211> LENGTH: 21
<212> TYPE: RNA
<213> ORGANISM: Homo sapiens

<400> SEQUENCE: 140
agggagggac gggggcugug c                                              21

<210> SEQ ID NO 141
<211> LENGTH: 21
<212> TYPE: RNA
<213> ORGANISM: Homo sapiens

<400> SEQUENCE: 141
aucacauugc cagggauuac c                                              21

<210> SEQ ID NO 142
<211> LENGTH: 22
<212> TYPE: RNA
<213> ORGANISM: Homo sapiens

<400> SEQUENCE: 142
ggcuggagcg agugcagugg ug                                             22

<210> SEQ ID NO 143
<211> LENGTH: 23
<212> TYPE: RNA
<213> ORGANISM: Homo sapiens

<400> SEQUENCE: 143 uggggcugg gaugggccau ggu                                             23

<210> SEQ ID NO 144
<211> LENGTH: 21
<212> TYPE: RNA
<213> ORGANISM: Homo sapiens

<400> SEQUENCE: 144
agguggguau ggaggagccc u                                              21

<210> SEQ ID NO 145
<211> LENGTH: 19
<212> TYPE: RNA
<213> ORGANISM: Homo sapiens

<400> SEQUENCE: 145
ggcuugcaug ggggacugg                                                 19

<210> SEQ ID NO 146
<211> LENGTH: 21
<212> TYPE: RNA
<213> ORGANISM: Homo sapiens

<400> SEQUENCE: 146
ucaccuggcu ggcccgccca g                                              21

<210> SEQ ID NO 147
<211> LENGTH: 20
<212> TYPE: RNA
<213> ORGANISM: Homo sapiens

<400> SEQUENCE: 147
```

```
ugggaauggg gguaagggcc                                           20

<210> SEQ ID NO 148
<211> LENGTH: 22
<212> TYPE: RNA
<213> ORGANISM: Homo sapiens

<400> SEQUENCE: 148
agggccgaag gguggaagcu gc                                        22

<210> SEQ ID NO 149
<211> LENGTH: 23
<212> TYPE: RNA
<213> ORGANISM: Homo sapiens

<400> SEQUENCE: 149
cucggggcag gcggcuggga gcg                                       23

<210> SEQ ID NO 150
<211> LENGTH: 17
<212> TYPE: RNA
<213> ORGANISM: Homo sapiens

<400> SEQUENCE: 150
ggauggagga ggggucu                                              17

<210> SEQ ID NO 151
<211> LENGTH: 23
<212> TYPE: RNA
<213> ORGANISM: Homo sapiens

<400> SEQUENCE: 151
gaacgccugu ucuugccagg ugg                                       23

<210> SEQ ID NO 152
<211> LENGTH: 21
<212> TYPE: RNA
<213> ORGANISM: Homo sapiens

<400> SEQUENCE: 152
gugccagcug caguggggga g                                         21

<210> SEQ ID NO 153
<211> LENGTH: 19
<212> TYPE: RNA
<213> ORGANISM: Homo sapiens

<400> SEQUENCE: 153
gagccaguug gacaggagc                                            19

<210> SEQ ID NO 154
<211> LENGTH: 19
<212> TYPE: RNA
<213> ORGANISM: Homo sapiens

<400> SEQUENCE: 154 uggggagau gggguuga                                              19

<210> SEQ ID NO 155
<211> LENGTH: 22
<212> TYPE: RNA
<213> ORGANISM: Homo sapiens

<400> SEQUENCE: 155
```

```
ugcaggggu c ggugggcca gg                                             22

<210> SEQ ID NO 156
<211> LENGTH: 18
<212> TYPE: RNA
<213> ORGANISM: Homo sapiens

<400> SEQUENCE: 156
uucccagcca acgcacca                                                  18

<210> SEQ ID NO 157
<211> LENGTH: 24
<212> TYPE: RNA
<213> ORGANISM: Homo sapiens

<400> SEQUENCE: 157
ugggcgaggg gugggcucuc agag                                           24

<210> SEQ ID NO 158
<211> LENGTH: 22
<212> TYPE: RNA
<213> ORGANISM: Homo sapiens

<400> SEQUENCE: 158
ggggcuguga uugaccagca gg                                             22

<210> SEQ ID NO 159
<211> LENGTH: 21
<212> TYPE: RNA
<213> ORGANISM: Homo sapiens

<400> SEQUENCE: 159
acggcccagg cggcauuggu g                                              21

<210> SEQ ID NO 160
<211> LENGTH: 21
<212> TYPE: RNA
<213> ORGANISM: Homo sapiens

<400> SEQUENCE: 160
cugggagggg cuggguuugg c                                              21

<210> SEQ ID NO 161
<211> LENGTH: 19
<212> TYPE: RNA
<213> ORGANISM: Homo sapiens

<400> SEQUENCE: 161
gggggaagaa aaggugggg                                                 19

<210> SEQ ID NO 162
<211> LENGTH: 18
<212> TYPE: RNA
<213> ORGANISM: Homo sapiens

<400> SEQUENCE: 162
cggggcggca ggggccuc                                                  18

<210> SEQ ID NO 163
<211> LENGTH: 22
<212> TYPE: RNA
<213> ORGANISM: Homo sapiens
```

```
<400> SEQUENCE: 163 cuggggugg ggggcugggc gu                                            22

<210> SEQ ID NO 164
<211> LENGTH: 24
<212> TYPE: RNA
<213> ORGANISM: Homo sapiens

<400> SEQUENCE: 164 guagggcgu cccgggcgcg cggg                                          24

<210> SEQ ID NO 165
<211> LENGTH: 20
<212> TYPE: RNA
<213> ORGANISM: Homo sapiens

<400> SEQUENCE: 165
ugugggacug caaaugggag                                              20

<210> SEQ ID NO 166
<211> LENGTH: 17
<212> TYPE: RNA
<213> ORGANISM: Homo sapiens

<400> SEQUENCE: 166
gcggggcugg gcgcgcg                                                 17

<210> SEQ ID NO 167
<211> LENGTH: 22
<212> TYPE: RNA
<213> ORGANISM: Homo sapiens

<400> SEQUENCE: 167
ugcggggaca ggccagggca uc                                           22

<210> SEQ ID NO 168
<211> LENGTH: 18
<212> TYPE: RNA
<213> ORGANISM: Homo sapiens

<400> SEQUENCE: 168
aggcugggcu gggacgga                                                18

<210> SEQ ID NO 169
<211> LENGTH: 22
<212> TYPE: RNA
<213> ORGANISM: Homo sapiens

<400> SEQUENCE: 169 uggggagug cagugauugu gg                                            22

<210> SEQ ID NO 170
<211> LENGTH: 20
<212> TYPE: RNA
<213> ORGANISM: Homo sapiens

<400> SEQUENCE: 170
ccugagcccg ggccgcgcag                                              20

<210> SEQ ID NO 171
<211> LENGTH: 24
<212> TYPE: RNA
<213> ORGANISM: Homo sapiens
```

```
<400> SEQUENCE: 171
aggcaggggc uggugcuggg cggg                                         24

<210> SEQ ID NO 172
<211> LENGTH: 20
<212> TYPE: RNA
<213> ORGANISM: Homo sapiens

<400> SEQUENCE: 172
gugucugggc ggacagcugc                                              20

<210> SEQ ID NO 173
<211> LENGTH: 22
<212> TYPE: RNA
<213> ORGANISM: Homo sapiens

<400> SEQUENCE: 173
agugggaggc cagggcacgg ca                                           22

<210> SEQ ID NO 174
<211> LENGTH: 22
<212> TYPE: RNA
<213> ORGANISM: Homo sapiens

<400> SEQUENCE: 174
cugguacagg ccuggggac ag                                            22

<210> SEQ ID NO 175
<211> LENGTH: 22
<212> TYPE: RNA
<213> ORGANISM: Homo sapiens

<400> SEQUENCE: 175
ugagccccug ugccgccccc ag                                           22

<210> SEQ ID NO 176
<211> LENGTH: 22
<212> TYPE: RNA
<213> ORGANISM: Homo sapiens

<400> SEQUENCE: 176 gggugggau uuguugcauu ac                                            22

<210> SEQ ID NO 177
<211> LENGTH: 23
<212> TYPE: RNA
<213> ORGANISM: Homo sapiens

<400> SEQUENCE: 177 ugagggcag agagcgagac uuu                                           23

<210> SEQ ID NO 178
<211> LENGTH: 18
<212> TYPE: RNA
<213> ORGANISM: Homo sapiens

<400> SEQUENCE: 178
cgggcguggu ggugggg                                                 18

<210> SEQ ID NO 179
<211> LENGTH: 23
<212> TYPE: RNA
```

<213> ORGANISM: Homo sapiens

<400> SEQUENCE: 179
gggggccgau acacuguacg aga        23

<210> SEQ ID NO 180
<211> LENGTH: 22
<212> TYPE: RNA
<213> ORGANISM: Homo sapiens

<400> SEQUENCE: 180
uggcucaguu cagcaggaac ag        22

<210> SEQ ID NO 181
<211> LENGTH: 22
<212> TYPE: RNA
<213> ORGANISM: Homo sapiens

<400> SEQUENCE: 181 aggggcgca gucacugacg ug        22

<210> SEQ ID NO 182
<211> LENGTH: 23
<212> TYPE: RNA
<213> ORGANISM: Homo sapiens

<400> SEQUENCE: 182
ggaggcgcag gcucggaaag gcg        23

<210> SEQ ID NO 183
<211> LENGTH: 23
<212> TYPE: RNA
<213> ORGANISM: Homo sapiens

<400> SEQUENCE: 183
uggugcggag agggcccaca gug        23

<210> SEQ ID NO 184
<211> LENGTH: 17
<212> TYPE: RNA
<213> ORGANISM: Homo sapiens

<400> SEQUENCE: 184
gcugggcgag gcuggca        17

<210> SEQ ID NO 185
<211> LENGTH: 22
<212> TYPE: RNA
<213> ORGANISM: Homo sapiens

<400> SEQUENCE: 185
ucggccuggg gaggaggaag gg        22

<210> SEQ ID NO 186
<211> LENGTH: 21
<212> TYPE: RNA
<213> ORGANISM: Homo sapiens

<400> SEQUENCE: 186
aucacauugc cagggauuuc c        21

<210> SEQ ID NO 187
<211> LENGTH: 22

<212> TYPE: RNA
<213> ORGANISM: Homo sapiens

<400> SEQUENCE: 187 acugggagc agaaggagaa cc                                              22

<210> SEQ ID NO 188
<211> LENGTH: 22
<212> TYPE: RNA
<213> ORGANISM: Homo sapiens

<400> SEQUENCE: 188
aaaccguuac cauuacugag uu                                             22

<210> SEQ ID NO 189
<211> LENGTH: 20
<212> TYPE: RNA
<213> ORGANISM: Homo sapiens

<400> SEQUENCE: 189
guggguuggg gcgggcucug                                                20

<210> SEQ ID NO 190
<211> LENGTH: 22
<212> TYPE: RNA
<213> ORGANISM: Homo sapiens

<400> SEQUENCE: 190 gggaacugu agaugaaaag gc                                              22

<210> SEQ ID NO 191
<211> LENGTH: 23
<212> TYPE: RNA
<213> ORGANISM: Homo sapiens

<400> SEQUENCE: 191
caggggcugg gguuucaggu ucu                                            23

<210> SEQ ID NO 192
<211> LENGTH: 17
<212> TYPE: RNA
<213> ORGANISM: Homo sapiens

<400> SEQUENCE: 192
ggggcugggc gcgcgcc                                                   17

<210> SEQ ID NO 193
<211> LENGTH: 22
<212> TYPE: RNA
<213> ORGANISM: Homo sapiens

<400> SEQUENCE: 193
caggaaggau uuagggacag gc                                             22

<210> SEQ ID NO 194
<211> LENGTH: 19
<212> TYPE: RNA
<213> ORGANISM: Homo sapiens

<400> SEQUENCE: 194
ggggagcgag gggcgggc                                                  19

<210> SEQ ID NO 195

```
<211> LENGTH: 61
<212> TYPE: RNA
<213> ORGANISM: Homo sapiens

<400> SEQUENCE: 195
gggggcggga gcuggggucu gcagguucgc acugaugccu gcucgcccug ucucccgcua    60
g                                                                    61

<210> SEQ ID NO 196
<211> LENGTH: 86
<212> TYPE: RNA
<213> ORGANISM: Homo sapiens

<400> SEQUENCE: 196
ggcuuagaaa cagucccuag guaggauuug gggaggagcu aagaagcccc uacagggccc    60
agaggugggg acugagccuu aguugg                                         86

<210> SEQ ID NO 197
<211> LENGTH: 61
<212> TYPE: RNA
<213> ORGANISM: Homo sapiens

<400> SEQUENCE: 197
ucggcuggcg gggguagagc uggcugcagg cccggcccu cucagcugcu gcccucucca    60
g                                                                    61

<210> SEQ ID NO 198
<211> LENGTH: 79
<212> TYPE: RNA
<213> ORGANISM: Homo sapiens

<400> SEQUENCE: 198
cagccugggg aaggcuuggc agggaagaca caugagcagu gccuccacuu cacgccucuc    60
ccuugucucc uuucccuag                                                 79

<210> SEQ ID NO 199
<211> LENGTH: 63
<212> TYPE: RNA
<213> ORGANISM: Homo sapiens

<400> SEQUENCE: 199
gagucgagga cugguggaag ggccuuuccc cucagaccaa ggcccuggcc ccagcuucuu    60
cuc                                                                  63

<210> SEQ ID NO 200
<211> LENGTH: 87
<212> TYPE: RNA
<213> ORGANISM: Homo sapiens

<400> SEQUENCE: 200
guguggccgg caggcgggug ggcggggggcg gccgguggga accccgcccc gccccgcgcc    60
cgcacucacc cgcccgucuc cccacag                                        87

<210> SEQ ID NO 201
<211> LENGTH: 84
<212> TYPE: RNA
<213> ORGANISM: Homo sapiens

<400> SEQUENCE: 201
gcuggcgucg gugcugggga gcggcccccg ggugggccuc ugcucuggcc ccuccugggg    60
```

```
cccgcacucu cgcucgggc ccgc                                          84

<210> SEQ ID NO 202
<211> LENGTH: 136
<212> TYPE: RNA
<213> ORGANISM: Homo sapiens

<400> SEQUENCE: 202
ccgcuugccu cgcccagcgc agcccggcc gcugggcgca cccgucccgu ucgucccgg    60 acguugcucu cuaccccggg aacgucgaga cuggagcgcc cgaacugagc caccuucgcg  120
gaccccgaga gcggcg                                                  136

<210> SEQ ID NO 203
<211> LENGTH: 73
<212> TYPE: RNA
<213> ORGANISM: Homo sapiens

<400> SEQUENCE: 203
cggcgacggc gggugggug aggucgggcc ccaagacucg ggguugccgg ggcgccucag   60
uucaccgcgg ccg                                                     73

<210> SEQ ID NO 204
<211> LENGTH: 69
<212> TYPE: RNA
<213> ORGANISM: Homo sapiens

<400> SEQUENCE: 204
gggcuuaggg augggaggcc aggaugaaga uuaauccccua auccccaaca cuggccuugc 60
uaucccag                                                           69

<210> SEQ ID NO 205
<211> LENGTH: 68
<212> TYPE: RNA
<213> ORGANISM: Homo sapiens

<400> SEQUENCE: 205
cguggugagg auauggcagg gaagggagu ucccucuau ucccuucccc ccaguaaucu    60
ucaucaug                                                           68

<210> SEQ ID NO 206
<211> LENGTH: 61
<212> TYPE: RNA
<213> ORGANISM: Homo sapiens

<400> SEQUENCE: 206
ucucguuuga ucucggaagc uaagcagggu ugggccuggu aguacuugg augggaaacu   60 u                                                                  61

<210> SEQ ID NO 207
<211> LENGTH: 53
<212> TYPE: RNA
<213> ORGANISM: Homo sapiens

<400> SEQUENCE: 207
guuugaucuc ggaagcuaag cagggucggg ccugguuagu acuuggauggg gag        53

<210> SEQ ID NO 208
<211> LENGTH: 63
<212> TYPE: RNA
```

<213> ORGANISM: Homo sapiens

<400> SEQUENCE: 208
cuugcccggg agaaggaggu ggccuggaga gcugcugucu ccagccgccg ccugucucca    60
cag    63

<210> SEQ ID NO 209
<211> LENGTH: 80
<212> TYPE: RNA
<213> ORGANISM: Homo sapiens

<400> SEQUENCE: 209
gcgucaagau ggcggcgggg agguaggcag agcaggacgc cgcugcugcc gccgccaccg    60
ccgccuccgc uccagucgcc    80

<210> SEQ ID NO 210
<211> LENGTH: 63
<212> TYPE: RNA
<213> ORGANISM: Homo sapiens

<400> SEQUENCE: 210 aaugggugggg ugcugguggg agccgugccc uggccacuca uucggcucuc ucccucaccc    60
uag    63

<210> SEQ ID NO 211
<211> LENGTH: 80
<212> TYPE: RNA
<213> ORGANISM: Homo sapiens

<400> SEQUENCE: 211
cgggaaugcc gcggcgggga cggcgauugg uccguaugug uggugccacc ggccgccggc    60
uccgccccgg ccccgcccc    80

<210> SEQ ID NO 212
<211> LENGTH: 93
<212> TYPE: RNA
<213> ORGANISM: Homo sapiens

<400> SEQUENCE: 212
gcuuguuggg gauuggguca ggccagguguu caagggcccc uccucuagua cucccuguuu    60
guguucugcc acugacugag cuucuccccca cag    93

<210> SEQ ID NO 213
<211> LENGTH: 71
<212> TYPE: RNA
<213> ORGANISM: Homo sapiens

<400> SEQUENCE: 213
gugucugugc cgguccuagg agaaccugca gaggcaucgg gucagcggug cuccugcggg    60
ccgacacuca c    71

<210> SEQ ID NO 214
<211> LENGTH: 98
<212> TYPE: RNA
<213> ORGANISM: Homo sapiens

<400> SEQUENCE: 214
uugggcaagg ugcggggcua gggcuaacag cagucuuacu gaagguuucc uggaaaccac    60
gcacaugcug uugccacuaa ccucaaccuu acucggguc    98

<210> SEQ ID NO 215
<211> LENGTH: 74
<212> TYPE: RNA
<213> ORGANISM: Homo sapiens

<400> SEQUENCE: 215
gcagcccggu gagcgcucgc uggccuggca gugcgucgga agaacagggc ggguggggcc      60
gcgcacaucu cugc      74

<210> SEQ ID NO 216
<211> LENGTH: 94
<212> TYPE: RNA
<213> ORGANISM: Homo sapiens

<400> SEQUENCE: 216
cgggcagcgg gugccaggca cggugucagc aggcaacaug gccgagaggc cggggccucc      60
gggcggcgcc guguccgcga ccgcguaccc ugac      94

<210> SEQ ID NO 217
<211> LENGTH: 67
<212> TYPE: RNA
<213> ORGANISM: Homo sapiens

<400> SEQUENCE: 217
ccagaccccu ggggcugggc aggcggaaag aggucugaac ugccucugcc uccuuggucu      60
ccggcag      67

<210> SEQ ID NO 218
<211> LENGTH: 66
<212> TYPE: RNA
<213> ORGANISM: Homo sapiens

<400> SEQUENCE: 218
gggcaugggg aggugugggag ucagcauggg gcuaggaggc cccgcgcuga cccgccuucu      60
ccgcag      66

<210> SEQ ID NO 219
<211> LENGTH: 98
<212> TYPE: RNA
<213> ORGANISM: Homo sapiens

<400> SEQUENCE: 219
cuuggucaau aggaaagagg ugggaccucc uggcuuuucc ucugcagcau ggcucggacc      60
uagugcaaug uuuaagcucc ccucucuuuc cguucag      98

<210> SEQ ID NO 220
<211> LENGTH: 79
<212> TYPE: RNA
<213> ORGANISM: Homo sapiens

<400> SEQUENCE: 220
cucgaggugc uggggacgc gugagcgcga gccgcuuccu cacggcucgg ccgcggcgcg      60 uagccccgc cacaucggg      79

<210> SEQ ID NO 221
<211> LENGTH: 63
<212> TYPE: RNA
<213> ORGANISM: Homo sapiens

```
<400> SEQUENCE: 221
ugguggcggc gguaguuaug ggcuucucuu ucucaccagc agcccugggg ccgccgccuc    60
ccu                                                                  63

<210> SEQ ID NO 222
<211> LENGTH: 85
<212> TYPE: RNA
<213> ORGANISM: Homo sapiens

<400> SEQUENCE: 222
ggcgccuccu gcucugcugu gccgccaggg ccuccccuag cgcgccuucu ggagaggcuu    60
ugugcggaua cggggcugga ggccu                                          85

<210> SEQ ID NO 223
<211> LENGTH: 96
<212> TYPE: RNA
<213> ORGANISM: Homo sapiens

<400> SEQUENCE: 223
gcucuggggc gugccgccgc cgucgcugcc accuccccua ccgcuagugg aagaagaugg    60
cggaaggcgg agcggcggau cuggacaccc agcggu                              96

<210> SEQ ID NO 224
<211> LENGTH: 63
<212> TYPE: RNA
<213> ORGANISM: Homo sapiens

<400> SEQUENCE: 224
acccuagggu ggggcuggag gugggcuga ggcugagucu uccuccccuu ccucccugcc     60
cag                                                                  63

<210> SEQ ID NO 225
<211> LENGTH: 73
<212> TYPE: RNA
<213> ORGANISM: Homo sapiens

<400> SEQUENCE: 225
gugggcgggg gcaggugugu gguggguggu ggccugcggu gagcagggcc cucacaccug    60
ccucgccccc cag                                                       73

<210> SEQ ID NO 226
<211> LENGTH: 81
<212> TYPE: RNA
<213> ORGANISM: Homo sapiens

<400> SEQUENCE: 226
uagaggcagu uucaacagau guguagacuu uugauaugag aaauuggeuu caaaaucagg    60 agucggggcu uuacugcuuu u                                              81

<210> SEQ ID NO 227
<211> LENGTH: 86
<212> TYPE: RNA
<213> ORGANISM: Homo sapiens

<400> SEQUENCE: 227
cgccugagcg ugcagcagga caucuuccug accugguaau aauuaggega gaaggauggu    60 uggggggcggu cggcguaacu caggga                                        86
```

```
<210> SEQ ID NO 228
<211> LENGTH: 72
<212> TYPE: RNA
<213> ORGANISM: Homo sapiens

<400> SEQUENCE: 228
gagucugagg gacccaggac aggagaaggc cuauggugau uugcauucuu ccugcccugg    60
cuccauccuc ag                                                       72

<210> SEQ ID NO 229
<211> LENGTH: 68
<212> TYPE: RNA
<213> ORGANISM: Homo sapiens

<400> SEQUENCE: 229
gaauggaaga agaaggcggu cggucugcgg gagccaggcc gcagagccau ccgccuucug    60
uccauguc                                                            68

<210> SEQ ID NO 230
<211> LENGTH: 102
<212> TYPE: RNA
<213> ORGANISM: Homo sapiens

<400> SEQUENCE: 230
uguguucccu auccuccuua ugucccaccc ccacuccugu uugaauauuu caccagaaac    60
aggagugggg ggugggacgu aaggaggaug ggggaaagaa ca                      102

<210> SEQ ID NO 231
<211> LENGTH: 65
<212> TYPE: RNA
<213> ORGANISM: Homo sapiens

<400> SEQUENCE: 231 gagaauggggg ggacagaugg agaggacaca ggcuggcacu gagguccccu ccacuuuccu   60
ccuag                                                               65

<210> SEQ ID NO 232
<211> LENGTH: 82
<212> TYPE: RNA
<213> ORGANISM: Homo sapiens

<400> SEQUENCE: 232
ugagcuguug gauucggggc cguagcacug ucgagaggu uuacauuucu cacagugaac     60
cggucucuuu uucagcugcu uc                                            82

<210> SEQ ID NO 233
<211> LENGTH: 92
<212> TYPE: RNA
<213> ORGANISM: Homo sapiens

<400> SEQUENCE: 233
cgcugcgcuu cugggcccgc ggcgggcgug gggcugcccg ggccggucga ccagcgcgcc    60
guagcucccg aggcccgagc cgcgacccgc gg                                 92

<210> SEQ ID NO 234
<211> LENGTH: 80
<212> TYPE: RNA
<213> ORGANISM: Homo sapiens

<400> SEQUENCE: 234
```

```
cgugugagcc cgcccugugc ccggcccacu ucugcuuccu cuuagcgcag gaggggcccc      60
gcacugggag gggcccucac                                                 80

<210> SEQ ID NO 235
<211> LENGTH: 90
<212> TYPE: RNA
<213> ORGANISM: Homo sapiens

<400> SEQUENCE: 235
guggguacgg cccagugggg gggagaggga cacgcccugg gcucugccca gggugcagcc      60
ggacugacug agccccugug ccgccccag                                       90

<210> SEQ ID NO 236
<211> LENGTH: 68
<212> TYPE: RNA
<213> ORGANISM: Homo sapiens

<400> SEQUENCE: 236
cucaggcuca guggugcaug cuuauagucc cagccacucu ggaggcugaa ggaagauggc      60
uugagccu                                                              68

<210> SEQ ID NO 237
<211> LENGTH: 86
<212> TYPE: RNA
<213> ORGANISM: Homo sapiens

<400> SEQUENCE: 237
ggggcugggg gugugggggag agagagugca cagccagcuc agggauuaaa gcucuuucuc     60
ucucucucuc ucccacuucc cugcag                                          86

<210> SEQ ID NO 238
<211> LENGTH: 109
<212> TYPE: RNA
<213> ORGANISM: Homo sapiens

<400> SEQUENCE: 238
ggucgggcuc accaugacac agugugagac cucgggcuac aacacaggac ccgggcgcug      60
cucugacccc ucgugucuug uguugcagcc ggagggacgc agguccgca                 109

<210> SEQ ID NO 239
<211> LENGTH: 75
<212> TYPE: RNA
<213> ORGANISM: Homo sapiens

<400> SEQUENCE: 239
aagcaagacu gaggggccuc agaccgagcu uuuggaaaau agaaaagucu cgcucucugc      60
cccucagccu aacuu                                                      75

<210> SEQ ID NO 240
<211> LENGTH: 110
<212> TYPE: RNA
<213> ORGANISM: Homo sapiens

<400> SEQUENCE: 240
ggcuacaguc uuucuucaug ugacucgugg acuccccuuu gucauccuau gccugagaau      60
auaugaagga ggcugggaag gcaaagggac guucaauugu caucacuggc                110

<210> SEQ ID NO 241
<211> LENGTH: 137
```

```
<212> TYPE: RNA
<213> ORGANISM: Homo sapiens

<400> SEQUENCE: 241
agccagacaa gagggucaug gggagucacu gucaacccag agcaggcacu gccccugcga    60
ccagccuggg gcaucgguug ggugcaggg gucugcuggu gaugcuuucc aucucuuugc    120
uuuguccuga uuguagc                                                   137

<210> SEQ ID NO 242
<211> LENGTH: 65
<212> TYPE: RNA
<213> ORGANISM: Homo sapiens

<400> SEQUENCE: 242
gagggugggc gagggcggcu gagcggcucc auccccggc cugcucaucc cccucgcccu    60
cucag                                                                65

<210> SEQ ID NO 243
<211> LENGTH: 96
<212> TYPE: RNA
<213> ORGANISM: Homo sapiens

<400> SEQUENCE: 243
cucgggaggg gcgggagggg ggucccccggu gcucggaucu cgagggugcu uauuguucgg    60
uccgagccug ggucucccuc uuccccccaa cccccc                              96

<210> SEQ ID NO 244
<211> LENGTH: 69
<212> TYPE: RNA
<213> ORGANISM: Homo sapiens

<400> SEQUENCE: 244
ggcccucggg ccuggggrug ggggagcucu guccugcucu acucauugcu ccuccccugc    60
cuggcccag                                                            69

<210> SEQ ID NO 245
<211> LENGTH: 57
<212> TYPE: RNA
<213> ORGANISM: Homo sapiens

<400> SEQUENCE: 245
cauuggaggg uguggaagac aucugggcca acucugaucu cuucaucuac ccccag        57

<210> SEQ ID NO 246
<211> LENGTH: 106
<212> TYPE: RNA
<213> ORGANISM: Homo sapiens

<400> SEQUENCE: 246
agaagaaugc ccaaccagcc cucaguugcu acaguucccu guuguuucag cucgacaaca    60
acaggcggcu guagcaaugg ggggcuggau gggcaucuca augugc                   106

<210> SEQ ID NO 247
<211> LENGTH: 71
<212> TYPE: RNA
<213> ORGANISM: Homo sapiens

<400> SEQUENCE: 247
ugaccacccc cgggcaaaga ccugcagauc cccuguuaga gacgggccca ggacuuugug    60
```
cggggugccc a                                                  71

<210> SEQ ID NO 248
<211> LENGTH: 69
<212> TYPE: RNA
<213> ORGANISM: Homo sapiens

<400> SEQUENCE: 248
ccgggcaggc agguguaggg uggagcccac ugugguccu gacucagccc ugcugccuuc    60
accugccag                                                     69

<210> SEQ ID NO 249
<211> LENGTH: 67
<212> TYPE: RNA
<213> ORGANISM: Homo sapiens

<400> SEQUENCE: 249
gugggagggg agaggcagca agcacacagg gccugggacu agcaugcuga ccucccuccu    60
gccccag                                                       67

<210> SEQ ID NO 250
<211> LENGTH: 73
<212> TYPE: RNA
<213> ORGANISM: Homo sapiens

<400> SEQUENCE: 250
cugguguuug aggcgaugug gggauguaga gacaacuucc cagucucauu uccucauccu    60
gccaggccac cau                                                73

<210> SEQ ID NO 251
<211> LENGTH: 59
<212> TYPE: RNA
<213> ORGANISM: Homo sapiens

<400> SEQUENCE: 251
cuccagggag acagugugug aggccucuug ccauggccuc ccugcccgcc ucucugcag     59

<210> SEQ ID NO 252
<211> LENGTH: 77
<212> TYPE: RNA
<213> ORGANISM: Homo sapiens

<400> SEQUENCE: 252
gaguugggag guucccucuc caaauguguc uugaucccccc accccaagac acauuggag    60 agggacccuc ccaacuc                                            77

<210> SEQ ID NO 253
<211> LENGTH: 65
<212> TYPE: RNA
<213> ORGANISM: Homo sapiens

<400> SEQUENCE: 253
gucuccuggg gggaggagac ccugcucucc cuggcagcaa gccucuccug cccuuccaga    60
uuagc                                                         65

<210> SEQ ID NO 254
<211> LENGTH: 65
<212> TYPE: RNA
<213> ORGANISM: Homo sapiens

<400> SEQUENCE: 254

```
agcccugggg guggucucua gccaaggcuc uggggucuca cccuuggcug gucucugcuc    60
cgcag                                                                65

<210> SEQ ID NO 255
<211> LENGTH: 67
<212> TYPE: RNA
<213> ORGANISM: Homo sapiens

<400> SEQUENCE: 255
gcgcccuccc ucucuccccg gugugcaaau gugugugugc gguguuaugc cggacaagag    60
ggaggug                                                              67

<210> SEQ ID NO 256
<211> LENGTH: 81
<212> TYPE: RNA
<213> ORGANISM: Homo sapiens

<400> SEQUENCE: 256
cauccuccuu acgucccacc ccccacuccu guuucggug aaauauucaa acaggagugg     60 ggugggaca uaaggaggau a                                               81

<210> SEQ ID NO 257
<211> LENGTH: 80
<212> TYPE: RNA
<213> ORGANISM: Homo sapiens

<400> SEQUENCE: 257
gguuccggag ccccggcgcg ggcggguucu gggguguaga cgcugcuggc cagcccgccc    60
cagccgaggu ucucggcacc                                                80

<210> SEQ ID NO 258
<211> LENGTH: 89
<212> TYPE: RNA
<213> ORGANISM: Homo sapiens

<400> SEQUENCE: 258
agccugnggg aaagagaaga gcagggcagg gugaaggccc ggcggagaca cucugcccac    60
cccacacccu gccuaugggc cacacagcu                                      89

<210> SEQ ID NO 259
<211> LENGTH: 66
<212> TYPE: RNA
<213> ORGANISM: Homo sapiens

<400> SEQUENCE: 259
agcagcccuc ggcggcccgg ggggcgggcg gcggugcccg ucccggggcu gcgcgaggca    60
caggcg                                                               66

<210> SEQ ID NO 260
<211> LENGTH: 82
<212> TYPE: RNA
<213> ORGANISM: Homo sapiens

<400> SEQUENCE: 260
gcuacgggga gcggggagga agugggcgcu gcuucugcgu uaucuggaag gagcagccca    60
cuccuguccu gggcucugug gu                                             82

<210> SEQ ID NO 261
```

```
<211> LENGTH: 80
<212> TYPE: RNA
<213> ORGANISM: Homo sapiens

<400> SEQUENCE: 261
accucuaccu cccggcagag gaggcugcag aggcuggcuu uccaaaacuc ugcccccucc    60
gcugcugcca aguggcuggu                                               80

<210> SEQ ID NO 262
<211> LENGTH: 98
<212> TYPE: RNA
<213> ORGANISM: Homo sapiens

<400> SEQUENCE: 262
uucucacccc cgccugacac gggcgacagc ugcggcccgc uguuucacu cgggccgagu     60 gcgucuccug ucaggcaagg gagagcagag ccccccug                           98

<210> SEQ ID NO 263
<211> LENGTH: 82
<212> TYPE: RNA
<213> ORGANISM: Homo sapiens

<400> SEQUENCE: 263
ugugggcagg gcccugggga gcugaggcuc uggggguggc cggggcugac ccugggccuc    60
ugcuccccag ugucugaccg cg                                            82

<210> SEQ ID NO 264
<211> LENGTH: 74
<212> TYPE: RNA
<213> ORGANISM: Homo sapiens

<400> SEQUENCE: 264
ccugcaggag gcaguggggcg agcaggcggg gcagcccaau gccaugggcc ugaucucacc   60
gcugccuccu uccc                                                     74

<210> SEQ ID NO 265
<211> LENGTH: 76
<212> TYPE: RNA
<213> ORGANISM: Homo sapiens

<400> SEQUENCE: 265
acugacuuug agucucuccu cagggugcug caggcaaagc uggggaccca gggagagacg    60
uaagugaggg gagaug                                                   76

<210> SEQ ID NO 266
<211> LENGTH: 66
<212> TYPE: RNA
<213> ORGANISM: Homo sapiens

<400> SEQUENCE: 266
ccgagugggg cggggcaggu cccugcaggg acugugacac ugaaggaccu gcaccuucgc    60
ccacag                                                              66

<210> SEQ ID NO 267
<211> LENGTH: 61
<212> TYPE: RNA
<213> ORGANISM: Homo sapiens

<400> SEQUENCE: 267
gagggcagcg uggguguggc ggaggcaggc gugaccguuu gccgcccucu cgcugcucua    60
```

```
g                                                              61

<210> SEQ ID NO 268
<211> LENGTH: 87
<212> TYPE: RNA
<213> ORGANISM: Homo sapiens

<400> SEQUENCE: 268
cccucaucuc ugggcagggg cuuauuguag gagucucuga agagagcugu ggacugaccu    60
gcuuuaaccc uuccccaggu ucccauu                                       87

<210> SEQ ID NO 269
<211> LENGTH: 103
<212> TYPE: RNA
<213> ORGANISM: Homo sapiens

<400> SEQUENCE: 269
gugucggcug uggcgugacu gucccucugu gucccccacu aggcccacug cucaguggag    60
cguggaggac gaggaggagg ccguccacga gcaaugccag cau                     103

<210> SEQ ID NO 270
<211> LENGTH: 109
<212> TYPE: RNA
<213> ORGANISM: Homo sapiens

<400> SEQUENCE: 270
ugcuauuguc uuacugcuac agcagggcug gggauugcag uaccgcugu ugcugcugcu     60 cccaguccug ccccugcugc uaccuagucc agccucaccg caucccaga              109

<210> SEQ ID NO 271
<211> LENGTH: 79
<212> TYPE: RNA
<213> ORGANISM: Homo sapiens

<400> SEQUENCE: 271
gugcagaucc uugggagccc uguuagacuc uggauuuuac acuggagug aacgggcgcc     60 aucccgaggc uuugcacag                                                79

<210> SEQ ID NO 272
<211> LENGTH: 67
<212> TYPE: RNA
<213> ORGANISM: Homo sapiens

<400> SEQUENCE: 272
uacaggccgg ggcuuugggu gagggacccc cggagucugu cacggucuca ccccaacucu    60
gccccag                                                             67

<210> SEQ ID NO 273
<211> LENGTH: 66
<212> TYPE: RNA
<213> ORGANISM: Homo sapiens

<400> SEQUENCE: 273
gggaggaggg aggagauggg ccaaguuccc ucuggcugga acgcccuucc cccccuucuu    60
caccug                                                              66

<210> SEQ ID NO 274
<211> LENGTH: 86
<212> TYPE: RNA
```

```
<213> ORGANISM: Homo sapiens

<400> SEQUENCE: 274
agcacugccc ccggugaguc agggugggge uggcccccug cuucgugccc auccgcgcuc    60
ugacucucug cccaccugca ggagcu                                         86

<210> SEQ ID NO 275
<211> LENGTH: 115
<212> TYPE: RNA
<213> ORGANISM: Homo sapiens

<400> SEQUENCE: 275
gagcaaaaac cagagaacaa caugggagcg uccuaaccc cuaaggcaac uggaugggag      60
accugaccca uccaguucuc ugagggggcu cuugugguu cuacaagguu guuca          115

<210> SEQ ID NO 276
<211> LENGTH: 60
<212> TYPE: RNA
<213> ORGANISM: Homo sapiens

<400> SEQUENCE: 276
aggccuaggg gguggcaggc uggccaucag uguggcuaa cccuguccuc ucccucccag      60

<210> SEQ ID NO 277
<211> LENGTH: 73
<212> TYPE: RNA
<213> ORGANISM: Homo sapiens

<400> SEQUENCE: 277
gaaaacaacc aggugggcuu cccggagggc ggaacaccca gccccagcau ccagggcuca    60
ccuaccacgu uug                                                       73

<210> SEQ ID NO 278
<211> LENGTH: 62
<212> TYPE: RNA
<213> ORGANISM: Homo sapiens

<400> SEQUENCE: 278
gcuggggguc ccccgacagu guggagcugg ggccgggucc cggggagggg gguucgggc      60 ag                                                                   62

<210> SEQ ID NO 279
<211> LENGTH: 70
<212> TYPE: RNA
<213> ORGANISM: Homo sapiens

<400> SEQUENCE: 279
cucgggcccg accgcgccgg cccgcaccuc ccggcccgga gcugcgggcu gcggucaggg    60
cgaucccggg                                                           70

<210> SEQ ID NO 280
<211> LENGTH: 72
<212> TYPE: RNA
<213> ORGANISM: Homo sapiens

<400> SEQUENCE: 280
augagcgggu gggagcagau cuuauugaga guuccuucuc cugcuccuga uugucuuccc    60
ccacccucac ag                                                        72
```

<210> SEQ ID NO 281
<211> LENGTH: 93
<212> TYPE: RNA
<213> ORGANISM: Homo sapiens

<400> SEQUENCE: 281
ccuuccggcg ucccaggcgg ggcgccgcgg gaccgcccuc ugucucugugg cgguggggauc    60 ccgcggccgu guuuuccugg uggcccggcc aug                                   93

<210> SEQ ID NO 282
<211> LENGTH: 86
<212> TYPE: RNA
<213> ORGANISM: Homo sapiens

<400> SEQUENCE: 282
auucuaggug gggagacuga cggcuggagg cccauaagcu gucuaaaacu ucggccccca    60
gauuucuggu cuccccacuu cagaac                                          86

<210> SEQ ID NO 283
<211> LENGTH: 64
<212> TYPE: RNA
<213> ORGANISM: Homo sapiens

<400> SEQUENCE: 283
aaccccgggc cggaggucaa gggcgucgcu ucucccuaau guugccucuu uuccacggcc    60
ucag                                                                  64

<210> SEQ ID NO 284
<211> LENGTH: 88
<212> TYPE: RNA
<213> ORGANISM: Homo sapiens

<400> SEQUENCE: 284
guggggccag gcgguggugg gcacugcugg ggugggcaca gcagccaugc agagcgggca    60
uuugaccccg ugccacccuu uucccag                                         88

<210> SEQ ID NO 285
<211> LENGTH: 61
<212> TYPE: RNA
<213> ORGANISM: Homo sapiens

<400> SEQUENCE: 285
aacugcgggg ccagagcaga gagcccuugc acaccaccag ccucuccucc cugugcccca    60
g                                                                     61

<210> SEQ ID NO 286
<211> LENGTH: 67
<212> TYPE: RNA
<213> ORGANISM: Homo sapiens

<400> SEQUENCE: 286
ggcagccagg gggaugggcg agcuugggcc cauuccuuuc cuuacccuac cccccauccc    60
ccuguag                                                               67

<210> SEQ ID NO 287
<211> LENGTH: 79
<212> TYPE: RNA
<213> ORGANISM: Homo sapiens

<400> SEQUENCE: 287

-continued

```
gugaggugggg ggccagcagg gagugggcug ggcugggcug ggccaaggua caaggccuca    60
cccugcaucc cgcacccag                                                  79

<210> SEQ ID NO 288
<211> LENGTH: 80
<212> TYPE: RNA
<213> ORGANISM: Homo sapiens

<400> SEQUENCE: 288
ugagaggccg caccuugccu ugcugcccgg gccgugcacc cgugggcccc agggcgacgc    60 ggcggggcg gcccuagcga                                                 80

<210> SEQ ID NO 289
<211> LENGTH: 76
<212> TYPE: RNA
<213> ORGANISM: Homo sapiens

<400> SEQUENCE: 289
ccgaugccuc gggagucuac agcagggcca ugucugugag ggcccaaggg ugcaugoguc    60 ucccagguuu cggugc                                                    76

<210> SEQ ID NO 290
<211> LENGTH: 97
<212> TYPE: RNA
<213> ORGANISM: Homo sapiens

<400> SEQUENCE: 290
aucugaguug ggagggucccc ucuccaaaug ugucuugggg uggggauca agacacauuu    60 ggagagggaa ccucccaacu cggccucugc caucauu                             97

<210> SEQ ID NO 291
<211> LENGTH: 67
<212> TYPE: RNA
<213> ORGANISM: Homo sapiens

<400> SEQUENCE: 291
guggcacuca aacugugggg gcacuuucug cucucuggug aaagugccgc caucuuuuga    60
guguuac                                                              67

<210> SEQ ID NO 292
<211> LENGTH: 94
<212> TYPE: RNA
<213> ORGANISM: Homo sapiens

<400> SEQUENCE: 292
gugaggugug ggcccggccc caggagcggg gccugggcag ccccgugugu ugaggaagga    60
aggcagggcc cccgcucccc gggccugacc ccac                                94

<210> SEQ ID NO 293
<211> LENGTH: 65
<212> TYPE: RNA
<213> ORGANISM: Homo sapiens

<400> SEQUENCE: 293
ugucugggga uuuggagaag uggugagcgc aggucuuugg caccaucucc ccugguccccu   60 uggcu                                                                65

<210> SEQ ID NO 294
<211> LENGTH: 81
```

<212> TYPE: RNA
<213> ORGANISM: Homo sapiens

<400> SEQUENCE: 294 aguuggugggg ggagccauga gauaagagca ccuccuagag aauguugaac uaaaggugcc    60
cucucuggcu ccuccccaaa g                                               81

<210> SEQ ID NO 295
<211> LENGTH: 47
<212> TYPE: RNA
<213> ORGANISM: Homo sapiens

<400> SEQUENCE: 295
cucggcgcgg ggcgcgggcu ccggguuggg gcgagccaac gccgggg                   47

<210> SEQ ID NO 296
<211> LENGTH: 64
<212> TYPE: RNA
<213> ORGANISM: Homo sapiens

<400> SEQUENCE: 296
gaggcacugg guaggugggg cuccagggcu ccugacaccu ggaccucucc uccccaggcc    60
caca                                                                  64

<210> SEQ ID NO 297
<211> LENGTH: 68
<212> TYPE: RNA
<213> ORGANISM: Homo sapiens

<400> SEQUENCE: 297
gugcaaagag caggaggaca ggggauuuau cucccaaggg aggucccug auccaguca       60 cggcacca                                                              68

<210> SEQ ID NO 298
<211> LENGTH: 66
<212> TYPE: RNA
<213> ORGANISM: Homo sapiens

<400> SEQUENCE: 298
cagagcaggg cagggaaggu gggagagggg cccagcugac ccuccuguca cccgcuccuu    60
gcccag                                                                66

<210> SEQ ID NO 299
<211> LENGTH: 65
<212> TYPE: RNA
<213> ORGANISM: Homo sapiens

<400> SEQUENCE: 299
gagggcuagg uggggggcuu gaagcccga gaugccucac gucuucaccc cucucaccua    60
agcag                                                                 65

<210> SEQ ID NO 300
<211> LENGTH: 50
<212> TYPE: RNA
<213> ORGANISM: Homo sapiens

<400> SEQUENCE: 300
acccgggcgu ggugguggggg gugggugccu guaauuccag cuaguuggga              50

<210> SEQ ID NO 301

```
<211> LENGTH: 115
<212> TYPE: RNA
<213> ORGANISM: Homo sapiens

<400> SEQUENCE: 301
ggugccgagg gccguccggc auccuaggcg ggucgcugcg guaccucccu ccugucugug      60 gcgguggau cccguggccg uguuuccug guggcccggc cgugccgag guuuc             115

<210> SEQ ID NO 302
<211> LENGTH: 86
<212> TYPE: RNA
<213> ORGANISM: Homo sapiens

<400> SEQUENCE: 302
ugccagucuc uaggucccug agacccuuua accugugagg acauccaggg ucacagguga      60
gguucuuggg agccuggcgu cuggcc                                          86

<210> SEQ ID NO 303
<211> LENGTH: 90
<212> TYPE: RNA
<213> ORGANISM: Homo sapiens

<400> SEQUENCE: 303
ggcgccucug cagcuccggc uccccuggc cucucgggaa cuacaaguccc caggggggccu     60 ggcgguggc ggcgggcgga agaggcgggg                                       90

<210> SEQ ID NO 304
<211> LENGTH: 51
<212> TYPE: RNA
<213> ORGANISM: Homo sapiens

<400> SEQUENCE: 304
agagaugaag cggggggggcg gggucuugcu cuauugccua cgcugaucuc a              51

<210> SEQ ID NO 305
<211> LENGTH: 71
<212> TYPE: RNA
<213> ORGANISM: Homo sapiens

<400> SEQUENCE: 305 ggugagugg agccgguggg gcuggaguaa gggcacgccc ggggcugccc caccugcuga       60
ccacccuccc c                                                          71

<210> SEQ ID NO 306
<211> LENGTH: 80
<212> TYPE: RNA
<213> ORGANISM: Homo sapiens

<400> SEQUENCE: 306
aggacccuuc cagaggggccc ccccucaauc cuguugugcc uaauucagag gguugggugg     60
aggcucuccu gaagggcucu                                                 80

<210> SEQ ID NO 307
<211> LENGTH: 64
<212> TYPE: RNA
<213> ORGANISM: Homo sapiens

<400> SEQUENCE: 307
gaaggcgagg gguagaagag cacaggggguu cugauaaacc cuucugccug cauucuacuc     60
ccag                                                                  64
```

<210> SEQ ID NO 308
<211> LENGTH: 118
<212> TYPE: RNA
<213> ORGANISM: Homo sapiens

<400> SEQUENCE: 308
gcaggugaac uggcaggcca ggaagaggag gaagcccugg aggggcugga ggugauggau      60
guuuuccucc gguucucagg gcuccaccuc uuucgggccg uagagccagg gcuggugc       118

<210> SEQ ID NO 309
<211> LENGTH: 55
<212> TYPE: RNA
<213> ORGANISM: Homo sapiens

<400> SEQUENCE: 309
ccggauccga gucacggcac caaauuucau gcgguccgu gugaagagac cacca            55

<210> SEQ ID NO 310
<211> LENGTH: 86
<212> TYPE: RNA
<213> ORGANISM: Homo sapiens

<400> SEQUENCE: 310
agggagaagg gucggggcag ggagggcagg gcaggcucug ggguggggg ucugugaguc       60 agccacggcu cugcccacgu cucccc                                           86

<210> SEQ ID NO 311
<211> LENGTH: 99
<212> TYPE: RNA
<213> ORGANISM: Homo sapiens

<400> SEQUENCE: 311
gcaagggaca gggagggucg uggcgacacu cgcgccagcu cccgggacgg cugggcucgg      60
gcuggucgcc gaccuccgac ccuccacuag augccuggc                             99

<210> SEQ ID NO 312
<211> LENGTH: 90
<212> TYPE: RNA
<213> ORGANISM: Homo sapiens

<400> SEQUENCE: 312 cgggcgggc gggguccggcc gccuccgagc ccggccggca gccccggcc uuaaagcgcg       60 ggcuguccgg aggggucggc uuucccaccg                                       90

<210> SEQ ID NO 313
<211> LENGTH: 96
<212> TYPE: RNA
<213> ORGANISM: Homo sapiens

<400> SEQUENCE: 313
cgggccccgg gcgggcggga gggacgggac gcggugcagu guuguuuuuu ccccgccaa       60 uauugcacuc gucccggccu ccggcccccc cggccc                                96

<210> SEQ ID NO 314
<211> LENGTH: 68
<212> TYPE: RNA
<213> ORGANISM: Homo sapiens

<400> SEQUENCE: 314 agggUUggggg ggacaggaug agaggcuguc uucauucccu cuugaccacc ccucguuucu    60
uccccag    68

<210> SEQ ID NO 315
<211> LENGTH: 62
<212> TYPE: RNA
<213> ORGANISM: Homo sapiens

<400> SEQUENCE: 315
uggccuaggg ggcggcuugu ggaguguaug ggcugagccu ugcucugcuc cccgccccc    60 ag    62

<210> SEQ ID NO 316
<211> LENGTH: 90
<212> TYPE: RNA
<213> ORGANISM: Homo sapiens

<400> SEQUENCE: 316
gugucucucu ggagacccug cagccuuccc acccaccagg gagcuuucca ugggcugugg    60
ggaaggcguc agugucgggu gagggaacac    90

<210> SEQ ID NO 317
<211> LENGTH: 69
<212> TYPE: RNA
<213> ORGANISM: Homo sapiens

<400> SEQUENCE: 317
uggggUaggg gugggggaau cagggguguu cgaacucaug gcugccaccu uugugucccc    60
auccugcag    69

<210> SEQ ID NO 318
<211> LENGTH: 83
<212> TYPE: RNA
<213> ORGANISM: Homo sapiens

<400> SEQUENCE: 318
gucuacuccc agggugccaa gcuguuucgu guucccuccc uaggggauccc cagguagggg    60 cagcagagga ccugggccug gac    83

<210> SEQ ID NO 319
<211> LENGTH: 61
<212> TYPE: RNA
<213> ORGANISM: Homo sapiens

<400> SEQUENCE: 319
gugcggaacg cuggccgggg cgggagggga agggacgccc ggccggaacg ccgcacucac    60
g    61

<210> SEQ ID NO 320
<211> LENGTH: 66
<212> TYPE: RNA
<213> ORGANISM: Homo sapiens

<400> SEQUENCE: 320
ucaagacggg gagucaggca gugguggaga uggagagccc ugagccucca cucuccuggc    60
ccccag    66

<210> SEQ ID NO 321
<211> LENGTH: 81

```
<212> TYPE: RNA
<213> ORGANISM: Homo sapiens

<400> SEQUENCE: 321
cucccuggga gggcguggau gaugguggga gaggagcccc acuguggaag ucgaccccc    60 acaucgcccc accuucccca g                                            81

<210> SEQ ID NO 322
<211> LENGTH: 65
<212> TYPE: RNA
<213> ORGANISM: Homo sapiens

<400> SEQUENCE: 322
gcuucuggga ggaggggauc uugggaguga ucccaacagc ugagcucccu gaaucccugu    60
cccag                                                               65

<210> SEQ ID NO 323
<211> LENGTH: 97
<212> TYPE: RNA
<213> ORGANISM: Homo sapiens

<400> SEQUENCE: 323
cccgggaccu ugguccaggc gcuggucugc guggugcucg gguggauaag ucgaucuga    60 gcaccacaca ggccgggcgc cgggaccaag ggggcuc                            97

<210> SEQ ID NO 324
<211> LENGTH: 109
<212> TYPE: RNA
<213> ORGANISM: Homo sapiens

<400> SEQUENCE: 324
ucccgcauuc ccucugcuuu ggucaggugg ugcccuccuu ccaugggag agccagagau    60 ggugggsuucu ggcuggucag augggagugg acagagaccc ggggguccuc             109

<210> SEQ ID NO 325
<211> LENGTH: 51
<212> TYPE: RNA
<213> ORGANISM: Homo sapiens

<400> SEQUENCE: 325
acagaccccg gggagcccgg cggugaagcu ccugguaucc ggggugucug a             51

<210> SEQ ID NO 326
<211> LENGTH: 62
<212> TYPE: RNA
<213> ORGANISM: Homo sapiens

<400> SEQUENCE: 326
ccuucugcgg cagagcuggg gucaccagcc cucauguacu ugugacuucu ccccugccac    60
ag                                                                  62

<210> SEQ ID NO 327
<211> LENGTH: 70
<212> TYPE: RNA
<213> ORGANISM: Homo sapiens

<400> SEQUENCE: 327
gguuucuccu ugaggagaca uggugggggc cggucaggca gcccaugcca uguguccuca    60
uggagaggcc                                                          70
```

```
<210> SEQ ID NO 328
<211> LENGTH: 68
<212> TYPE: RNA
<213> ORGANISM: Homo sapiens

<400> SEQUENCE: 328
gacucggcug cgguggacaa guccggcucc agaaccugga caccgcucag ccggccgcgg    60
cagggguc                                                            68

<210> SEQ ID NO 329
<211> LENGTH: 69
<212> TYPE: RNA
<213> ORGANISM: Homo sapiens

<400> SEQUENCE: 329
cuuucggcca gcgggacggc auccgaggug ggcuaggcuc gggcccgugg cgggugcggg    60
ggugggagg                                                           69

<210> SEQ ID NO 330
<211> LENGTH: 85
<212> TYPE: RNA
<213> ORGANISM: Homo sapiens

<400> SEQUENCE: 330
gugagcugcu ggggacgcgg gucggggucu gcagggcggu gcggcagccg ccaccgacg    60 ccgcgccuuu gucugugucc cacag                                         85

<210> SEQ ID NO 331
<211> LENGTH: 62
<212> TYPE: RNA
<213> ORGANISM: Homo sapiens

<400> SEQUENCE: 331
cuuccuggug ggugggagg agaagugccg uccucaugag ccccucucug ucccacccau    60
ag                                                                  62

<210> SEQ ID NO 332
<211> LENGTH: 89
<212> TYPE: RNA
<213> ORGANISM: Homo sapiens

<400> SEQUENCE: 332
gccggcgccc gagcucuggc uccgugucuu cacuccgug cuuguccgag gagggaggga    60
gggacggggg cugugcuggg gcagcugga                                     89

<210> SEQ ID NO 333
<211> LENGTH: 97
<212> TYPE: RNA
<213> ORGANISM: Homo sapiens

<400> SEQUENCE: 333
cucaggugcu cuggcugcuu ggguuccugg caugcugauu ugugacuuaa gauuaaaauc    60
acauugccag ggauuaccac gcaaccacga ccuuggc                            97

<210> SEQ ID NO 334
<211> LENGTH: 68
<212> TYPE: RNA
<213> ORGANISM: Homo sapiens

<400> SEQUENCE: 334
```

```
ugcccaggcu ggagcgagug caguggugca gucaguccua gcucacugca gccucgaacu    60
ccugggcu                                                              68

<210> SEQ ID NO 335
<211> LENGTH: 70
<212> TYPE: RNA
<213> ORGANISM: Homo sapiens

<400> SEQUENCE: 335
gucccugggg gcugggaugg gccauggugu gcucugaucc cccugguguc ucuuggcccc    60
caggaacucc                                                            70

<210> SEQ ID NO 336
<211> LENGTH: 73
<212> TYPE: RNA
<213> ORGANISM: Homo sapiens

<400> SEQUENCE: 336
aggccaggug gguauggagg agcccucaua uggcaguugg cgagggccca gugagcccu     60 cucugcucuc cag                                                        73

<210> SEQ ID NO 337
<211> LENGTH: 85
<212> TYPE: RNA
<213> ORGANISM: Homo sapiens

<400> SEQUENCE: 337
ggccugggua ggcuugcaug ggggacuggg aagagaccau gaacagguua guccagggag    60
uucucaucaa gccuuuacuc aguag                                           85

<210> SEQ ID NO 338
<211> LENGTH: 87
<212> TYPE: RNA
<213> ORGANISM: Homo sapiens

<400> SEQUENCE: 338
gugaggcggg gccaggaggg uguguggcgu gggugcugcg gggccgucag ggugccugcg    60
ggacgcucac cuggcuggcc cgcccag                                         87

<210> SEQ ID NO 339
<211> LENGTH: 80
<212> TYPE: RNA
<213> ORGANISM: Homo sapiens

<400> SEQUENCE: 339
gagaggccaa gaccuuggga auggggguaa gggccuucug agcccagguc cgaacucucc    60 auccucugc agagcgcucu                                                  80

<210> SEQ ID NO 340
<211> LENGTH: 64
<212> TYPE: RNA
<213> ORGANISM: Homo sapiens

<400> SEQUENCE: 340
aguucagggc cgaaggguug aagcugcugg ugcucaucuc agccucugcc cuuggccucc    60
ccag                                                                  64

<210> SEQ ID NO 341
```

```
<211> LENGTH: 65
<212> TYPE: RNA
<213> ORGANISM: Homo sapiens

<400> SEQUENCE: 341
gggugcucgg ggcaggcggc ugggagcggc ccucacauug auggcuccug ccaccuccuc    60
cgcag                                                                65

<210> SEQ ID NO 342
<211> LENGTH: 60
<212> TYPE: RNA
<213> ORGANISM: Homo sapiens

<400> SEQUENCE: 342
ugugaaugac ccccuuccag agccaaaauc accagggaug gaggaggggu cuugggua cu   60

<210> SEQ ID NO 343
<211> LENGTH: 90
<212> TYPE: RNA
<213> ORGANISM: Homo sapiens

<400> SEQUENCE: 343
ucuaagaaac gcaguggucu cugaagccug caggggcagg ccagcccugc acugaacgcc    60
uguucuugcc agguggcaga agguugcugc                                     90

<210> SEQ ID NO 344
<211> LENGTH: 83
<212> TYPE: RNA
<213> ORGANISM: Homo sapiens

<400> SEQUENCE: 344
ccugcugcag aggugccagc ugcagugggg gaggcacugc cagggcugcc cacucugcuu    60
agccagcagg ugccaagaac agg                                            83

<210> SEQ ID NO 345
<211> LENGTH: 94
<212> TYPE: RNA
<213> ORGANISM: Homo sapiens

<400> SEQUENCE: 345
aauucagccc ugccacuggc uuaugucaug accuugggcu acucaggcug ucugcacaau    60
gagccaguug gacaggagca gugccacuca acuc                                94

<210> SEQ ID NO 346
<211> LENGTH: 60
<212> TYPE: RNA
<213> ORGANISM: Homo sapiens

<400> SEQUENCE: 346
caaggugggg gagauggggg uugaacuuca uuucucaugc ucaucccau cuccuuucag      60

<210> SEQ ID NO 347
<211> LENGTH: 78
<212> TYPE: RNA
<213> ORGANISM: Homo sapiens

<400> SEQUENCE: 347
ggccucaggc aggcgcaccc gaccacaugc auggcuggug gcggcgugca ggggucgggu    60
gggccaggcu gugggggcg                                                 78
```

-continued

```
<210> SEQ ID NO 348
<211> LENGTH: 49
<212> TYPE: RNA
<213> ORGANISM: Homo sapiens

<400> SEQUENCE: 348
uucccagcca acgcaccaaa aaugauaugg gucuguuguc uggagaaac          49

<210> SEQ ID NO 349
<211> LENGTH: 64
<212> TYPE: RNA
<213> ORGANISM: Homo sapiens

<400> SEQUENCE: 349
ucugggcgag ggguggcuc ucagagggc uggcaguacu gcucugaggc cugccucucc     60
ccag                                                                64

<210> SEQ ID NO 350
<211> LENGTH: 77
<212> TYPE: RNA
<213> ORGANISM: Homo sapiens

<400> SEQUENCE: 350
caugagaaau ccugcugguc aaccauagcc cuggucagac ucuccggggc ugugauugac    60
cagcaggacu ucucaug                                                   77

<210> SEQ ID NO 351
<211> LENGTH: 95
<212> TYPE: RNA
<213> ORGANISM: Homo sapiens

<400> SEQUENCE: 351
gacaccacau gcuccuccag gccugccugc ccuccagguc auguuccagu gucccacaga    60
ugcagcacca cggcccaggc ggcauuggug ucacc                               95

<210> SEQ ID NO 352
<211> LENGTH: 64
<212> TYPE: RNA
<213> ORGANISM: Homo sapiens

<400> SEQUENCE: 352
gagcucuggg aggggcuggg uuuggcagga caguuccaa gcccugcuc cucccaucuu      60 ccag                                                                 64

<210> SEQ ID NO 353
<211> LENGTH: 67
<212> TYPE: RNA
<213> ORGANISM: Homo sapiens

<400> SEQUENCE: 353
aaaucucucu ccauaucuuu ccugcagccc ccagguggg gggaagaaaa gguggggaau     60
uagauuc                                                              67

<210> SEQ ID NO 354
<211> LENGTH: 64
<212> TYPE: RNA
<213> ORGANISM: Homo sapiens

<400> SEQUENCE: 354 ggguggggc ggggcggcag gggccucccc cagugccagg ccccauucug cuucucuccc     60
```

```
agcu                                                             64

<210> SEQ ID NO 355
<211> LENGTH: 65
<212> TYPE: RNA
<213> ORGANISM: Homo sapiens

<400> SEQUENCE: 355
cuccucuggg gguggggggc ugggcguggu ggacagcgau gcaucccucg ccuucucacc    60
cucag                                                             65

<210> SEQ ID NO 356
<211> LENGTH: 98
<212> TYPE: RNA
<213> ORGANISM: Homo sapiens

<400> SEQUENCE: 356
cgagguaggg gcgucccggg cgcgcgggcg ggucccaggc ugggcccuc ggaggccggg    60 ugcucacugc cccgucccgg cgcccguguc uccuccag                         98

<210> SEQ ID NO 357
<211> LENGTH: 72
<212> TYPE: RNA
<213> ORGANISM: Homo sapiens

<400> SEQUENCE: 357
ugugggacug caaaugggag cucagcaccu gccugccacc cacgcagacc agccccugcu    60
cuguucccac ag                                                     72

<210> SEQ ID NO 358
<211> LENGTH: 70
<212> TYPE: RNA
<213> ORGANISM: Homo sapiens

<400> SEQUENCE: 358
aggacccagc ggggcugggc gcgcggagca gcgcugggug cagcgccugc gccggcagcu    60
gcaagggccg                                                        70

<210> SEQ ID NO 359
<211> LENGTH: 61
<212> TYPE: RNA
<213> ORGANISM: Homo sapiens

<400> SEQUENCE: 359
ccugcgggga caggccaggg caucuaggcu gugcacagug acgccccucc ugccccaca    60 g                                                                 61

<210> SEQ ID NO 360
<211> LENGTH: 73
<212> TYPE: RNA
<213> ORGANISM: Homo sapiens

<400> SEQUENCE: 360
ggaggcuggg cuggacggga cacccggccu ccacuuucug uggcagguac cuccuccaug    60
ucggcccgcc uug                                                    73

<210> SEQ ID NO 361
<211> LENGTH: 72
<212> TYPE: RNA
<213> ORGANISM: Homo sapiens
```

```
<400> SEQUENCE: 361
cugugcaccu gggggagugc agugauugug gaaugcaaag ucccacaauc acuguacucc      60
ccaggugcac ag                                                         72

<210> SEQ ID NO 362
<211> LENGTH: 119
<212> TYPE: RNA
<213> ORGANISM: Homo sapiens

<400> SEQUENCE: 362
agccugcgcc ggagccgggg ccugagcccg ggccgcgcag gccgugaacu cgucgagcug      60
cgcgugcggc cggugcucaa ccugccgggu ccuggccccg cgcucccgcg cgcccugga     119

<210> SEQ ID NO 363
<211> LENGTH: 92
<212> TYPE: RNA
<213> ORGANISM: Homo sapiens

<400> SEQUENCE: 363
ccugucccuc cugcccugcg ccugcccagc ccuccugcuc uggugacuga ggaccgccag      60
gcaggggcug gugcugggcg gggggcggcg gg                                   92

<210> SEQ ID NO 364
<211> LENGTH: 92
<212> TYPE: RNA
<213> ORGANISM: Homo sapiens

<400> SEQUENCE: 364
gucagugucu gggcggacag cugcaggaaa gggaagacca aggcuugcug ucuguccagu      60
cugccacccu acccugucug uucuugccac ag                                   92

<210> SEQ ID NO 365
<211> LENGTH: 82
<212> TYPE: RNA
<213> ORGANISM: Homo sapiens

<400> SEQUENCE: 365
gugaguggga ggccagggca cggcaggggg agcugcaggg cuaugggagg ggccccagcg      60
ucugagcccu guccucccgc ag                                              82

<210> SEQ ID NO 366
<211> LENGTH: 82
<212> TYPE: RNA
<213> ORGANISM: Homo sapiens

<400> SEQUENCE: 366
gugaguggga ggccagggca cggcaggggg agcugcaggg cuaugggagg ggccccagcg      60
ucugagcccu guccucccgc ag                                              82

<210> SEQ ID NO 367
<211> LENGTH: 84
<212> TYPE: RNA
<213> ORGANISM: Homo sapiens

<400> SEQUENCE: 367
cuccccaugg cccugucucc caacccuugu accagugcug ggcucagacc cugguacagg      60 ccuggggac agggaccugg ggac                                             84
```

```
<210> SEQ ID NO 368
<211> LENGTH: 75
<212> TYPE: RNA
<213> ORGANISM: Homo sapiens

<400> SEQUENCE: 368
ucaucccugg gugggauuuu guugcauuac uguguucua uauaaaguau ugcacuuguc    60
ccggccugug gaaga                                                    75

<210> SEQ ID NO 369
<211> LENGTH: 94
<212> TYPE: RNA
<213> ORGANISM: Homo sapiens

<400> SEQUENCE: 369
auaaaggaag uuaggcugag gggcagagag cgagacuuuu cuauuuucca aaagcucggu    60
cugaggcccc ucagucuugc uuccuaaccc gcgc                               94

<210> SEQ ID NO 370
<211> LENGTH: 52
<212> TYPE: RNA
<213> ORGANISM: Homo sapiens

<400> SEQUENCE: 370
uagccgggcg ugguggugg ggccuguggu cccagcuacu uuggaggcug ag             52

<210> SEQ ID NO 371
<211> LENGTH: 84
<212> TYPE: RNA
<213> ORGANISM: Homo sapiens

<400> SEQUENCE: 371
ugugcagugg aaggggggc cgauacacug uacgagagug aguagcaggu cucacaguga    60
accggucucu uucccuacug uguc                                          84

<210> SEQ ID NO 372
<211> LENGTH: 68
<212> TYPE: RNA
<213> ORGANISM: Homo sapiens

<400> SEQUENCE: 372
cuccggugcc uacugagcug auaucaguuc ucauuuuaca cacuggcuca guucagcagg    60
aacaggag                                                            68

<210> SEQ ID NO 373
<211> LENGTH: 73
<212> TYPE: RNA
<213> ORGANISM: Homo sapiens

<400> SEQUENCE: 373
cucugccucc cgugccuacu gagcugaaac acaguugguu uguguacacu ggcucaguuc    60
agcaggaaca ggg                                                      73

<210> SEQ ID NO 374
<211> LENGTH: 78
<212> TYPE: RNA
<213> ORGANISM: Homo sapiens

<400> SEQUENCE: 374
gggcccagaa gggggcgcag ucacugacgu gaagggacca caucccgcuu caugucagug    60
```
acuccugccc cuuggucu                                              78

<210> SEQ ID NO 375
<211> LENGTH: 73
<212> TYPE: RNA
<213> ORGANISM: Homo sapiens

<400> SEQUENCE: 375
ggcgagggga ggcgcaggcu cggaaaggcg cgcgaggcuc caggcuccuu cccgauccac    60
cgcucuccuc gcu                                                       73

<210> SEQ ID NO 376
<211> LENGTH: 73
<212> TYPE: RNA
<213> ORGANISM: Homo sapiens

<400> SEQUENCE: 376
cccagggucu ggugcggaga gggcccacag uggacuuggu gacgcuguau gcccucaccg    60
cucagccccu ggg                                                       73

<210> SEQ ID NO 377
<211> LENGTH: 63
<212> TYPE: RNA
<213> ORGANISM: Homo sapiens

<400> SEQUENCE: 377
gcaugcuggg cgaggcuggc aucuagcaca ggcgguagau gcuugcucuu gccauugcaa    60
uga                                                                  63

<210> SEQ ID NO 378
<211> LENGTH: 80
<212> TYPE: RNA
<213> ORGANISM: Homo sapiens

<400> SEQUENCE: 378
ugccgucggc cugggagga ggaagggcaa guccaaaggu auacaguugg ucguucauu      60 cucucuuuuu ggccuacaag                                                80

<210> SEQ ID NO 379
<211> LENGTH: 73
<212> TYPE: RNA
<213> ORGANISM: Homo sapiens

<400> SEQUENCE: 379
ggccggcugg gguuccuggg gaugggauuu gcuuccuguc acaaaucaca uugccaggga    60
uuuccaaccg acc                                                       73

<210> SEQ ID NO 380
<211> LENGTH: 66
<212> TYPE: RNA
<213> ORGANISM: Homo sapiens

<400> SEQUENCE: 380
ugacugggga gcagaaggag aacccaagaa aagcugacuu ggagguccu ccuucugucc     60 ccacag                                                               66

<210> SEQ ID NO 381
<211> LENGTH: 72
<212> TYPE: RNA

<213> ORGANISM: Homo sapiens

<400> SEQUENCE: 381
cuugggaaug gcaaggaaac cguuaccauu acugaguuua guaaugguaa ugguucucuu    60
gcuauaccca ga    72

<210> SEQ ID NO 382
<211> LENGTH: 102
<212> TYPE: RNA
<213> ORGANISM: Homo sapiens

<400> SEQUENCE: 382
gcuuaucgag gaaaagaucg agguggguug gggcgggcuc uggggauuug gucucacagc    60
ccggauccca gcccacuuac cuugguuacu cuccuuccuu cu    102

<210> SEQ ID NO 383
<211> LENGTH: 81
<212> TYPE: RNA
<213> ORGANISM: Homo sapiens

<400> SEQUENCE: 383
uacaggugca ggggaacugu agaugaaaag gcuuggcacu ugagggaaag ccucaguuca    60
uucucauuuu gcucaccugu u    81

<210> SEQ ID NO 384
<211> LENGTH: 56
<212> TYPE: RNA
<213> ORGANISM: Homo sapiens

<400> SEQUENCE: 384
guaggcaggg gcuggggauuu cagguucuca gucagaaccu uggccccucu ccccag    56

<210> SEQ ID NO 385
<211> LENGTH: 80
<212> TYPE: RNA
<213> ORGANISM: Homo sapiens

<400> SEQUENCE: 385
cugcagcgug cuucuccagg ccccgcgcgc ggacagacac acggacaagu cccgccaggg    60
gcugggcgcg cgccagccgg    80

<210> SEQ ID NO 386
<211> LENGTH: 70
<212> TYPE: RNA
<213> ORGANISM: Homo sapiens

<400> SEQUENCE: 386
aaaagccugu cccuaagucc cucccagccu uccagaguug gugccaggaa ggauuuaggg    60
acaggcuuug    70

<210> SEQ ID NO 387
<211> LENGTH: 60
<212> TYPE: RNA
<213> ORGANISM: Homo sapiens

<400> SEQUENCE: 387
cgcuggguuc gcgcgcccug ggccgggcga uguccgcuug ggggagcgag gggcggggcg    60

<210> SEQ ID NO 388
<211> LENGTH: 24

```
<212> TYPE: RNA
<213> ORGANISM: Homo sapiens

<400> SEQUENCE: 388
ucgaggacug guggaagggc cuuu                                          24

<210> SEQ ID NO 389
<211> LENGTH: 16
<212> TYPE: RNA
<213> ORGANISM: Homo sapiens

<400> SEQUENCE: 389
ucgaggacug guggaa                                                   16

<210> SEQ ID NO 390
<211> LENGTH: 23
<212> TYPE: RNA
<213> ORGANISM: Homo sapiens

<400> SEQUENCE: 390
cuccuggggc ccgcacucuc gcu                                           23

<210> SEQ ID NO 391
<211> LENGTH: 18
<212> TYPE: RNA
<213> ORGANISM: Homo sapiens

<400> SEQUENCE: 391
cuccuggggc ccgcacuc                                                 18

<210> SEQ ID NO 392
<211> LENGTH: 22
<212> TYPE: RNA
<213> ORGANISM: Homo sapiens

<400> SEQUENCE: 392
ccgggaacgu cgagacugga gc                                            22

<210> SEQ ID NO 393
<211> LENGTH: 15
<212> TYPE: RNA
<213> ORGANISM: Homo sapiens

<400> SEQUENCE: 393
cgggaacguc gagac                                                    15

<210> SEQ ID NO 394
<211> LENGTH: 23
<212> TYPE: RNA
<213> ORGANISM: Homo sapiens

<400> SEQUENCE: 394 gguggugag gucgggcccc aag                                            23

<210> SEQ ID NO 395
<211> LENGTH: 20
<212> TYPE: RNA
<213> ORGANISM: Homo sapiens

<400> SEQUENCE: 395
cggggugggu gaggucgggc                                               20

<210> SEQ ID NO 396
```

```
<211> LENGTH: 23
<212> TYPE: RNA
<213> ORGANISM: Homo sapiens

<400> SEQUENCE: 396
ugaggauaug gcagggaagg gga                                           23

<210> SEQ ID NO 397
<211> LENGTH: 19
<212> TYPE: RNA
<213> ORGANISM: Homo sapiens

<400> SEQUENCE: 397
ugaggauaug gcagggaag                                                19

<210> SEQ ID NO 398
<211> LENGTH: 22
<212> TYPE: RNA
<213> ORGANISM: Homo sapiens

<400> SEQUENCE: 398
cgcggcgggg acggcgauug gu                                            22

<210> SEQ ID NO 399
<211> LENGTH: 17
<212> TYPE: RNA
<213> ORGANISM: Homo sapiens

<400> SEQUENCE: 399
cggcggggac ggcgauu                                                  17

<210> SEQ ID NO 400
<211> LENGTH: 25
<212> TYPE: RNA
<213> ORGANISM: Homo sapiens

<400> SEQUENCE: 400
ugcggggcua gggcuaacag caguc                                         25

<210> SEQ ID NO 401
<211> LENGTH: 15
<212> TYPE: RNA
<213> ORGANISM: Homo sapiens

<400> SEQUENCE: 401
ugcggggcua gggcu                                                    15

<210> SEQ ID NO 402
<211> LENGTH: 17
<212> TYPE: RNA
<213> ORGANISM: Homo sapiens

<400> SEQUENCE: 402
ggugagcgcu cgcuggc                                                  17

<210> SEQ ID NO 403
<211> LENGTH: 15
<212> TYPE: RNA
<213> ORGANISM: Homo sapiens

<400> SEQUENCE: 403
cggugagcgc ucgcu                                                    15
```

```
<210> SEQ ID NO 404
<211> LENGTH: 18
<212> TYPE: RNA
<213> ORGANISM: Homo sapiens

<400> SEQUENCE: 404
cuccgggcgg cgccgugu                                                    18

<210> SEQ ID NO 405
<211> LENGTH: 18
<212> TYPE: RNA
<213> ORGANISM: Homo sapiens

<400> SEQUENCE: 405
cuccgggcgg cgccgugu                                                    18

<210> SEQ ID NO 406
<211> LENGTH: 25
<212> TYPE: RNA
<213> ORGANISM: Homo sapiens

<400> SEQUENCE: 406
uggcggcggu aguaugggc uucuc                                             25

<210> SEQ ID NO 407
<211> LENGTH: 25
<212> TYPE: RNA
<213> ORGANISM: Homo sapiens

<400> SEQUENCE: 407
uggcggcggu aguaugggc uucuc                                             25

<210> SEQ ID NO 408
<211> LENGTH: 26
<212> TYPE: RNA
<213> ORGANISM: Homo sapiens

<400> SEQUENCE: 408
ccuucuggag aggcuuugug cggaua                                           26

<210> SEQ ID NO 409
<211> LENGTH: 15
<212> TYPE: RNA
<213> ORGANISM: Homo sapiens

<400> SEQUENCE: 409
ccuucuggag aggcu                                                       15

<210> SEQ ID NO 410
<211> LENGTH: 23
<212> TYPE: RNA
<213> ORGANISM: Homo sapiens

<400> SEQUENCE: 410
cuaguggaag aagauggcgg aag                                              23

<210> SEQ ID NO 411
<211> LENGTH: 15
<212> TYPE: RNA
<213> ORGANISM: Homo sapiens

<400> SEQUENCE: 411
uaguggaaga agaug                                                       15
```

```
<210> SEQ ID NO 412
<211> LENGTH: 22
<212> TYPE: RNA
<213> ORGANISM: Homo sapiens

<400> SEQUENCE: 412
ccucacaccu gccucgcccc cc                                              22

<210> SEQ ID NO 413
<211> LENGTH: 15
<212> TYPE: RNA
<213> ORGANISM: Homo sapiens

<400> SEQUENCE: 413
ucacaccugc cucgc                                                      15

<210> SEQ ID NO 414
<211> LENGTH: 23
<212> TYPE: RNA
<213> ORGANISM: Homo sapiens

<400> SEQUENCE: 414
agaagaaggc ggucggucug cgg                                             23

<210> SEQ ID NO 415
<211> LENGTH: 21
<212> TYPE: RNA
<213> ORGANISM: Homo sapiens

<400> SEQUENCE: 415
aagaaggcgg ucggucugcg g                                               21

<210> SEQ ID NO 416
<211> LENGTH: 23
<212> TYPE: RNA
<213> ORGANISM: Homo sapiens

<400> SEQUENCE: 416
cggggccgua gcacugucug aga                                             23

<210> SEQ ID NO 417
<211> LENGTH: 20
<212> TYPE: RNA
<213> ORGANISM: Homo sapiens

<400> SEQUENCE: 417
cggggccgua gcacugucug                                                 20

<210> SEQ ID NO 418
<211> LENGTH: 25
<212> TYPE: RNA
<213> ORGANISM: Homo sapiens

<400> SEQUENCE: 418
uucugggccc gcggcgggcg ugggg                                           25

<210> SEQ ID NO 419
<211> LENGTH: 15
<212> TYPE: RNA
<213> ORGANISM: Homo sapiens

<400> SEQUENCE: 419
cgcggcgggc guggg                                                      15
```

```
<210> SEQ ID NO 420
<211> LENGTH: 23
<212> TYPE: RNA
<213> ORGANISM: Homo sapiens

<400> SEQUENCE: 420 aggaggggguc ccgcacuggg agg                                    23

<210> SEQ ID NO 421
<211> LENGTH: 15
<212> TYPE: RNA
<213> ORGANISM: Homo sapiens

<400> SEQUENCE: 421
ugggaggggc ccuca                                              15

<210> SEQ ID NO 422
<211> LENGTH: 18
<212> TYPE: RNA
<213> ORGANISM: Homo sapiens

<400> SEQUENCE: 422
gaggcugaag gaagaugg                                           18

<210> SEQ ID NO 423
<211> LENGTH: 15
<212> TYPE: RNA
<213> ORGANISM: Homo sapiens

<400> SEQUENCE: 423
gaggcugaag gaaga                                              15

<210> SEQ ID NO 424
<211> LENGTH: 23
<212> TYPE: RNA
<213> ORGANISM: Homo sapiens

<400> SEQUENCE: 424
ggcuacaaca caggacccgg gcg                                     23

<210> SEQ ID NO 425
<211> LENGTH: 21
<212> TYPE: RNA
<213> ORGANISM: Homo sapiens

<400> SEQUENCE: 425
ggcuacaaca caggacccgg g                                       21

<210> SEQ ID NO 426
<211> LENGTH: 24
<212> TYPE: RNA
<213> ORGANISM: Homo sapiens

<400> SEQUENCE: 426
gaggcuggga aggcaaaggg acgu                                    24

<210> SEQ ID NO 427
<211> LENGTH: 15
<212> TYPE: RNA
<213> ORGANISM: Homo sapiens

<400> SEQUENCE: 427
```
gaaggaggcu gggaa                                                           15

<210> SEQ ID NO 428
<211> LENGTH: 16
<212> TYPE: RNA
<213> ORGANISM: Homo sapiens

<400> SEQUENCE: 428
ugcuggugau gcuuuc                                                          16

<210> SEQ ID NO 429
<211> LENGTH: 16
<212> TYPE: RNA
<213> ORGANISM: Homo sapiens

<400> SEQUENCE: 429
ugcuggugau gcuuuc                                                          16

<210> SEQ ID NO 430
<211> LENGTH: 23
<212> TYPE: RNA
<213> ORGANISM: Homo sapiens

<400> SEQUENCE: 430
gggggucccc ggugcucgga ucu                                                  23

<210> SEQ ID NO 431
<211> LENGTH: 16
<212> TYPE: RNA
<213> ORGANISM: Homo sapiens

<400> SEQUENCE: 431
ucgggagggg cgggag                                                          16

<210> SEQ ID NO 432
<211> LENGTH: 21
<212> TYPE: RNA
<213> ORGANISM: Homo sapiens

<400> SEQUENCE: 432
caacucugau cucuucaucu a                                                    21

<210> SEQ ID NO 433
<211> LENGTH: 20
<212> TYPE: RNA
<213> ORGANISM: Homo sapiens

<400> SEQUENCE: 433
ucucuucauc uaccccccag                                                      20

<210> SEQ ID NO 434
<211> LENGTH: 22
<212> TYPE: RNA
<213> ORGANISM: Homo sapiens

<400> SEQUENCE: 434
ugggagggga gaggcagcaa gc                                                   22

<210> SEQ ID NO 435
<211> LENGTH: 22
<212> TYPE: RNA
<213> ORGANISM: Homo sapiens

<400> SEQUENCE: 435

```
ugggagggga gaggcagcaa gc                                              22

<210> SEQ ID NO 436
<211> LENGTH: 21
<212> TYPE: RNA
<213> ORGANISM: Homo sapiens

<400> SEQUENCE: 436
gaggcgaugu ggggauguag a                                               21

<210> SEQ ID NO 437
<211> LENGTH: 20
<212> TYPE: RNA
<213> ORGANISM: Homo sapiens

<400> SEQUENCE: 437
cccagucuca uuuccucauc                                                 20

<210> SEQ ID NO 438
<211> LENGTH: 23
<212> TYPE: RNA
<213> ORGANISM: Homo sapiens

<400> SEQUENCE: 438 cuggggacg cgugagcgcg agc                                              23

<210> SEQ ID NO 439
<211> LENGTH: 21
<212> TYPE: RNA
<213> ORGANISM: Homo sapiens

<400> SEQUENCE: 439 cuggggacg cgugagcgcg a                                                21

<210> SEQ ID NO 440
<211> LENGTH: 20
<212> TYPE: RNA
<213> ORGANISM: Homo sapiens

<400> SEQUENCE: 440
aagacacauu uggagaggga                                                 20

<210> SEQ ID NO 441
<211> LENGTH: 16
<212> TYPE: RNA
<213> ORGANISM: Homo sapiens

<400> SEQUENCE: 441
agacacauuu ggagag                                                     16

<210> SEQ ID NO 442
<211> LENGTH: 20
<212> TYPE: RNA
<213> ORGANISM: Homo sapiens

<400> SEQUENCE: 442
cuccccggug ugcaaaugug                                                 20

<210> SEQ ID NO 443
<211> LENGTH: 15
<212> TYPE: RNA
<213> ORGANISM: Homo sapiens
```

```
<400> SEQUENCE: 443
gugugcggug uuaug                                                    15

<210> SEQ ID NO 444
<211> LENGTH: 23
<212> TYPE: RNA
<213> ORGANISM: Homo sapiens

<400> SEQUENCE: 444
acaggagugg ggugggaca uaa                                            23

<210> SEQ ID NO 445
<211> LENGTH: 20
<212> TYPE: RNA
<213> ORGANISM: Homo sapiens

<400> SEQUENCE: 445
acaggagugg ggugggaca                                                20

<210> SEQ ID NO 446
<211> LENGTH: 23
<212> TYPE: RNA
<213> ORGANISM: Homo sapiens

<400> SEQUENCE: 446
gccccggcgc gggcggguuc ugg                                           23

<210> SEQ ID NO 447
<211> LENGTH: 16
<212> TYPE: RNA
<213> ORGANISM: Homo sapiens

<400> SEQUENCE: 447
ggagccccgg cgcggg                                                   16

<210> SEQ ID NO 448
<211> LENGTH: 16
<212> TYPE: RNA
<213> ORGANISM: Homo sapiens

<400> SEQUENCE: 448
gugaaggccc ggcgga                                                   16

<210> SEQ ID NO 449
<211> LENGTH: 15
<212> TYPE: RNA
<213> ORGANISM: Homo sapiens

<400> SEQUENCE: 449
gugaaggccc ggcgg                                                    15

<210> SEQ ID NO 450
<211> LENGTH: 26
<212> TYPE: RNA
<213> ORGANISM: Homo sapiens

<400> SEQUENCE: 450
gucccggggc ugcgcgaggc acaggc                                        26

<210> SEQ ID NO 451
<211> LENGTH: 15
<212> TYPE: RNA
<213> ORGANISM: Homo sapiens
```

```
<400> SEQUENCE: 451
ggcccggggg gcggg                                                  15

<210> SEQ ID NO 452
<211> LENGTH: 25
<212> TYPE: RNA
<213> ORGANISM: Homo sapiens

<400> SEQUENCE: 452
agcggggagg aagugggcgc ugcuu                                       25

<210> SEQ ID NO 453
<211> LENGTH: 21
<212> TYPE: RNA
<213> ORGANISM: Homo sapiens

<400> SEQUENCE: 453
agcggggagg aagugggcgc u                                           21

<210> SEQ ID NO 454
<211> LENGTH: 22
<212> TYPE: RNA
<213> ORGANISM: Homo sapiens

<400> SEQUENCE: 454
ccggcagagg aggcugcaga gg                                          22

<210> SEQ ID NO 455
<211> LENGTH: 19
<212> TYPE: RNA
<213> ORGANISM: Homo sapiens

<400> SEQUENCE: 455
ccggcagagg aggcugcag                                              19

<210> SEQ ID NO 456
<211> LENGTH: 24
<212> TYPE: RNA
<213> ORGANISM: Homo sapiens

<400> SEQUENCE: 456 ugggagcug aggcucuggg ggug                                         24

<210> SEQ ID NO 457
<211> LENGTH: 15
<212> TYPE: RNA
<213> ORGANISM: Homo sapiens

<400> SEQUENCE: 457
ggcccugggg agcug                                                  15

<210> SEQ ID NO 458
<211> LENGTH: 21
<212> TYPE: RNA
<213> ORGANISM: Homo sapiens

<400> SEQUENCE: 458
aggaggcagu gggcgagcag g                                           21

<210> SEQ ID NO 459
<211> LENGTH: 21
<212> TYPE: RNA
```

<213> ORGANISM: Homo sapiens

<400> SEQUENCE: 459
aggaggcagu gggcgagcag g            21

<210> SEQ ID NO 460
<211> LENGTH: 16
<212> TYPE: RNA
<213> ORGANISM: Homo sapiens

<400> SEQUENCE: 460
ggacccaggg agagac            16

<210> SEQ ID NO 461
<211> LENGTH: 16
<212> TYPE: RNA
<213> ORGANISM: Homo sapiens

<400> SEQUENCE: 461
ggacccaggg agagac            16

<210> SEQ ID NO 462
<211> LENGTH: 21
<212> TYPE: RNA
<213> ORGANISM: Homo sapiens

<400> SEQUENCE: 462
gagggcagcg uggguguggc g            21

<210> SEQ ID NO 463
<211> LENGTH: 21
<212> TYPE: RNA
<213> ORGANISM: Homo sapiens

<400> SEQUENCE: 463
gagggcagcg uggguguggc g            21

<210> SEQ ID NO 464
<211> LENGTH: 25
<212> TYPE: RNA
<213> ORGANISM: Homo sapiens

<400> SEQUENCE: 464
ugggcagggg cuuauuguag gaguc            25

<210> SEQ ID NO 465
<211> LENGTH: 19
<212> TYPE: RNA
<213> ORGANISM: Homo sapiens

<400> SEQUENCE: 465
ugggcagggg cuuauugua            19

<210> SEQ ID NO 466
<211> LENGTH: 23
<212> TYPE: RNA
<213> ORGANISM: Homo sapiens

<400> SEQUENCE: 466
acagcagggc uggggauugc agu            23

<210> SEQ ID NO 467
<211> LENGTH: 19

```
<212> TYPE: RNA
<213> ORGANISM: Homo sapiens

<400> SEQUENCE: 467
ugcugcuccc aguccugcc                                              19

<210> SEQ ID NO 468
<211> LENGTH: 27
<212> TYPE: RNA
<213> ORGANISM: Homo sapiens

<400> SEQUENCE: 468
gugaacgggc gccaucccga ggcuuug                                     27

<210> SEQ ID NO 469
<211> LENGTH: 16
<212> TYPE: RNA
<213> ORGANISM: Homo sapiens

<400> SEQUENCE: 469
gugaacgggc gccauc                                                 16

<210> SEQ ID NO 470
<211> LENGTH: 21
<212> TYPE: RNA
<213> ORGANISM: Homo sapiens

<400> SEQUENCE: 470 cuuccccca guaaucuuca u                                            21

<210> SEQ ID NO 471
<211> LENGTH: 21
<212> TYPE: RNA
<213> ORGANISM: Homo sapiens

<400> SEQUENCE: 471 cuuccccca guaaucuuca u                                            21

<210> SEQ ID NO 472
<211> LENGTH: 26
<212> TYPE: RNA
<213> ORGANISM: Homo sapiens

<400> SEQUENCE: 472
aggagggagg agaugggcca aguucc                                      26

<210> SEQ ID NO 473
<211> LENGTH: 15
<212> TYPE: RNA
<213> ORGANISM: Homo sapiens

<400> SEQUENCE: 473
gggaggaggg aggag                                                  15

<210> SEQ ID NO 474
<211> LENGTH: 21
<212> TYPE: RNA
<213> ORGANISM: Homo sapiens

<400> SEQUENCE: 474
gugagucagg gugggggcugg c                                          21

<210> SEQ ID NO 475
```

```
<211> LENGTH: 21
<212> TYPE: RNA
<213> ORGANISM: Homo sapiens

<400> SEQUENCE: 475
gugagucagg gugggcugg c                                              21

<210> SEQ ID NO 476
<211> LENGTH: 21
<212> TYPE: RNA
<213> ORGANISM: Homo sapiens

<400> SEQUENCE: 476
auccaguucu cugaggggc u                                              21

<210> SEQ ID NO 477
<211> LENGTH: 21
<212> TYPE: RNA
<213> ORGANISM: Homo sapiens

<400> SEQUENCE: 477
auccaguucu cugaggggc u                                              21

<210> SEQ ID NO 478
<211> LENGTH: 18
<212> TYPE: RNA
<213> ORGANISM: Homo sapiens

<400> SEQUENCE: 478
ggugggcuuc ccggaggg                                                 18

<210> SEQ ID NO 479
<211> LENGTH: 15
<212> TYPE: RNA
<213> ORGANISM: Homo sapiens

<400> SEQUENCE: 479
ggugggcuuc ccgga                                                    15

<210> SEQ ID NO 480
<211> LENGTH: 16
<212> TYPE: RNA
<213> ORGANISM: Homo sapiens

<400> SEQUENCE: 480 cuggggucc cccgac                                                    16

<210> SEQ ID NO 481
<211> LENGTH: 15
<212> TYPE: RNA
<213> ORGANISM: Homo sapiens

<400> SEQUENCE: 481
guguggagcu ggggc                                                    15

<210> SEQ ID NO 482
<211> LENGTH: 24
<212> TYPE: RNA
<213> ORGANISM: Homo sapiens

<400> SEQUENCE: 482
gcugcgggcu gcggucaggg cgau                                          24
```

```
<210> SEQ ID NO 483
<211> LENGTH: 20
<212> TYPE: RNA
<213> ORGANISM: Homo sapiens

<400> SEQUENCE: 483
gcugcgggcu gcggucaggg                                              20

<210> SEQ ID NO 484
<211> LENGTH: 26
<212> TYPE: RNA
<213> ORGANISM: Homo sapiens

<400> SEQUENCE: 484 cgugggauc ccgcggccgu guuuuc                                        26

<210> SEQ ID NO 485
<211> LENGTH: 15
<212> TYPE: RNA
<213> ORGANISM: Homo sapiens

<400> SEQUENCE: 485
ggggcgccgc gggac                                                   15

<210> SEQ ID NO 486
<211> LENGTH: 18
<212> TYPE: RNA
<213> ORGANISM: Homo sapiens

<400> SEQUENCE: 486 ucuaggugg gagacuga                                                 18

<210> SEQ ID NO 487
<211> LENGTH: 16
<212> TYPE: RNA
<213> ORGANISM: Homo sapiens

<400> SEQUENCE: 487 gugggagac ugacgg                                                   16

<210> SEQ ID NO 488
<211> LENGTH: 23
<212> TYPE: RNA
<213> ORGANISM: Homo sapiens

<400> SEQUENCE: 488
gugggcuggg cugggcuggg cca                                          23

<210> SEQ ID NO 489
<211> LENGTH: 15
<212> TYPE: RNA
<213> ORGANISM: Homo sapiens

<400> SEQUENCE: 489
gggcugggcu gggcu                                                   15

<210> SEQ ID NO 490
<211> LENGTH: 23
<212> TYPE: RNA
<213> ORGANISM: Homo sapiens

<400> SEQUENCE: 490
caccuugccu ugcugcccgg gcc                                          23
```

```
<210> SEQ ID NO 491
<211> LENGTH: 22
<212> TYPE: RNA
<213> ORGANISM: Homo sapiens

<400> SEQUENCE: 491
caccuugccu ugcugcccgg gc                                        22

<210> SEQ ID NO 492
<211> LENGTH: 24
<212> TYPE: RNA
<213> ORGANISM: Homo sapiens

<400> SEQUENCE: 492
agacacauuu ggagagggaa ccuc                                      24

<210> SEQ ID NO 493
<211> LENGTH: 16
<212> TYPE: RNA
<213> ORGANISM: Homo sapiens

<400> SEQUENCE: 493
agacacauuu ggagag                                               16

<210> SEQ ID NO 494
<211> LENGTH: 22
<212> TYPE: RNA
<213> ORGANISM: Homo sapiens

<400> SEQUENCE: 494
acucaaacug uggggcacu uu                                         22

<210> SEQ ID NO 495
<211> LENGTH: 19
<212> TYPE: RNA
<213> ORGANISM: Homo sapiens

<400> SEQUENCE: 495
acucaaacug uggggcac                                             19

<210> SEQ ID NO 496
<211> LENGTH: 25
<212> TYPE: RNA
<213> ORGANISM: Homo sapiens

<400> SEQUENCE: 496
aaggcagggc ccccgcuccc cgggc                                     25

<210> SEQ ID NO 497
<211> LENGTH: 15
<212> TYPE: RNA
<213> ORGANISM: Homo sapiens

<400> SEQUENCE: 497
guguguugag gaagg                                                15

<210> SEQ ID NO 498
<211> LENGTH: 22
<212> TYPE: RNA
<213> ORGANISM: Homo sapiens

<400> SEQUENCE: 498
uggggauuug gagaaguggu ga                                        22
```

<210> SEQ ID NO 499
<211> LENGTH: 22
<212> TYPE: RNA
<213> ORGANISM: Homo sapiens

<400> SEQUENCE: 499
uggggauuug gagaaguggu ga                                              22

<210> SEQ ID NO 500
<211> LENGTH: 25
<212> TYPE: RNA
<213> ORGANISM: Homo sapiens

<400> SEQUENCE: 500
gggggagcca ugagauaaga gcacc                                           25

<210> SEQ ID NO 501
<211> LENGTH: 20
<212> TYPE: RNA
<213> ORGANISM: Homo sapiens

<400> SEQUENCE: 501 uggggagcc augagauaag                                                  20

<210> SEQ ID NO 502
<211> LENGTH: 17
<212> TYPE: RNA
<213> ORGANISM: Homo sapiens

<400> SEQUENCE: 502
uccuagucac ggcacca                                                    17

<210> SEQ ID NO 503
<211> LENGTH: 17
<212> TYPE: RNA
<213> ORGANISM: Homo sapiens

<400> SEQUENCE: 503
uccuagucac ggcacca                                                    17

<210> SEQ ID NO 504
<211> LENGTH: 24
<212> TYPE: RNA
<213> ORGANISM: Homo sapiens

<400> SEQUENCE: 504
cgggcguggu ggugggggug ggug                                            24

<210> SEQ ID NO 505
<211> LENGTH: 15
<212> TYPE: RNA
<213> ORGANISM: Homo sapiens

<400> SEQUENCE: 505
cgggcguggu ggugg                                                      15

<210> SEQ ID NO 506
<211> LENGTH: 23
<212> TYPE: RNA
<213> ORGANISM: Homo sapiens

<400> SEQUENCE: 506

```
ggcccggccg ugccugaggu uuc                                              23

<210> SEQ ID NO 507
<211> LENGTH: 15
<212> TYPE: RNA
<213> ORGANISM: Homo sapiens

<400> SEQUENCE: 507
ggcgguggga ucccg                                                       15

<210> SEQ ID NO 508
<211> LENGTH: 23
<212> TYPE: RNA
<213> ORGANISM: Homo sapiens

<400> SEQUENCE: 508
cacaggugag guucuuggga gcc                                              23

<210> SEQ ID NO 509
<211> LENGTH: 15
<212> TYPE: RNA
<213> ORGANISM: Homo sapiens

<400> SEQUENCE: 509
acaggugagg uucuu                                                       15

<210> SEQ ID NO 510
<211> LENGTH: 16
<212> TYPE: RNA
<213> ORGANISM: Homo sapiens

<400> SEQUENCE: 510 ggcgguggc ggcggg                                                       16

<210> SEQ ID NO 511
<211> LENGTH: 15
<212> TYPE: RNA
<213> ORGANISM: Homo sapiens

<400> SEQUENCE: 511
ggccucucgg gaacu                                                       15

<210> SEQ ID NO 512
<211> LENGTH: 15
<212> TYPE: RNA
<213> ORGANISM: Homo sapiens

<400> SEQUENCE: 512
ugaagcgggg gggcg                                                       15

<210> SEQ ID NO 513
<211> LENGTH: 15
<212> TYPE: RNA
<213> ORGANISM: Homo sapiens

<400> SEQUENCE: 513
ugaagcgggg gggcg                                                       15

<210> SEQ ID NO 514
<211> LENGTH: 24
<212> TYPE: RNA
<213> ORGANISM: Homo sapiens

<400> SEQUENCE: 514
```

```
gugaguggga gccgguggggg cugg                                         24

<210> SEQ ID NO 515
<211> LENGTH: 15
<212> TYPE: RNA
<213> ORGANISM: Homo sapiens

<400> SEQUENCE: 515
ggggcuggag uaagg                                                    15

<210> SEQ ID NO 516
<211> LENGTH: 22
<212> TYPE: RNA
<213> ORGANISM: Homo sapiens

<400> SEQUENCE: 516 gagguuggg uggaggcucu cc                                             22

<210> SEQ ID NO 517
<211> LENGTH: 15
<212> TYPE: RNA
<213> ORGANISM: Homo sapiens

<400> SEQUENCE: 517 gagguuggg uggag                                                     15

<210> SEQ ID NO 518
<211> LENGTH: 25
<212> TYPE: RNA
<213> ORGANISM: Homo sapiens

<400> SEQUENCE: 518
aggaagcccu ggaggggcug gaggu                                         25

<210> SEQ ID NO 519
<211> LENGTH: 15
<212> TYPE: RNA
<213> ORGANISM: Homo sapiens

<400> SEQUENCE: 519
aggaagagga ggaag                                                    15

<210> SEQ ID NO 520
<211> LENGTH: 21
<212> TYPE: RNA
<213> ORGANISM: Homo sapiens

<400> SEQUENCE: 520
cggauccgag ucacggcacc a                                             21

<210> SEQ ID NO 521
<211> LENGTH: 15
<212> TYPE: RNA
<213> ORGANISM: Homo sapiens

<400> SEQUENCE: 521
ggauccgagu cacgg                                                    15

<210> SEQ ID NO 522
<211> LENGTH: 23
<212> TYPE: RNA
<213> ORGANISM: Homo sapiens
```

```
<400> SEQUENCE: 522
agggucgggg cagggagggc agg                                         23

<210> SEQ ID NO 523
<211> LENGTH: 15
<212> TYPE: RNA
<213> ORGANISM: Homo sapiens

<400> SEQUENCE: 523
gggagaaggg ucggg                                                  15

<210> SEQ ID NO 524
<211> LENGTH: 26
<212> TYPE: RNA
<213> ORGANISM: Homo sapiens

<400> SEQUENCE: 524
gcgggcuguc cggagggguc ggcuuu                                      26

<210> SEQ ID NO 525
<211> LENGTH: 16
<212> TYPE: RNA
<213> ORGANISM: Homo sapiens

<400> SEQUENCE: 525
gcuguccgga gggguc                                                 16

<210> SEQ ID NO 526
<211> LENGTH: 26
<212> TYPE: RNA
<213> ORGANISM: Homo sapiens

<400> SEQUENCE: 526
agggacggga cgcggugcag uguugu                                      26

<210> SEQ ID NO 527
<211> LENGTH: 15
<212> TYPE: RNA
<213> ORGANISM: Homo sapiens

<400> SEQUENCE: 527
ggcgggcggg aggga                                                  15

<210> SEQ ID NO 528
<211> LENGTH: 23
<212> TYPE: RNA
<213> ORGANISM: Homo sapiens

<400> SEQUENCE: 528
uggggaaggc gucagugucg ggu                                         23

<210> SEQ ID NO 529
<211> LENGTH: 16
<212> TYPE: RNA
<213> ORGANISM: Homo sapiens

<400> SEQUENCE: 529
uggggaaggc gucagu                                                 16

<210> SEQ ID NO 530
<211> LENGTH: 23
<212> TYPE: RNA
<213> ORGANISM: Homo sapiens
```

```
<400> SEQUENCE: 530
uaggggcagc agaggaccug ggc                                              23

<210> SEQ ID NO 531
<211> LENGTH: 20
<212> TYPE: RNA
<213> ORGANISM: Homo sapiens

<400> SEQUENCE: 531
uaggggcagc agaggaccug                                                  20

<210> SEQ ID NO 532
<211> LENGTH: 20
<212> TYPE: RNA
<213> ORGANISM: Homo sapiens

<400> SEQUENCE: 532
ggcuggucag augggagugg                                                  20

<210> SEQ ID NO 533
<211> LENGTH: 20
<212> TYPE: RNA
<213> ORGANISM: Homo sapiens

<400> SEQUENCE: 533
ggcuggucag augggagugg                                                  20

<210> SEQ ID NO 534
<211> LENGTH: 20
<212> TYPE: RNA
<213> ORGANISM: Homo sapiens

<400> SEQUENCE: 534
ccccagggcg acgcggcggg                                                  20

<210> SEQ ID NO 535
<211> LENGTH: 15
<212> TYPE: RNA
<213> ORGANISM: Homo sapiens

<400> SEQUENCE: 535
cgcggcgggg gcggc                                                       15

<210> SEQ ID NO 536
<211> LENGTH: 20
<212> TYPE: RNA
<213> ORGANISM: Homo sapiens

<400> SEQUENCE: 536
ccccggggag cccggcggug                                                  20

<210> SEQ ID NO 537
<211> LENGTH: 15
<212> TYPE: RNA
<213> ORGANISM: Homo sapiens

<400> SEQUENCE: 537
accccgggga gcccg                                                       15

<210> SEQ ID NO 538
<211> LENGTH: 21
<212> TYPE: RNA
```

```
<213> ORGANISM: Homo sapiens

<400> SEQUENCE: 538
uugaggagac auggugggg c                                        21

<210> SEQ ID NO 539
<211> LENGTH: 15
<212> TYPE: RNA
<213> ORGANISM: Homo sapiens

<400> SEQUENCE: 539
uugaggagac auggu                                              15

<210> SEQ ID NO 540
<211> LENGTH: 22
<212> TYPE: RNA
<213> ORGANISM: Homo sapiens

<400> SEQUENCE: 540
acucggcugc gguggacaag uc                                      22

<210> SEQ ID NO 541
<211> LENGTH: 20
<212> TYPE: RNA
<213> ORGANISM: Homo sapiens

<400> SEQUENCE: 541
acucggcugc gguggacaag                                         20

<210> SEQ ID NO 542
<211> LENGTH: 19
<212> TYPE: RNA
<213> ORGANISM: Homo sapiens

<400> SEQUENCE: 542
uggcgggugc ggggguggg                                          19

<210> SEQ ID NO 543
<211> LENGTH: 15
<212> TYPE: RNA
<213> ORGANISM: Homo sapiens

<400> SEQUENCE: 543
uggcgggugc ggggg                                              15

<210> SEQ ID NO 544
<211> LENGTH: 23
<212> TYPE: RNA
<213> ORGANISM: Homo sapiens

<400> SEQUENCE: 544
gagggaggga cggggcugu gcu                                      23

<210> SEQ ID NO 545
<211> LENGTH: 15
<212> TYPE: RNA
<213> ORGANISM: Homo sapiens

<400> SEQUENCE: 545
gaggagggag ggagg                                              15

<210> SEQ ID NO 546
<211> LENGTH: 26
```

```
<212> TYPE: RNA
<213> ORGANISM: Homo sapiens

<400> SEQUENCE: 546
aaaaucacau ugccagggau uaccac                                       26

<210> SEQ ID NO 547
<211> LENGTH: 15
<212> TYPE: RNA
<213> ORGANISM: Homo sapiens

<400> SEQUENCE: 547
aaucacauug ccagg                                                   15

<210> SEQ ID NO 548
<211> LENGTH: 21
<212> TYPE: RNA
<213> ORGANISM: Homo sapiens

<400> SEQUENCE: 548
cccaggcugg agcgagugca g                                            21

<210> SEQ ID NO 549
<211> LENGTH: 15
<212> TYPE: RNA
<213> ORGANISM: Homo sapiens

<400> SEQUENCE: 549
agcucacugc agccu                                                   15

<210> SEQ ID NO 550
<211> LENGTH: 21
<212> TYPE: RNA
<213> ORGANISM: Homo sapiens

<400> SEQUENCE: 550
ugggaauggg gguaagggcc u                                            21

<210> SEQ ID NO 551
<211> LENGTH: 15
<212> TYPE: RNA
<213> ORGANISM: Homo sapiens

<400> SEQUENCE: 551
cuucugagcc caggu                                                   15

<210> SEQ ID NO 552
<211> LENGTH: 17
<212> TYPE: RNA
<213> ORGANISM: Homo sapiens

<400> SEQUENCE: 552
ugcaggggca ggccagc                                                 17

<210> SEQ ID NO 553
<211> LENGTH: 17
<212> TYPE: RNA
<213> ORGANISM: Homo sapiens

<400> SEQUENCE: 553
ugcaggggca ggccagc                                                 17

<210> SEQ ID NO 554
```

```
<211> LENGTH: 16
<212> TYPE: RNA
<213> ORGANISM: Homo sapiens

<400> SEQUENCE: 554
agcugcagug ggggag                                                          16

<210> SEQ ID NO 555
<211> LENGTH: 15
<212> TYPE: RNA
<213> ORGANISM: Homo sapiens

<400> SEQUENCE: 555
gcugcagugg gggag                                                           15

<210> SEQ ID NO 556
<211> LENGTH: 15
<212> TYPE: RNA
<213> ORGANISM: Homo sapiens

<400> SEQUENCE: 556
ucugggcgag gggug                                                           15

<210> SEQ ID NO 557
<211> LENGTH: 15
<212> TYPE: RNA
<213> ORGANISM: Homo sapiens

<400> SEQUENCE: 557
ucugggcgag gggug                                                           15

<210> SEQ ID NO 558
<211> LENGTH: 16
<212> TYPE: RNA
<213> ORGANISM: Homo sapiens

<400> SEQUENCE: 558 uggggggaa gaaaag                                                           16

<210> SEQ ID NO 559
<211> LENGTH: 16
<212> TYPE: RNA
<213> ORGANISM: Homo sapiens

<400> SEQUENCE: 559 uggggggaa gaaaag                                                           16

<210> SEQ ID NO 560
<211> LENGTH: 17
<212> TYPE: RNA
<213> ORGANISM: Homo sapiens

<400> SEQUENCE: 560
gcggggcggc agggggcc                                                        17

<210> SEQ ID NO 561
<211> LENGTH: 15
<212> TYPE: RNA
<213> ORGANISM: Homo sapiens

<400> SEQUENCE: 561
gggggcgggg cggca                                                           15
```

-continued

```
<210> SEQ ID NO 562
<211> LENGTH: 22
<212> TYPE: RNA
<213> ORGANISM: Homo sapiens

<400> SEQUENCE: 562
ugugggacug caaaugggag cu                                              22

<210> SEQ ID NO 563
<211> LENGTH: 22
<212> TYPE: RNA
<213> ORGANISM: Homo sapiens

<400> SEQUENCE: 563
ugugggacug caaaugggag cu                                              22

<210> SEQ ID NO 564
<211> LENGTH: 18
<212> TYPE: RNA
<213> ORGANISM: Homo sapiens

<400> SEQUENCE: 564
cagcggggcu gggcgcgc                                                   18

<210> SEQ ID NO 565
<211> LENGTH: 15
<212> TYPE: RNA
<213> ORGANISM: Homo sapiens

<400> SEQUENCE: 565
cagcggggcu gggcg                                                      15

<210> SEQ ID NO 566
<211> LENGTH: 24
<212> TYPE: RNA
<213> ORGANISM: Homo sapiens

<400> SEQUENCE: 566
cugcggggac aggccagggc aucu                                            24

<210> SEQ ID NO 567
<211> LENGTH: 20
<212> TYPE: RNA
<213> ORGANISM: Homo sapiens

<400> SEQUENCE: 567
cugcggggac aggccagggc                                                 20

<210> SEQ ID NO 568
<211> LENGTH: 30
<212> TYPE: RNA
<213> ORGANISM: Homo sapiens

<400> SEQUENCE: 568
gcugggcugg gacggacacc cggccuccac                                      30

<210> SEQ ID NO 569
<211> LENGTH: 19
<212> TYPE: RNA
<213> ORGANISM: Homo sapiens

<400> SEQUENCE: 569
gaggcugggc ugggacgga                                                  19
```

```
<210> SEQ ID NO 570
<211> LENGTH: 24
<212> TYPE: RNA
<213> ORGANISM: Homo sapiens

<400> SEQUENCE: 570 uggggggagug cagugauugu ggaa                                          24

<210> SEQ ID NO 571
<211> LENGTH: 19
<212> TYPE: RNA
<213> ORGANISM: Homo sapiens

<400> SEQUENCE: 571 uggggggagug cagugauug                                                19

<210> SEQ ID NO 572
<211> LENGTH: 24
<212> TYPE: RNA
<213> ORGANISM: Homo sapiens

<400> SEQUENCE: 572
aggcaggggc uggugcuggg cggg                                           24

<210> SEQ ID NO 573
<211> LENGTH: 15
<212> TYPE: RNA
<213> ORGANISM: Homo sapiens

<400> SEQUENCE: 573 gggcggggggg cggcg                                                    15

<210> SEQ ID NO 574
<211> LENGTH: 19
<212> TYPE: RNA
<213> ORGANISM: Homo sapiens

<400> SEQUENCE: 574
agugggaggc cagggcacg                                                 19

<210> SEQ ID NO 575
<211> LENGTH: 15
<212> TYPE: RNA
<213> ORGANISM: Homo sapiens

<400> SEQUENCE: 575 aggggggagcu gcagg                                                    15

<210> SEQ ID NO 576
<211> LENGTH: 24
<212> TYPE: RNA
<213> ORGANISM: Homo sapiens

<400> SEQUENCE: 576
cugguacagg ccuggggac aggg                                            24

<210> SEQ ID NO 577
<211> LENGTH: 18
<212> TYPE: RNA
<213> ORGANISM: Homo sapiens

<400> SEQUENCE: 577
cugguacagg ccuggggg                                                  18
```

<210> SEQ ID NO 578
<211> LENGTH: 25
<212> TYPE: RNA
<213> ORGANISM: Homo sapiens

<400> SEQUENCE: 578
ggguggggau uuguugcauu acuug 25

<210> SEQ ID NO 579
<211> LENGTH: 20
<212> TYPE: RNA
<213> ORGANISM: Homo sapiens

<400> SEQUENCE: 579
ggguggggau uuguugcauu 20

<210> SEQ ID NO 580
<211> LENGTH: 30
<212> TYPE: RNA
<213> ORGANISM: Homo sapiens

<400> SEQUENCE: 580
ugaggggcag agagcgagac uuuucuauuu 30

<210> SEQ ID NO 581
<211> LENGTH: 15
<212> TYPE: RNA
<213> ORGANISM: Homo sapiens

<400> SEQUENCE: 581
ugaggggcag agagc 15

<210> SEQ ID NO 582
<211> LENGTH: 21
<212> TYPE: RNA
<213> ORGANISM: Homo sapiens

<400> SEQUENCE: 582
gccgggcgug gugguggggg c 21

<210> SEQ ID NO 583
<211> LENGTH: 15
<212> TYPE: RNA
<213> ORGANISM: Homo sapiens

<400> SEQUENCE: 583
uagccgggcg uggug 15

<210> SEQ ID NO 584
<211> LENGTH: 23
<212> TYPE: RNA
<213> ORGANISM: Homo sapiens

<400> SEQUENCE: 584
gggggccgau acacuguacg aga 23

<210> SEQ ID NO 585
<211> LENGTH: 20
<212> TYPE: RNA
<213> ORGANISM: Homo sapiens

<400> SEQUENCE: 585

```
gggggccgau acacuguacg                                              20

<210> SEQ ID NO 586
<211> LENGTH: 24
<212> TYPE: RNA
<213> ORGANISM: Homo sapiens

<400> SEQUENCE: 586
acuggcucag uucagcagga acag                                         24

<210> SEQ ID NO 587
<211> LENGTH: 15
<212> TYPE: RNA
<213> ORGANISM: Homo sapiens

<400> SEQUENCE: 587
uggcucaguu cagca                                                   15

<210> SEQ ID NO 588
<211> LENGTH: 23
<212> TYPE: RNA
<213> ORGANISM: Homo sapiens

<400> SEQUENCE: 588
ggaggcgcag gcucggaaag gcg                                          23

<210> SEQ ID NO 589
<211> LENGTH: 15
<212> TYPE: RNA
<213> ORGANISM: Homo sapiens

<400> SEQUENCE: 589
gcaggcucgg aaagg                                                   15

<210> SEQ ID NO 590
<211> LENGTH: 23
<212> TYPE: RNA
<213> ORGANISM: Homo sapiens

<400> SEQUENCE: 590
uggugcggag agggcccaca gug                                          23

<210> SEQ ID NO 591
<211> LENGTH: 15
<212> TYPE: RNA
<213> ORGANISM: Homo sapiens

<400> SEQUENCE: 591
gggucuggug cggag                                                   15

<210> SEQ ID NO 592
<211> LENGTH: 19
<212> TYPE: RNA
<213> ORGANISM: Homo sapiens

<400> SEQUENCE: 592
gcugggcgag gcuggcauc                                               19

<210> SEQ ID NO 593
<211> LENGTH: 17
<212> TYPE: RNA
<213> ORGANISM: Homo sapiens

<400> SEQUENCE: 593
```

| | |
|---|---|
| gcugggcgag gcuggca | 17 |

<210> SEQ ID NO 594
<211> LENGTH: 27
<212> TYPE: RNA
<213> ORGANISM: Homo sapiens

<400> SEQUENCE: 594

| | |
|---|---|
| aucacauugc cagggauuuc caaccga | 27 |

<210> SEQ ID NO 595
<211> LENGTH: 15
<212> TYPE: RNA
<213> ORGANISM: Homo sapiens

<400> SEQUENCE: 595

| | |
|---|---|
| aaucacauug ccagg | 15 |

<210> SEQ ID NO 596
<211> LENGTH: 24
<212> TYPE: RNA
<213> ORGANISM: Homo sapiens

<400> SEQUENCE: 596

| | |
|---|---|
| ugacugggga gcagaaggag aacc | 24 |

<210> SEQ ID NO 597
<211> LENGTH: 15
<212> TYPE: RNA
<213> ORGANISM: Homo sapiens

<400> SEQUENCE: 597

| | |
|---|---|
| gacuggggag cagaa | 15 |

<210> SEQ ID NO 598
<211> LENGTH: 27
<212> TYPE: RNA
<213> ORGANISM: Homo sapiens

<400> SEQUENCE: 598

| | |
|---|---|
| aaaccguuac cauuacugag uuuagua | 27 |

<210> SEQ ID NO 599
<211> LENGTH: 15
<212> TYPE: RNA
<213> ORGANISM: Homo sapiens

<400> SEQUENCE: 599

| | |
|---|---|
| gaaaccguua ccauu | 15 |

<210> SEQ ID NO 600
<211> LENGTH: 19
<212> TYPE: RNA
<213> ORGANISM: Homo sapiens

<400> SEQUENCE: 600

| | |
|---|---|
| guggguuggg gcgggcucu | 19 |

<210> SEQ ID NO 601
<211> LENGTH: 19
<212> TYPE: RNA
<213> ORGANISM: Homo sapiens

```
<400> SEQUENCE: 601
guggguuggg gcgggcucu                                              19

<210> SEQ ID NO 602
<211> LENGTH: 17
<212> TYPE: RNA
<213> ORGANISM: Homo sapiens

<400> SEQUENCE: 602
aggggcuggg cgcgcgc                                                17

<210> SEQ ID NO 603
<211> LENGTH: 15
<212> TYPE: RNA
<213> ORGANISM: Homo sapiens

<400> SEQUENCE: 603
caggggcugg gcgcg                                                  15

<210> SEQ ID NO 604
<211> LENGTH: 25
<212> TYPE: RNA
<213> ORGANISM: Homo sapiens

<400> SEQUENCE: 604
caggaaggau uagggacag gcuuu                                        25

<210> SEQ ID NO 605
<211> LENGTH: 19
<212> TYPE: RNA
<213> ORGANISM: Homo sapiens

<400> SEQUENCE: 605
caggaaggau uagggaca                                               19

<210> SEQ ID NO 606
<211> LENGTH: 21
<212> TYPE: RNA
<213> ORGANISM: Homo sapiens

<400> SEQUENCE: 606
augccucccc cggccccgca g                                           21

<210> SEQ ID NO 607
<211> LENGTH: 17
<212> TYPE: RNA
<213> ORGANISM: Homo sapiens

<400> SEQUENCE: 607
cgcgccgggc ccggguu                                                17

<210> SEQ ID NO 608
<211> LENGTH: 21
<212> TYPE: RNA
<213> ORGANISM: Homo sapiens

<400> SEQUENCE: 608
cuuccgcccc gccgggcguc g                                           21

<210> SEQ ID NO 609
<211> LENGTH: 17
<212> TYPE: RNA
<213> ORGANISM: Homo sapiens
```

```
<400> SEQUENCE: 609
ggggcgcggc cggaucg                                                    17

<210> SEQ ID NO 610
<211> LENGTH: 25
<212> TYPE: RNA
<213> ORGANISM: Homo sapiens

<400> SEQUENCE: 610
agggaucgcg ggcggguggc ggccu                                           25

<210> SEQ ID NO 611
<211> LENGTH: 17
<212> TYPE: RNA
<213> ORGANISM: Homo sapiens

<400> SEQUENCE: 611
cuccgggacg gcugggc                                                    17

<210> SEQ ID NO 612
<211> LENGTH: 19
<212> TYPE: RNA
<213> ORGANISM: Homo sapiens

<400> SEQUENCE: 612
aaggggcugg gggagcaca                                                  19

<210> SEQ ID NO 613
<211> LENGTH: 22
<212> TYPE: RNA
<213> ORGANISM: Homo sapiens

<400> SEQUENCE: 613 gggggggugug gagccagggg gc                                             22

<210> SEQ ID NO 614
<211> LENGTH: 22
<212> TYPE: RNA
<213> ORGANISM: Homo sapiens

<400> SEQUENCE: 614
uauagggauu ggagccgugg cg                                              22

<210> SEQ ID NO 615
<211> LENGTH: 63
<212> TYPE: RNA
<213> ORGANISM: Homo sapiens

<400> SEQUENCE: 615
ggcuccgcag ggcccuggcg caggcaucca gacagcgggc gaaugccucc cccggccccg     60
cag                                                                   63

<210> SEQ ID NO 616
<211> LENGTH: 84
<212> TYPE: RNA
<213> ORGANISM: Homo sapiens

<400> SEQUENCE: 616
ccgcagccgc cgcgccgggc ccggguuggc cgcugacccc cgcggggccc cggcggccg      60 gggcggggc gggggcugcc ccgg                                             84
```

```
<210> SEQ ID NO 617
<211> LENGTH: 70
<212> TYPE: RNA
<213> ORGANISM: Homo sapiens

<400> SEQUENCE: 617
ggccgcggcg cgcaagaugg cggcgggccc gggcaccgcc ccuuccgccc cgccgggcgu    60
cgcacgaggc                                                          70

<210> SEQ ID NO 618
<211> LENGTH: 84
<212> TYPE: RNA
<213> ORGANISM: Homo sapiens

<400> SEQUENCE: 618 gaggcuggc ggggcgcggc cggaucgguc gagagcgucc uggcugauga cggucucccg    60
ugcccacgcc ccaaacgcag ucuc                                          84

<210> SEQ ID NO 619
<211> LENGTH: 100
<212> TYPE: RNA
<213> ORGANISM: Homo sapiens

<400> SEQUENCE: 619
gugagcgggc gcggcaggga ucgcgggcgg guggcggccu agggcgcgga gggcggaccg    60
ggaauggcgc gccgugcgcc gccggcguaa cugcggcgcu                         100

<210> SEQ ID NO 620
<211> LENGTH: 89
<212> TYPE: RNA
<213> ORGANISM: Homo sapiens

<400> SEQUENCE: 620
accuccggga cggcugggcg ccggcggccg ggagauccgc gcuuccugaa ucccggccgg    60
cccgcccggc gcccguccgc ccgcgggguc                                    89

<210> SEQ ID NO 621
<211> LENGTH: 110
<212> TYPE: RNA
<213> ORGANISM: Homo sapiens

<400> SEQUENCE: 621
gucuaccagg ugugggccca gcuuuacaua guucaugcug aggccgggau uucaugcaga    60
aaacugguug caaaaggugc ugaaggggcu gggggagcac aagggagaag              110

<210> SEQ ID NO 622
<211> LENGTH: 71
<212> TYPE: RNA
<213> ORGANISM: Homo sapiens

<400> SEQUENCE: 622
auggaggggg guguggagcc aggggggccca ggucuacagc uucucccgc ucccugcccc    60 cauacuccca g                                                        71

<210> SEQ ID NO 623
<211> LENGTH: 90
<212> TYPE: RNA
<213> ORGANISM: Homo sapiens

<400> SEQUENCE: 623
```

```
aggccucgcu guucucuaug gcuuuuuauu ccuaugugau ucuacugcuc acucauauag    60
ggauuggagc cguggcgcac ggcggggaca                                     90

<210> SEQ ID NO 624
<211> LENGTH: 17
<212> TYPE: RNA
<213> ORGANISM: Homo sapiens

<400> SEQUENCE: 624
ggggcggggg cgggggc                                                   17

<210> SEQ ID NO 625
<211> LENGTH: 15
<212> TYPE: RNA
<213> ORGANISM: Homo sapiens

<400> SEQUENCE: 625
cgcgccgggc ccggg                                                     15

<210> SEQ ID NO 626
<211> LENGTH: 15
<212> TYPE: RNA
<213> ORGANISM: Homo sapiens

<400> SEQUENCE: 626
ggcggcgggc ccggg                                                     15

<210> SEQ ID NO 627
<211> LENGTH: 15
<212> TYPE: RNA
<213> ORGANISM: Homo sapiens

<400> SEQUENCE: 627
ggcggcgggc ccggg                                                     15

<210> SEQ ID NO 628
<211> LENGTH: 24
<212> TYPE: RNA
<213> ORGANISM: Homo sapiens

<400> SEQUENCE: 628
gaucggucga gagcguccug gcug                                           24

<210> SEQ ID NO 629
<211> LENGTH: 15
<212> TYPE: RNA
<213> ORGANISM: Homo sapiens

<400> SEQUENCE: 629
gcugggcggg gcgcg                                                     15

<210> SEQ ID NO 630
<211> LENGTH: 16
<212> TYPE: RNA
<213> ORGANISM: Homo sapiens

<400> SEQUENCE: 630
ggcgcggagg gcggac                                                    16

<210> SEQ ID NO 631
<211> LENGTH: 15
<212> TYPE: RNA
```

```
<213> ORGANISM: Homo sapiens

<400> SEQUENCE: 631
ggcgcggagg gcgga                                                    15

<210> SEQ ID NO 632
<211> LENGTH: 17
<212> TYPE: RNA
<213> ORGANISM: Homo sapiens

<400> SEQUENCE: 632
ccuccgggac ggcuggg                                                  17

<210> SEQ ID NO 633
<211> LENGTH: 15
<212> TYPE: RNA
<213> ORGANISM: Homo sapiens

<400> SEQUENCE: 633
cuccgggacg gcugg                                                    15

<210> SEQ ID NO 634
<211> LENGTH: 22
<212> TYPE: RNA
<213> ORGANISM: Homo sapiens

<400> SEQUENCE: 634
auauagggau uggagccgug gc                                            22

<210> SEQ ID NO 635
<211> LENGTH: 20
<212> TYPE: RNA
<213> ORGANISM: Homo sapiens

<400> SEQUENCE: 635
auauagggau uggagccgug                                               20
```